US010954232B2

(12) United States Patent
Lee et al.

(10) Patent No.: US 10,954,232 B2
(45) Date of Patent: Mar. 23, 2021

(54) PYRAZOLE DERIVATIVE AS ALK5 INHIBITOR AND USES THEREOF

(71) Applicant: HANMI PHARMACEUTICAL CO., LTD., Hwaseong-si (KR)

(72) Inventors: Kyung Ik Lee, Hwaseong-si (KR); Young Hee Jung, Hwaseong-si (KR); Ji Young Song, Hwaseong-si (KR); Seung Ah Jun, Hwaseong-si (KR)

(73) Assignee: HANMI PHARMACEUTICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/313,948

(22) PCT Filed: Jun. 30, 2017

(86) PCT No.: PCT/KR2017/006940
§ 371 (c)(1),
(2) Date: Dec. 28, 2018

(87) PCT Pub. No.: WO2018/004290
PCT Pub. Date: Jan. 4, 2018

(65) Prior Publication Data
US 2019/0194198 A1    Jun. 27, 2019

(30) Foreign Application Priority Data

Jun. 30, 2016  (KR) .................. 10-2016-0082824
Dec. 27, 2016  (KR) .................. 10-2016-0180401
Jun. 29, 2017  (KR) .................. 10-2017-0082868

(51) Int. Cl.
| | |
|---|---|
| *C07D 471/04* | (2006.01) |
| *C07D 417/14* | (2006.01) |
| *C07D 401/14* | (2006.01) |
| *C07D 405/14* | (2006.01) |
| *C07D 413/14* | (2006.01) |
| *C07D 403/04* | (2006.01) |
| *A61K 31/4155* | (2006.01) |
| *C07D 495/04* | (2006.01) |
| *A61K 31/428* | (2006.01) |
| *A61K 31/4725* | (2006.01) |
| *A61P 19/04* | (2006.01) |
| *A61P 17/02* | (2006.01) |
| *A61P 11/00* | (2006.01) |
| *A61P 19/10* | (2006.01) |
| *A61P 35/00* | (2006.01) |

(52) U.S. Cl.
CPC ........ *C07D 471/04* (2013.01); *A61K 31/4155* (2013.01); *A61K 31/428* (2013.01); *A61K 31/4725* (2013.01); *C07D 401/14* (2013.01); *C07D 403/04* (2013.01); *C07D 405/14* (2013.01); *C07D 413/14* (2013.01); *C07D 417/14* (2013.01); *C07D 495/04* (2013.01); *A61P 11/00* (2018.01); *A61P 17/02* (2018.01); *A61P 19/04* (2018.01); *A61P 19/10* (2018.01); *A61P 35/00* (2018.01); *Y02A 50/30* (2018.01)

(58) Field of Classification Search
CPC ............ A61P 19/10; A61P 19/04; A61P 17/04
See application file for complete search history.

(56) References Cited

U.S. PATENT DOCUMENTS

2006/0100208 A1*  5/2006  Makriyannis ........ C07D 231/12
                                                                                514/241

FOREIGN PATENT DOCUMENTS

| CN | 101062916 | * 10/2007 |
|---|---|---|
| CN | 101062916 A | 10/2007 |
| CN | 101544631 A | 9/2009 |
| JP | 2003-524010 A | 8/2003 |
| JP | 2006-517592 A | 7/2006 |
| JP | 2006-527720 A | 12/2006 |
| JP | 2007-533734 A | 11/2007 |
| JP | 2008-506787 A | 3/2008 |
| JP | 2009-519977 A | 5/2009 |
| JP | 2010-506895 A | 3/2010 |
| KR | 10-2007-0107045 A | 11/2007 |
| WO | 2005/085241 A1 | 9/2005 |
| WO | 2008/047198 A1 | 4/2008 |
| WO | 2012/002680 A1 | 1/2012 |

OTHER PUBLICATIONS

Xian Ping Dai et al., "Synthesis and Biological Evaluation of Novel 1, 5-Diarylpyrazole-3-carboxamide Compounds as Inhibitors of ALK5", Chinese Chemical Letters, 2006, pp. 609-612, vol. 17, No. 5
Dai Xian-Ping et al., "Synthesis of Novel 1, 5-diarylpyrazole-3-carboxamide derivatives and their biological activities", Chinese Journal of Medical Chemistry, Dec. 2006, pp. 331-335, vol. 16, No. 6.
N. J. Laping et al., "Inhibition of Transforming Growth Factor (TGF)-β1-Induced Extracellular Matrix with a Novel Inhibitor of the TGF-β Type I Receptor Kinase Activity: SB-431542", Molecular Pharmacology, 2002, pp. 58-64, vol. 62, No. 1.

(Continued)

*Primary Examiner* — Mark L Shibuya
*Assistant Examiner* — Ebenezer O Sackey
(74) *Attorney, Agent, or Firm* — Sughrue Mion, PLLC

(57) ABSTRACT

The present disclosure relates to a novel substituted pyrazole derivative having an effect of inhibiting serine/threonine kinase activity targeting receptor ALK5 of TGF-β, and a pharmaceutical composition including the compound of the present disclosure as an active ingredient may be useful in preventing and/or treating cancers, autoimmune diseases, fibrotic diseases, inflammatory diseases, neurodegenerative diseases, infectious diseases, pulmonary diseases, cardiovascular diseases or metabolic diseases, or other diseases associated with a decrease in TGF family signaling activity.

13 Claims, No Drawings

(56) References Cited

OTHER PUBLICATIONS

International Search Report for PCT/KR2017/006940, dated Oct. 18, 2017.
Terashima et al., "R-268712, an orally active transforming growth factor-β type I receptor inhibitor, prevents glomerular sclerosis in a Thy1 nephritis model", European journal of Pharmacology, vol. 734, pp. 60-66, 2014, 7 pages total.

* cited by examiner

PYRAZOLE DERIVATIVE AS ALK5 INHIBITOR AND USES THEREOF

This Application is a National Stage of International Application No. PCT/KR2017/006940 filed Jun. 30, 2017, claiming priority based on Korean Patent Application No. 10-2016-0082824 filed Jun. 30, 2016, 10-2016-0180401 filed Dec. 27, 2016, and 10-2017-0082868 filed Jun. 29, 2017.

TECHNICAL FIELD

The present disclosure relates to a novel pyrazole derivative compound and use thereof, and in particular, to a novel pyrazole derivative having an ALK5 activity inhibiting effect, a pharmaceutically acceptable salt or solvate thereof, a pharmaceutical composition including such a compound as an active ingredient, and use thereof.

BACKGROUND ART

A transforming growth factor-β (TGF-β) signal regulates a developmental stage and cell activity in various ways, and thereby regulates various cell responses such as cell proliferation, differentiation, cell migration and cell death. TGF-β has at least 3 isoforms called TGF-β1, TGF-β2 and TGF-β3, and TGF-β1 may be divided into two well-preserved single membrane serine/threonine kinase type I (ALK5) and formulation TGF-β receptor. When oligomerization is induced by a ligand, the formulation receptor induces activation of ALK5 by hyperphosphorylating serine/threonine residues of ALK5 and producing Smad protein bonding sites. Activated ALK5 phosphorylates Smad2 and Smad3 to form a complex with Smad4, and migrates into the nucleus to regulate gene expression (Pennison, M. Pasche, B., Curr Opin Oncol (2007) 19, 579-85, Attisano, L., Wrana, J L. Science (2002) 296, 1646-47). Accordingly, abnormality in the TGF-β signaling function causes a number of human diseases (for example, deposition of extracellular matrix, inflammatory response, fibrotic dysfunction and advanced cancer).

Meanwhile, TGF-β responds to cancer formation in an early stage of cancer, and facilitates metastasis formation in cancer growing and late tumor stages. For cancer cells, TGF-β facilitates proliferation, epithelial mesenchymal transition (EMT), penetration and metastasis, acts as a major regulator of autocrine and paracrine between a cancer and microenvironments around the cancer, and acts on changes in the microenvironment, neovascularization and immunosuppression, which is effective in inhibiting tumor proliferation and cancer metastasis. An important role played by TGF-β in facilitating cancer growth also indicates a correlation between potent TGF-β expression and poor prognosis.

In addition, fibrosis of organs and tissues is considered to be well-known as a relation between the TGF-β and diseases. EMT activity has been known to be a main mechanism causing fibrosis to date. An inhibitor of intercellular signaling pathways is a useful therapeutic for fibroplasia. It is known to be centrally related to fibrosis of organs such as kidney, liver, lung, heart, bone marrow and skin. From such a point, it has become clear that inhibiting TGF-β is useful for preventing and treating all diseases accompanying fibrosis including chronic renal disease.

A compound according to the present disclosure and a salt thereof have been found to have very important pharmacological properties while being highly tolerant. Particularly, these exhibit TGF-β receptor I kinase (ALK5)-inhibiting properties. Accordingly, for signaling pathway ingredients of the TGF-β family, development of inhibitors in treating or preventing diseases associated with an abnormal behavior of this signaling pathway has been required.

DISCLOSURE

Technical Problem

The present disclosure is directed to providing a compound capable of selectively and effectively inhibiting ALK5 and/or ALK4, or a pharmaceutically acceptable salt thereof.

The present disclosure is also directed to providing a pharmaceutical composition including the compound as an active ingredient.

The present disclosure is also directed to providing a pharmaceutical composition capable of, by including the compound as an active ingredient, selectively and effectively inhibiting ALK5 and/or ALK4 and thereby preventing or treating various diseases mediated thereby.

Technical Solution

In view of the above, one embodiment of the present disclosure provides a compound represented by the following Chemical Formula 1, or a pharmaceutically acceptable salt thereof:

[Chemical Formula 1]

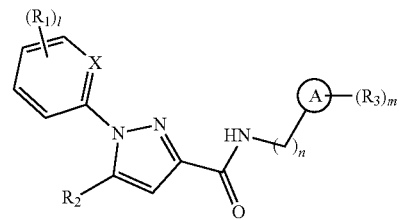

in Chemical Formula 1,

X is N or CH;

a ring A is $C_{3-6}$ cycloalkylene, $C_{6-10}$ arylene, $C_{5-10}$ heteroarylene containing 1 to 4 heteroatoms selected from among N, O and S atoms, or a non-aromatic fused heteropolycyclic ring containing 1 to 4 heteroatoms selected from among N, O and S;

$R_1$s are each independently hydrogen, halogen, or linear or branched $C_{1-6}$ alkyl, or halo $C_{1-6}$ alkyl, and when there are a plurality of $R_1$s, these are the same as or different from each other;

$R_2$s are each independently

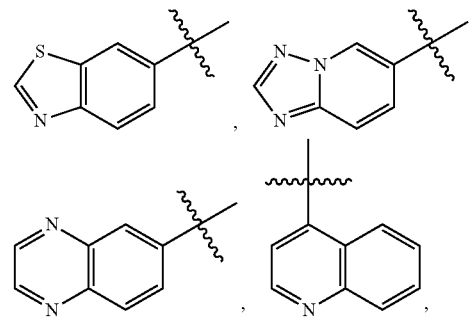

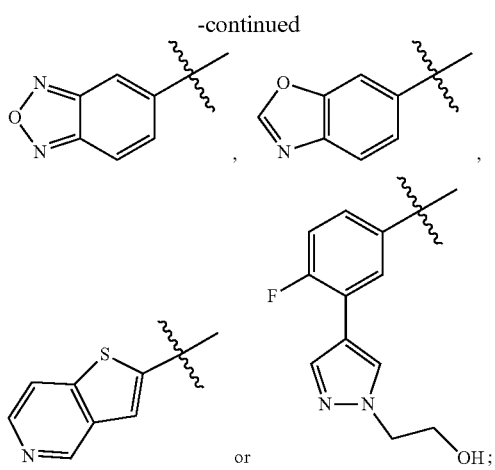

$R_3$ is hydrogen, halogen, linear or branched $C_{1-6}$ alkyl, linear or branched halo $C_{1-6}$ alkyl, $C_{3-10}$ cycloalkyl, $C_{3-10}$ heterocycloalkyl unsubstituted or substituted with $R_4$, $C_{6-10}$ heterobicycloalkyl, linear or branched $C_{2-6}$ alkenyl, $C_{2-6}$ alkynyl, —$(CH_2)_a$—$R_4$, —$(CH_2)_a$—$OR_4$, —$(CH_2)_a$—O—$(CH_2)_a$—$R_4$, —$(CH_2)_a$—S—$(CH_2)_a$—$R_4$, —$(CH_2)_a$—O—$(CH_2)_a$—$OR_4$, —$(CH_2)_a$ $NR_4R_5$, —$(CH_2)_a$—$NO_2$, —$(CH_2)_a$—CN, —$(CH_2)_a$—$COR_4$, —$(CH_2)_a$—$CO_2R_4$, —$(CH_2)_a$—$CONR_4R_5$, —$(CH_2)_a$—$NHCOR_4$, —$(CH_2)_a$—$SR_4$, —$(CH_2)_a$—$NHSO_2R_4$, —$(CH_2)_aSOR_6$, —$(CH_2)_a$—$SO_2R_6$, —$(CH_2)_a$—$SO_2NHR_6$, —$(CH_2)_a$—$SO(NH)R_6$ or —$(CH_2)_a$—$SO_2NR_4R_5$, or when there are a plurality of $R_3$s and they are adjacent to each other, they may be linked to each other to form a 5-membered or 6-membered ring with the ring A, one or more heteroatoms selected from among N, O and S atoms may be included in the ring, and the heteroatoms may be further oxidized;

$R_4$ and $R_5$ are each independently hydrogen, linear or branched $C_{1-6}$ alkyl, linear or branched halo $C_{1-6}$ alkyl, $C_{3-10}$ cycloalkyl, $C_{3-6}$ cycloalkenyl, $C_{1-6}$ carbonyl, $C_{6-12}$ aryl, —$(CH_2)_b$—$NR_6R_7$, or saturated or partially unsaturated 5-membered to 10-membered monocyclic or bicyclic heterocycloalkyl or heteroaryl containing 1 to 4 heteroatoms selected from among N, O and S;

$R_6$ and $R_7$ are each independently hydrogen, hydroxy, $C_{1-6}$ alkyl, halo $C_{1-6}$ alkyl or $C_{3-6}$ cycloalkyl;

a and b are an integer of 0 to 4; and l, m and n are each independently an integer of 0 to 4.

Another embodiment of the present disclosure provides a preventive or therapeutic use for diseases mediated by an ALK5 and/or ALK4 receptor in a pharmaceutical composition including the compound of Chemical Formula 1 or a pharmaceutically acceptable salt thereof as an active ingredient.

The disease is particularly preferably selected from the group consisting of fibrotic diseases (for example, scleroderma, lupus nephritis, connective tissue disease, wound healing, surgical trauma, spinal trauma, CNS injury, acute lung injury, idiopathic pulmonary fibrosis, chronic obstructive pulmonary disease, adult respiratory distress syndrome, acute lung injury, drug-induced lung injury, glomerulonephritis, diabetic renal disorder, hypertension-induced renal disorder, liver or biliary fibrosis, liver cirrhosis, primary biliary sclerosis, fatty liver disease, primary sclerogenous cholangitis, recurrent stenosis, cardiac fibrosis, ocular damage, fibrosclerosis, fibrous cancer, fibromyoma, fibroma, fibroadenoma, fibrosarcoma, grafted arterial disorder, and keloid); dehydration of nerve multiple sclerosis; Alzheimer's disease; great sinus vasculopathy; and tumor cells (for example, squamous cell carcinoma, multiple myeloma, melanoma, glioma, glioblastoma, leukemia, and carcinomas of lung, breast, ovary, cervix, liver, biliary duct, gastrointestinal tract, pancreas, prostate, and head and neck).

Advantageous Effects

A novel pyrazole derivative according to the present disclosure is capable of selectively or simultaneously inhibiting various diseases mediated by TGF-β, particularly ALK5 and/or ALK4. Accordingly, the novel derivative according to the present invention is useful in treating or preventing fibrotic diseases (for example, scleroderma, lupus nephritis, connective tissue disease, wound healing, surgical trauma, spinal trauma, CNS injury, acute lung injury, idiopathic pulmonary fibrosis, chronic obstructive pulmonary disease, adult respiratory distress syndrome, acute lung injury, drug-induced lung injury, glomerulonephritis, diabetic renal disorder, hypertension-induced renal disorder, liver or biliary fibrosis, liver cirrhosis, primary biliary sclerosis, fatty liver disease, primary sclerogenous cholangitis, recurrent stenosis, cardiac fibrosis, ocular damage, fibrosclerosis, fibrous cancer, fibromyoma, fibroma, fibroadenoma, fibrosarcoma, grafted arterial disorder, and keloid); dehydration of nerve multiple sclerosis; Alzheimer's disease; great sinus vasculopathy; and tumor cells (for example, squamous cell carcinoma, multiple myeloma, melanoma, glioma, glioblastoma, leukemia, and carcinomas of lung, breast, ovary, cervix, liver, biliary duck, gastrointestinal tract, pancreas, prostate, and head and neck).

MODE FOR DISCLOSURE

Definitions listed below are definitions of various terms used for describing the present disclosure. These definitions are used throughout the specification individually or as a part of terms including these unless limited otherwise.

The term 'halogen' used in the present specification means, unless mentioned otherwise, any one of fluorine, chlorine, bromine, iodine, or all of these.

The term 'alkyl' used in the present specification refers to, unless mentioned otherwise, a saturated linear or branched hydrocarbon radical expressed by $C_nH_{2n+1}$, and specifically, refers to a saturated linear or branched hydrocarbon radical each including carbon atoms between 1 to 6, 1 to 8, 1 to 10, or 1 to 20. Examples of these radicals include methyl, ethyl, propyl, isopropyl, n-butyl, tert-butyl, neopentyl, n-hexyl, heptyl and octyl radicals, but are not limited thereto.

The term 'alkenyl' used in the present specification refers to, unless mentioned otherwise, a monovalent group derived from an unsaturated linear or branched hydrocarbon moiety having at least one carbon-carbon double bond, and specifically, refers to an unsaturated linear or branched monovalent group each including carbon atoms between 2 to 6, 2 to 8, 2 to 10, or 2 to 20. Examples thereof include ethenyl, propenyl, butenyl, 1-methyl-2-buten-1-yl, heptenyl and octenyl radicals, but are not limited thereto.

The term 'cycloalkyl' used in the present specification refers to, unless mentioned otherwise, a monovalent group derived from a monocyclic or polycyclic saturated or partially unsaturated carbocyclic ring compound. For example, examples of C3-C8-cycloalkyl include, but are not limited to, cyclopropyl, cyclobutyl, cyclopentyl, cyclohexyl, cyclopentyl and cyclooctyl; and examples of C3-C12-cycloalkyl include, but are not limited to, cyclopropyl, cyclobutyl, cyclopentyl, cyclohexyl, bicyclo[2.2.1]heptyl, and bicyclo[2.2.2]octyl. A monovalent group derived from a monocyclic or polycyclic carbocyclic ring compound having at least one carbon-carbon double bond obtained by removing a single hydrogen atom is also considered. Examples of such a group include, but are not limited to, cyclopropenyl, cyclobutenyl, cyclopentenyl, cyclohexenyl and cycloheptenyl, cyclooctenyl and the like.

The term 'cycloalkenyl' used in the present specification refers to, unless mentioned otherwise, a partially unsaturated carbocyclic ring containing 3 to 6 carbon atoms and having a carbon-carbon double bond in the ring. Examples of such a group include, but are not limited to, cyclopentenyl, cyclohexenyl and the like.

The term 'aryl' used in the present specification refers to, unless mentioned otherwise, a mono- or poly-cyclic carbocyclic ring system having fused or non-fused one or more aromatic rings, and although not limited thereto, includes phenyl, naphthyl, tetrahydronaphthyl, indenyl, idenyl and the like.

The term 'heterocycloalkyl' used in the present specification refers to, unless mentioned otherwise, a saturated or partially unsaturated 3-membered to 10-membered monocyclic or polycyclic substituent containing one or more, for example, 1 to 4 heteroatoms selected from among N, O and S. Examples of the monocyclic heterocycloalkyl may include piperidinyl, morpholinyl, thiamorpholinyl, pyrrolidinyl, imidazolidinyl, tetrahydrofuranyl, piperazinyl and groups similar thereto, but are not limited thereto.

The term 'heteroaryl' used in the present specification means, unless mentioned otherwise, a 5-membered to 12-membered monocyclic, or bicyclic or higher aromatic group containing one or more, for example, 1 to 4 heteroatoms selected from among O, N and S. Examples of the monocyclic heteroaryl may include thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl and groups similar thereto, but are not limited thereto. Examples of the bicyclic heteroaryl may include indolyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, furinyl, furopyridinyl and groups similar thereto, but are not limited thereto.

The term 'non-aromatic fused heteropolycyclic ring' used in the present specification means a group having two or more rings fused to each other, including a heteroatom selected from among N, O and S as a ring-forming atom other than carbon, and having the whole molecule exhibiting non-aromacity (for example, having 5 to 10 nuclear atoms). Examples of the non-aromatic fused heteropolycyclic ring may include benzo[d][1,3]dioxol and the like, but are not limited thereto.

Hereinafter, the present disclosure will be described in more detail.

One embodiment of the present disclosure provides a compound of the following Chemical Formula 1, or a pharmaceutically acceptable salt thereof:

[Chemical Formula 1]

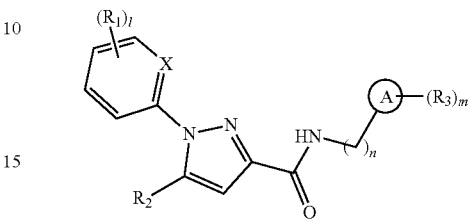

in Chemical Formula 1,

X is N or CH;

a ring A is $C_{3-6}$ cycloalkylene, $C_{6-10}$ arylene, $C_{5-10}$ heteroarylene containing 1 to 4 heteroatoms selected from among N, O and S atoms, or a non-aromatic fused heteropolycyclic ring containing 1 to 4 heteroatoms selected from among N, O and S;

$R_1$s are each independently hydrogen, halogen, or linear or branched $C_{1-6}$ alkyl, or halo $C_{1-6}$ alkyl, and when there are a plurality of $R_1$s, these are the same as or different from each other;

$R_2$s are each independently

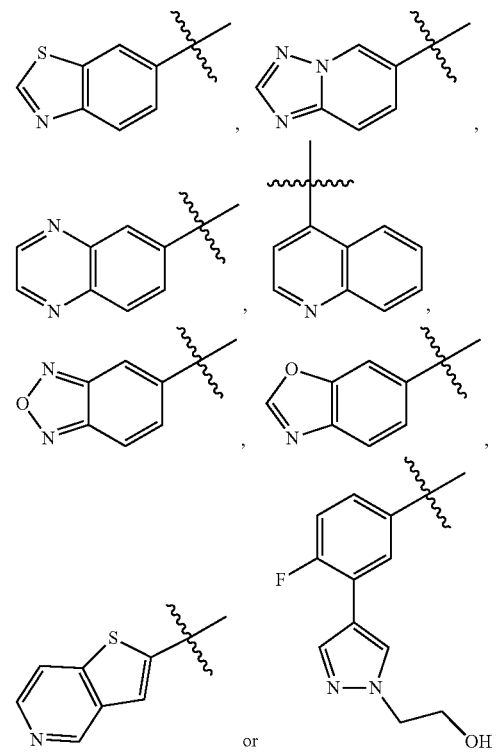

$R_3$ is hydrogen, halogen, linear or branched $C_{1-6}$ alkyl, linear or branched halo $C_{1-6}$ alkyl, $C_{3-10}$ cycloalkyl, $C_{3-10}$ heterocycloalkyl unsubstituted or substituted with $R_4$, $C_{6-10}$ heterobicycloalkyl, linear or branched $C_{2-6}$ alkenyl, $C_{2-6}$ alkynyl, —$(CH_2)_a$—$R_4$, —$(CH_2)_a$—$OR_4$, —$(CH_2)_a$—O—

—(CH$_2$)$_a$—R$_4$, —(CH$_2$)$_a$—S—(CH$_2$)$_a$—R$_4$, —(CH$_2$)$_a$—O—(CH$_2$)$_a$—R$_4$, —(CH$_2$)$_a$—OR$_4$, —(CH$_2$)$_a$NR$_4$R$_5$, —(CH$_2$)$_a$—NO$_2$, —(CH$_2$)$_a$—CN, —(CH$_2$)$_a$—COR$_4$, —(CH$_2$)$_a$—CO$_2$R$_4$, —(CH$_2$)$_a$—CONR$_4$R$_5$, —(CH$_2$)$_a$—NHCOR$_4$, —(CH$_2$)$_a$—SR$_4$, —(CH$_2$)$_a$—NHSO$_2$R$_4$, —(CH$_2$)$_a$SOR$_6$, —(CH$_2$)$_a$—SO$_2$R$_6$, —(CH$_2$)$_a$—SO$_2$NHR$_6$, —(CH$_2$)$_a$—SO(NH)R$_6$ or —(CH$_2$)$_a$—SO$_2$NR$_4$R$_5$, or when there are a plurality of R$_3$s and they are adjacent to each other, they may be linked to each other to form a 5-membered or 6-membered ring with the ring A, one or more heteroatoms selected from among N, O and S atoms may be included in the ring, and the heteroatoms may be further oxidized;

R$_4$ and R$_5$ are each independently hydrogen, linear or branched C$_{1-6}$ alkyl, linear or branched halo C$_{1-6}$ alkyl, C$_{3-10}$ cycloalkyl, C$_{3-6}$ cycloalkenyl, C$_{1-6}$ carbonyl, C$_{6-12}$ aryl, —(CH$_2$)$_b$—NR$_6$R$_7$, or saturated or partially unsaturated 5-membered to 10-membered monocyclic or bicyclic heterocycloalkyl or heteroaryl containing 1 to 4 heteroatoms selected from among N, O and S;

R$_6$ and R$_7$ are each independently hydrogen, hydroxy, C$_{1-6}$ alkyl, halo C$_{1-6}$ alkyl or C$_{3-6}$ cycloalkyl;

a and b are an integer of 0 to 4; and l, m and n are each independently an integer of 0 to 4.

In one specific embodiment of the present disclosure, X may be N, and R$_1$ may be C$_{1-6}$ alkyl.

In one specific embodiment of the present disclosure, the ring A may be phenyl, pyrazole, pyridinyl or benzo[d][1,3]dioxol.

In one specific embodiment of the present disclosure, the compound of Chemical Formula 1 may be selected from the group consisting of the following compounds, but is not limited thereto:

(1) 5-(benzo[d]thiazol-6-yl)-N-(4-methoxyphenyl)-1-(6-methylpyridin-2-yl)-1H-pyrazole-3-carboxamide;
(2) 5-(benzo[d]thiazol-6-yl)-N-(4-ethoxyphenyl)-1-(6-methylpyridin-2-yl)-1H-pyrazole-3-carboxamide;
(3) 5-(benzo[d]thiazol-6-yl)-N-(4-(cyclopropylmethoxy)phenyl)-1-(6-methylpyridin-2-yl)-1H-pyrazole-3-carboxamide;
(4) 5-(benzo[d]thiazol-6-yl)-N-(4-(2-methoxyethoxy)phenyl)-1-(6-methylpyridin-2-yl)-1H-pyrazole-3-carboxamide;
(5) 5-(benzo[d]thiazol-6-yl)-1-(6-methylpyridin-2-yl)-N-(4-(trifluoromethoxy)phenyl)-1H-pyrazole-3-carboxyamide;
(6) 5-(benzo[d]thiazol-6-yl)-N-(4-(benzyloxy)phenyl)-1-(6-methylpyridin-2-yl)-1H-pyrazole-3-carboxamide;
(7) N-(benzo[d][1,3]dioxol-5-yl)-5-(benzo[d]thiazol-6-yl)-1-(6-methylpyridin-2-yl)-1-H-pyrazole-3-carboxamide;
(8) 5-(benzo[d]thiazol-6-yl)-N-(4-fluoro-3-methoxyphenyl)-1-(6-methylpyridin-2-yl)-1H-pyrazole-3-carboxamide;
(9) 5-(benzo[d]thiazol-6-yl)-N-(2-fluoro-4-methoxyphenyl)-1-(6-methylpyridin-2-yl)-1H-pyrazole-3-carboxamide;
(10) 5-(benzo[d]thiazol-6-yl)-N-(3-fluoro-4-methoxyphenyl)-1-(6-methylpyridin-2-yl)-1H-pyrazole-3-carboxamide;
(11) 5-(benzo[d]thiazol-6-yl)-N-(3-aminophenyl)-1-(6-methylpyridin-2-yl)-1H-pyrazole-3-carboxamide;
(12) 5-(benzo[d]thiazol-6-yl)-N-(3-(methylamino)phenyl)-1-(6-methylpyridin-2-yl)-1H-pyrazole-3-carboxamide;
(13) 5-(benzo[d]thiazol-6-yl)-N-(4-(dimethylamino)phenyl)-1-(6-methylpyridin-2-yl)-1H-pyrazole-3-carboxamide;
(14) 5-(benzo[d]thiazol-6-yl)-1-(6-methylpyridin-2-yl)-N-(4-nitrophenyl)-1H-pyrazole-3-carboxamide;
(15) 5-(benzo[d]thiazol-6-yl)-N-(4-((2-(dimethylamino)ethyl)(methyl)amino) phenyl)-1-(6-methylpyridin-2-yl)-1H-pyrazole-3-carboxyamide;
(16) 5-(benzo[d]thiazol-6-yl)-N-(4-(3-(dimethylamino)pyrrolidin-1-yl)phenyl)-1-(6-methylpyridin-2-yl)-1H-pyrazole-3-carboxamide;
(17) 5-(benzo[d]thiazol-6-yl)-N-(3-chloro-4-(octahydro-6H-pyrrolo[3,4-b]pyridin-6-yl)phenyl)-1-(6-methylpyridin-2-yl)-1H-pyrazole-3-carboxamide;
(18) 5-(benzo[d]thiazol-6-yl)-1-(6-methylpyridin-2-yl)-N-phenyl-1H-pyrazole-3-carboxamide;
(19) 5-(benzo[d]thiazol-6-yl)-N-(3-tolyl)-1-(6-methylpyridin-2-yl)-1H-pyrazole-3-carboxamide;
(20) 5-(benzo[d]thiazol-6-yl)-1-(6-methylpyridin-2-yl)-N-(3-vinylphenyl)-1H-pyrazole-3-carboxamide;
(21) 5-(benzo[d]thiazol-6-yl)-N-(3-(trifluoromethyl)phenyl)-1-(6-methylpyridin-2-yl)-1H-pyrazole-3-carboxyamide;
(22) 5-(benzo[d]thiazol-6-yl)-N-(3-(cyanophenyl)-1-(6-methylpyridin-2-yl)-1H-pyrazole-3-carboxamide;
(23) 5-(benzo[d]thiazol-6-yl)-N-(3-acetylphenyl)-1-(6-methylpyridin-2-yl)-1H-pyrazole-3-carboxamide;
(24) ethyl 3-(5-(benzo[d]thiazol-6-yl)-1-(6-methylpyridin-2-yl)-1H-pyrazole-3-carboxyamido)benzoate;
(25) 5-(benzo[d]thiazol-6-yl)-N-(4-(methylcarbamoyl)phenyl)-1-(6-methylpyridin-2-yl)-1H-pyrazole-3-carboxyamide;
(26) 5-(benzo[d]thiazol-6-yl)-N-(4-acetamidophenyl)-1-(6-methylpyridin-2-yl)-1H-pyrazole-3-carboxamide;
(27) 5-(benzo[d]thiazol-6-yl)-N-(2-fluorophenyl)-1-(6-methylpyridin-2-yl)-1H-pyrazole-3-carboxamide;
(28) 5-(benzo[d]thiazol-6-yl)-N-(3-fluorophenyl)-1-(6-methylpyridin-2-yl)-1H-pyrazole-3-carboxamide;
(29) 5-(benzo[d]thiazol-6-yl)-N-(4-fluorophenyl)-1-(6-methylpyridin-2-yl)-1H-pyrazole-3-carboxamide;
(30) 5-(benzo[d]thiazol-6-yl)-N-(3,4-difluorophenyl)-1-(6-methylpyridin-2-yl)-1H-pyrazole-3-carboxamide;
(31) 5-(benzo[d]thiazol-6-yl)-N-(2-chlorophenyl)-1-(6-methylpyridin-2-yl)-1H-pyrazole-3-carboxamide;
(32) 5-(benzo[d]thiazol-6-yl)-N-(3-chlorophenyl)-1-(6-methylpyridin-2-yl)-1H-pyrazole-3-carboxamide;
(33) 5-(benzo[d]thiazol-6-yl)-N-(4-chlorophenyl)-1-(6-methylpyridin-2-yl)-1H-pyrazole-3-carboxamide;
(34) 5-(benzo[d]thiazol-6-yl)-N-(4-bromophenyl)-1-(6-methylpyridin-2-yl)-1H-pyrazole-3-carboxamide;
(35) 5-(benzo[d]thiazol-6-yl)-1-(6-methylpyridin-2-yl)-N-(3-(methylthio)phenyl)-1H-pyrazole-3-carboxamide;
(36) 5-(benzo[d]thiazol-6-yl)-1-(6-methylpyridin-2-yl)-N-(4-(methylthio)phenyl)-1H-pyrazole-3-carboxamide;
(37) 5-(benzo[d]thiazol-6-yl)-N-(4-(cyclopropylthio)phenyl)-1-(6-methylpyridin-2-yl)-1H-pyrazole-3-carboxyamide;
(38) 5-(benzo[d]thiazol-6-yl)-1-(6-methylpyridin-2-yl)-N-(3-(methylsulfinyl)phenyl)-1H-pyrazole-3-carboxyamide;
(39) 5-(benzo[d]thiazol-6-yl)-1-(6-methylpyridin-2-yl)-N-(4-(methylsulfinyl)phenyl)-1H-pyrazole-3-carboxyamide;
(40) 5-(benzo[d]thiazol-6-yl)-1-(6-methylpyridin-2-yl)-N-(3-(methylsulfonyl)phenyl)-1H-pyrazole-3-carboxyamide;
(41) 5-(benzo[d]thiazol-6-yl)-1-(6-methylpyridin-2-yl)-N-(4-(methylsulfonyl)phenyl)-1H-pyrazole-3-carboxyamide;
(42) 5-(benzo[d]thiazol-6-yl)-1-(6-methylpyridin-2-yl)-N-(4-(propylsulfonyl)phenyl)-1H-pyrazole-3-carboxyamide;

(43) 5-(benzo[d]thiazol-6-yl)-N-(4-(cyclopropylsulfonyl)phenyl)-1-(6-methylpyridin-2-yl)-1H-pyrazole-3-carboxamide;
(44) 5-(benzo[d]thiazol-6-yl)-N-(2-fluoro-4-(methylsulfonyl)phenyl)-1-(6-methylpyridin-2-yl)-1H-pyrazole-3-carboxamide;
(45) 5-(benzo[d]thiazol-6-yl)-1-(6-methylpyridin-2-yl)-N-(3-sulfamoylphenyl)-1H-pyrazole-3-carboxamide;
(46) 5-(benzo[d]thiazol-6-yl)-1-(6-methylpyridin-2-yl)-N-(4-sulfamoylphenyl)-1H-pyrazole-3-carboxamide;
(47) 5-(benzo[d]thiazol-6-yl)-1-(6-methylpyridin-2-yl)-N-(3-(N-methylsulfamoyl)phenyl)-1H-pyrazole-3-carboxamide;
(48) 5-(benzo[d]thiazol-6-yl)-1-(6-methylpyridin-2-yl)-N-(4-(N-methylsulfamoyl)phenyl)-1H-pyrazole-3-carboxamide;
(49) 5-(benzo[d]thiazol-6-yl)-N-(3-(N-cyclopropylsulfamoyl)phenyl)-1-(6-methylpyridin-2-yl)-1H-pyrazole-3-carboxamide;
(50) 5-(benzo[d]thiazol-6-yl)-N-(4-(N-cyclopropylsulfamoyl)phenyl)-1-(6-methylpyridin-2-yl)-1H-pyrazole-3-carboxamide;
(51) 5-(benzo[d]thiazol-6-yl)-N-(3-(N,N-dimethylsulfamoyl)phenyl)-1-(6-methylpyridin-2-yl)-1H-pyrazole-3-carboxamide;
(52) 5-(benzo[d]thiazol-6-yl)-N-(4-(N,N-dimethylsulfamoyl)phenyl)-1-(6-methylpyridin-2-yl)-1H-pyrazole-3-carboxamide;
(53) 5-(benzo[d]thiazol-6-yl)-1-(6-methylpyridin-2-yl)-N-(3-(methylsulfonamido)phenyl)-1H-pyrazole-3-carboxamide;
(54) 5-(benzo[d]thiazol-6-yl)-N-(3-(cyclopropanesulfonamido)phenyl)-1-(6-methylpyridin-2-yl)-1H-pyrazole-3-carboxamide;
(55) 5-(benzo[d]thiazol-6-yl)-N-(4-(cyclopropanesulfonamido)phenyl)-1-(6-methylpyridin-2-yl)-1H-pyrazole-3-carboxamide;
(56) 4-(5-(benzo[d]thiazol-6-yl)-1-(6-methylpyridin-2-yl)-1H-pyrazole-3-carboxamido)benzenesulfonic acid;
(57) 5-(benzo[d]thiazol-6-yl)-1-(6-methylpyridin-2-yl)-N-(4-((trifluoromethyl)sulfonyl)phenyl)-1H-pyrazole-3-carboxamide;
(58) 5-(benzo[d]thiazol-6-yl)-1-(6-methylpyridin-2-yl)-N-(4-(N-(2,2,2-trifluoroethyl)sulfamoyl)phenyl)-1H-pyrazole-3-carboxamide;
(59) 5-(benzo[d]thiazol-6-yl)-1-(6-methylpyridin-2-yl)-N-(4-((methylsulfonyl)methyl)phenyl)-1H-pyrazole-3-carboxamide;
(60) 5-(benzo[d]thiazol-6-yl)-1-(6-methylpyridin-2-yl)-N-(3-(sulfamoylmethyl)phenyl)-1H-pyrazole-3-carboxamide;
(61) 5-(benzo[d]thiazol-6-yl)-1-(6-methylpyridin-2-yl)-N-(4-(sulfamoylmethyl)phenyl)-1H-pyrazole-3-carboxamide;
(62) 5-(benzo[d]thiazol-6-yl)-N-(4-fluoro-3-(sulfamoylmethyl)phenyl)-1-(6-methylpyridin-2-yl)-1H-pyrazole-3-carboxamide;
(63) 5-(benzo[d]thiazol-6-yl)-N-(4-(((1,1-dioxidotetrahydrothiophen-3-yl)amino)phenyl)-1-(6-methylpyridin-2-yl)-1H-pyrazole-3-carboxamide;
(64) 5-(benzo[d]thiazol-6-yl)-1-(6-methylpyridin-2-yl)-N-(pyridin-4-yl)-1H-pyrazole-3-carboxamide;
(65) 5-(benzo[d]thiazol-6-yl)-N-(6-methoxypyridin-3-yl)-1-(6-methylpyridin-2-yl)-1H-pyrazole-3-carboxamide;
(66) 5-(benzo[d]thiazol-6-yl)-N-(2-methoxypyridin-4-yl)-1-(6-methylpyridin-2-yl)-1H-pyrazole-3-carboxamide;
(67) 5-(benzo[d]thiazol-6-yl)-N-(6-(methylthio)pyridin-3-yl)-1-(6-methylpyridin-2-yl)-1H-pyrazole-3-carboxamide;
(68) 5-(benzo[d]thiazol-6-yl)-1-(6-methylpyridin-2-yl)-N-(6-(methylsulfonyl)pyridin-3-yl)-1H-pyrazole-3-carboxamide;
(69) 5-(benzo[d]thiazol-6-yl)-N-(6-(methylsulfonyl)pyridin-3-yl)-1-(6-methylpyridin-2-yl)-1H-pyrazole-3-carboxamide;
(70) 5-(benzo[d]thiazol-6-yl)-1-(6-methylpyridin-2-yl)-N-(2-(methylsulfonyl)pyridin-4-yl)-1H-pyrazole-3-carboxamide;
(71) 5-(benzo[d]thiazol-6-yl)-N-(6-fluoropyridin-3-yl)-1-(6-methylpyridin-2-yl)-1H-pyrazole-3-carboxamide;
(72) 5-(benzo[d]thiazol-6-yl)-N-(2-fluoropyridin-4-yl)-1-(6-methylpyridin-2-yl)-1H-pyrazole-3-carboxamide;
(73) 5-(benzo[d]thiazol-6-yl)-N-(6-chloropyridin-3-yl)-1-(6-methylpyridin-2-yl)-1H-pyrazole-3-carboxamide;
(74) 5-(benzo[d]thiazol-6-yl)-N-(2-chloropyridin-4-yl)-1-(6-methylpyridin-2-yl)-1H-pyrazole-3-carboxamide;
(75) 5-(benzo[d]thiazol-6-yl)-1-(6-methylpyridin-2-yl)-N-(thiazol-2-yl)-1H-pyrazole-3-carboxamide;
(76) 5-(benzo[d]thiazol-6-yl)-N-benzyl-1-(6-methylpyridin-2-yl)-1H-pyrazole-3-carboxamide;
(77) 5-(benzo[d]thiazol-6-yl)-N-(2-fluorobenzyl)-1-(6-methylpyridin-2-yl)-1H-pyrazole-3-carboxamide;
(78) 5-(benzo[d]thiazol-6-yl)-N-(3-fluorobenzyl)-1-(6-methylpyridin-2-yl)-1H-pyrazole-3-carboxamide;
(79) 5-(benzo[d]thiazol-6-yl)-N-(4-fluorobenzyl)-1-(6-methylpyridin-2-yl)-1H-pyrazole-3-carboxamide;
(80) 5-(benzo[d]thiazol-6-yl)-1-(6-methylpyridin-2-yl)-N-(1-(methylsulfonyl)-1H-pyrazol-4-yl)-1H-pyrazole-3-carboxamide;
(81) 5-(benzo[d]thiazol-6-yl)-N-(1-(cyclopropylsulfonyl)-1H-pyrazol-4-yl)-1-(6-methylpyridin-2-yl)-1H-pyrazole-3-carboxamide;
(82) 5-(benzo[d]thiazol-6-yl)-N-(3-hydroxyphenyl)-1-(6-methylpyridin-2-yl)-1H-pyrazole-3-carboxamide;
(83) 5-(benzo[d]thiazol-6-yl)-N-(4-hydroxyphenyl)-1-(6-methylpyridin-2-yl)-1H-pyrazole-3-carboxamide;
(84) 5-(benzo[d]thiazol-6-yl)-N-(3-(hydroxymethyl)phenyl)-1-(6-methylpyridin-2-yl)-1H-pyrazole-3-carboxamide;
(85) 5-(benzo[d]thiazol-6-yl)-N-(4-(hydroxymethyl)phenyl)-1-(6-methylpyridin-2-yl)-1H-pyrazole-3-carboxamide;
(86) N-(4-aminophenyl)-5-(benzo[d]thiazol-6-yl)-1-(6-methylpyridin-2-yl)-1H-pyrazole-3-carboxamide;
(87) 5-(benzo[d]thiazol-6-yl)-N-(4-(butylamino)phenyl)-1-(6-methylpyridin-2-yl)-1H-pyrazole-3-carboxamide;
(88) 5-(benzo[d]thiazol-6-yl)-N-(4-(cyclopropylamino)phenyl)-1-(6-methylpyridin-2-yl)-1H-pyrazole-3-carboxamide;
(89) 5-(benzo[d]thiazol-6-yl)-1-(6-methylpyridin-2-yl)-N-(4-(S-methylsulfonimidoyl)phenyl)-1H-pyrazole-3-carboxamide;
(90) 5-([1,2,4]triazolo[1,5-α]pyridin-6-yl)-N-(2-methoxyphenyl)-1-(6-methylpyridin-2-yl)-1H-pyrazole-3-carboxamide;
(91) 5-([1,2,4]triazolo[1,5-α]pyridin-6-yl)-N-(3-methoxyphenyl)-1-(6-methylpyridin-2-yl)-1H-pyrazole-3-carboxamide;
(92) 5-([1,2,4]triazolo[1,5-α]pyridin-6-yl)-N-(2-methoxyphenyl)-1-(6-methylpyridin-2-yl)-1H-pyrazole-3-carboxamide;

(93) 5-([1,2,4]triazolo[1,5-α]pyridin-6-yl)-N-(4-hydroxyphenyl)-1-(6-methylpyridin-2-yl)-1H-pyrazole-3-carboxyamide;

(94) 5-([1,2,4]triazolo[1,5-α]pyridin-6-yl)-N-(4-isopropylphenyl)-1-(6-methylpyridin-2-yl)-1H-pyrazole-3-carboxyamide;

(95) 5-([1,2,4]triazolo[1,5-α]pyridin-6-yl)-N-(4-(2-methoxyethoxy)phenyl)-1-(6-methylpyridin-2-yl)-1H-pyrazole-3-carboxyamide;

(96) 5-([1,2,4]triazolo[1,5-α]pyridin-6-yl)-N-(benzo[d][1,3]dioxol-5-yl)-1-(6-methylpyridin-2-yl)-1H-pyrazole-3-carboxyamide;

(97) 5-([1,2,4]triazolo[1,5-α]pyridin-6-yl)-N-(2-fluoro-4-methoxyphenyl)-1-(6-methylpyridin-2-yl)-1H-pyrazole-3-carboxyamide;

(98) 5-([1,2,4]triazolo[1,5-α]pyridin-6-yl)-N-(3-fluoro-4-methoxyphenyl)-1-(6-methylpyridin-2-yl)-1H-pyrazole-3-carboxyamide;

(99) 5-([1,2,4]triazolo[1,5-α]pyridin-6-yl)-1-(6-methylpyridin-2-yl)-N-(2-(trifluoromethoxy)phenyl)-1H-pyrazole-3-carboxyamide;

(100) 5-([1,2,4]triazolo[1,5-α]pyridin-6-yl)-1-(6-methylpyridin-2-yl)-N-(3-(trifluoromethoxy)phenyl)-1H-pyrazole-3-carboxyamide;

(101) 5-([1,2,4]triazolo[1,5-α]pyridin-6-yl)-1-(6-methylpyridin-2-yl)-N-(4-(trifluoromethoxy)phenyl)-1H-pyrazole-3-carboxyamide;

(102) 5-([1,2,4]triazolo[1,5-α]pyridin-6-yl)-N-(3-(dimethylamino)phenyl)-1-(6-methylpyridin-2-yl)-1H-pyrazole-3-carboxyamide;

(103) 5-([1,2,4]triazolo[1,5-α]pyridin-6-yl)-N-(4-aminophenyl)-1-(6-methylpyridin-2-yl)-1H-pyrazole-3-carboxyamide;

(104) 5-([1,2,4]triazolo[1,5-α]pyridin-6-yl)-N-(4-(dimethylamino)phenyl)-1-(6-methylpyridin-2-yl)-1-H-pyrazole-3-carboxyamide;

(105) 5-([1,2,4]triazolo[1,5-α]pyridin-6-yl)-N-(4-(pyrrolidin-1-yl)phenyl) 1-(6-methylpyridin-2-yl)-1H-pyrazole-3-carboxyamide;

(106) 5-([1,2,4]triazolo[1,5-α]pyridin-6-yl)-N-(4-((2-(dimethylamino) ethyl)(methyl)amino)phenyl)-1-(6-methylpyridin-2-yl)-1H-pyrazole-3-carboxyamide;

(107) 5-([1,2,4]triazolo[1,5-α]pyridin-6-yl)-N-(4-(4-methylpiperazin-1-yl)phenyl)-1-(6-methylpyridin-2-yl)-1H-pyrazole-3-carboxyamide;

(108) 5-([1,2,4]triazolo[1,5-α]pyridin-6-yl)-N-(4-(4-acetylpiperazin-1-yl)phenyl)-1-(6-methylpyridin-2-yl)-1H-pyrazole-3-carboxyamide;

(109) 5-([1,2,4]triazolo[1,5-α]pyridin-6-yl)-N-(4-((1,1-dioxidotetrahydrothiophen-3-yl)amino)phenyl)-1-(6-methylpyridin-2-yl)-1H-pyrazole-3-carboxyamide;

(110) 5-([1,2,4]triazolo[1,5-α]pyridin-6-yl)-N-(4-acetamidophenyl)-1-(6-methylpyridin-2-yl)-1H-pyrazole-3-carboxyamide;

(111) 5-([1,2,4]triazolo[1,5-α]pyridin-6-yl)-N-(4-((dimethylamino)methyl)phenyl)-1-(6-methylpyridin-2-yl)-1H-pyrazole-3-carboxyamide;

(112) 5-([1,2,4]triazolo[1,5-α]pyridin-6-yl)-N-(2-(methylcarbamoyl)phenyl)-1-(6-methylpyridin-2-yl)-1H-pyrazole-3-carboxyamide;

(113) 5-([1,2,4]triazolo[1,5-α]pyridin-6-yl)-N-(4-(methylcarbamoyl)phenyl)-1-(6-methylpyridin-2-yl)-1H-pyrazole-3-carboxyamide;

(114) 5-([1,2,4]triazolo[1,5-α]pyridin-6-yl)-1-(6-methylpyridin-2-yl)-N-phenyl-1H-pyrazole-3-carboxyamide;

(115) 5-([1,2,4]triazolo[1,5-α]pyridin-6-yl)-1-(6-methylpyridin-2-yl)-N-(o-tolyl)-1H-pyrazole-3-carboxyamide;

(116) 5-([1,2,4]triazolo[1,5-α]pyridin-6-yl)-1-(6-methylpyridin-2-yl)-N-(m-tolyl)-1H-pyrazole-3-carboxyamide;

(117) 5-([1,2,4]triazolo[1,5-α]pyridin-6-yl)-1-(6-methylpyridin-2-yl)-N-(p-tolyl)-1H-pyrazole-3-carboxyamide;

(118) 5-([1,2,4]triazolo[1,5-α]pyridin-6-yl)-1-(6-methylpyridin-2-yl)-N-(3-(trifluoromethyl)phenyl)-1H-pyrazole-3-carboxyamide;

(119) 5-([1,2,4]triazolo[1,5-α]pyridin-6-yl)-1-(6-methylpyridin-2-yl)-N-(4-vinylphenyl)-1H-pyrazole-3-carboxyamide;

(120) 5-([1,2,4]triazolo[1,5-α]pyridin-6-yl)-N-(3-cyanophenyl)-1-(6-methylpyridin-2-yl)-1H-pyrazole-3-carboxyamide;

(121) 5-([1,2,4]triazolo[1,5-α]pyridin-6-yl)-N-(4-cyanophenyl)-1-(6-methylpyridin-2-yl)-1-H-pyrazole-3-carboxyamide;

(122) 5-([1,2,4]triazolo[1,5-α]pyridin-6-yl)-N-(3-acetylphenyl)-1-(6-methylpyridin-2-yl)-1H-pyrazole-3-carboxyamide;

(123) 5-([1,2,4]triazolo[1,5-α]pyridin-6-yl)-N-(4-acetylphenyl)-1-(6-methylpyridin-2-yl)-1H-pyrazole-3-carboxyamide;

(124) 5-([1,2,4]triazolo[1,5-α]pyridin-6-yl)-N-(2-fluorophenyl)-1-(6-methylpyridin-2-yl)-1H-pyrazole-3-carboxyamide;

(125) 5-([1,2,4]triazolo[1,5-α]pyridin-6-yl)-N-(3-fluorophenyl)-1-(6-methylpyridin-2-yl)-1H-pyrazole-3-carboxyamide;

(126) 5-([1,2,4]triazolo[1,5-α]pyridin-6-yl)-N-(4-fluorophenyl)-1-(6-methylpyridin-2-yl)-1H-pyrazole-3-carboxyamide;

(127) 5-([1,2,4]triazolo[1,5-α]pyridin-6-yl)-N-(2-chlorophenyl)-1-(6-methylpyridin-2-yl)-1H-pyrazole-3-carboxyamide;

(128) 5-([1,2,4]triazolo[1,5-α]pyridin-6-yl)-N-(3-chlorophenyl)-1-(6-methylpyridin-2-yl)-1H-pyrazole-3-carboxyamide;

(129) 5-([1,2,4]triazolo[1,5-α]pyridin-6-yl)-N-(4-chlorophenyl)-1-(6-methylpyridin-2-yl)-1H-pyrazole-3-carboxyamide;

(130) 5-([1,2,4]triazolo[1,5-α]pyridin-6-yl)-N-(2-bromophenyl)-1-(6-methylpyridin-2-yl)-1H-pyrazole-3-carboxyamide;

(131) 5-([1,2,4]triazolo[1,5-α]pyridin-6-yl)-N-(3-bromophenyl)-1-(6-methylpyridin-2-yl)-1H-pyrazole-3-carboxyamide;

(132) 5-([1,2,4]triazolo[1,5-α]pyridin-6-yl)-N-(4-bromophenyl)-1-(6-methylpyridin-2-yl)-1H-pyrazole-3-carboxyamide;

(133) 5-([1,2,4]triazolo[1,5-α]pyridin-6-yl)-N-(2,3-difluorophenyl)-1-(6-methylpyridin-2-yl)-1H-pyrazole-3-carboxyamide;

(134) 5-([1,2,4]triazolo[1,5-α]pyridin-6-yl)-N-(2,4-difluorophenyl)-1-(6-methylpyridin-2-yl)-1H-pyrazole-3-carboxyamide;

(135) 5-([1,2,4]triazolo[1,5-α]pyridin-6-yl)-N-(2,5-difluorophenyl)-1-(6-methylpyridin-2-yl)-1H-pyrazole-3-carboxyamide;

(136) 5-([1,2,4]triazolo[1,5-α]pyridin-6-yl)-N-(3,4-difluorophenyl)-1-(6-methylpyridin-2-yl)-1H-pyrazole-3-carboxyamide;

(137) 5-([1,2,4]triazolo[1,5-α]pyridin-6-yl)-N-(3,5-difluorophenyl)-1-(6-methylpyridin-2-yl)-1H-pyrazole-3-carboxamide;
(138) 5-([1,2,4]triazolo[1,5-α]pyridin-6-yl)-N-(3-chloro-2-fluorophenyl)-1-(6-methylpyridin-2-yl)-1H-pyrazole-3-carboxamide;
(139) 5-([1,2,4]triazolo[1,5-α]pyridin-6-yl)-N-(4-chloro-2-fluorophenyl)-1-(6-methylpyridin-2-yl)-1H-pyrazole-3-carboxamide;
(140) 5-([1,2,4]triazolo[1,5-α]pyridin-6-yl)-N-(3-chloro-4-fluorophenyl)-1-(6-methylpyridin-2-yl)-1H-pyrazole-3-carboxamide;
(141) 5-([1,2,4]triazolo[1,5-α]pyridin-6-yl)-N-(3,4-dichlorophenyl)-1-(6-methylpyridin-2-yl)-1H-pyrazole-3-carboxamide;
(142) 5-([1,2,4]triazolo[1,5-α]pyridin-6-yl)-N-(2-bromo-4-fluorophenyl)-1-(6-methylpyridin-2-yl)-1H-pyrazole-3-carboxamide;
(143) 5-([1,2,4]triazolo[1,5-α]pyridin-6-yl)-N-(3-(methoxythio)phenyl)-1-(6-methylpyridin-2-yl)-1H-pyrazole-3-carboxamide;
(144) 5-([1,2,4]triazolo[1,5-α]pyridin-6-yl)-N-(4-(methoxythio)phenyl)-1-(6-methylpyridin-2-yl)-1H-pyrazole-3-carboxamide;
(145) 5-([1,2,4]triazolo[1,5-α]pyridin-6-yl)-N-(3-(methylsulfinyl)phenyl)-1-(6-methylpyridin-2-yl)-1H-pyrazole-3-carboxamide;
(146) 5-([1,2,4]triazolo[1,5-α]pyridin-6-yl)-N-(4-(methylsulfinyl)phenyl)-1-(6-methylpyridin-2-yl)-1H-pyrazole-3-carboxamide;
(147) 5-([1,2,4]triazolo[1,5-α]pyridin-6-yl)-N-(4-(methylsulfonyl)phenyl)-1-(6-methylpyridin-2-yl)-1H-pyrazole-3-carboxamide;
(148) 5-([1,2,4]triazolo[1,5-α]pyridin-6-yl)-N-(4-sulfamoylphenyl)-1-(6-methylpyridin-2-yl)-1H-pyrazole-3-carboxamide;
(149) 5-([1,2,4]triazolo[1,5-α]pyridin-6-yl)-N-(4-(S-methylsulfonimidoyl)phenyl)-1-(6-methylpyridin-2-yl)-1H-pyrazole-3-carboxamide;
(150) 5-([1,2,4]triazolo[1,5-α]pyridin-6-yl)-N-(4-(propylsulfonyl)phenyl)-1-(6-methylpyridin-2-yl)-1H-pyrazole-3-carboxamide;
(151) 5-([1,2,4]triazolo[1,5-α]pyridin-6-yl)-N-(4-(propylsulfonyl)phenyl)-1-(6-methylpyridin-2-yl)-1H-pyrazole-3-carboxamide;
(152) 5-([1,2,4]triazolo[1,5-α]pyridin-6-yl)-N-(6-fluoropyridin-3-yl)-1-(6-methylpyridin-2-yl)-1H-pyrazole-3-carboxamide;
(153) 5-([1,2,4]triazolo[1,5-α]pyridin-6-yl)-N-(6-chloropyridin-3-yl)-1-(6-methylpyridin-2-yl)-1H-pyrazole-3-carboxamide;
(154) 5-([1,2,4]triazolo[1,5-α]pyridin-6-yl)-N-(6-methoxypyridin-3-yl)-1-(6-methylpyridin-2-yl)-1H-pyrazole-3-carboxamide;
(155) 5-([1,2,4]triazolo[1,5-α]pyridin-6-yl)-N-(2-fluorobenzyl)-1-(6-methylpyridin-2-yl)-1H-pyrazole-3-carboxamide;
(156) 5-([1,2,4]triazolo[1,5-α]pyridin-6-yl)-N-(3-fluorobenzyl)-1-(6-methylpyridin-2-yl)-1H-pyrazole-3-carboxamide;
(157) 5-([1,2,4]triazolo[1,5-α]pyridin-6-yl)-N-(4-fluorobenzyl)-1-(6-methylpyridin-2-yl)-1H-pyrazole-3-carboxamide;
(158) 5-([1,2,4]triazolo[1,5-α]pyridin-6-yl)-N-(3-methoxybenzyl)-1-(6-methylpyridin-2-yl)-1H-pyrazole-3-carboxamide;
(159) 5-([1,2,4]triazolo[1,5-α]pyridin-6-yl)-N-(4-methoxybenzyl)-1-(6-methylpyridin-2-yl)-1H-pyrazole-3-carboxamide;
(160) 5-([1,2,4]triazolo[1,5-α]pyridin-6-yl)-N-(4-(dimethylamino)benzyl)-1-(6-methylpyridin-2-yl)-1H-pyrazole-3-carboxamide;
(161) 5-([1,2,4]triazolo[1,5-α]pyridin-6-yl)-N-(-acetamidobenzyl)-1-(6-methylpyridin-2-yl)-1H-pyrazole-3-carboxamide;
(162) 5-([1,2,4]triazolo[1,5-α]pyridin-6-yl)-1-(6-methylpyridin-2-yl)-N-(1-(methylsulfonyl)-1H-pyrazol-4-yl)-1H-pyrazole-3-carboxamide;
(163) 5-([1,2,4]triazolo[1,5-α]pyridin-6-yl)-N-(1-cyclopropyl sulfonyl)-1H-pyrazol-4-yl)-1-(6-methylpyridin-2-yl)-1H-pyrazole-3-carboxamide;
(164) N-(4-methoxyphenyl)-1-(6-methylpyridin-2-yl)-5-(quinoxalin-6-yl)-1H-pyrazole-3-carboxamide;
(165) N-(3-methoxyphenyl)-1-(6-methylpyridin-2-yl)-5-(quinoxalin-6-yl)-1H-pyrazole-3-carboxamide;
(166) N-(2-methoxyphenyl)-1-(6-methylpyridin-2-yl)-5-(quinoxalin-6-yl)-1H-pyrazole-3-carboxamide;
(167) N-(4-(2-methoxyethoxy)phenyl)-1-(6-methylpyridin-2-yl)-5-(quinoxalin-6-yl)-1H-pyrazole-3-carboxamide;
(168) N-(benzo[d][1,3]dioxol-5-yl)-1-(6-methylpyridin-2-yl)-5-(quinoxalin-6-yl)-1H-pyrazole-3-carboxamide;
(169) N-(2,3-dihydrobenzo[b][1,4]dioxin-6-yl)-1-(6-methylpyridin-2-yl)-5-(quinoxalin-6-yl)-1H-pyrazole-3-carboxamide;
(170) N-(4-(dimethylamino)phenyl)-1-(6-methylpyridin-2-yl)-5-(quinoxalin-6-yl)-1H-pyrazole-3-carboxamide;
(171) 1-(6-methylpyridin-2-yl)-N-(4-morpholinophenyl)-5-(quinoxalin-6-yl)-1H-pyrazole-3-carboxamide;
(172) N-(4-(4-methylpiperazin-1-yl)phenyl)-1-(6-methylpyridin-2-yl)-5-(quinoxalin-6-yl)-1H-pyrazole-3-carboxamide;
(173) N-(4-(4-acetylpiperazin-1-yl)phenyl)-1-(6-methylpyridin-2-yl)-5-(quinoxalin-6-yl)-1H-pyrazole-3-carboxamide;
(174) N-(4-cyanophenyl)-1-(6-methylpyridin-2-yl)-5-(quinoxalin-6-yl)-1H-pyrazole-3-carboxamide;
(175) N-(3-cyanophenyl)-1-(6-methylpyridin-2-yl)-5-(quinoxalin-6-yl)-1H-pyrazole-3-carboxamide;
(176) N-(2-cyanophenyl)-1-(6-methylpyridin-2-yl)-5-(quinoxalin-6-yl)-1H-pyrazole-3-carboxamide;
(177) 1-(6-methylpyridin-2-yl)-N-(4-(morpholinomethyl)phenyl)-5-(quinoxalin-6-yl)-1H-pyrazole-3-carboxamide;
(178) N-(4-acetylphenyl)-1-(6-methylpyridin-2-yl)-5-(quinoxalin-6-yl)-1H-pyrazole-3-carboxamide;
(179) N-(3-acetylphenyl)-1-(6-methylpyridin-2-yl)-5-(quinoxalin-6-yl)-1H-pyrazole-3-carboxamide;
(180) 1-(6-methylpyridin-2-yl)-5-(quinoxalin-6-yl)-N-(4-(trifluoromethyl)phenyl)-1H-pyrazole-3-carboxamide;
(181) 1-(6-methylpyridin-2-yl)-5-(quinoxalin-6-yl)-N-(3-(trifluoromethyl)phenyl)-1H-pyrazole-3-carboxamide;
(182) N-(4-(methylcarbamoyl)phenyl)-1-(6-methylpyridin-2-yl)-5-(quinoxalin-6-yl)-1H-pyrazole-3-carboxamide;
(183) N-(4-fluorophenyl)-1-(6-methylpyridin-2-yl)-5-(quinoxalin-6-yl)-1H-pyrazole-3-carboxamide;
(184) N-(3-fluorophenyl)-1-(6-methylpyridin-2-yl)-5-(quinoxalin-6-yl)-1H-pyrazole-3-carboxamide;
(185) N-(2-fluorophenyl)-1-(6-methylpyridin-2-yl)-5-(quinoxalin-6-yl)-1H-pyrazole-3-carboxamide;
(186) N-(3,4-difluorophenyl)-1-(6-methylpyridin-2-yl)-5-(quinoxalin-6-yl)-1H-pyrazole-3-carboxamide;
(187) N-(2,4-difluorophenyl)-1-(6-methylpyridin-2-yl)-5-(quinoxalin-6-yl)-1H-pyrazole-3-carboxamide;

(188) N-(2,3-difluorophenyl)-1-(6-methylpyridin-2-yl)-5-(quinoxalin-6-yl)-1H-pyrazole-3-carboxamide;
(189) N-(4-chlorophenyl)-1-(6-methylpyridin-2-yl)-5-(quinoxalin-6-yl)-1H-pyrazole-3-carboxamide;
(190) N-(2-chlorophenyl)-1-(6-methylpyridin-2-yl)-5-(quinoxalin-6-yl)-1H-pyrazole-3-carboxamide;
(191) N-(4-bromophenyl)-1-(6-methylpyridin-2-yl)-5-(quinoxalin-6-yl)-1H-pyrazole-3-carboxamide;
(192) N-(6-methoxypyridin-3-yl)-1-(6-methylpyridin-2-yl)-5-(quinoxalin-6-yl)-1H-pyrazole-3-carboxamide;
(193) N-(4-methoxybenzyl)-1-(6-methylpyridin-2-yl)-5-(quinoxalin-6-yl)-1H-pyrazole-3-carboxamide;
(194) N-(4-cyanobenzyl)-1-(6-methylpyridin-2-yl)-5-(quinoxalin-6-yl)-1H-pyrazole-3-carboxamide;
(195) N-(3-acetylbenzyl)-1-(6-methylpyridin-2-yl)-5-(quinoxalin-6-yl)-1H-pyrazole-3-carboxamide;
(196) N-(4-fluorobenzyl)-1-(6-methylpyridin-2-yl)-5-(quinoxalin-6-yl)-1H-pyrazole-3-carboxamide;
(197) N-(3-fluorobenzyl)-1-(6-methylpyridin-2-yl)-5-(quinoxalin-6-yl)-1H-pyrazole-3-carboxamide;
(198) N-(2-fluorobenzyl)-1-(6-methylpyridin-2-yl)-5-(quinoxalin-6-yl)-1H-pyrazole-3-carboxamide;
(199) N-(4-chlorobenzyl)-1-(6-methylpyridin-2-yl)-5-(quinoxalin-6-yl)-1H-pyrazole-3-carboxamide;
(200) N-(3-chlorobenzyl)-1-(6-methylpyridin-2-yl)-5-(quinoxalin-6-yl)-1H-pyrazole-3-carboxamide;
(201) N-(2-chlorobenzyl)-1-(6-methylpyridin-2-yl)-5-(quinoxalin-6-yl)-1H-pyrazole-3-carboxamide;
(202) N-(2-fluorophenyl)-5-(quinoxalin-6-yl)-1-(m-tolyl)-1H-pyrazole-3-carboxamide;
(203) 1-(5-chloro-2-fluorophenyl)-N-(4-methoxyphenyl)-5-(quinoxalin-6-yl)-1H-pyrazole-3-carboxamide;
(204) 1-(5-chloro-2-fluorophenyl)-N-(4-(dimethylamino)phenyl)-5-(quinoxalin-6-yl)-1H-pyrazole-3-carboxamide;
(205) N-(4-methoxyphenyl)-5-(quinoxalin-6-yl)-1-(6-trifluoromethyl)pyridin-2-yl)-1H-pyrazole-3-carboxamide;
(206) N-(4-(dimethylamino)phenyl)-5-(quinoxalin-6-yl)-1-(6-trifluoromethyl)pyridin-2-yl)-1H-pyrazole-3-carboxamide;
(207) 1-(6-bromopyridin-2-yl)-N-(4-methoxyphenyl)-5-(quinoxalin-6-yl)-1H-pyrazole-3-carboxamide;
(208) 1-(6-bromopyridin-2-yl)-N-(4-(dimethylamino)phenyl)-5-(quinoxalin-6-yl)-1H-pyrazole-3-carboxamide;
(209) N-(2-fluorophenyl)-1-(6-methylpyridin-2-yl)-5-(quinolin-4-yl)-1H-pyrazole-3-carboxamide;
(210) N-(4-methoxyphenyl)-1-(6-methylpyridin-2-yl)-5-(quinolin-4-yl)-1H-pyrazole-3-carboxamide;
(211) 1-(6-methylpyridin-2-yl)-N-(4-(methylsulfonyl)phenyl)-5-(quinolin-4-yl)-1H-pyrazole-3-carboxamide;
(212) N-(6-methoxypyridin-3-yl)-1-(6-methylpyridin-2-yl)-5-(quinolin-4-yl)-1H-pyrazole-3-carboxamide;
(213) N-(6-chloropyridin-3-yl)-1-(6-methylpyridin-2-yl)-5-(quinolin-4-yl)-1H-pyrazole-3-carboxamide;
(214) N-(benzo[d][1,3]dioxol-5-yl)-1-(6-methylpyridin-2-yl)-5-(quinolin-4-yl)-1H-pyrazole-3-carboxamide;
(215) N-(3-fluoro-4-methoxyphenyl)-1-(6-methylpyridin-2-yl)-5-(quinolin-4-yl)-1H-pyrazole-3-carboxamide;
(216) N-(2-fluoro-4-methoxyphenyl)-1-(6-methylpyridin-2-yl)-5-(quinolin-4-yl)-1H-pyrazole-3-carboxamide;
(217) N-(4-(2-methoxyethoxy)phenyl)-1-(6-methylpyridin-2-yl)-5-(quinolin-4-yl)-1H-pyrazole-3-carboxamide;
(218) 5-(benzo[c][1,2,5]oxadiazol-5-yl)-N-(4-(cyclopropylsulfonyl)phenyl)-1-(6-methylpyridin-2-yl)-1H-pyrazole-3-carboxamide;
(219) 5-(benzo[d]oxazol-6-yl)-N-(2-fluorophenyl)-1-(6-methylpyridin-2-yl)-1H-pyrazole-3-carboxamide;
(220) 5-(benzo[d]oxazol-6-yl)-N-(4-(cyclopropylsulfonyl)phenyl)-1-(6-methylpyridin-2-yl)-1H-pyrazole-3-carboxamide;
(221) N-cyclopropyl-5-(4-fluoro-3-(1-(2-hydroxyethyl)-1H-pyrazol-4-yl)phenyl)-1-(6-methylpyridin-2-yl)-1H-pyrazole-3-carboxamide;
(222) N-(1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxamide;
(223) N-(1-methyl-1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxamide;
(224) N-(1-(methylsulfonyl)-1H-pyrazol-4-yl)-5-(4-fluoro-3-(1-(2-hydroxy ethyl)-1H-pyrazol-4-yl)phenyl)-1-(6-methylpyridin-2-yl)-1H-pyrazole-3-carboxamide;
(225) N-(4-chlorophenyl)-5-(4-fluoro-3-(1-(2-hydroxyethyl)-1H-pyrazol-4-yl)phenyl)-1-(6-methylpyridin-2-yl)-1H-pyrazole-3-carboxamide;
(226) N-(4-(methylsulfonyl)phenyl)-5-(4-fluoro-3-(1-(2-hydroxyethyl)-1H-pyrazol-4-yl)phenyl)-1-(6-methylpyridin-2-yl)-1H-pyrazole-3-carboxamide; and
(227) N-(2-fluorophenyl)-5-(thieno[3,2,c]pyridin-2-yl)-1-(m-tolyl)-1H-pyrazole-3-carboxamide.

The compound of Chemical Formula 1 according to the present disclosure may be prepared using a method representatively illustrated in the following Reaction Formula 1:

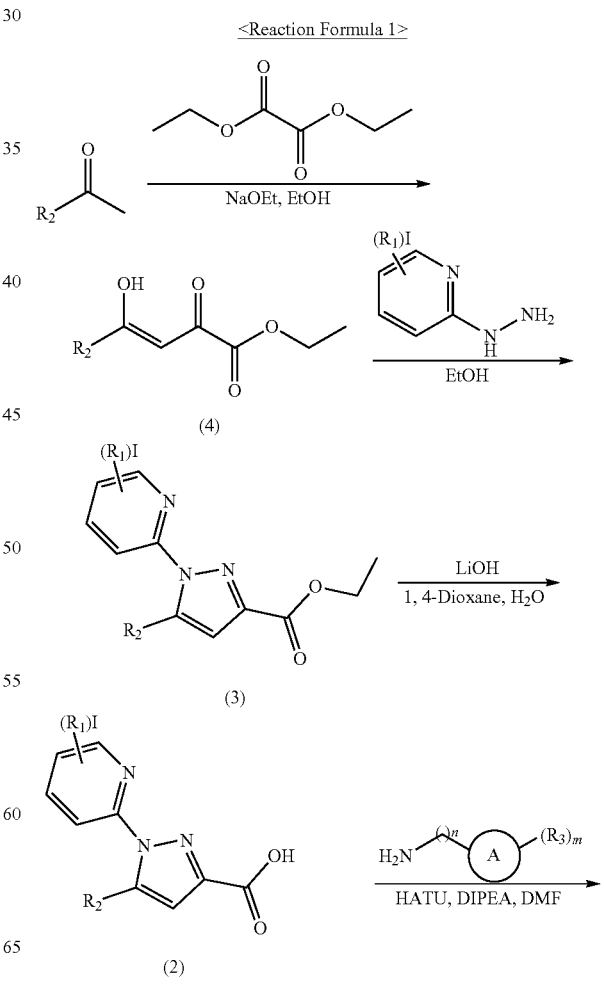

-continued

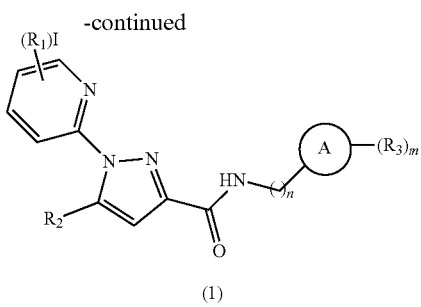

(1)

In Reaction Formula 1, $R_1$, $R_2$, $R_3$, A, l, m and n each have the same definitions as in Chemical Formula 1.

When describing the reaction in more detail with reference to Reaction Formula 1, an acetyl compound having $R_2$, diethyl oxalate and ethoxysodium solution are refluxed in an organic solvent (for example, ethanol) to obtain Compound (4). Compound (4) is refluxed with a hydrazinyl material having an $(R_1)_l$ group and the like to obtain Compound (3), and this may be stirred under 1,4-dioxane and lithium hydroxide to obtain Intermediate Compound (2). Next, Compound (2) may be reacted with an aniline derivative having an $R_3$ group together with HATU and DIPEA in N,N-dimethylformamide to obtain a target compound of Chemical Formula 1 of the present disclosure.

The compound of Chemical Formula 1 according to the present disclosure may be prepared to a pharmaceutically acceptable salt form having an inorganic acid or an organic acid added thereto, and herein, examples of the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, toluenesulfonic acid or the like.

Specifically, the pharmaceutically acceptable salt according to the present disclosure may be prepared by dissolving the compound of Chemical Formula 1 in an organic solvent such as acetone, methanol, ethanol or acetonitrile, adding an organic acid or an inorganic acid thereto, and filtering crystals precipitated therefrom. Alternatively, the pharmaceutically acceptable salt may be prepared by vacuuming a solvent or excess acid in an acid-added reaction mixture to dry the residue, or prepared by filtering a salt precipitated from adding other organic solvents.

The compound of Chemical Formula 1 or a pharmaceutically acceptable salt thereof according to the present disclosure may have a form of a hydrate or solvate, and such compounds are also included in the present disclosure.

The compound of Chemical Formula 1 or a pharmaceutically acceptable salt thereof according to the present disclosure may effectively inhibit protein kinase. In one embodiment, the compound of the present disclosure may effectively prevent or treat diseases mediated by the ALK5 receptor or the ALK4 receptor, or both the ALK5 receptor and the ALK4 receptor. Specifically, the disease may be selected from the group consisting of kidney-, liver- or lung-fibrosis, glomerulonephritis, diabetic renal disease, erythematous nephritis, hypertension-induced renal disease, kidney interstitial fibrosis, kidney fibrosis derived from drug exposure complications, HIV-related renal disease, organ transplantation gangrene, liver fibrosis caused by all diseases, hepatic dysfunction caused by infection, alcohol-induced hepatitis, biliary disorder, pulmonary fibrosis, acute lung injury, adult respiratory pain syndrome, idiopathic pulmonary fibrosis, chronic obstructive pulmonary disease, pulmonary fibrosis caused by infection or toxic factors, cardiac fibrosis after myocardial infarction, congestive heart failure, dilated cardiomyopathy, myocarditis, vascular stenosis, restenosis, atherosclerosis, visual impairment, corneal injury, proliferative vitreoretinopathy, excessive or exacerbated scar or keloid formation in the dermis occurring during wound healing from trauma or surgical wounds, peritoneum and subcutaneous adhesion, skin sclerosis, fibrosclerosis, progressive systemic sclerosis, dermatomyositis, multiple myositis, arthritis, osteoporosis, ulcer, impaired nerve function, male impotence, Alzheimer's disease, Raynaud's disease, fibrous cancer, metastasis growth of tumors, radiation-induced fibrosis and thrombosis, but is not limited thereto.

In one specific embodiment of the present disclosure, the compound of Chemical Formula 1 or a pharmaceutically acceptable salt thereof may prevent or treat fibrotic diseases or fibrotic conditions. Herein, the fibrotic disease or the fibrotic condition may be selected from the group consisting of liver fibrosis, kidney fibrosis, pulmonary fibrosis, irritable pneumonia, interstitial fibrosis, systematic sclerodermie, macular degeneration, pancreas fibrosis, splenic fibrosis, cardiac fibrosis, species septic fibrosis, bone marrow fibrosis, vascular fibrosis, skin fibrosis, eye fibrosis, joint fibrosis, muscle fibrosis, thyroid fibrosis, endocardial myocardial fibrosis, peritoneal fibrosis, after peritoneal fibrosis, progressive congenital trophoblastic fibrosis, allogeneic systematic fibrosis, fibrotic complications of surgery and infection fibrosis, but is not limited thereto.

In one specific embodiment of the present disclosure, the compound of Chemical Formula 1 or a pharmaceutically acceptable salt thereof may effectively prevent or treat cancers or tumors, and may further effectively inhibit cancer cell metastasis as well. Herein, the cancer may be selected from the group consisting of liver cancer, hepatocellular carcinoma, thyroid cancer, colorectal cancer, testicular cancer, bone cancer, oral cancer, basal cell carcinoma, ovarian cancer, brain tumor, gallbladder carcinoma, biliary tract cancer, head and neck cancer, colorectal cancer, vesical carcinoma, tongue cancer, esophageal cancer, glioma, glioblastoma, renal cancer, malignant melanoma, gastric cancer, breast cancer, sarcoma, pharynx carcinoma, uterine cancer, cervical cancer, prostate cancer, rectal cancer, pancreatic cancer, lung cancer, skin cancer and other solid cancers, but is not limited thereto.

In one specific embodiment of the present disclosure, the compound of Chemical Formula 1 or a pharmaceutically acceptable salt thereof may effectively prevent or treat a carcinoma mediated by overexpression of TGFβ. Herein, the carcinoma may be selected from the group consisting of carcinomas of lung, breast, liver, biliary, gastrointestinal tract, head and neck, pancreas, prostate and cervix, multiple myeloma, melanoma, glioma and glioblastoma, but is not limited thereto.

The compound of Chemical Formula 1 or a pharmaceutically acceptable salt thereof according to the present disclosure may strengthen therapeutic effects by being co-administered with other drugs for treating fibrotic diseases, cancers or tumors, inflammatory diseases, autoimmune diseases, proliferative diseases, hyperproliferative diseases or immunologically-mediated diseases.

Examples of the other drugs for treating cancers or tumors may include drugs such as cell signaling inhibitors (gleevec, iressa, tarceva and the like), mitotic inhibitors (vincristine, vinblastine and the like), alkylating agents (cyclophosphamide, thiotepa, busulfan and the like), anti-metabolites (tergaflor-based, methotrexate, gemcitabine and the like), topoisomerase inhibitors (irinotecan, topotecan, amsacrine, etoposide, teniposide and the like), immunotherapeutic agents (interferon α, β, γ, interleukin and the like) or anti-hormones (tamoxifen, leuprorelin, anastrozole and the like), but are not limited thereto, and one or more drugs selected from among these may be included in the pharmaceutical composition of the present disclosure.

Examples of the other drugs for treating inflammatory diseases, autoimmune diseases, proliferative diseases, hyperproliferative diseases or immunologically-mediated diseases may include drugs such as steroid drugs (prednisone, prednisolone, methylprednisolone, cortisone, hydroxycortisone, betamethasone, dexamethasone and the like), methotrexate, leflunomide, anti-TNFα drugs (etanercept, infliximab, adalimumab and the like), calcineurin inhibitors (tacrolimus, pimecrolimus and the like) and antihistamine drugs (diphenhydramine, hydroxygene, loratadine, avastin, ketotifen, cetirizine, levocetirizine, fexofenadine and the like), but are not limited thereto, and one or more drugs selected from among these may be included in the pharmaceutical composition of the present disclosure.

The compound of Chemical Formula 1, a pharmaceutically acceptable salt thereof, or the like according to the present disclosure may be administered to a subject to prevent or treat the above-mentioned diseases. Herein, the dosage may vary depending on the subject to be treated, the severity of disease or condition, the rate of administration and the judgement of prescribing physician, however, the compound of Chemical Formula 1 may be commonly administered to a person as an active ingredient via an oral or parenteral route 1 to 4 times a day or on an on/off schedule with an amount of 0.1 mg to 2,000 mg and preferably 1 mg to 1,000 mg per day based on a body weight of 70 kg. In some cases, dosage less than the above-mentioned range may be more suited, and more dosage may be used without causing harmful side effects. More dosage may be dispensed in several smaller dosage over a day.

The pharmaceutical composition according to the present disclosure may be formulated using common methods, and may be prepared in various oral administration forms such as tablets, pills, powders, capsules, syrups, emulsions or microemulsions, or parenteral administration forms such as intramuscular, intravenous or subcutaneous administration.

When the pharmaceutical composition according to the present disclosure is prepared in the form of oral formulation, examples of a carrier to be used may include cellulose, calcium silicate, corn starch, lactose, sucrose, dextrose, calcium phosphate, stearic acid, magnesium stearate, calcium stearate, gelatin, talc, a surfactant, a suspension, an emulsifier, a diluent and the like. When the pharmaceutical composition according to the present disclosure is prepared in the form of an injection, water, a saline solution, an aqueous glucose solution, an aqueous pseudo-sugar solution, alcohol, glycol, ether (for example: polyethylene glycol 400), oil, fatty acid, fatty acid ester, glyceride, a surfactant, a suspension, an emulsifier and the like may be used as the carrier.

The compound of Chemical Formula 1 of the present disclosure may be used in studies on kinases for biological and pathological phenomena, studies on intracellular signaling pathways mediated by kinases, and comparative evaluations on novel kinase inhibitors.

Hereinafter, the present disclosure will be described in detail with reference to examples. However, the following examples are for illustrative purposes only, and the present disclosure is not limited to the following examples.

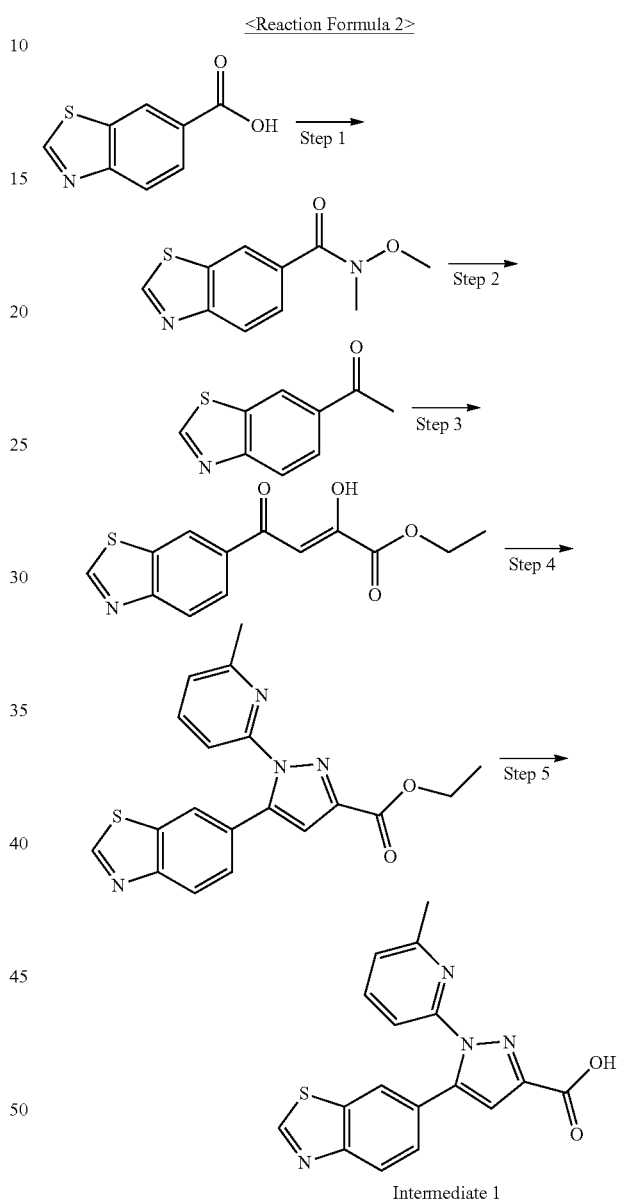

<Reaction Formula 2>

Intermediate 1

[Preparation Example 1] 5-(Benzo[d]thiazol-6-yl)-1-(6-methylpyridin-2-yl)-1H-pyrazole-3-carboxylic acid Step 1. Preparation of N-methoxy-N-methylbenzo[d]thiazole-6-carboxyamide After adding benzothiazole-6-carboxylic acid (5.0 g, 27.9 mmol), HATU (15.9 g, 41.9 mmol) and DIPEA (11.7 mL, 83.7 mmol) to dichloromethane (87 mL) and N,N-dimethylformamide (22 mL), the result was stirred for 30 minutes.

To the reaction solution, an N,O-dimethylhydroxylamine salt (3.0 g, 30.7 mmol) was introduced, and the result was stirred for 12 hours at room temperature. After terminating the reaction, the reaction solution was removed, and ethyl acetate was added thereto. The result was washed with water and saline, then dried using anhydrous magnesium sulfate, and filtered. The filtrate was concentrated and purified using column chromatography to obtain a target compound (6.2 g).

1H NMR spectrum (300 MHz, CDCl$_3$) δ 9.13 (s, 1H), 8.36 (d, 1H), 8.16 (d, 1H), 7.87 (dd, 1H), 3.57 (s, 3H), 3.42 (s, 3H).

Step 2. 1-(Benzo[d]thiazol-6-yl)ethan-1-one

After dissolving N-methoxy-N-methylbenzo[d]thiazole-6-carboxyamide (6.2 g, 27.9 mmol) synthesized in Step 1 in anhydrous tetrahydrofuran (84 mL) under argon, 3 M methyl magnesium bromide (13.9 mL, 41.8 mmol) dissolved in diethyl ether was added dropwise thereto at 0° C. The reaction solution was warmed to room temperature and stirred for 12 hours. After terminating the reaction by introducing a saturated ammonium chloride solution thereto, ethyl acetate was introduced thereto, and the result was extracted. The organic layer was dried using anhydrous magnesium sulfate, and then filtered. The filtrate was concentrated and then purified using column chromatography to obtain a target compound (3.1 g).

1H NMR spectrum (300 MHz, CDCl$_3$) δ 9.17 (s, 1H), 8.62 (s, 1H), 8.16 (q, 2H), 2.71 (s, 3H).

Step 3. Ethyl (Z)-4-(benzo[d]thiazol-6-yl)-4-hydroxy-2-oxo-3-butenoate

After dissolving 1-(benzo[d]thiazol-6-yl)ethan-1-one (1.0 g, 5.6 mmol) synthesized in Step 2 and diethyl oxalate (1.5 mL, 11.3 mmol) in ethanol (2 mL), a 2 M ethoxysodium solution (5.6 mL, 11.3 mmol) was slowly added dropwise thereto at 50° C., and the result was refluxed for 2 hours. After cooling the result to room temperature, the solvent was vacuum concentrated, and the result was acidified by adding 2 M HCl dropwise thereto. Dichloromethane was introduced thereto for extraction, and the organic layer was dried using anhydrous magnesium sulfate and then filtered. The filtrate was concentrated and purified using column chromatography to obtain a target compound (597 mg).

1H NMR spectrum (300 MHz, CDCl$_3$) δ 9.19 (s, 1H), 8.68 (s, 1H), 8.20 (q, 2H), 7.17 (s, 1H), 4.43 (q, 2H), 1.43 (t, 3H).

Step 4. Ethyl 5-(benzo[d]thiazol-6-yl)-1-(6-methylpyridin-2-yl)-1H-pyrazole-3-carboxylate After dissolving ethyl (Z)-4-(benzo[d]thiazol-6-yl)-4-hydroxy-2-oxo-3-butenoate (580 mg, 2.1 mmol) synthesized in Step 3 and 2-hydrazinyl-6-methylpyridine hydrochloric acid (350 mg, 2.2 mmol) in ethanol (10 mL), the result was refluxed for 2 hours. After terminating the reaction, the reaction solution was removed under vacuum, and ethyl acetate was added thereto. The organic layer was washed with saline and then dried using anhydrous magnesium sulfate, and after filtering, the filtrate was concentrated. The filtrate was purified using column chromatography to obtain a target compound (525 mg).

$^1$H NMR spectrum (300 MHz, CDCl$_3$) δ 9.04 (s, 1H), 8.04 (d, 1H), 7.97 (d, 1H), 7.67 (t, 1H), 7.41-7.33 (m, 2H), 7.14-7.10 (m, 2H), 7.47 (q, 2H), 2.32 (s, 3H), 1.43 (t, 3H).

Step 5. 5-(Benzo[d]thiazol-6-yl)-1-(6-methylpyridin-2-yl)-1H-pyrazole-3-carboxylic acid After dissolving ethyl 5-(benzo[d]thiazol-6-yl)-1-(6-methylpyridin-2-yl)-1H-pyrazole-3-carboxylate (520 mg, 1.4 mmol) synthesized in Step 4 in 1,4-dioxane (11 mL), a 2 N lithium hydroxide solution dissolved in water was introduced thereto, and the result was stirred for 2 hours at 70° C. After terminating the reaction, the reaction solution was removed under vacuum. The result was acidified by adding 12 N hydrochloric acid thereto, and then extracted by introducing chloroform/isopropanol (3:1) thereto. The organic layer was dried using anhydrous magnesium sulfate, and after filtering, the filtrate was concentrated. The filtrate was purified using column chromatography to obtain Intermediate 1 (394 mg).

$^1$H NMR spectrum (300 MHz, CDCl$_3$) δ 9.34 (s, 1H), 8.09 (d, 1H), 8.05 (s, 1H), 7.75 (t, 1H), 7.44-7.39 (m, 2H), 7.21 (d, 1H), 7.13 (s, 1H), 2.36 (s, 3H).

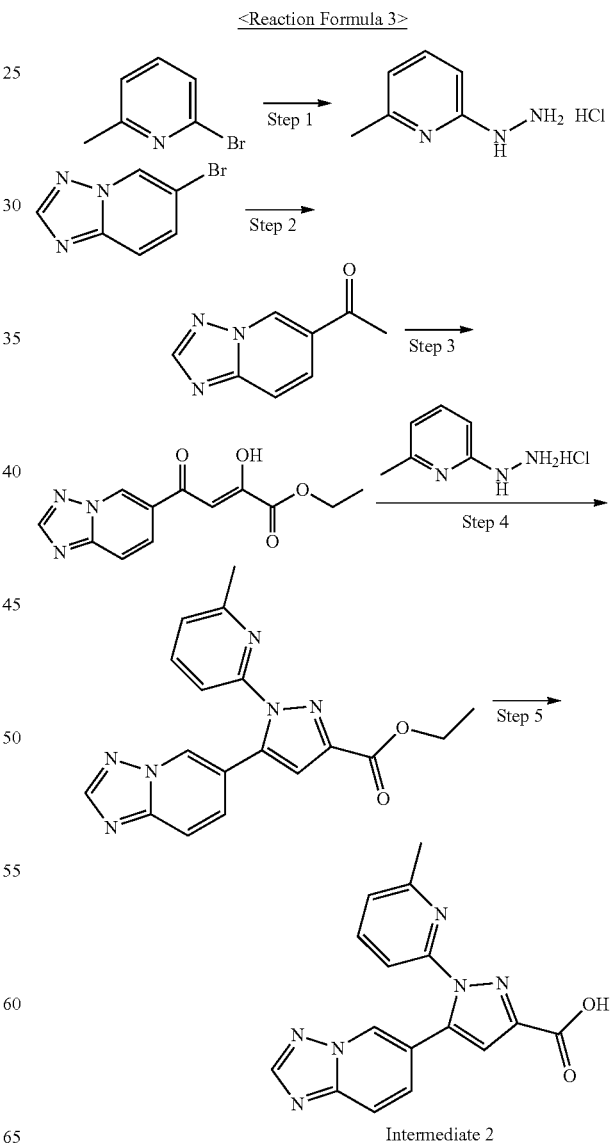

<Reaction Formula 3>

Intermediate 2

[Preparation Example] 2 Preparation of 5-([1,2,4]triazolo[1,5-α]pyridin-6-yl)-1-(6-methylpyridin-2-yl)-1H-pyrazole-3-carboxylic acid Step 1. Preparation of 2-hydrazinyl-6-methylpyridine hydrochloric acid salt A hydrazine hydrate (60 mL) was added to 2-bromo-6-methylpyridine (10.0 g, 58.1 mmol), and the result was heated under reflux for 4 hours. After terminating the reaction, the result was extracted with ethyl acetate, and the obtained organic layer was vacuum concentrated, and acidified with 4 N-hydrochloric acid/dioxane (30 mL). The produced solids were filtered, and the obtained solids were dried to obtain a target compound (9.3 g).

1H NMR (300 MHz, DMSO-$d_6$) δ 9.65 (brs, 3H), 7.60 (t, 1H), 6.75 (d, 1H), 6.69 (d, 1H), 2.41 (s, 3H).

MS (ESI$^+$): m/z 124 [M+H]$^+$

Step 2. Preparation of 1-([1,2,4]triazolo[1,5-α]pyridin-6-yl)ethan-1-one

After dissolving 1-bromo-[1,2,4]triazolo[1,5-α]pyridine (1.1 g, 5.6 mmol) in N,N-dimethylformamide (15 mL) in a sealed tube, n-butyl vinyl ether (3.6 mL, 27.8 mmol), 1,3-bis(diphenylphosphino)propane (161 mg, 0.4 mmol), palladium(II) acetate (37 mg, 0.2 mmol), potassium carbonate (922 mg, 6.7 mmol) and water (1.6 mL) were added thereto, and the result was heated under reflux for 16 hours. After lowering the temperature to room temperature, an aqueous 2 N-hydrochloric acid solution (10 mL) was added thereto, and the result was stirred for 30 minutes at room temperature. After terminating the reaction, the result was extracted with ethyl acetate, and the obtained organic layer was dried using anhydrous magnesium sulfate and then filtered. The filtrate was concentrated and purified using column chromatography to obtain a target compound (410 mg).

1H NMR (300 MHz, CDCl$_3$) δ 9.23 (s, 1H), 8.46 (s, 1H), 8.09 (d, 1H), 7.81 (d, 1H), 2.67 (s, 3H).

MS (ESI$^+$): m/z 162 [M+H]$^+$

Step 3. Preparation of (Z)-ethyl-4-([1,2,4]triazolo[1,5-α]pyridin-6-yl)-2-hydroxy-4-oxo-2-butenoate After adding diethyl oxalate (1.3 mL, 9.9 mmol) to a 2 M ethoxysodium solution (5.0 mL, 9.9 mmol), a solution dissolving 1-([1,2,4]triazolo[1,5-α]pyridin-6-yl)ethan-1-one (400 mg, 2.5 mmol) synthesized in Step 1 in ethanol (3 mL) was added thereto, and the result was stirred for 2 hours at room temperature. The result was vacuum concentrated, and acidified by adding an aqueous 2 N hydrochloric acid solution dropwise thereto at 0□. The result was extracted with ethyl acetate, and the obtained organic layer was dried using anhydrous magnesium sulfate and then filtered. The filtrate was concentrated and recrystallized with ether to obtain a target compound (444 mg).

$^1$H NMR (300 MHz, DMSO-$d_6$) δ 9.95 (s, 1H), 8.69 (s, 1H), 8.16 (d, 1H), 7.95 (d, 1H), 7.30 (brs, 1H), 4.30 (q, 2H), 1.31 (t, 3H).

MS (ESI$^+$): m/z 262 [M+H]$^+$

Step 4. Preparation of ethyl-5-([1,2,4]triazolo[1,5-α]pyridin-6-yl)-1-(6-methylpyridin-2-yl)-1H-pyrazole-3-carboxylate After dissolving (Z)-ethyl-4-([1,2,4]triazolo[1,5-α]pyridin-6-yl)-2-hydroxy-4-oxo-2-butenoate (440 mg, 1.7 mmol) synthesized in Step 3 and the 2-hydrazinyl-6-methylpyridine hydrochloric acid salt (268 mg, 1.7 mmol) synthesized in Step 1 in ethanol (6 mL), the result was stirred for 2 hours at 50□. The result was vacuum concentrated, extracted with ethyl acetate, and the obtained organic layer was dried using anhydrous magnesium sulfate and then filtered. The filtrate was concentrated and purified using column chromatography to obtain a target compound (446 mg).

1H NMR (300 MHz, CDCl$_3$) δ 8.73 (s, 1H), 8.39 (s, 1H), 7.77-7.67 (m, 3H), 7.47 (d, 1H), 7.18-7.09 (m, 2H), 4.46 (q, 2H), 2.26 (s, 3H), 1.45 (t, 3H).

MS (ESI$^+$): m/z 349 [M+H]$^+$

Step 5. Preparation of 5-([1,2,4]triazolo[1,5-α]pyridin-6-yl)-1-(6-methylpyridin-2-yl)-1H-pyrazole-3-carboxylic acid After adding an aqueous 50% ethanol solution (5 mL) to ethyl-5-([1,2,4]triazolo[1,5-α]pyridin-6-yl)-1-(6-methylpyridin-2-yl)-1H-pyrazole-3-carboxylate (440 mg, 1.3 mmol) synthesized in Step 4, the result was stirred for 1 hour at 50° C. The result was vacuum concentrated and acidified with an aqueous 2 N hydrochloric acid solution, and produced solids were filtered and dried to obtain Intermediate 2 (386 mg).

1H NMR (300 MHz, DMSO-$d_6$) δ 13.2 (brs, 1H), 9.15 (s, 1H), 8.52 (s, 1H), 7.91 (t, 1H), 7.78 (d, 1H), 7.73 (d, 1H), 7.29 (d, 1H), 2.13 (s, 3H).

MS (ESI$^+$): m/z 321 [M+H]$^+$

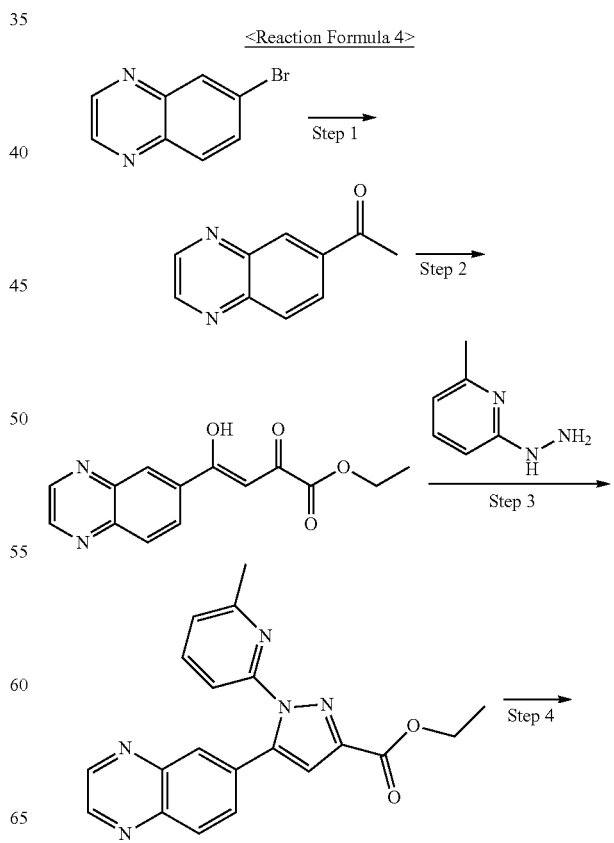

<Reaction Formula 4>

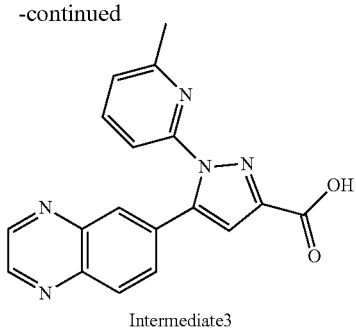

Intermediate 3

Preparation Example 3 Synthesis of 1-(6-methylpyridin-2-yl)-5-(quinoxalin-6-yl)-1H-pyrazole-3-carboxylic acid

Step 1. Preparation of 1-(quinoxalin-6-yl)ethan-1-one

After adding 6-bromoquinoxaline (3.8 g, 18.2 mmol), n-butyl vinyl ether (12.3 mL, 95.2 mmol), potassium carbonate (3.1 g, 22.8 mmol), 1,3-bis(diphenylphosphino)propane (504 mg, 1.3 mmol) and palladium(II) acetate (124 mg, 0.5 mmol) to N,N-dimethylformamide (47 mL) and water (6 mL), the result was stirred and refluxed for 6 hours. After terminating the reaction, the result was cooled to room temperature, 2 N hydrochloric acid was added thereto, and the result was stirred for 0.5 hours. Ethyl acetate was added thereto, the organic layer was washed with water and sodium bicarbonate, dried using anhydrous magnesium sulfate, and filtered. The filtrate was concentrated and purified using column chromatography to obtain a target compound (2.4 g).

1H NMR spectrum (300 MHz, DMSO-$d_6$) δ 10.05 (d, 1H), 9.73 (t, 1H), 8.71 (s, 1H), 7.97 (d, 1H), 3.16 (s, 3H).

Step 2. Preparation of ethyl (Z)-4-hydroxy-2-oxo-4-(quinoxalin-6-yl)-3-butenoate After dissolving 6-(quinoxalin-6-yl)ethan-1-one (4.6 g, 27.0 mmol) synthesized in Step 1 and diethyl oxalate (7.3 mL, 53.9 mmol) in ethanol (9 mL), a 2 M ethoxysodium solution (26.9 mL, 53.9 mmol) was slowly added dropwise thereto at 50° C., and the result was refluxed for 2 hours. After cooling the result to room temperature, the solvent was vacuum concentrated, and the result was acidified by adding 2 M HCl dropwise thereto. Dichloromethane was introduced thereto for extraction, and the organic layer was dried using anhydrous magnesium sulfate and then filtered. The filtrate was concentrated and purified using column chromatography to obtain a target compound (6.7 g).

$^1$H NMR spectrum (300 MHz, CDCl$_3$) δ 8.96 (s, 2H), 8.78 (s, 1H), 8.35 (dd, 1H), 8.24 (d, 1H), 7.27 (s, 1H), 4.44 (q, 2H), 1.45 (t, 3H).

Step 3. Preparation of ethyl 1-(6-methylpyridin-2-yl)-5-(quinoxalin-6-yl)-1H-pyrazole-3-carboxylate After dissolving (Z)-4-hydroxy-2-oxo-4-(quinoxalin-6-yl)-3-butenoate (2.7 g, 10.1 mmol) synthesized in Step 2 and 2-hydrazinyl-6-methylpyridine hydrochloric acid (1.3 g, 10.6 mmol) in ethanol, the result was refluxed for 2 hours. After terminating the reaction, the reaction solution was removed under vacuum, and ethyl acetate was added thereto. The organic layer was washed with sodium bicarbonate, dried using anhydrous magnesium sulfate, and filtered. The filtrate was concentrated and purified using column chromatography to obtain a target compound (2.7 g).

$^1$H NMR spectrum (300 MHz, CDCl$_3$) δ 8.86 (s, 2H), 8.09 (d, 1H), 8.01 (d, 1H), 7.73-7.62 (m, 1H), 7.55 (d, 1H), 7.20 (s, 1H), 7.13 (d, 1H), 4.48 (q, 2H), 2.24 (s, 3H), 1.45 (s, 3H).

Step 4. Preparation of 1-(6-methylpyridin-2-yl)-5-(quinoxalin-6-yl)-1H-pyrazole-3-carboxylic acid After dissolving ethyl 1-(6-methylpyridin-2-yl)-5-(quinoxalin-6-yl)-1H-pyrazole-3-carboxylate (2.6 g, 7.2 mmol) synthesized in Step 3 in 1,4-dioxane (40 mL), a 2 N lithium hydroxide solution dissolved in water was introduced thereto, and the result was stirred for 3 hours at 70° C. After terminating the reaction, the reaction solution was removed under vacuum, and water was added thereto. Ethyl acetate was introduced thereto for extraction, the water layer was acidified to a pH of 2 to 3, and the result was stirred for 1 hour at room temperature. Produced solids were filtered, washed with water, and dried to obtain Intermediate 3 (2.3 g).

$^1$H NMR spectrum (300 MHz, DMSO-$d_6$) δ 13.17 (br, 1H), 8.96 (s, 2H), 8.06-7.92 (m, 3H), 7.72 (dd, 1H), 7.60 (d, 1H), 7.35-7.32 (m, 2H), 2.15 (s, 3H).

<Reaction Formula 5>

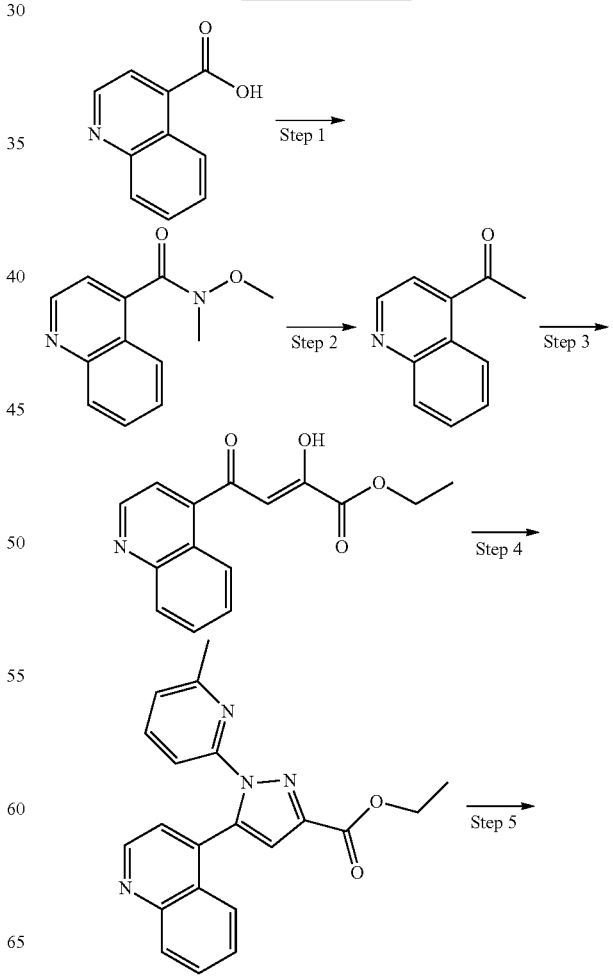

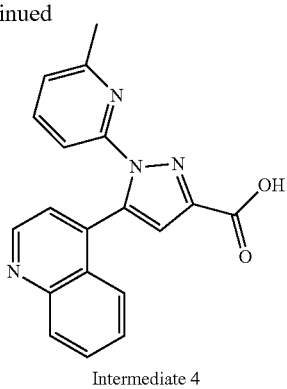

Intermediate 4

[Preparation Example 4] 1-(6-Methylpyridin-2-yl)-5-(quinolin-4-yl)-1H-pyrazole-3-carboxylic acid Step 1. Preparation of N-methoxy-N-methylquinoline-4-carboxyamide After adding quinoline-4-carboxylic acid (2.2 g, 12.8 mmol), HATU (5.8 g, 15.3 mmol) and DIPEA (6.7 mL, 38.4 mmol) to dichloromethane (25 mL), the result was stirred for 30 minutes. To the reaction solution, an N,O-dimethylhydroxylamine salt (1.9 g, 19.2 mmol) was introduced, and the result was stirred for 12 hours at room temperature. After terminating the reaction, the reaction solution was removed, and ethyl acetate was added thereto. The result was washed with water and saline, then dried using anhydrous magnesium sulfate, and filtered. The filtrate was concentrated and purified using column chromatography to obtain a target compound (2.8 g).
$^1$H NMR spectrum (300 MHz, CDCl$_3$) δ 8.96 (d, 1H), 8.15 (d, 1H), 7.86 (d, 1H), 7.76 (t, 1H), 7.59 (t, 1H), 7.39 (d, 1H), 3.48-3.40 (m, 6H).

Step 2. Preparation of 1-(quinolin-4-yl)ethan-1-one

After dissolving N-methoxy-N-methylquinoline-4-carboxamide (2.8 g, 12.9 mmol) synthesized in Step 1 in anhydrous tetrahydrofuran (100 mL) under argon, 3 M methyl magnesium bromide (6.5 mL, 19.4 mmol) dissolved in diethyl ether was added dropwise thereto at 0° C. The reaction solution was warmed to room temperature, and stirred for 3 hours. 3M methyl magnesium bromide (3.0 mL, 9.0 mmol) dissolved in diethyl ether was further added dropwise thereto at 0□. The reaction solution was warmed to room temperature and stirred for 12 hours. After terminating the reaction by introducing a saturated ammonium chloride solution thereto, ethyl acetate was introduced thereto, and the result was extracted. The organic layer was dried using anhydrous magnesium sulfate, and then filtered. The filtrate was concentrated and then purified using column chromatography to obtain a target compound (1.8 g).
$^1$H NMR spectrum (300 MHz, CDCl$_3$) δ 9.03 (d, 1H), 8.46 (d, 1H), 8.17 (d, 1H), 7.77 (t, 1H), 7.67-7.61 (m, 2H), 2.75 (s, 3H).

Step 3. Preparation of ethyl (Z)-2-hydroxy-4-oxo-4-(quinolin-4-yl)but-2-enoate

After dissolving 1-(quinolin-4-yl)ethan-1-one (1.0 g, 5.8 mmol) synthesized in Step 2 and diethyl oxalate (1.6 mL, 11.7 mmol) in ethanol (3 mL), a 2 M ethoxysodium solution (5.8 mL, 11.7 mmol) was slowly added dropwise thereto at 50□, and the result was refluxed for 1 hour. After cooling the result to room temperature, the solvent was vacuum concentrated, and the result was acidified by adding 2 M hydrochloric acid dropwise thereto. Dichloromethane was introduced thereto for extraction, and the organic layer was dried using anhydrous magnesium sulfate, and then filtered. The filtrate was concentrated and then crystallized using a 1:1 mixed solution of hexane and ether to obtain a target compound (1.1 g).
$^1$H NMR spectrum (300 MHz, CDCl$_3$) δ 9.06 (d, 1H), 8.40 (d, 1H), 8.20 (d, 1H), 7.81 (t, 1H), 7.70-7.63 (m, 2H), 6.95 (s, 1H), 4.42 (q, 2H), 1.41 (t, 3H).

Step 4. Preparation of ethyl 1-(6-methylpyridin-2-yl)-5-(quinolin-4-yl)-1H-pyrazole-3-carboxylate After dissolving ethyl (Z)-2-hydroxy-4-oxo-4-(quinolin-4-yl)but-2-enoate (1.1 g, 4.2 mmol) synthesized in Step 3 and 2-hydrazinyl-6-methylpyridine hydrochloric acid (677 mg, 4.2 mmol) in ethanol (12 mL), the result was refluxed for 3 hours. After terminating the reaction, the reaction solution was removed under vacuum, and ethyl acetate was added thereto. The organic layer was washed with water and saline, then dried using anhydrous magnesium sulfate, and after filtering, the filtrate was concentrated. The filtrate was purified using column chromatography to obtain a target compound (1.1 g).
$^1$H NMR spectrum (300 MHz, CDCl$_3$) δ 8.92 (d, 1H), 8.13 (d, 1H), 7.70-7.56 (m, 4H), 7.39 (t, 1H), 7.31 (t, 1H), 7.13 (s, 1H), 6.89 (d, 1H), 4.50 (q, 2H), 1.79 (s, 3H), 1.46 (t, 3H).

Step 5. Preparation of 1-(6-methylpyridin-2-yl)-5-(quinolin-4-vyl)-H-pyrazole-3-carboxylic acid After dissolving ethyl 1-(6-methylpyridin-2-yl)-5-(quinolin-4-yl)-1H-pyrazole-3-carboxylate (1.1 g, 3.2 mmol) synthesized in Step 4 in 1,4-dioxane (11 mL), a 2 N lithium hydroxide solution (4.8 mL, 9.5 mmol) dissolved in water was introduced thereto, and the result was stirred for 2 hours at 45□. After terminating the reaction, the reaction solution was removed under vacuum, and the result was acidified to a pH of 2 to 3 by adding 2 N hydrochloric acid thereto, and then stirred for 1 hour at room temperature. The result was vacuum filtered to obtain Intermediate 4 (960 mg).
$^1$H NMR spectrum (300 MHz, DMSO-d$_6$) δ 13.0 (bs, 1H), 8.92 (d, 1H), 8.07 (d, 1H), 7.81 (t, 1H), 7.71-7.65 (m, 2H), 7.50-7.44 (m, 3H), 7.06 (s, 1H), 7.05 (d, 1H), 1.64 (t, 3H).

<Reaction Formula 6>

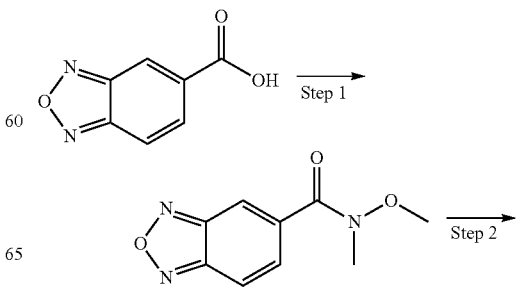

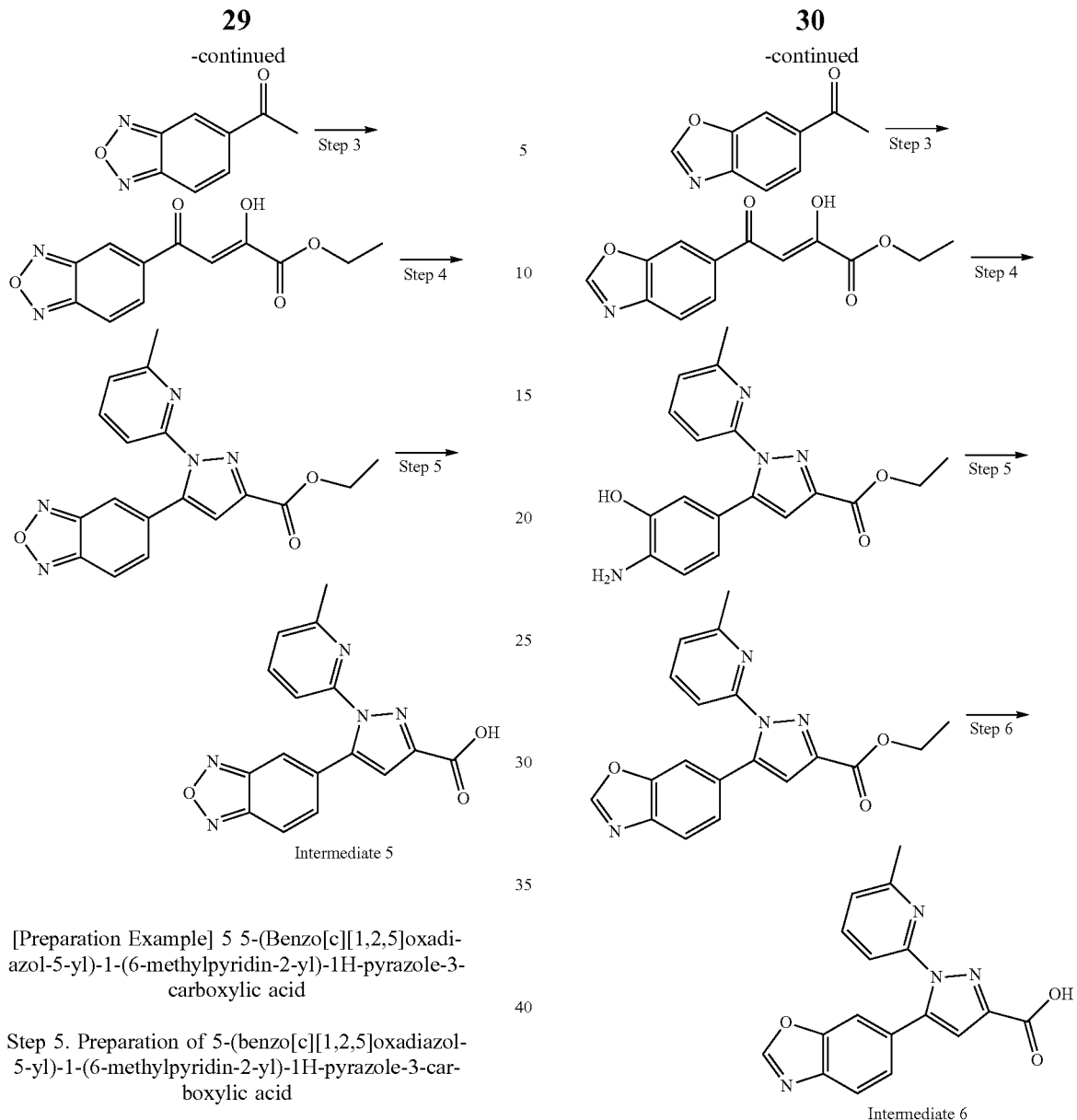

[Preparation Example] 5 5-(Benzo[c][1,2,5]oxadiazol-5-yl)-1-(6-methylpyridin-2-yl)-1H-pyrazole-3-carboxylic acid Step 5. Preparation of 5-(benzo[c][1,2,5]oxadiazol-5-yl)-1-(6-methylpyridin-2-yl)-1H-pyrazole-3-carboxylic acid Intermediate 5 (30 mg) was obtained through the methods of Step 1 to Step 5 of Preparation Example 4 using benzo[c][1,2,5]oxadiazole-5-carboxylic acid instead of quinoline-4-carboxylic acid of Step 1.

$^1$H NMR spectrum (300 MHz, DMSO-$d_6$) δ 8.14 (s, 1H), 7.97-7.92 (m, 2H), 7.71 (d, 1H), 7.40 (d, 1H), 7.31-7.28 (m, 2H), 2.10 (s, 3H).

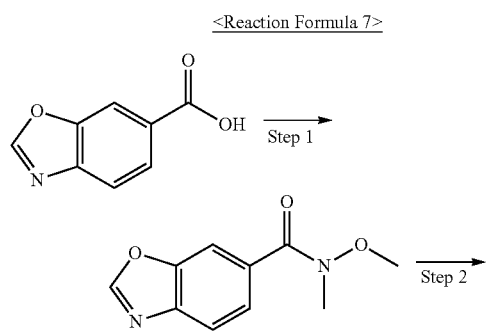

<Reaction Formula 7>

[Preparation Example] 6 5-(Benzo[d]oxazol-6-yl)-1-(6-methylpyridin-2-yl)-1H-pyrazole-3-carboxylic acid Step 3. Preparation of ethyl (Z)-4-(benzo[d]oxazol-6-yl)-2-hydroxy-4-oxobut-2-enoate A target compound (1.2 g) was obtained through the methods of Step 1 to Step 3 of Preparation Example 4 using benzo[d]oxazole-6-carboxylic acid instead of quinoline-4-carboxylic acid of Step 1.

$^1$H NMR spectrum (300 MHz, CDCl$_3$) δ 8.28-8.26 (m, 2H), 8.06 (d, 1H), 7.90 (d, 1H), 7.27 (s, 1H), 7.14 (s, 1H), 4.42 (q, 2H), 1.44 (t, 3H).

Step 4. Preparation of ethyl 5-(4-amino-3-hydroxyphenyl)-1-(6-methylpyridin-2-yl)-1H-pyrazole-3-carboxylate After dissolving ethyl (Z)-4-(benzo[d]oxazol-6-yl)-2-hydroxy-4-oxobut-2-enoate (1.2 g, 4.8 mmol) synthesized in Step 3 and 2-hydrazinyl-6-methylpyridine hydrochloric acid (915 mg, 5.7 mmol) in ethanol (15 mL), the result was refluxed for 2 hours. After terminating the reaction, the reaction solution was removed under vacuum, and a saturated sodium bicarbonate solution was added thereto. The result was stirred for 1 hour at room temperature, and then vacuum filtered. Obtained solids were crystallized with dichloromethane and vacuum filtered to obtain a target compound (1.5 g).

$^1$H NMR spectrum (300 MHz, DMSO-$d_6$) δ 9.11 (s, 1H), 7.84 (t, 1H), 7.37 (d, 1H), 7.20 (d, 1H), 6.83 (s, 1H), 6.49-6.41 (m, 3H), 4.79 (bs, 2H), 4.31 (q, 2H), 1.33 (t, 3H).

Step 5. Preparation of ethyl 5-(benzo[d]oxazol-6-yl)-1-(6-methylpyridin-2-yl)-1H-pyrazole-3-carboxylate After dissolving ethyl 5-(4-amino-3-hydroxyphenyl)-1-(6-methylpyridin-2-yl)-1H-pyrazole-3-carboxylate (1.0 g, 3.0 mmol) synthesized in Step 4 in trimethyl orthoformate (1.5 mL), the result was stirred for 2 hours at 100□. After terminating the reaction, the reaction solution was removed under vacuum, and the result was purified using column chromatography to obtain a target compound (930 mg).

$^1$H NMR spectrum (300 MHz, CDCl$_3$) δ 8.12 (s, 1H), 7.72-7.63 (m, 2H), 7.55 (d, 1H), 7.36 (d, 1H), 7.25 (m, 1H), 7.13 (d, 1H), 7.07 (s, 1H), 4.46 (q, 2H), 2.33 (s, 3H), 1.43 (t, 3H).

Step 6. Preparation of 5-(benzo[d]oxazol-6-yl)-1-(6-methylpyridin-2-yl)-1H-pyrazole-3-carboxylic acid After dissolving ethyl 5-(benzo[d]oxazol-6-yl)-1-(6-methylpyridin-2-yl)-1H-pyrazole-3-carboxylate (300 mg, 0.9 mmol) synthesized in Step 5 in 1,4-dioxane (3 mL), a 1 N lithium hydroxide solution (1.5 mL, 1.5 mmol) dissolved in water was introduced thereto, and the result was stirred for 2 hours at room temperature. After terminating the reaction, the reaction solution was removed under vacuum, and the result was acidified to a pH of 2 to 3 by adding 1 N hydrochloric acid thereto, and then stirred for 1 hour at room temperature. The result was vacuum filtered and then purified using column chromatography to obtain Intermediate 6 (100 mg).

$^1$H NMR spectrum (300 MHz, DMSO-$d_6$) δ 8.75 (s, 1H), 7.85 (t, 1H), 7.72-7.68 (m, 2H), 7.45 (d, 1H), 7.24-7.17 (m, 2H), 6.84 (s, 1H), 2.14 (s, 3H).

<Reaction Formula 8>

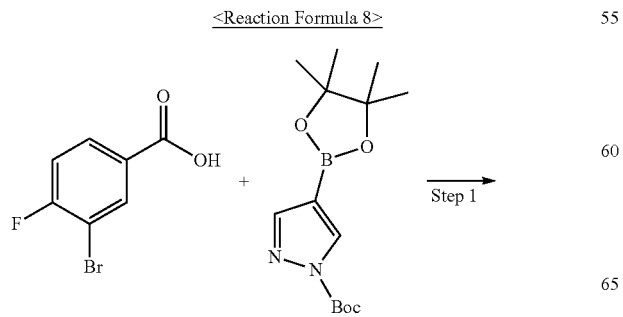

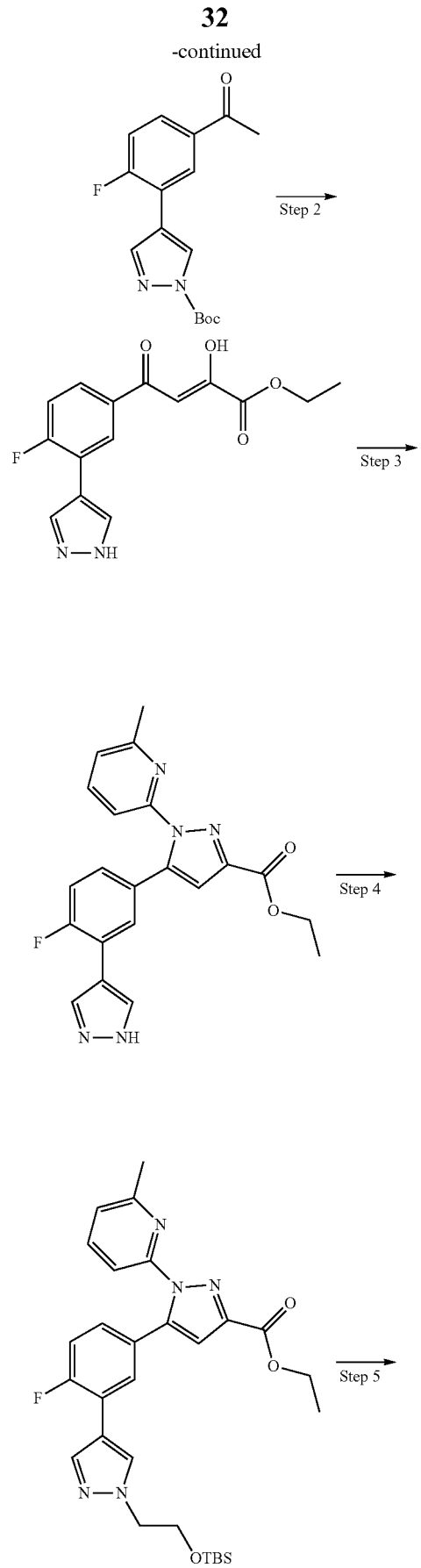

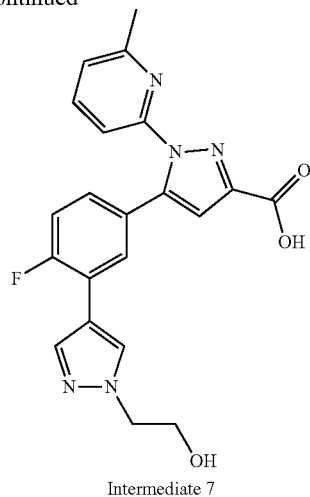

Intermediate 7

[Preparation Example 7] 1-(6-Methylpyridin-2-yl)-5-(4-fluoro-3-(1-(2-hydroxyethyl)-1H-pyrazol-4-yl)-1H-pyrazole-3-carboxylic acid Step 1. Preparation of t-butyl 4-(5-acetyl-2-fluorophenyl)-1H-pyrazole-1-carboxylate After dissolving 1-(3-bromo-4-fluorophenyl)ethan-1-one (1.0 g, 4.6 mmol) in 1,4-dioxane (20 mL) and water (4 mL), t-butyl 4-(4,4,5,5-tetramethyl-1,3,2-dioxaboran-2-yl)-1H-pyrazole-1-carboxylate (2.0 g, 6.9 mmol), tripotassium phosphate (2.0 g, 9.2 mmol) and XPhos (156 mg, 0.2 mmol) were added thereto under nitrogen, and the result was heated under reflux for 5 hours at 100□. The result was cooled to room temperature, then extracted with ethyl acetate, dried and concentrated. The result was purified using column chromatography to obtain a target compound (960 mg).
$^1$H NMR (300 MHz, CDCl$_3$) δ 8.51 (s, 1H), 8.21 (d, 1H), 8.14 (s, 1H), 7.23 (d, 1H), 2.64 (s, 3H), 1.70 (s, 9H).
MS (ESI$^+$): [M+H]$^+$ m/z 305

Step 2. Preparation of ethyl-4-(4-fluoro-3-(1H-pyrazol-4-yl)phenyl)-2-hydroxy-4-oxobute-2-noate After adding ethanol (15 mL) to diethyl oxalate (1.7 mL, 12.6 mmol), a 2 M ethoxysodium solution (6.3 mL, 12.6 mmol) was added thereto. t-Butyl 4-(5-acetyl-2-fluorophenyl)-1H-pyrazole-1-carboxylate (1.0 g, 4.6 mmol) was slowly added thereto, and the result was stirred for 3 hours at room temperature. The solvent was vacuum concentrated, and the result was acidified by adding 2 N hydrochloric acid dropwise thereto. The result was extracted with ethyl acetate, the organic layer was dried using anhydrous magnesium sulfate and then filtered. The filtrate was concentrated to obtain a target compound (958 mg).
$^1$H NMR (300 MHz, CDCl$_3$) δ 8.24 (d, 1H), 8.07 (s, 2H), 7.90-7.84 (m, 1H), 7.29-7.23 (m, 1H), 7.07 (s, 1H), 4.42 (q, 2H), 1.43 (t, 3H).
MS (ESI$^+$): [M+H]$^+$ m/z 305

Step 3. Preparation of ethyl 5-(4-fluoro-3-(1H-pyrazol-4-yl)phenyl)-1-(6-methylpyridin-2-yl)-1H-pyrazole-3-carboxylate After dissolving ethyl-4-(4-fluoro-3-(1H-pyrazol-4-yl)phenyl)-2-hydroxy-4-oxobute-2-noate (955 mg, 3.1 mmol) and a 2-hydrazinyl-6-methylpyridine hydrochloric acid salt (751 mg, 4.7 mmol) in ethanol (15 mL), the result was stirred for 2 hours at 50□. After terminating the reaction, the reaction solution was removed under vacuum. The result was extracted with ethyl acetate, dried using anhydrous magnesium sulfate, and then filtered. The filtrate was concentrated and purified using column chromatography to obtain a target compound (658 mg).
$^1$H NMR (300 MHz, CDCl$_3$) δ 7.90 (s, 2H), 7.72 (t, 1H), 7.53 (d, 1H), 7.40 (d, 1H), 7.18 (d, 1H), 7.12-7.09 (m, 3H), 4.49 (q, 2H), 2.42 (s, 3H), 1.46 (t, 3H).
MS (ESI$^+$): [M+H]$^+$ m/z 392

Step 4. Preparation of ethyl 5-(3-(1-(2-((t-butyldimethylsilyl)oxy)ethyl)-1H-pyrazol-4-yl)-4-fluorophenyl)-1-(6-methylpyridin-2-yl)-1H-pyrazole-3-carboxylate After dissolving ethyl 5-(4-fluoro-3-(1H-pyrazol-4-yl)phenyl)-1-(6-methylpyridin-2-yl)-1H-pyrazole-3-carboxylate (650 mg, 1.7 mmol), (2-bromoethoxy)(t-butyl)dimethylsilane (477 mg, 2.0 mmol) and potassium carbonate (688 mg, 5.0 mmol) in N,N-dimethylformamide (15 mL), the result was stirred for 16 hours at 800. The result was cooled to room temperature, then extracted with ethyl acetate, dried using anhydrous magnesium sulfate, and filtered. The filtrate was concentrated and purified using column chromatography to obtain a target compound (740 mg).
$^1$H NMR (300 MHz, CDCl$_3$) δ 7.88 (s, 1H), 7.75-7.70 (m, 2H), 7.51 (d, 1H), 7.41 (d, 1H), 7.19 (d, 1H), 7.11-7.08 (m, 3H), 4.51 (q, 2H), 4.29 (t, 2H), 4.00 (t, 2H), 2.44 (s, 3H), 1.47 (t, 3H), 0.88 (s, 9H), 0.02 (s, 6H).
MS (ESI$^+$): [M+H]$^+$ m/z 550

Step 5. Preparation of 5-(4-fluoro-3-(1-(2-hydroxyethyl)-1H-pyrazol-4-yl)phenyl)-1-(6-methylpyridin-2-yl)-1H-pyrazole-3-carboxylic acid After adding an aqueous 50% ethanol solution (8 mL) to ethyl 5-(3-(1-(2-((t-butyldimethylsilyl)oxy)ethyl)-1H-pyrazol-4-yl)-4-fluorophenyl)-1-(6-methylpyridin-2-yl)-1H-pyrazole-3-carboxylate (700 mg, 1.3 mmol), the result was stirred for 2 hours at 50□. The result was vacuum concentrated and acidified with 2 N hydrochloric acid, and then produced solids were filtered and dried to obtain Intermediate 7 (460 mg).
$^1$H NMR (300 MHz, CDCl$_3$) δ 7.84 (s, 1H), 7.74-7.69 (m, 2H), 7.50 (d, 1H), 7.40 (d, 1H), 7.18 (d, 1H), 7.08-7.05 (m, 3H), 4.32 (t, 2H), 4.06 (t, 2H), 2.40 (s, 3H).
MS (ESI$^+$): m/z 408 [M+H]$^+$ <Reaction Formula 9>

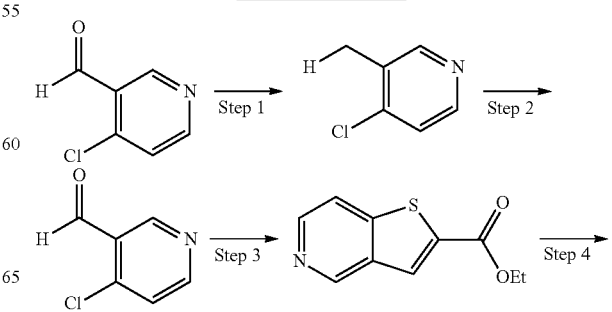

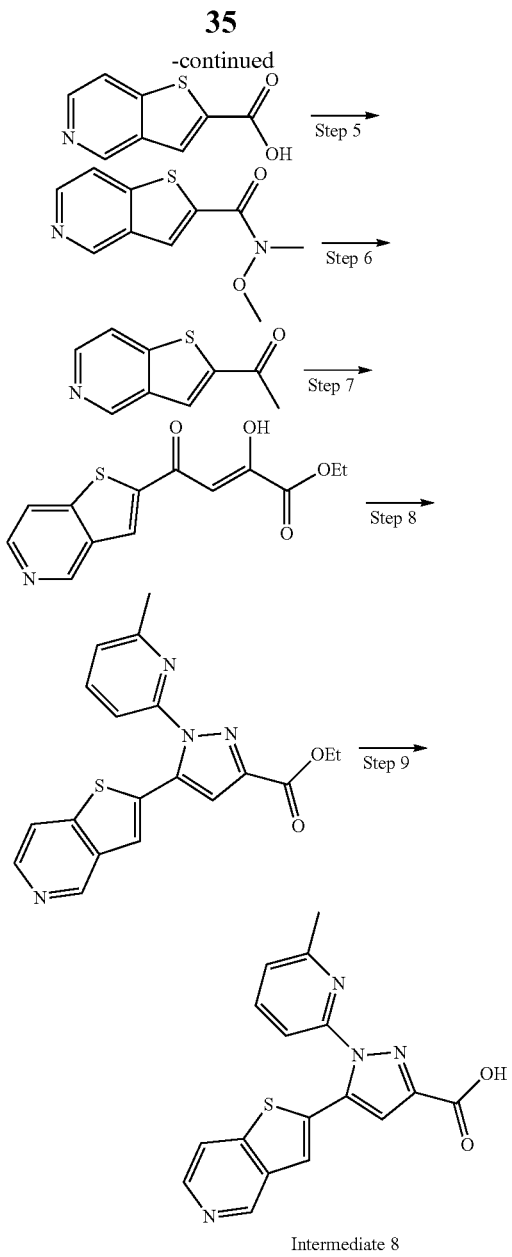

Intermediate 8

[Preparation Example 8] 1-(6-Methylpyridin-2-yl)-5-(thieno[3,2-c]pyridin-2-yl)-1H-pyrazole-3-carboxylic acid Step 1. Preparation of (4-chloropyridin-3-yl)methanol After dissolving 4-chloronicotinic acid (7.0 g, 44.4 mmol) in tetrahydrofuran (500 mL), lithium aluminum hydride (1.68 g, 44.4 mmol) was introduced thereto, and the result was stirred for 1 hour at room temperature. After terminating the reaction, the reaction solution was removed under vacuum, and the result was extracted by introducing ethyl acetate and water thereto. The organic layer was dried using anhydrous magnesium sulfate, and after filtering, the filtrate was concentrated. The filtrate was purified using column chromatography to obtain an intermediate (2.6 g).

$^1$H NMR spectrum (300 MHz, CDCl$_3$) δ 8.62 (s, 1H), 8.42 (s, 1H), 7.48 (s, 1H), 7.53 (s, 2H).

Step 2. Preparation of 4-chloronicotinaldehyde

After dissolving (4-chloropyridin-3-yl)methanol (2.6 g, 18.0 mmol) synthesized in Step 1 in dichloromethane (26 mL), manganese (IV) oxide (23.5 g, 270.5 mmol) was introduced thereto, and the result was stirred for 12 hours at 50□. After terminating the reaction, the result was extracted by introducing water thereto. The organic layer was dried using anhydrous magnesium sulfate, and after filtering, the filtrate was concentrated. The filtrate was purified using column chromatography to obtain an intermediate (1.37 g).

$^1$H NMR spectrum (300 MHz, CDCl$_3$) δ 10.51 (s, 1H), 9.05 (s, 1H), 8.67 (s, 1H), 7.42 (s, 1H).

Step 3. Preparation of ethylthieno[3,2,c]pyridine-2-carboxylate

After dissolving 4-chloronicotinaldehyde (3.3 g, 23.3 mmol) synthesized in Step 2 in N,N-dimethylformamide (33 mL) and water (3.3 mL), potassium carbonate (3.1 g, 23.3 mmol) was introduced thereto, and the result was stirred for 5 minutes at room temperature. After adding ethyl 2-mercaptoacetate (2.8 g, 23.3 mmol) dropwise thereto, the result was stirred for 12 hours at 50□. After the reaction was completed, water was added dropwise thereto, the result was stirred for 1 hour, and solids were filtered to obtain an intermediate (2.3 g).

$^1$H NMR spectrum (300 MHz, CDCl$_3$) δ 9.26 (s, 1H), 8.54 (s, 1H), 8.32 (s, 1H), 0.13 (s, 1H), 4.39 (q, 2H), 1.33 (t, 3H).

Step 4. Preparation of thieno[3,2-c]pyridine-2-carboxylic acid

After dissolving ethylthieno[3,2-c]pyridine-2-carboxylate (2.3 g, 11.0 mmol) synthesized in Step 3 in methanol (25 mL), a 2 N lithium hydroxide solution dissolved in water was introduced thereto, and the result was stirred for 2 hours at 700. After terminating the reaction, the reaction solution was removed under vacuum. The result was acidified by adding 12 N hydrochloric acid thereto, and then extracted by introducing chloroform/isopropanol (3:1) thereto. The organic layer was dried using anhydrous magnesium sulfate, and after filtering, the filtrate was concentrated. The filtrate was purified using column chromatography to obtain an intermediate (1.89 g).

$^1$H NMR spectrum (300 MHz, CDCl$_3$) δ 9.24 (s, 1H), 8.52 (s, 1H), 8.23 (s, 1H), 8.10 (s, 1H).

Step 5. Preparation of N-methoxy-N-methylthieno[3,2-c]pyridine-2-carboxyamide

After adding thieno[3,2-c]pyridine-2-carboxylic acid (1.9 g, 10.5 mmol), HATU (6.0 g, 15.8 mmol) and TEA (3.2 g, 31.6 mmol) to dichloromethane (38 mL) and N,N-dimethylformamide (7.5 mL), the result was stirred for 30 minutes. To the reaction solution, an N, O-dimethylhydroxylamine salt (1.1 g, 11.6 mmol) was introduced, and the result was stirred for 12 hours at room temperature. After terminating the reaction, the reaction solution was removed, and ethyl acetate was added thereto. The result was washed with water and saline, then dried using anhydrous magnesium sulfate, and filtered. The filtrate was concentrated and purified using column chromatography to obtain a target compound (1.4 g).

¹H NMR spectrum (300 MHz, CDCl₃) δ 9.19 (s, 1H), 8.50 (s, 1H), 8.27 (s, 1H), 7.80 (s, 1H), 3.83 (s, 3H), 3.42 (s, 3H).

Step 6. Preparation of 1-(thieno[3,2-c]pyridin-2-yl)ethan-1-one

After dissolving N-methoxy-N-methylthieno[3,2-c]pyridine-2-carboxyamide (0.4 g, 1.7 mmol) synthesized in Step 5 in anhydrous tetrahydrofuran (5.1 mL) under argon, 3 M methyl magnesium bromide (2.8 mL, 2.5 mmol) dissolved in diethyl ether was added dropwise thereto at 0° C. After terminating the reaction by introducing a saturated ammonium chloride solution thereto, ethyl acetate was introduced thereto, and the result was extracted. The organic layer was dried using anhydrous magnesium sulfate, and then filtered. The filtrate was concentrated and then purified using column chromatography to obtain a target compound (250 mg).

¹H NMR spectrum (300 MHz, CDCl₃) δ 9.19 (s, 1H), 8.54 (s, 1H), 7.80 (s, 1H), 7.78 (s, 1H), 2.68 (s, 3H).

Step 7. Preparation of (Z)-ethyl 2-hydroxy-4-oxo-4-(thieno[3,2-c]pyridin-2-yl)2-butenoate After dissolving 1-(thieno[3,2-c]pyridin-2-yl)ethan-1-one (0.3 g, 1.4 mmol) synthesized in Step 6 and diethyl oxalate (0.8 g, 5.6 mmol) in ethanol (2.5 mL), ethoxysodium (0.4 g, 5.6 mmol) was slowly added dropwise thereto at 50□, and the result was refluxed for 2 hours. After cooling the result to room temperature, the solvent was vacuum concentrated, and the result was acidified by adding 2 M hydrochloric acid dropwise thereto. Dichloromethane was introduced thereto for extraction, and the organic layer was dried using anhydrous magnesium sulfate, and then filtered. The filtrate was concentrated and purified using column chromatography to obtain a target compound (0.2 g).

¹H NMR spectrum (300 MHz, CDCl₃) δ 9.51 (s, 1H), 8.43 (s, 1H), 8.16 (s, 1H), 7.38 (s, 1H), 7.38 (s, 1H), 4.23 (q, 2H), 1.21 (t, 3H).

Step 8. Preparation of ethyl 1-(6-methylpyridin-2-yl)-5-(thieno[3,2,c]pyridin-2-yl)-1H-pyrazole-3-carboxylate After dissolving (Z)-ethyl 2-hydroxy-4-oxo-4-(thieno[3,2-c]pyridin-2-yl)2-butenoate (0.2 g, 0.6 mmol) synthesized in Step 7 and 2-hydrazinyl-6-methylpyridine hydrochloric acid (0.1 g, 0.6 mmol) in ethanol (1.5 mL), the result was refluxed for 2 hours. After terminating the reaction, the reaction solution was removed under vacuum, and ethyl acetate was added thereto. The organic layer was washed with saline and then dried using anhydrous magnesium sulfate, and after filtering, the filtrate was concentrated. The filtrate was purified using column chromatography to obtain a target compound (98 mg).

¹H NMR spectrum (300 MHz, CDCl₃) δ 9.02 (s, 1H), 8.45 (s, 1H), 7.84-7.70 (m, 2H), 7.61 (t, 1H), 7.52 (s, 1H), 7.39-7.20 (m, 2H), 4.50 (q, 2H), 2.32 (s, 3H), 1.43 (t, 3H).

Step 9. Preparation of 1-(6-methylpyridin-2-yl)-5-(thieno[3,2-c]pyridin-2-yl)-1H-pyrazole-3-carboxylic acid After dissolving ethyl 1-(6-methylpyridin-2-yl)-5-(thieno[3,2,c]pyridin-2-yl)-1H-pyrazole-3-carboxylate (98 mg, 0.3 mmol) synthesized in Step 8 in 1,4-dioxane (1 mL), a 2 N lithium hydroxide solution dissolved in water was introduced thereto, and the result was stirred for 2 hours at 70□. After terminating the reaction, the reaction solution was removed under vacuum. The result was acidified by adding 12 N hydrochloric acid thereto, and then extracted by introducing chloroform/isopropanol (3:1) thereto. The organic layer was dried using anhydrous magnesium sulfate, and after filtering, the filtrate was concentrated. The filtrate was purified using column chromatography to obtain Intermediate 8 (82 mg).

¹H NMR spectrum (300 MHz, CDCl₃) δ 9.50 (s, 1H), 8.69 (d, 2H), 8.06 (s, 1H), 7.99 (t, 1H), 7.64-7.61 (m, 2H), 7.43 (d, 1H), 2.37 (s, 3H).

[Example 1] 5-(Benzo[d]thiazol-6-yl)-N-(4-methoxyphenyl)-1-(6-methylpyridin-2-yl)-1H-pyrazole-3-carboxyamide

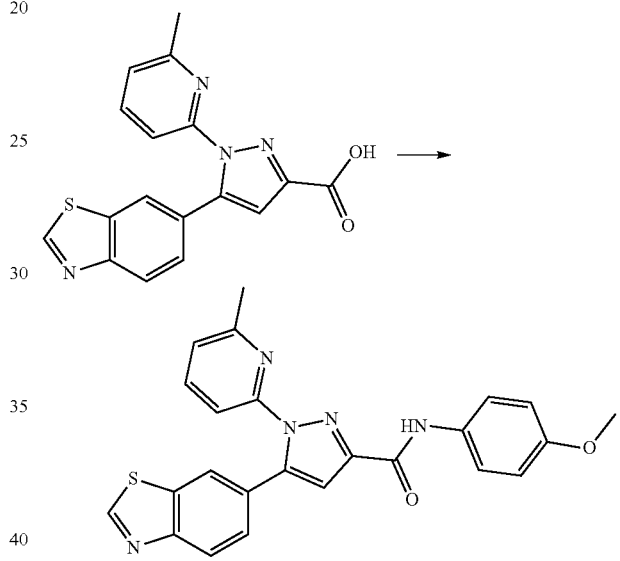

After dissolving 1-(6-methylpyridin-2-yl)-5-(quinoxalin-6-yl)-1H-pyrazole-3-carboxylic acid (40 mg, 0.1 mmol) synthesized in Step 5 of Preparation Example 1 in dichloromethane, HATU (54 mg, 0.1 mmol) and DIPEA (60 µL, 0.4 mmol) were introduced thereto, and the result was stirred for 20 minutes at room temperature. To the reaction solution, p-anisidine (16 mg, 0.1 mmol) was introduced, and the result was stirred for 12 hours at room temperature. After terminating the reaction, ethyl acetate was added thereto. The result was washed with sodium bicarbonate, then dried using anhydrous magnesium sulfate, and after filtering, the filtrate was concentrated. The filtrate was purified using column chromatography to obtain a target compound (22 mg).

¹H NMR spectrum (300 MHz, CDCl₃) δ 9.05 (s, 1H), 8.76 (s, 1H), 8.05 (d, 1H), 7.98 (d, 1H), 7.66-7.63 (m, 3H), 7.35 (dd, 1H), 7.20 (t, 3H), 7.20 (dd, 2H), 3.82 (s, 3H), 2.43 (s, 3H).

MS (ESI⁺): [M+H]⁺ m/z 442.1

Examples 2 to 81

Compounds of Examples 2 to 79 listed in the following [Table 1] were obtained in the same manner as in Step 1) of Example 1 using various amine derivatives instead of p-anisidine.

TABLE 1

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 2 | 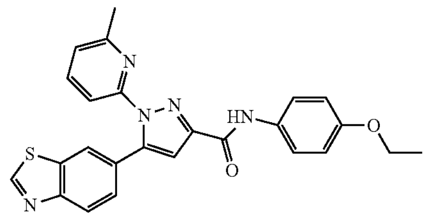 [SMILES: CCOc1ccc(NC(=O)c2cc(-c3ccc4ncsc4c3)n(-c3cccc(C)n3)n2)cc1] | 5-(benzo[d]thiazol-6-yl)-N-(4-ethoxyphenyl)-1-(6-methylpyridin-2-yl)-1H-pyrazole-3-carboxamide | 9.04(s, 1H), 8.73(s, 1H), 8.06(d, 1H), 7.98(d, 1H), 7.69-7.60(m, 3H), 7.36(dd, 1H), 7.19(t, 3H), 6.90 (d, 2H), 4.04(q, 2H), 2.42(s, 3H), 1.41(t, 3H) | 456.1/455.1 |
| 3 | 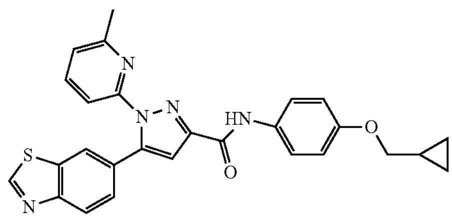 [SMILES: Cc1cccc(-n2nc(C(=O)Nc3ccc(OCC4CC4)cc3)cc2-c2ccc3ncsc3c2)n1] | 5-(benzo[d]thiazol-6-yl)-N-(4-(cyclopropylmethoxy)phenyl)-1-(6-methylpyridin-2-yl)-1H-pyrazole-3-carboxamide | 9.05(s, 1H), 8.74(s, 1H), 8.05(d, 1H), 7.98(d, 1H), 7.69-7.61(m, 3H), 7.36(dd, 1H), 7.22(t, 3H), 6.92(d, 2H), 3.80(d, 2H), 2.44(s, 3H), 1.28-1.21(m, 1H, 0.66(q, 2H), 0.36(q, 2H) | 482.2/481.2 |
| 4 | 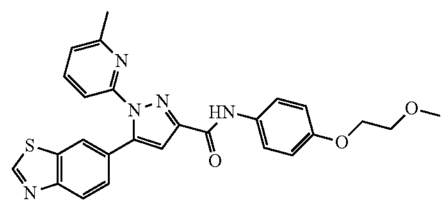 [SMILES: COCCOc1ccc(NC(=O)c2cc(-c3ccc4ncsc4c3)n(-c3cccc(C)n3)n2)cc1] | 5-(benzo[d]thiazol-6-yl)-N-(4-(2-methoxyethoxy)phenyl)-1-(6-methylpyridin-2-yl)-1H-pyrazole-3-carboxamide | 9.04(s, 1H), 8.77(s, 1H), 8.05(d, 1H), 7.98(d, 1H), 7.68-7.61(m, 3H), 7.36(dd, 1H), 7.20(t, 3H), 6.95(d, 2H), 4.14-4.11(m, 2H), 3.77-3.73(m, 2H), 3.46(s, 3H), 2.42(s, 3H) | 486.2/485.2 |
| 5 | 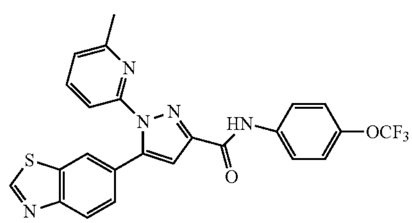 [SMILES: Cc1cccc(-n2nc(C(=O)Nc3ccc(OC(F)(F)F)cc3)cc2-c2ccc3ncsc3c2)n1] | 5-(benzo[d]thiazol-6-yl)-1-(6-methylpyridin-2-yl)-N-(4-(trifluoromethoxy)phenyl)-1H-pyrazole-3-carboxamide | 9.05(s, 1H), 8.88(s, 1H), 8.05(d, 1H), 7.98(d, 1H), 7.76(d, 2H), 7.67(t, 1H), 7.36(dd, 1H), 7.25-7.19(m, 5H), 2.45(s, 3H) | 496.1/495.1 |
| 6 | 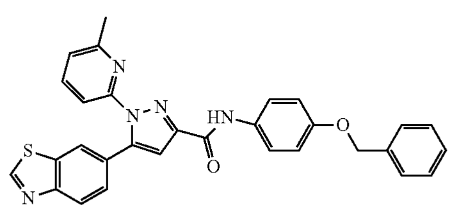 [SMILES: Cc1cccc(-n2nc(C(=O)Nc3ccc(OCc4ccccc4)cc3)cc2-c2ccc3ncsc3c2)n1] | 5-(benzo[d]thiazol-6-yl)-N-(4-(benzyloxy)phenyl)-1-(6-methylpyridin-2-yl)-1H-pyrazole-3-carboxamide | (300 MHz. DMSO-d₆)δ 10.15(s, 1H), 9.44(s, 1H), 8.26(d, 1H), 8.03(d, 1H), 7.92(t, 1H), 7.73(d, 2H), 7.61(d, 1H), 7.47-7.32(m, 6H), 7.20(s, 1H), 7.00(d, 2H), 5.10(s, 2H), 2.22(s, 3H) | 518.2/517.2 |
| 7 | 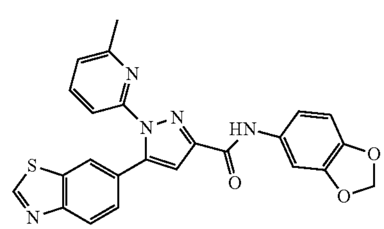 [SMILES: Cc1cccc(-n2nc(C(=O)Nc3ccc4c(c3)OCO4)cc2-c2ccc3ncsc3c2)n1] | N-(benzo[d][1,3]dioxol-5-yl)-5-(benzo[d]thiazol-6-yl)-1-(6-methylpyridin-2-yl)-1-H-pyrazole-3-carboxamide | 9.05(s, 1H), 8.75(s, 1H), 8.05(d, 1H), 7.98(d, 1H), 7.66(t, 1H), 7.45(d, 1H), 7.34(dd, 1H), 7.18(t, 3H), 7.00(d, 1H), 6.70(d, 1H), 5.97(s, 2H), 2.44(s, 3H) | 456.1/455.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 8 | 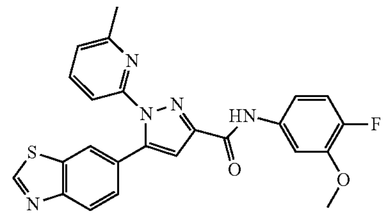 [SMILES: COc1cc(NC(=O)c2cc(-c3ccc4ncsc4c3)n(-c3cccc(C)n3)n2)ccc1F] | 5-(benzo[d]thiazol-6-yl)-N-(4-fluoro-3-methoxyphenyl)-1-(6-methylpyridin-2-yl)-1H-pyrazole-3-carboxamide | 9.05(s, 1H), 8.81(s, 1H), 8.05(d, 1H), 7.98(d, 1H), 7.74-7.64(m, 2H), 7.35(dd, 1H), 7.22(t, 3H), 7.02(d, 2H), 3.94(s, 3H), 2.44(s, 3H). | 460.1/459.1 |
| 9 | 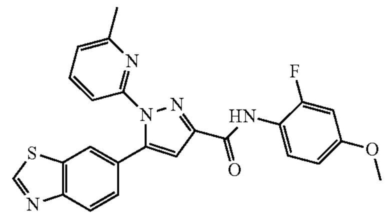 [SMILES: COc1ccc(NC(=O)c2cc(-c3ccc4ncsc4c3)n(-c3cccc(C)n3)n2)c(F)c1] | 5-(benzo[d]thiazol-6-yl)-N-(2-fluoro-4-methoxyphenyl)-1-(6-methylpyridin-2-yl)-1H-pyrazole-3-carboxyamide | 9.04(s, 1H), 8.88(s, 1H), 8.30(t, 1H), 8.05(d, 1H), 7.99(d, 1H), 7.69(t, 1H), 7.35(t, 2H), 7.18-7.15(m, 2H), 6.70(d, 2H), 3.80(s, 3H), 2.36(s, 3H) | 460.1/459.1 |
| 10 | 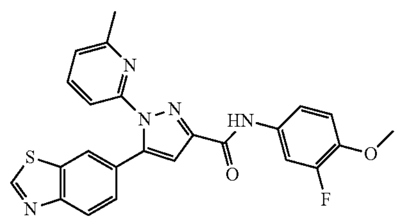 [SMILES: COc1ccc(NC(=O)c2cc(-c3ccc4ncsc4c3)n(-c3cccc(C)n3)n2)cc1F] | 5-(benzo[d]thiazol-6-yl)-N-(3-fluoro-4-methoxyphenyl)-1-(6-methylpyridin-2-yl)-1H-pyrazole-3-carboxyamide | 9.04(s, 1H), 8.77(s, 1H), 8.05(d, 1H), 7.98(d, 1H), 7.69-7.63(m, 2H), 7.35(d, 2H), 7.19(t, 3H), 6.95(t, 1H), 3.89(s, 3H), 2.43(s, 3H) | 460.1/459.1 |
| 11 | 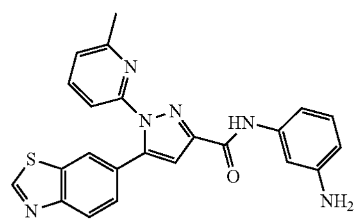 [SMILES: Cc1cccc(-n2nc(C(=O)Nc3cccc(N)c3)cc2-c2ccc3ncsc3c2)n1] | 5-(benzo[d]thiazol-6-yl)-N-(3-aminophenyl)-1-(6-methylpyridin-2-yl)-1H-pyrazole-3-carboxyamide | (300 MHz, DMSO-d₆) δ 10.50(s, 1H), 9.41(s, 1H), 8.25(s, 1H), 8.02(m, 1H), 7.91(t, 1H), 7.68(d, 1H), 7.59(d, 1H), 7.43-7.32(m, 4H), 7.03(d, 1H), 2.22(s, 3H) | 427.1/426.1 |
| 12 | 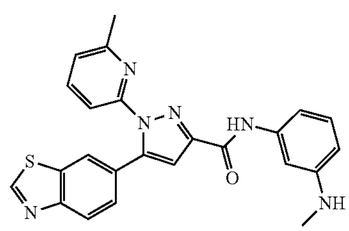 [SMILES: CNc1cccc(NC(=O)c2cc(-c3ccc4ncsc4c3)n(-c3cccc(C)n3)n2)c1] | 5-(benzo[d]thiazol-6-yl)-N-(3-(methylamino)phenyl)-1-(6-methylpyridin-2-yl)-1H-pyrazole-3-carboxyamide | (300 MHz, MeOD) δ 9.30(s, 1H), 8.11 (s, 1H), 8.02(d, 1H), 7.80(t, 1H), 7.42-7.37(m, 2H), 7.31(d, 1H), 7.17(s, 1H), 7.14-7.09(m, 2H), 7.00(d, 1H), 6.45(d, 1H), 2.80(d, 3H), 2.36(s, 3H) | 441.1/440.1 |
| 13 | 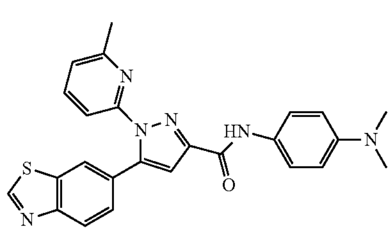 [SMILES: Cc1cccc(-n2nc(C(=O)Nc3ccc(N(C)C)cc3)cc2-c2ccc3ncsc3c2)n1] | 5-(benzo[d]thiazol-6-yl)-N-(4-(dimethylamino)phenyl)-1-(6-methylpyridin-2-yl)-1H-pyrazole-3-carboxyamide | 9.04(s, 1H), 8.71(s, 1H), 8.05(d, 1H), 7.98(d, 1H), 7.66(t, 1H), 7.59(d, 2H), 7.36(dd, 1H), 7.23-7.16(m, 3H), 6.76(d, 2H), 2.95(s, 6H), 2.05(s, 3H) | 455.2/454.2 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 14 | 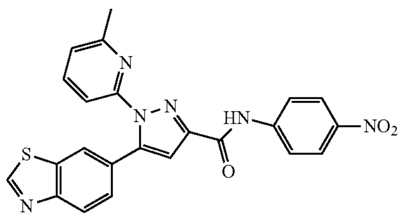 [SMILES: Cc1cccc(-n2nc(C(=O)Nc3ccc([N+](=O)[O-])cc3)cc2-c2ccc3ncsc3c2)n1] | 5-(benzo[d]thiazol-6-yl)-1-(6-methylpyridin-2-yl)-N-(4-nitrophenyl)-1H-pyrazole-3-carboxamide | (300 MHz, DMSO-d₆)δ 10.90(s, 1H), 9.45(s, 1H), 8.29-8.26(m, 3H), 8.15(d, 2H), 8.05(d, 1H), 7.93(t, 1H), 7.61(d, 1H), 7.38-7.34(m, 2H), 7.31(s, 1H), 2.27(s, 3H) | 457.1/456.1 |
| 15 | 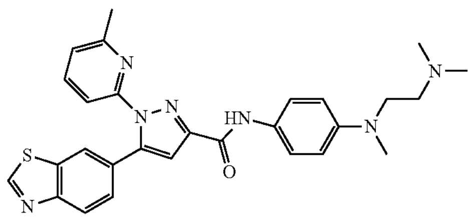 [SMILES: Cc1cccc(-n2nc(C(=O)Nc3ccc(N(C)CCN(C)C)cc3)cc2-c2ccc3ncsc3c2)n1] | 5-(benzo[d]thiazol-6-yl)-N-(4-((2-(dimethylamino)ethyl)(methyl)amino)phenyl)-1-(6-methylpyridin-2-yl)-1H-pyrazole-3-carboxamide | 9.04(s, 1H), 8.68(s, 1H), 8.04(d, 1H), 7.98(d, 1H), 7.66(t, 1H), 7.56(d, 2H), 7.35(d, 1H), 7.20(t, 3H), 6.74(d, 2H), 3.48(t, 2H), 2.96(s, 3H), 2.55(t, 2H), 2.43(s, 3H), 2.35(s, 6H) | 490.1/489.1 |
| 16 | 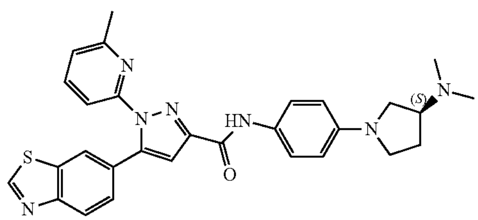 | 5-(benzo[d]thiazol-6-yl)-N-(4-(3-(dimethylamino)pyrrolidin-1-yl)phenyl)-1-(6-methylpyridin-2-yl)-1H-pyrazole-3-carboxamide | 9.05(s, 1H), 8.67(s, 1H), 8.07(d, 1H), 7.99(s, 1H), 7.67(t, 1H), 7.59(d, 2H), 7.38(d, 1H), 7.35-7.17(m, 3H), 6.58(d, 2H), 3.55-3.41(m, 2H), 3.37-3.34(m, 1H), 3.20(t, 1H), 2.93-2.91(m, 1H), 2.43(s, 3H), 2.36(s, 6H), 2.24-2.22(m, 1H) | 524.2/523.2 |
| 17 | 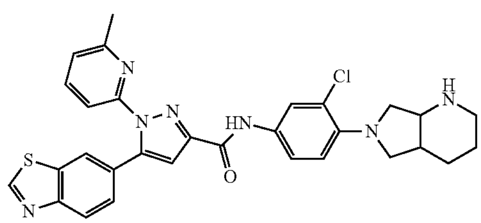 [SMILES: Cc1cccc(-n2nc(C(=O)Nc3ccc(N4CC5CCCNC5C4)c(Cl)c3)cc2-c2ccc3ncsc3c2)n1] | 5-(benzo[d]thiazol-6-yl)-N-(3-chloro-4-(octahydro-6H-pyrrolo[3.4-b]pyridin-6-yl)phenyl)-1-(6-methylpyridin-2-yl)-1H-pyrazole-3-carboxamide | 9.04(s, 1H), 8.70(s, 1H), 8.04(d, 1H), 7.97(s, 1H), 7.74(s, 1H), 7.60(t, 1H), 7.44(d, 1H), 7.34(d, 1H), 7.24-7.15(m, 3H), 6.86(d, 1H), 3.80-3.70(m, 2H), 3.47-3.45(m, 3H), 3.30-3.06(m, 2H), 2.70(t, 1H), 2.41(s, 3H), 2.39-2.36(m, 1H), 1.77-1.73(m, 3H) | 570.1/569.1 |
| 18 | 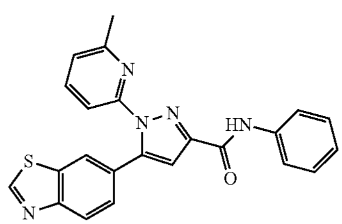 [SMILES: Cc1cccc(-n2nc(C(=O)Nc3ccccc3)cc2-c2ccc3ncsc3c2)n1] | 5-(benzo[d]thiazol-6-yl)-1-(6-methylpyridin-2-yl)-N-phenyl-1H-pyrazole-3-carboxamide | 9.08(s, 1H), 8.89(s, 1H), 8.05(d, 1H), 7.98(d, 1H), 7.74(d, 2H), 7.66(t, 1H), 7.38-7.35(m, 3H), 7.22-7.17(m, 4H), 2.43(s, 3H) | 412.1/411.1 |
| 19 | 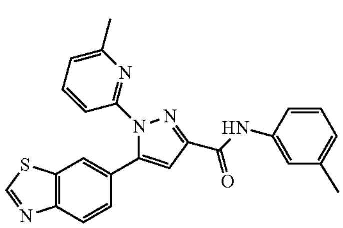 [SMILES: Cc1cccc(NC(=O)c2cc(-c3ccc4ncsc4c3)n(-c3cccc(C)n3)n2)c1] | 5-(benzo[d]thiazol-6-yl)-N-(3-tolyl)-1-(6-methylpyridin-2-yl)-1H-pyrazole-3-carboxamide | (300 MHz. MeOD) δ 9.28(s, 1H), 8.06(s, 1H), 7.98(d, 1H), 7.76(t, 1H), 7.56-7.53(m, 2H), 7.36(d, 2H), 7.30-7.20(m, 2H), 7.13(s, 1H), 6.96(d, 1H), 2.34(s, 3H), 2.33(s, 3H) | 426.1/425.1 |

TABLE 1-continued

| Example Number | Structure | Compound Name | ¹H NMR Spectrum (300 MHz, CDCl₃)δ | MS (ES) Actual Measurement Value [M + H]⁺/Required Value |
|---|---|---|---|---|
| 20 | 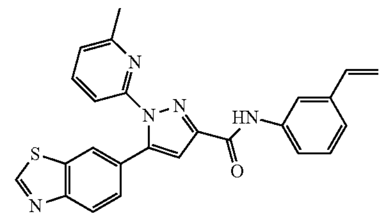 [SMILES: C=Cc1cccc(NC(=O)c2cc(-c3ccc4ncsc4c3)n(-c3cccc(C)n3)n2)c1] | 5-(benzo[d]thiazol-6-yl)-1-(6-methylpyridin-2-yl)-N-(3-vinylphenyl)-1H-pyrazole-3-carboxamide | 9.05(s, 1H), 8.85(s, 1H), 8.05(d, 1H), 7.99(d, 1H), 7.90(s, 1H), 7.70-7.62(m, 2H), 7.34(d, 2H), 7.21(t, 3H) 6.73(dd, 1H), 5.80(d, 1H), 5.28(d, 1H), 2.43(s, 3H) | 438.1/437.1 |
| 21 | 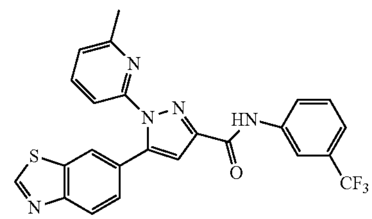 [SMILES: Cc1cccc(-n2nc(C(=O)Nc3cccc(C(F)(F)F)c3)cc2-c2ccc3ncsc3c2)n1] | 5-(benzo[d]thiazol-6-yl)-N-(3-(trifluoromethyl)phenyl)-1-(6-methylpyridin-2-yl)-1H-pyrazole-3-carboxamide | 9.06(s, 1H), 9.01(s, 1H), 8.08-8.05(m, 2H), 8.00-7.94(m, 2H), 7.68(t, 1H), 7.50(t, 1H), 7.41-7.34(m, 2H), 7.28-7.19(m, 3H), 2.45(s, 3H) | 480.4/479.1 |
| 22 | 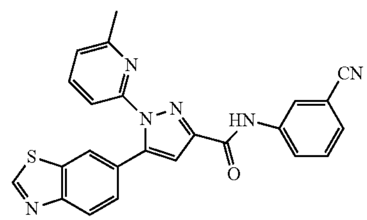 [SMILES: Cc1cccc(-n2nc(C(=O)Nc3cccc(C#N)c3)cc2-c2ccc3ncsc3c2)n1] | 5-(benzo[d]thiazol-6-yl)-N-(3-cyanophenyl)-1-(6-methylpyridin-2-yl)-1H-pyrazole-3-carboxamide | 9.06(s, 1H), 8.95(s, 1H), 8.15(d, 1H), 8.06(d, 1H), 7.99(d, 1H), 7.80(dd, 1H), 7.68(t, 1H), 7.47-7.43(m, 2H), 7.37(dd, 1H), 7.21-7.18(m, 3H), 2.45(s, 3H) | 437.1/436.1 |
| 23 | 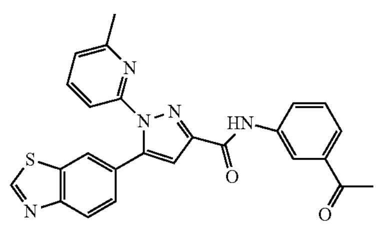 [SMILES: CC(=O)c1cccc(NC(=O)c2cc(-c3ccc4ncsc4c3)n(-c3cccc(C)n3)n2)c1] | 5-(benzo[d]thiaol-6-yl)-N-(3-acetylphenyl)-1-(6-methylpyridin-2-yl)-1H-pyrazole-3-carboxamide | 9.07(s, 1H), 9.01(s, 1H), 8.27(s, 1H), 8.26-8.06(m, 2H), 8.00(s, 1H), 7.74-7.67(m, 2H), 7.50(t, 1H), 7.38(d, 1H), 7.25-7.20(m, 2H), 2.66(s, 3H), 2.45(s, 3H) | 454.1/453.1 |
| 24 | 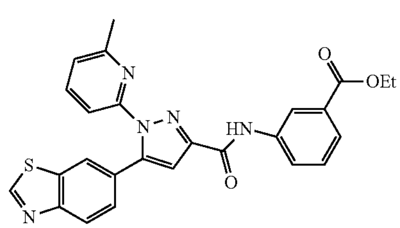 [SMILES: CCOC(=O)c1cccc(NC(=O)c2cc(-c3ccc4ncsc4c3)n(-c3cccc(C)n3)n2)c1] | ethyl 3-(5-(benzo[d]thiazol-6-yl)-1-(6-methylpyridin-2-yl)-1H-pyrazole-3-carboxamide)benzoate | 9.05(s, 1H), 8.95(s, 1H), 8.21(s, 1H), 8.16(d, 1H), 8.06(d, 1H), 7.99(d, 1H), 7.83(d, 1H), 7.66(t, 1H), 7.46(t, 1H), 7.37(dd, 1H), 7.21 (t, 3H), 4.40(q, 2H), 2.43(s, 3H), 4.41(t, 3H) | 484.1/483.1 |
| 25 | 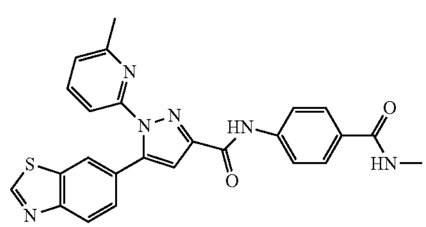 [SMILES: CNC(=O)c1ccc(NC(=O)c2cc(-c3ccc4ncsc4c3)n(-c3cccc(C)n3)n2)cc1] | 5-(benzo[d]thiazol-6-yl)-N-(4-(methylcarbamoyl)phenyl)-1-(6-methylpyridin-2-yl)1H-pyrazole-3-carboxamide | 9.05(s, 1H), 8.98(s, 1H), 8.07(d, 1H), 7.99(d, 1H), 7.80(s, 4H), 7.68(t, 1H), 7.35(dd, 1H), 7.21 (t, 3H), 6.10(s, 1H), 3.03(d, 3H), 2.44(s, 3H) | 469.1/468.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 26 | 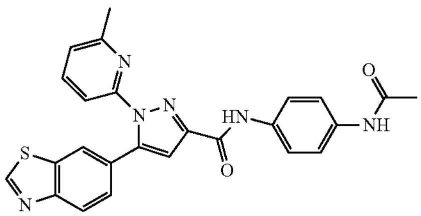 [SMILES: CC(=O)Nc1ccc(NC(=O)c2cc(-c3ccc4ncsc4c3)n(-c3cccc(C)n3)n2)cc1] | 5-(benzo[d]thiazol-6-yl)-N-(4-acetoamidophenyl)-1-(6-methylpyridin-2-yl)-1H-pyrazole-3-carboxyamide | (300 MHz, DMSO-d₆) δ 10.16(s, 1H), 9.90(s, 1H), 9.42(s, 1H), 8.85(d, 1H), 8.39(d, 1H), 8.25(s, 1H), 8.25-8.00(m, 2H), 7.90(t, 1H), 7.73(d, 2H), 7.60(d, 1H), 7.53(d, 2H), 7.34(t, 2H), 7.19(s, 1H), 2.21 (s, 3H), 2.01(s, 3H) | 469.1/468.1 |
| 27 | 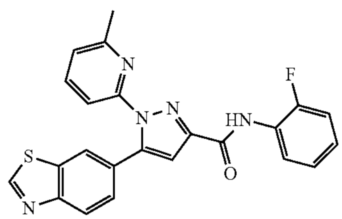 [SMILES: Cc1cccc(-n2nc(C(=O)Nc3ccccc3F)cc2-c2ccc3ncsc3c2)n1] | 5-(benzo[d]thiazol-6-yl)-N-(2-fluorophenyl)-1-(6-methylpyridin-2-yl)-1H-pyrazole-3-carboxyamide | 9.10(br, 1H), 9.05(s, 1H), 8.52(t, 1H), 8.06(d, 1H), 8.00(d, 1H), 7.70(t, 1H), 7.39-7.35(m, 2H), 7.20-7.09(m, 5H), 2.35(s, 3H) | 430.1/429.1 |
| 28 | 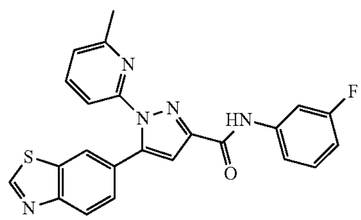 [SMILES: Cc1cccc(-n2nc(C(=O)Nc3cccc(F)c3)cc2-c2ccc3ncsc3c2)n1] | 5-(benzo[d]thiazol-6-yl)-N-(3-fluorophenyl)-1-(6-methylpyridin-2-yl)-1H-pyrazole-3-carboxyamide | 9.05(s, 1H), 8.91(s, 1H), 8.06(d, 1H), 7.98(d, 1H), 7.79-7.65(m, 2H), 7.37-7.30(m, 3H), 7.23-7.18(m, 3H), 6.84(t, 1H), 2.44(s, 3H) | 430.1/429.1 |
| 29 | 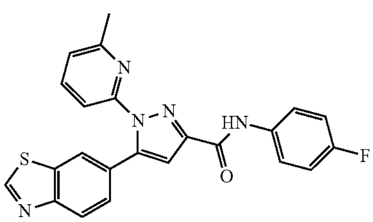 [SMILES: Cc1cccc(-n2nc(C(=O)Nc3ccc(F)cc3)cc2-c2ccc3ncsc3c2)n1] | 5-(benzo[d]thiazol-6-yl)-N-(4-fluorophenyl)-1-(6-methylpyridin-2-yl)-1H-pyraozle-3-carboxyamide | 9.05(s, 1H), 8.84(s, 1H), 8.06(d, 1H), 7.98(d, 1H), 7.72-7.67(m, 3H), 7.36(d, 1H), 7.22-7.18(m, 3H), 7.07(t, 2H), 2.44(s, 3H) | 430.1/429.1 |
| 30 | 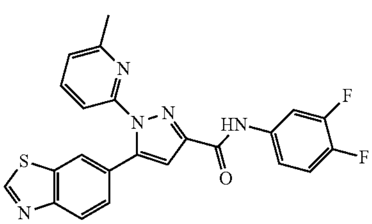 [SMILES: Cc1cccc(-n2nc(C(=O)Nc3ccc(F)c(F)c3)cc2-c2ccc3ncsc3c2)n1] | 5-(benzo[d]thiazol-6-yl)-N-(3,4-difluorophenyl)-1-(6-methylpyridin-2-yl)-1H-pyrazole-3-carboxyamide | 9.06(s, 1H), 8.86(s, 1H), 8.06(d, 1H), 7.98(d, 1H), 7.82-7.78(m, 1H), 7.67(t, 1H), 7.35(d, 1H), 7.30-7.28(m, 1H), 7.21-7.13(m, 4H), 2.45(s, 3H) | 448.1/447.1 |
| 31 | 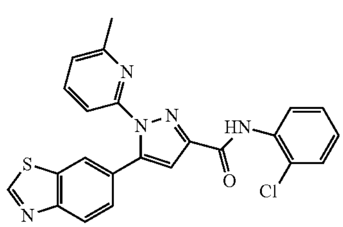 [SMILES: Cc1cccc(-n2nc(C(=O)Nc3ccccc3Cl)cc2-c2ccc3ncsc3c2)n1] | 5-(benzo[d]thiazol-6-yl)-N-(2-chlorophenyl)-1-(6-methylpyridin-2-yl)-1H-pyrazole-3-carboxyamide | 9.49(s, 1H), 9.05(s, 1H), 8.60(d, 1H), 8.05(d, 1H), 8.01(d, 1H), 7.73(t, 1H), 7.46-7.34(m, 4H), 7.19(s, 1H), 7.15 (d, 1H), 7.07(t, 1H), 2.30(s, 3H) | 446.1/445.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 32 | 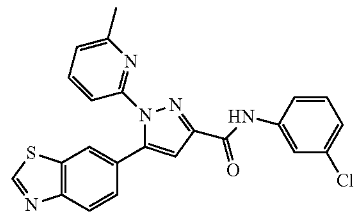 [SMILES: Cc1cccc(-n2nc(C(=O)Nc3cccc(Cl)c3)cc2-c2ccc3ncsc3c2)n1] | 5-(benzo[d]thiazol-6-yl)-N-(3-chlorophenyl)-1-(6-methylpyridin-2-yl)-1H-pyrazole-3-carboxyamide | 9.05(s, 1H), 8.85(s, 1H), 8.05(d, 1H), 7.98(d, 1H), 7.86(s, 1H), 7.67(t, 1H), 7.57(d, 1H). 7.36-7.30(m, 2H), 7.21-7.10(m, 4H), 2.44(s, 3H) | 446.1/445.1 |
| 33 | 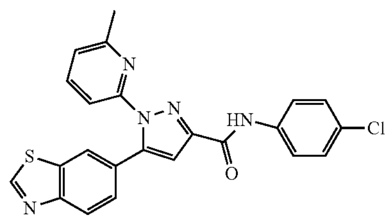 [SMILES: Cc1cccc(-n2nc(C(=O)Nc3ccc(Cl)cc3)cc2-c2ccc3ncsc3c2)n1] | 5-(benzo[d]thiazol-6-yl)-N-(4-chlorophenyl)-1-(6-methylpyridin-2-yl)-1H-pyrazole-3-carboxyamide | 9.05(s, 1H), 8.84(s, 1H), 8.05(d, 1H), 7.98(d, 1H), 7.70-7.64(m, 3H), 7.36-7.30(m, 3H), 7.21-7.18(m, 3H), 2.44(s, 3H) | 446.1/445.1 |
| 34 | 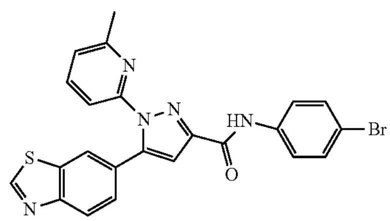 [SMILES: Cc1cccc(-n2nc(C(=O)Nc3ccc(Br)cc3)cc2-c2ccc3ncsc3c2)n1] | 5-(benzo[d]thiazol-6-yl)-N-(4-bromophenyl)-1-(6-methylpyridin-2-yl)-1H-pyrazole-3-carboxyamide | 9.05(s, 1H), 8.83(s, 1H), 8.05(d, 1H), 7.98(d, 1H), 7.69-7.62(m, 3H), 7.48(d, 2H), 7.34(d, 1H), 7.21-7.18(m, 3H), 2.44(s, 3H) | 490.0/489.0 |
| 35 | 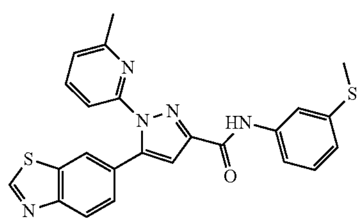 [SMILES: CSc1cccc(NC(=O)c2cc(-c3ccc4ncsc4c3)n(-c3cccc(C)n3)n2)c1] | 5-(benzo[d]thiazol-6-yl)-1-(6-methylpyridin-2-yl)-N-(3-(methylthio)phenyl)-1H-pyrazole-3-carboxyamide | 9.04(s, 1H), 8.84(s, 1H), 8.05(d, 1H), 7.98(d, 1H), 7.74(m, 1H), 7.67(t, 1H), 7.40(dd, 1H), 7.35(d, 1H), 7.27-7.17(m, 4H), 7.01(d, 1H), 2.52(s, 3H), 2.43(s, 3H) | 458.1/457.1 |
| 36 | 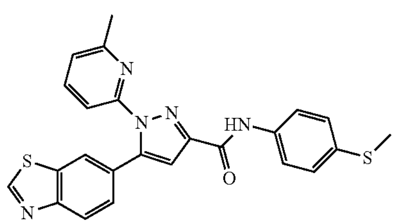 [SMILES: CSc1ccc(NC(=O)c2cc(-c3ccc4ncsc4c3)n(-c3cccc(C)n3)n2)cc1] | 5-(benzo[d]thiazol-6-yl)-1-(6-methylpyridin-2-yl)-N-(4-(methylthio)phenyl)-1H-pyrazole-3-carboxyamide | 9.05(s, 1H), 8.84(s, 1H), 8.05(d, 1H), 7.98(d, 1H), 7.69-7.64(m, 3H), 7.36-7.27(m, 4H), 7.21-7.18(m, 2H), 2.49(s, 3H), 2.44(s, 3H) | 458.1/457.1 |
| 37 | 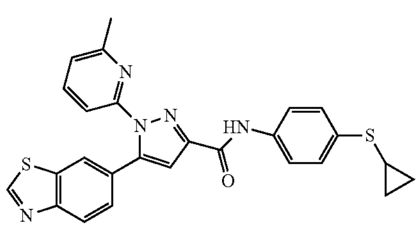 [SMILES: Cc1cccc(-n2nc(C(=O)Nc3ccc(SC4CC4)cc3)cc2-c2ccc3ncsc3c2)n1] | 5-(benzo[d]thiazol-6-yl)-N-(4-(cyclopropylthio)phenyl)-1-(6-methylpyridin-2-yl)-1H-pyrazole-3-carboxyamide | 9.04(s, 1H), 8.80(s, 1H), 8.05(d, 1H), 7.98(d, 1H), 7.69-7.64(m, 3H), 7.40-7.34(m, 4H), 7.26-7.17(m, 2H), 2.43(s, 3H), 2.23-2.19(m, 1H), 1.08-1.03(m, 2H), 0.73-0.69(m, 2H) | |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 38 | 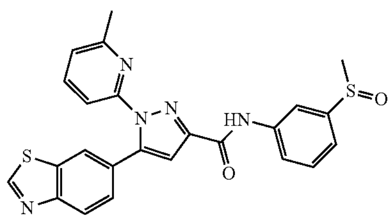 [SMILES: Cc1cccc(-n2nc(C(=O)Nc3cccc(S(C)=O)c3)cc2-c2ccc3ncsc3c2)n1] | 5-(benzo[d]thiazol-6-yl)-1-(6-methylpyridin-2-yl)-N-(3-(methylsulfinyl)phenyl)-1H-pyrazole-3-carboxamide | 9.09(s, 1H), 9.05(s, 1H), 8.07-7.98(m, 4H), 7.69(t, 1H), 7.54(t, 1H), 7.43-7.34(m, 2H), 7.20-7.18(m, 3H), 2.77(s, 3H), 2.42(s, 3H) | 474.1/473.1 |
| 39 | 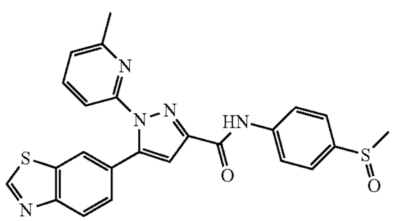 [SMILES: Cc1cccc(-n2nc(C(=O)Nc3ccc(S(C)=O)cc3)cc2-c2ccc3ncsc3c2)n1] | 5-(benzo[d]thiazol-6-yl)-1-(6-methylpyridin-2-yl)-N-(4-(methylsulfinyl)phenyl)-1H-pyrazole-3-carboxamide | 9.08(s, 1H), 9.06(s, 1H), 8.06(d, 1H), 7.98(d, 1H), 7.93(d, 2H), 7.69-7.64(m, 3H), 7.36(d, 1H), 7.22-7.17(m, 3H), 2.74(s, 3H), 2.46(s, 3H) | 474.1/473.1 |
| 40 | 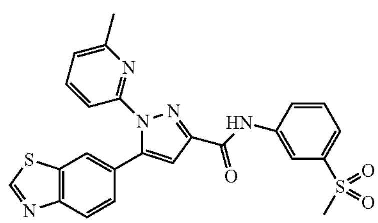 [SMILES: Cc1cccc(-n2nc(C(=O)Nc3cccc(S(C)(=O)=O)c3)cc2-c2ccc3ncsc3c2)n1] | 5-(benzo[d]thiazol-6-yl)-1-(6-methylpyridin-2-yl)-N-(3-(methylsulfonyl)phenyl)-1H-pyrazole-3-carboxamide | 9.07(m, 2H), 8.24(s, 1H), 8.15(d, 1H), 8.06(d, 1H), 7.99(d, 1H), 7.69(t, 2H), 7.59(t, 1H), 7.36(d, 1H), 7.22-7.19(m, 3H), 3.10(s, 3H), 2.44(s, 3H) | 490.1/489.1 |
| 41 | 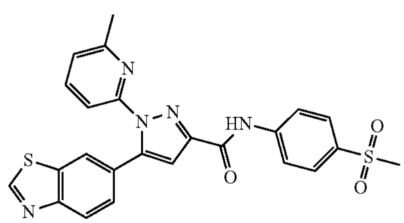 [SMILES: Cc1cccc(-n2nc(C(=O)Nc3ccc(S(C)(=O)=O)cc3)cc2-c2ccc3ncsc3c2)n1] | 5-(benzo[d]thiazol-6-yl)-1-(6-methylpyridin-2-yl)-N-(4-(methylsulfonyl)phenyl)-1H-pyrazole-3-carboxamide | 9.12(s, 1H), 9.06(s, 1H), 8.06(d, 1H), 7.98-7.95(m, 5H), 7.67(t, 1H), 7.35(d, 1H), 7.22-7.18(m, 3H), 3.07(s, 3H), 2.46(s, 3H) | 490.1/489.1 |
| 42 | 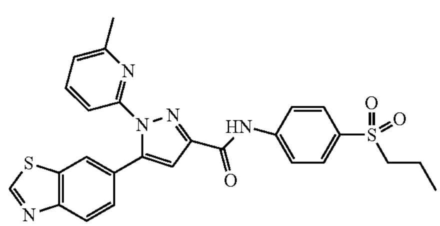 [SMILES: CCCS(=O)(=O)c1ccc(NC(=O)c2cc(-c3ccc4ncsc4c3)n(-c3cccc(C)n3)n2)cc1] | 5-(benzo[d]thiazol-6-yl)-1-(6-methylpyridin-2-yl)-N-(4-(propylsulfonyl)phenyl)-1H-pyrazole-3-carboxamide | 9.10(s, 1H), 9.06(s, 1H), 8.06(d, 1H), 7.99-7.89(m, 5H), 7.68(t, 1H), 7.35(d, 1H), 7.23-7.17(m, 3H), 3.10-3.05(m, 2H), 2.46(s, 3H), 1.80-1.72(m, 2H), 1.01(t, 3H) | 518.1/517.1 |
| 43 | 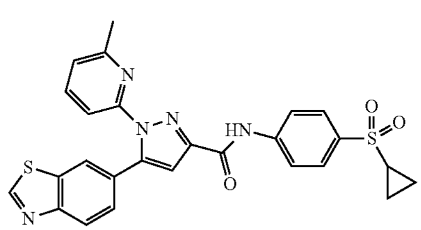 [SMILES: Cc1cccc(-n2nc(C(=O)Nc3ccc(S(=O)(=O)C4CC4)cc3)cc2-c2ccc3ncsc3c2)n1] | 5-(benzo[d]thiazol-6-yl)-N-(4-(cyclopropylsulfonyl)phenyl)-1-(6-methylpyridin-2-yl)-1H-pyrazole-3-carboxamide | 9.08(s, 1H), 9.06(s, 1H), 8.06(d, 1H), 7.98(d, 1H), 7.95-7.91(m, 4H), 7.68(t, 1H), 7.35(d, 1H), 7.22-7.18(m, 3H), 2.49-2.46(m, 4H), 1.37-1.35(m, 2H), 1.06-1.02(m, 2H) | 516.1/515.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 44 | 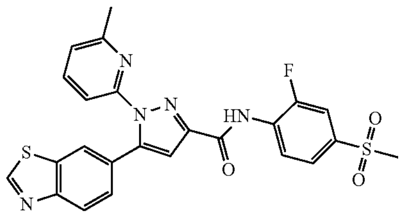 [SMILES: Cc1cccc(-n2nc(C(=O)Nc3ccc(S(C)(=O)=O)cc3F)cc2-c2ccc3ncsc3c2)n1] | 5-(benzo[d]thiazol-6-yl)-N-(2-fluoro-4-(methylsulfonyl)phenyl)-1-(6-methylpyridin-2-yl)-1H-pyrazole-3-carboxamide | 9.36(s, 1H), 9.07(s, 1H), 8.86(t, 1H), 8.07(d, 1H), 8.01(s, 1H). 7.82-7.70(m, 3H), 7.39-7.32(m, 3H), 7.22-7.20(m, 2H), 3.09(s, 3H), 2.39(s, 3H) | 508.0/507.0 |
| 45 | 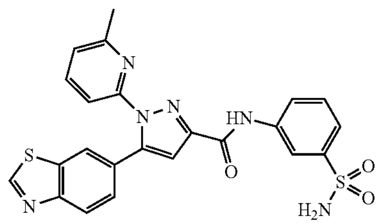 [SMILES: Cc1cccc(-n2nc(C(=O)Nc3cccc(S(N)(=O)=O)c3)cc2-c2ccc3ncsc3c2)n1] | 5-(benzo[d]thiazol-6-yl)-1-(6-methylpyridin-2-yl)-N-(3-sulfoamoylphenyl)-1H-pyrazole-3-carboxamide | 9.12(s, 1H), 8.34(m, 1H), 8.08(d, 1H), 8.02(d, 1H), 7.98(d, 1H), 7.70-7.60(m, 2H), 7.52(t, 1H), 7.37(d, 1H), 7.24(d, 1H), 7.20(s, 2H), 6.98(d, 1H), 2.56(s, 3H) | 491.1/490.1 |
| 46 | 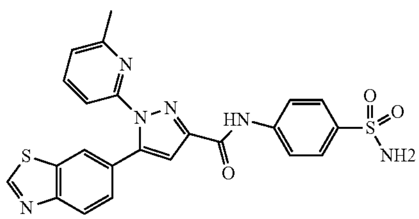 [SMILES: Cc1cccc(-n2nc(C(=O)Nc3ccc(S(N)(=O)=O)cc3)cc2-c2ccc3ncsc3c2)n1] | 5-(benzo[d]thiazol-6-yl)-1-(6-methylpyridin-2-yl)-N-(4-sulfamoylphenyl)-1H-pyrazole-3-carboxamide | 9.12(s, 1H), 8.07(d, 1H), 8.01(d, 1H), 7.93(s, 4H), 7.64(t, 1H), 7.39-7.26(m, 2H), 7.24(d, 1H), 7.21(s, 1H), 7.00(d, 1H), 2.56(s, 3H) | 491.1/490.1 |
| 47 | 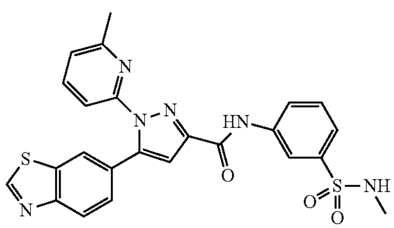 [SMILES: CNS(=O)(=O)c1cccc(NC(=O)c2cc(-c3ccc4ncsc4c3)n(-c3cccc(C)n3)n2)c1] | 5-(benzo[d]thiazol-6-yl)-1-(6-methylpyridin-2-yl)-N-(3-(N-methylsulfamoyl)phenyl)-1H-pyrazole-3-carboxamide | 9.06-7.05(m, 2H), 8.18(d, 1H), 8.05(d, 2H), 7.99(d, 1H), 7.71-7.54(m, 3H), 7.35(d, 1H), 7.24-7.20(m, 3H), 4.41-4.39(bs, 1H), 2.73(s, 3H), 2.44(s, 3H) | 505.1/504.1 |
| 48 | 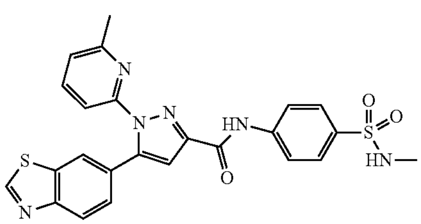 [SMILES: CNS(=O)(=O)c1ccc(NC(=O)c2cc(-c3ccc4ncsc4c3)n(-c3cccc(C)n3)n2)cc1] | 5-(benzo[d]thiazol-6-yl)-1-(6-methylpyridin-2-yl)-N-(4-(N-methylsulfamoyl)phenyl)-1H-pyrazole-3-carboxamide | 9.06 (m, 2H), 8.06(d, 1H), 7.99(d, 1H), 7.93-7.85(m, 3H), 7.68(t, 1H), 7.35(d, 1H), 7.22-7.18(m, 3H), 4.21-4.19(bs, 1H), 2.69(s, 3H), 2.46(s, 3H) | 505.1/504.1 |
| 49 | 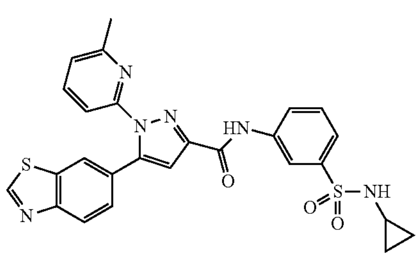 [SMILES: Cc1cccc(-n2nc(C(=O)Nc3cccc(S(=O)(=O)NC4CC4)c3)cc2-c2ccc3ncsc3c2)n1] | 5-(benzo[d]thiazol-6-yl)-N-(3-(N-cyclopropylsulfamoyl)phenyl)-1-(6-methylpyridin-2-yl)-1H-pyrazole-3-carboxamide | 9.06(s, 1H), 9.05(s, 1H), 8.19(d, 1H), 8.08(t, 2H), 7.99(d, 1H), 7.70-7.66(m, 2H), 7.55(t, 1H), 7.35(d, 1H), 7.22-7.19(m, 3H), 4.91(s, 1H), 2.44(s, 3H), 2.35-2.28(m, 1H), 0.68-0.64(m, 4H) | 531.1/530.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 50 | 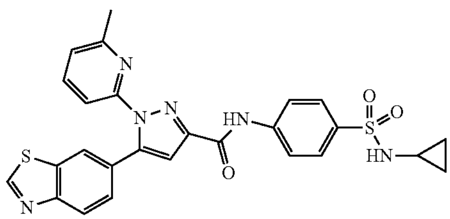 [SMILES: Cc1cccc(-n2nc(C(=O)Nc3ccc(S(=O)(=O)NC4CC4)cc3)cc2-c2ccc3ncsc3c2)n1] | 5-(benzo[d]thiazol-6-yl)-N-(4-(N-cyclopropylsulfamoyl)phenyl)-1-(6-methylpyridin-2-yl)-1H-pyrazole-3-carboxamide | 9.13(s, 1H), 9.06(s, 1H), 8.07(d, 1H), 8.00(d, 1H), 7.85(d, 2H), 7.71 (t, 1H), 7.42-7.34(m, 2H), 7.21-7.17(m, 4H), 4.90(s, 1H), 2.34(s, 3H), 2.25-2.22(m, 1H), 0.60-0.57(m. 4H) | 531.1/530.1 |
| 51 | 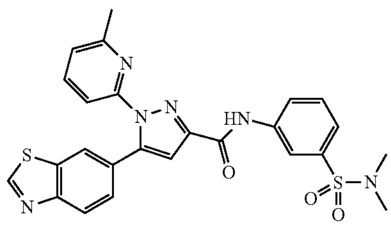 [SMILES: Cc1cccc(-n2nc(C(=O)Nc3cccc(S(=O)(=O)N(C)C)c3)cc2-c2ccc3ncsc3c2)n1] | 5-(benzo[d]thiazol-6-yl)-N-(3-(N,N-dimethylsulfamoyl)phenyl)-1-(6-methylpyridin-2-yl)-1H-pyrazole-3-carboxamide | 9.08(s, 1H), 9.06(s, 1H), 8.10-8.05(m, 3H), 7.98(d, 1H), 7.68(t, 1H), 7.56-7.54(m, 2H), 7.35(d, 1H), 7.25-7.19(m, 3H), 2.76(s, 6H), 2.44(s, 3H) | 519.1/518.1 |
| 52 | 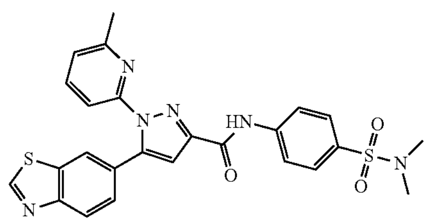 [SMILES: Cc1cccc(-n2nc(C(=O)Nc3ccc(S(=O)(=O)N(C)C)cc3)cc2-c2ccc3ncsc3c2)n1] | 5-(benzo[d]thiazol-6-yl)-N-(4-(N,N-dimethylsulfamoyl)phenyl)-1-(6-methylpyridin-2-yl)-1H-pyrazole-3-carboxamide | (300 MHz, DMSO-d₆) δ 10.50(s, 1H), 9.23(s, 1H), 8.46(s, 1H), 8.02(m, 1H), 7.96(d, 2H), 7.89-7.85(m, 3H), 7.60(d, 2H), 7.34-7.29 (m, 1H), 7.25-7.22(m, 1H), 2.66(s, 6H), 2.51(s, 3H) | 519.1/518.1 |
| 53 | 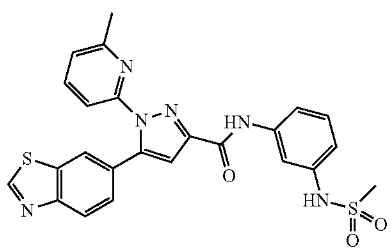 [SMILES: Cc1cccc(-n2nc(C(=O)Nc3cccc(NS(C)(=O)=O)c3)cc2-c2ccc3ncsc3c2)n1] | 5-(benzo[d]thiazol-6-yl)-1-(6-methylpyridin-2-yl)-N-(3-(methylsulfonamide)phenyl)-1H-pyrazole-3-carboxamide | 9.05(s, 1H), 8.90(s, 1H), 8.05(d, 1H), 7.98(d, 1H), 7.77(d, 1H), 7.68(t, 1H), 7.48(d, 1H), 7.38-7.34(m, 2H), 7.23-7.18(m, 3H), 7.00(d, 1H), 6.40(s, 1H), 3.06(s, 3H), 2.43(s, 3H) | 505.1/504.1 |
| 54 | 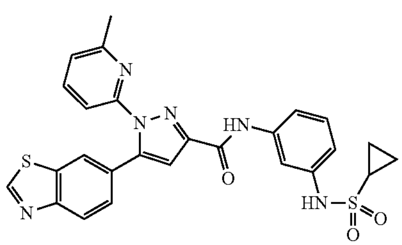 [SMILES: Cc1cccc(-n2nc(C(=O)Nc3cccc(NS(=O)(=O)C4CC4)c3)cc2-c2ccc3ncsc3c2)n1] | 5-(benzo[d]thiazol-6-yl)-N-(3-(cyclopropanesulfonamido)phenyl)-1-(6-methylpyridin-2-yl)-1H-pyrazole-3-carboxamide | 9.05(s, 1H), 8.89(s, 1H), 8.05(d, 1H), 7.98(d, 1H), 7.80(d, 1H), 7.67(t, 1H), 7.48(d, 1H), 7.35(d, 2H), 7.23-7.18(m, 3H), 7.06(d, 1H), 6.32(s, 1H), 2.56-2.54(m, 1H), 2.43(s, 3H), 1.28-1.21(m, 2H), 1.04-0.99(m, 2H) | 531.1/530.1 |
| 55 | 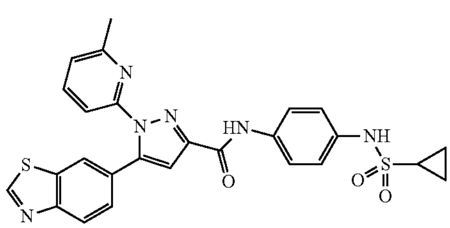 [SMILES: Cc1cccc(-n2nc(C(=O)Nc3ccc(NS(=O)(=O)C4CC4)cc3)cc2-c2ccc3ncsc3c2)n1] | 5-(benzo[d]thiazol-6-yl)-N-(4-(cyclopropanesulfonamido)phenyl)-1-(6-methylpyridin-2-yl)-1H-pyrazole-3-carboxamide | 9.06(s, 1H), 8.87(s, 1H), 8.05(d, 1H), 7.98(d, 1H), 7.72(d, 2H), 7.67(t, 1H), 7.35(d, 1H), 7.30(d, 2H), 7.23-7.18(m, 3H), 6.32(s, 1H), 2.49-2.44(s, 4H). 1.18-1.15(m, 2H), 1.00-0.95(m, 2H) | 531.1/530.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 56 | 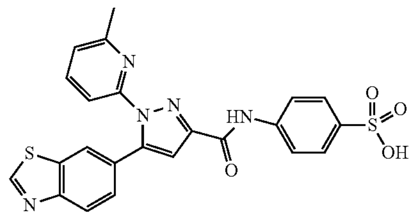 [SMILES: Cc1cccc(-n2nc(C(=O)Nc3ccc(S(=O)(=O)O)cc3)cc2-c2ccc3ncsc3c2)n1] | 4-(5-(benzo[d]thiazol-6-yl)-1-(6-methylpyridin-2-yl)-1H-pyrazole-3-carboxyamido) benzenesulfonic acid | (300 MHz, DMSO-d₆)δ 10.30(s, 1H), 9.44(s, 1H), 8.27(d, 1H), 8.03(d, 1H), 7.93(t, 1H), 7.77(d, 2H), 7.65(d, 1H), 7.56(d, 2H), 7.34(t, 2H), 7.23(s, 1H), 2.08(s, 3H) | 492.1/491.1 |
| 57 | 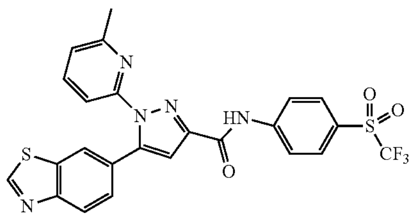 [SMILES: Cc1cccc(-n2nc(C(=O)Nc3ccc(S(=O)(=O)C(F)(F)F)cc3)cc2-c2ccc3ncsc3c2)n1] | 5-(benzo[d]thiazol-6-yl)-1-(6-methylpyridin-2-yl)-N-(4-((trifluoromethyl)sulfonyl)phenyl)-1H-pyrazole-3-carboxamide | 9.23(s, 1H), 9.06(s, 1H), 8.08-8.04(m, 5H), 7.99(d, 1H), 7.68(t, 1H), 7.35(d, 1H), 7.24-7.17(m, 3H), 2.47(s, 3H) | 544.1/543.1 |
| 58 | 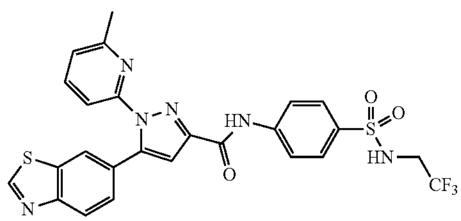 [SMILES: Cc1cccc(-n2nc(C(=O)Nc3ccc(S(=O)(=O)NCC(F)(F)F)cc3)cc2-c2ccc3ncsc3c2)n1] | 5-(benzo[d]thiazol-6-yl)-1-(6-methylpyridin-2-yl)-N-(4-(N-(2,2,2-trifluoroethyl)sulfamoyl)phenyl)-1H-pyrazole-3-carboxamide | 9.09(s, 1H), 9.06(s, 1H), 8.06(d, 1H), 7.98(d, 1H), 7.89(dd, 4H), 7.68(t, 1H), 7.36(d, 1H), 7.22-7.19(m, 3H), 4.97(t, 1H), 3.73-3.65(m, 2H), 2.45(s, 3H) | |
| 59 | 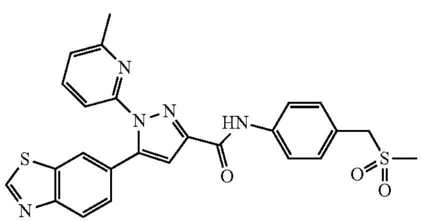 [SMILES: Cc1cccc(-n2nc(C(=O)Nc3ccc(CS(C)(=O)=O)cc3)cc2-c2ccc3ncsc3c2)n1] | 5-(benzo[d]thiazol-6-yl)-1-(6-methylpyridin-2-yl)-N-(4-((methylsulfonyl)methyl)phenyl)-1H-pyrazole-3-carboxamide | 9.05(s, 1H), 8.93(s, 1H), 8.06(d, 1H), 7.99(d, 1H), 7.85(d, 1H), 7.75(d, 1H), 7.68(t, 1H), 7.43(t, 2H), 7.37(d, 1H), 7.23-7.18(m, 3H), 4.27(s, 2H), 2.81(s, 3H), 2.43(s, 3H) | 504.1/503.1 |
| 60 | 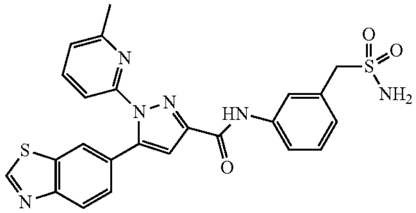 [SMILES: Cc1cccc(-n2nc(C(=O)Nc3cccc(CS(N)(=O)=O)c3)cc2-c2ccc3ncsc3c2)n1] | 5-(benzo[d]thiazol-6-yl)-1-(6-methylpyridin-2-yl)-N-(3-(sulfamoylmethyl)phenyl)-1H-pyrazole-3-carboxamide | (300 MHz, DMSO-d₆)δ 10.31 (s, 1H), 9.45(s, 1H), 8.27(d, 1H), 8.03(d, 1H), 7.95-7.84(m, 3H), 7.64(d, 1H), 7.39-7.33(m, 3H), 7.24(s, 1H), 7.12(d, 1H), 6.88(s, 2H), 4.25(s, 2H), 2.22(s, 3H) | 505.1/504.1 |
| 61 | 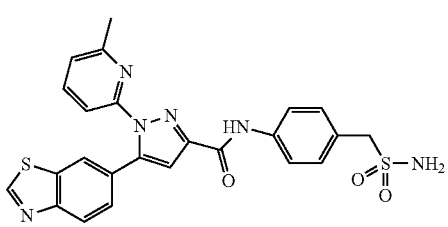 [SMILES: Cc1cccc(-n2nc(C(=O)Nc3ccc(CS(N)(=O)=O)cc3)cc2-c2ccc3ncsc3c2)n1] | 5-(benzo[d]thiazol-6-yl)-1-(6-methylpyridin-2-yl)-N-(4-(sulfamoylmethyl)phenyl)-1H-pyrazole-3-carboxamide | (300 MHz. DMSO-d₆)δ 10.32(s, 1H), 9.45(s, 1H), 8.27(d, 1H), 8.03(d, 1H), 7.92(t, 1H), 7.84(d, 2H), 7.61(d, 1H), 7.35-7.33(m, 4H), 7.24(s, 1H), 6.83(s, 2H), 4.23(s, 2H), 2.23(s, 3H) | 505.1/504.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 62 | 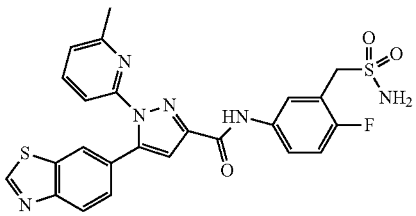 [SMILES: Cc1cccc(-n2nc(C(=O)Nc3ccc(F)c(CS(N)(=O)=O)c3)cc2-c2ccc3ncsc3c2)n1] | 5-(benzo[d]thiazol-6-yl)-N-(4-fluoro-3-(sulfamoylmethyl)phenyl)-1-(6-methylpyridin-2-yl)-1H-pyrazole-3-carboxamide | (300 MHz, DMSO-d₆)δ 10.40(s, 1H), 9.45(s, 1H), 8.27(d, 1H), 8.03(d, 1H), 7.97-7.90(m, 3H), 7.62(d, 1H), 7.35(dd, 2H), 7.23(dd, 2H), 7.06(s, 2H), 4.30(s, 2H), 2.23(s, 3H) | 523.1/522.1 |
| 63 | 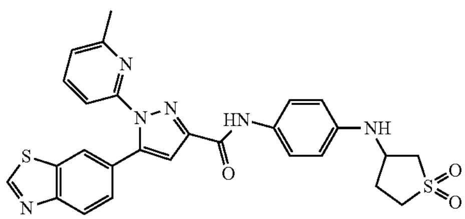 [SMILES: Cc1cccc(-n2nc(C(=O)Nc3ccc(NC4CCS(=O)(=O)C4)cc3)cc2-c2ccc3ncsc3c2)n1] | 5-(benzo[d]thiazol-6-yl)-N-(4-((1,1-dioxidotetrahydrothiophen-3-yl)amino)phenyl)-1-(6-methylpyridin-2-yl)-1H-pyrazole-3-carboxamide | 9.05(s, 1H), 8.85(s, 1H), 8.05(d, 1H), 7.98(d, 1H), 7.68(t, 1H), 7.62(d, 2H), 7.37(d, 1H), 7.23-7.18(m, 3H), 6.70(d, 2H), 4.25(s, 1H), 3.45-2.98(m, 5H), 2.55-2.50(m, 1H), 2.43(s, 3H), 2.33-2.30(m, 1H) | 545.1/544.1 |
| 64 | 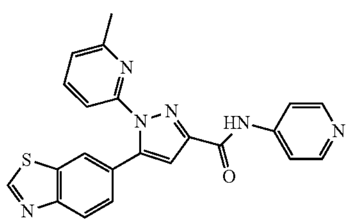 [SMILES: Cc1cccc(-n2nc(C(=O)Nc3ccncc3)cc2-c2ccc3ncsc3c2)n1] | 5-(benzo[d]thiazol-6-yl)-1-(6-methylpyridin-2-yl)-N-(pyridin-4-yl)-1H-pyrazole-3-carboxamide | 9.05(s, 1H), 8.96(s, 1H), 8.55(d, 2H), 8.05(d, 1H), 7.98(d, 1H), 7.70-7.65(m, 3H), 7.35(d, 1H), 7.22-7.19(m, 3H), 2.44(s, 3H) | 413.1/412.1 |
| 65 | 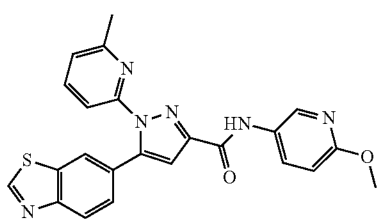 [SMILES: COc1ccc(NC(=O)c2cc(-c3ccc4ncsc4c3)n(-c3cccc(C)n3)n2)cn1] | 5-(benzo[d]thiazol-6-yl)-N-(6-methoxypyridin-3-yl)-1-(6-methylpyridin-2-yl)-1H-pyrazole-3-carboxamide | 9.05(s, 1H), 8.74(s, 1H), 8.38(d, 1H), 8.13(dd, 1H), 8.06(d, 1H), 7.98(d, 1H). 7.66(t, 1H), 7.35(d, 1H), 7.21(s, 2H), 7.18(dd, 1H), 6.79(d, 1H), 3.94(s, 3H), 2.45(s, 3H) | 443.1/442.1 |
| 66 | 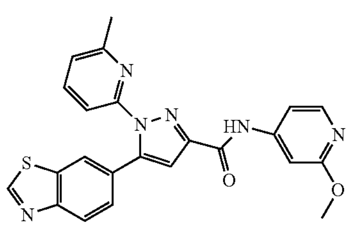 [SMILES: COc1cc(NC(=O)c2cc(-c3ccc4ncsc4c3)n(-c3cccc(C)n3)n2)ccn1] | 5-(benzo[d]thiazol-6-yl)-N-(2-methoxypyridin-4-yl)-1-(6-methylpyridin-2-yl)-1H-pyrazole-3-carboxamide | 9.06(s, 1H), 8.95(s, 1H), 8.11-8.04(m, 2H), 7.97(d, 1H), 7.67(t, 1H), 7.34(d, 1H), 7.22-7.17(m, 5H), 3.95(s, 3H), 2.45(s, 3H) | 443.1/442.1 |
| 67 | 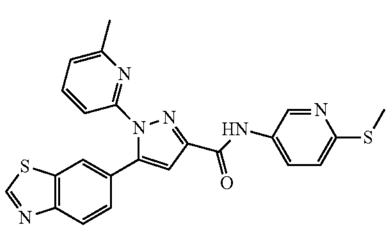 [SMILES: CSc1ccc(NC(=O)c2cc(-c3ccc4ncsc4c3)n(-c3cccc(C)n3)n2)cn1] | 5-(benzo[d]thiazol-6-yl)-N-(6-(methylthio)pyridin-3-yl)-1-(6-methylpyridin-2-yl)-1H-pyrazole-3-carboxamide | 9.07(s, 1H), 8.83(s, 1H), 8.67(s, 1H), 8.18(d, 1H), 8.07(d, 1H), 7.99(s, 1H), 7.68(t, 1H), 7.36(d, 1H), 7.24-7.20(m, 4H), 2.59(s, 3H), 2.46(s, 3H) | 459.1/458.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 68 | 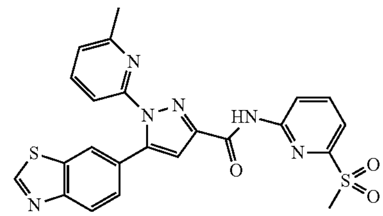 [SMILES: Cc1cccc(-n2nc(C(=O)Nc3cccc(S(C)(=O)=O)n3)cc2-c2ccc3ncsc3c2)n1] | 5-(benzo[d]thiazol-6-yl)-1-(6-methylpyridin-2-yl)-N-(6-(methylsulfonyl)pyridin-2-yl)-1H-pyrazole-3-carboxamide | 9.64(s, 1H), 9.06(s, 1H), 8.68(d, 1H), 8.08-7.99(m, 3H), 7.84(d, 1H), 7.73(t, 1H), 7.35(d, 2H), 7.22-7.13(m, 2H), 3.22(s, 3H), 2.32(s, 3H) | 491.1/490.1 |
| 69 | 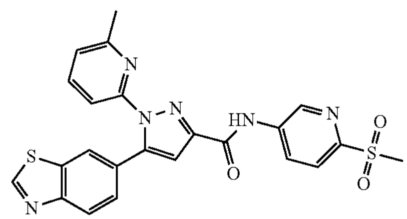 [SMILES: Cc1cccc(-n2nc(C(=O)Nc3ccc(S(C)(=O)=O)nc3)cc2-c2ccc3ncsc3c2)n1] | 5-(benzo[d]thiazol-6-yl)-N-(6-(methylsulfonyl)pyridin-3-yl)-1-(6-methylpyridin-2-yl)-1H-pyrazole-3-carboxamide | 9.16(s, 1H), 9.06(s, 1H), 8.92(s, 1H), 8.60(d, 1H), 8.12-8.05(m, 2H), 7.98(s, 1H), 7.67(t, 1H), 7.34(d, 1H), 7.23-7.16(m, 3H), 3.22(s, 3H), 2.46(s, 3H) | 491.1/490.1 |
| 70 | 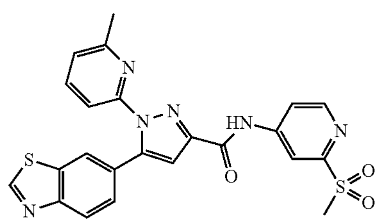 [SMILES: Cc1cccc(-n2nc(C(=O)Nc3ccnc(S(C)(=O)=O)c3)cc2-c2ccc3ncsc3c2)n1] | 5-(benzo[d]thiazol-6-yl)-1-(6-methylpyridin-2-yl)-N-(2-(methylsulfonyl)pyridin-4-yl)-1H-pyrazole-3-carboxamide | 9.30(s, 1H), 9.06(s, 1H), 8.66(d, 1H), 8.22(d, 1H), 8.17(d, 1H), 8.06(d, 1H), 7.98(d, 1H), 7.70(t, 1H), 7.35(d, 1H), 7.24-7.20(m, 3H), 3.24(s, 3H), 2.43(s, 3H) | 491.1/490.1 |
| 71 | 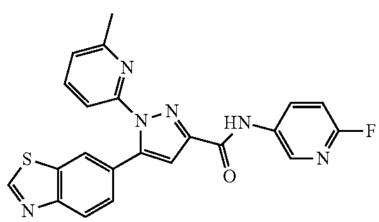 [SMILES: Cc1cccc(-n2nc(C(=O)Nc3ccc(F)nc3)cc2-c2ccc3ncsc3c2)n1] | 5-(benzo[d]thiazol-6-yl)-N-(6-fluoropyridin-3-yl)-1-(6-methylpyridin-2-yl)-1H-pyrazole-3-carboxamide | (300 MHz, DMSO-d₆)δ 10.67(s, 1H), 9.45(s, 1H), 8.67(d, 1H), 8.38(t, 1H), 8.27(d, 1H), 8.03(d, 1H), 7.93(t, 1H), 7.57(d, 1H), 7.37-7.32(m, 2H), 7.26-7.20(m, 2H), 2.25(s, 3H) | 431.1/430.1 |
| 72 | 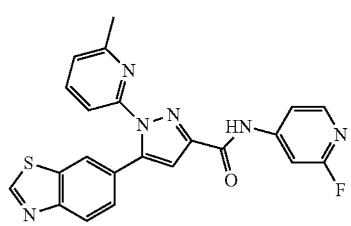 [SMILES: Cc1cccc(-n2nc(C(=O)Nc3ccnc(F)c3)cc2-c2ccc3ncsc3c2)n1] | 5-(benzo[d]thiazol-6-yl)-N-(2-fluoropyridin-4-yl)-1-(6-methylpyridin-2-yl)-1H-pyrazole-3-carboxamide | 9.15(s, 1H), 9.06(s, 1H), 8.16(d, 1H), 8.07(d, 1H), 7.98(d, 1H), 7.67(t, 1H), 7.52(d, 1H), 7.34(d, 1H), 7.30(d, 1H), 7.23-7.16(m, 3H), 2.46(s, 3H) | 431.1/430.1 |
| 73 | 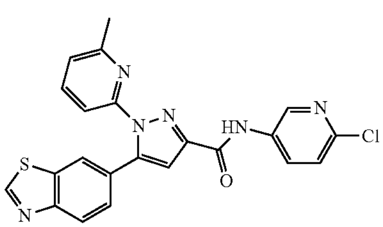 [SMILES: Cc1cccc(-n2nc(C(=O)Nc3ccc(Cl)nc3)cc2-c2ccc3ncsc3c2)n1] | 5-(benzo[d]thiazol-6-yl)-N-(6-chloropyridin-3-yl)-1-(6-methylpyridin-2-yl)-1H-pyrazole-3-carboxamide | 9.05(s, 1H), 8.92(s, 1H), 8.58(d, 1H), 8.36(dd, 1H), 8.06(d, 1H), 7.98(d, 1H), 7.67(t, 1H), 7.35(d, 2H), 7.22-7.19(m, 3H), 2.44(s, 3H) | 447.1/446.1 |

TABLE 1-continued

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 74 | 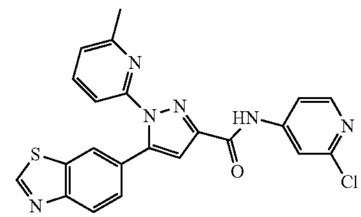 [SMILES: Cc1cccc(-n2nc(C(=O)Nc3ccnc(Cl)c3)cc2-c2ccc3ncsc3c2)n1] | 5-(benzo[d]thiazol-6-yl)-N-(2-chloropyridin-4-yl)-1-(6-methylpyridin-2-yl)-1H-pyrazole-3-carboxyamide | 9.09(s, 1H), 9.06(s, 1H), 8.31(d, 1H), 8.06(d, 1H), 7.98(d, 1H), 7.83(d, 1H), 7.67(t, 1H), 7.56(dd, 1H), 7.34(d, 1H), 7.23-7.16(m, 3H), 2.46(s, 3H) | 447.1/446.1 |
| 75 | 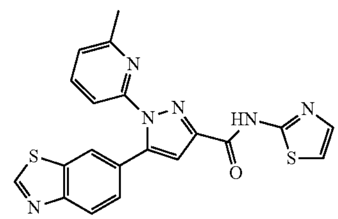 [SMILES: Cc1cccc(-n2nc(C(=O)Nc3nccs3)cc2-c2ccc3ncsc3c2)n1] | 5-(benzo[d]thiazol-6-yl)-1-(6-methylpyridin-2-yl)-N-(thiazol-2-yl)-1H-pyrazole-3-carboxyamide | 10.28(s, 1H), 9.05(s, 1H), 8.06(d, 1H), 8.00(d, 1H), 7.71(t, 1H), 7.51(d, 1H), 7.35(t, 2H), 7.21(s, 1H), 7.20(d, 1H), 7.03(d, 1H), 2.34(s, 3H) | 419.1/418.1 |
| 76 | 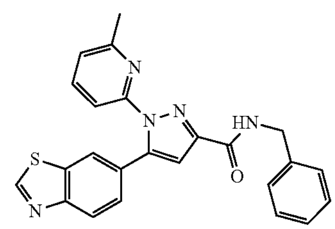 [SMILES: Cc1cccc(-n2nc(C(=O)NCc3ccccc3)cc2-c2ccc3ncsc3c2)n1] | 5-(benzo[d]thiazol-6-yl)-N-benzyl-1-(6-methylpyridin-2-yl)-1H-pyrazole-3-carboxyamide | 9.03(s, 1H), 8.04(d, 1H), 7.95(d, 1H), 7.61(t, 1H), 7.40-7.30(m, 7H), 4.67(d, 3H), 2.38(s, 3H) | 426.1/425.1 |
| 77 | 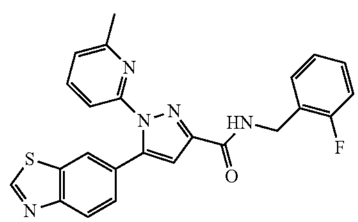 [SMILES: Cc1cccc(-n2nc(C(=O)NCc3ccccc3F)cc2-c2ccc3ncsc3c2)n1] | 5-(benzo[d]thiazol-6-yl)-N-(2-fluorobenzyl)-1-(6-methylpyridin-2-yl)-1H-pyrazole-3-carboxyamide | 9.03(s, 1H), 8.03(d, 1H), 7.95(d, 1H), 7.63(t, 1H), 7.48-7.44(m, 2H), 7.34(dd, 1H), 7.20-7.09(m, 5H), 4.72(d, 2H), 2.38(s, 3H) | 444.2/443.1 |
| 78 | 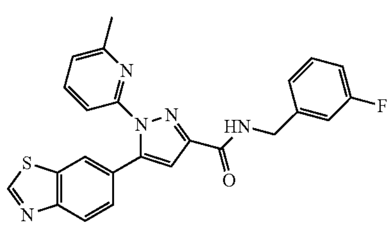 [SMILES: Cc1cccc(-n2nc(C(=O)NCc3cccc(F)c3)cc2-c2ccc3ncsc3c2)n1] | 5-(benzo[d]thiazol-6-yl)-N-(3-fluorobenzyl)-1-(6-methylpyridin-2-yl)-1H-pyrazole-3-carboxyamide | 9.04(s, 1H), 8.04(d, 1H), 7.96(d, 1H), 7.62(t, 1H), 7.45(t, 1H), 7.35-7.30(m, 2H), 7.19-7.13(m, 5H), 6.97(t, 1H), 4.66(d, 2H), 2.39(s, 3H) | 444.1/443.1 |
| 79 | 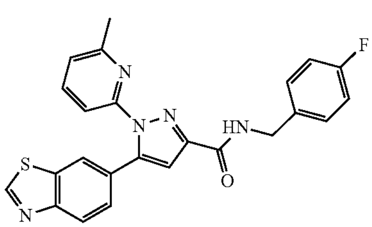 [SMILES: Cc1cccc(-n2nc(C(=O)NCc3ccc(F)cc3)cc2-c2ccc3ncsc3c2)n1] | 5-(benzo[d]thiazol-6-yl)-N-(4-fluorobenzyl)-1-(6-methylpyridin-2-yl)-1H-pyrazole-3-carboxyamide | 9.04(s, 1H), 8.04(d, 1H), 7.95(d, 1H), 7.61(t, 1H), 7.38-7.31(m, 4H), 7.17-7.13(m, 3H), 7.03(t, 2H), 4.63(d, 2H), 2.39(s, 3H) | 444.1/443.1 |

TABLE 1-continued

| Example Number | Structure | Compound Name | ¹H NMR Spectrum (300 MHz, CDCl₃) δ | MS (ES) Actual Measurement Value [M + H]⁺/ Required Value |
|---|---|---|---|---|
| 80 | 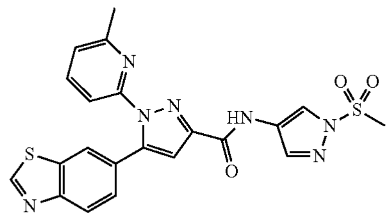 [SMILES: Cc1cccc(-n2nc(C(=O)Nc3cnn(S(C)(=O)=O)c3)cc2-c2ccc3ncsc3c2)n1] | 5-(benzo[d]thiazol-6-yl)-1-(6-methylpyridin-2-yl)-N-(1-(methylsulfonyl)-1H-pyrazol-4-yl)-1H-pyrazole-3-carboxyamide | 9.06(s, 1H), 8.90(s, 1H), 8.61(s, 1H), 8.06(d, 1H), 7.99-7.97(m, 2H), 7.66(t, 1H), 7.35(d, 1H), 7.21-7.14(m, 3H), 3.49(s, 3H), 2.46(s, 3H) | 480.1/479.1 |
| 81 | 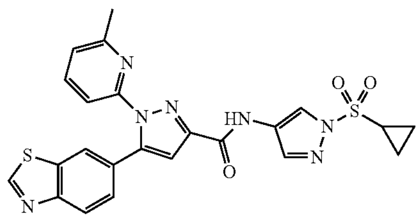 [SMILES: Cc1cccc(-n2nc(C(=O)Nc3cnn(S(=O)(=O)C4CC4)c3)cc2-c2ccc3ncsc3c2)n1] | 5-(benzo[d]thiazol-6-yl)-N-(1-(cyclopropylsulfonyl)-1H-pyrazol-4-yl)-1-(6-methylpyridin-2-yl)-1H-pyrazole-3-carboxyamide | 9.05(s, 1H), 8.85(s, 1H), 8.58(s, 1H), 8.06(d, 1H), 7.97(m, 2H), 7.66(t, 1H), 7.36-7.33(m, 1H), 7.21-7.16(m, 3H), 2.79-2.74(m, 1H), 2.45(s, 3H), 1.54-1.49(m, 2H), 1.23-1.16(m, 2H) | 506.1/505.1 |

[Example 82] 5-(Benzo[d]thiazol-6-yl)-N-(3-hydroxyphenyl)-1-(6-methylpyridin-2-yl)-1H-pyrazole-3-carboxyamide

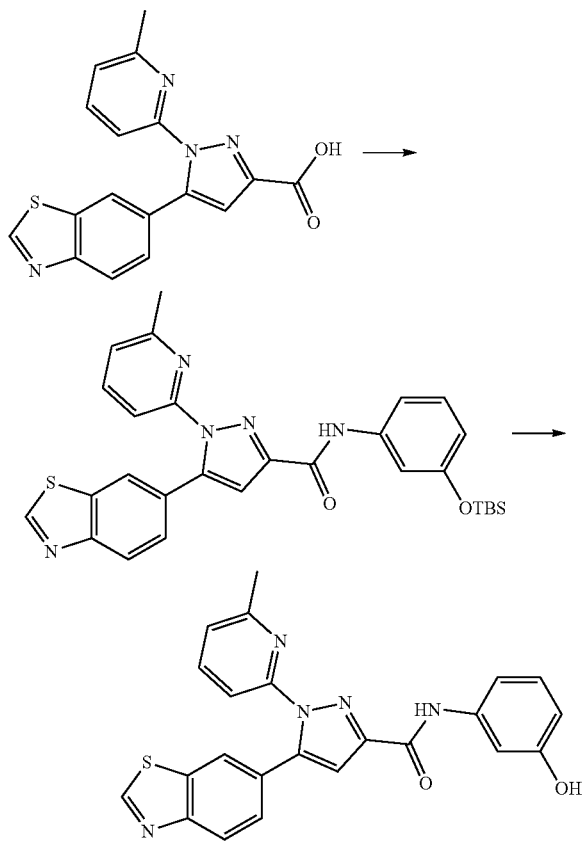

Step 1. 5-(Benzo[d]thiazol-6-yl)-N-(3-((tert-butyldimethylsilyl)oxy)phenyl)-1-(6-methylpyridin-2-yl)-1H-pyrazole-3-carboxyamide A target compound (140 mg) was obtained in the same manner as in Example 1 except that 3-((tert-butyldimethylsilyl)oxy)aniline was used instead of p-anisidine.

¹H NMR spectrum (300 MHz, CDCl₃) δ 9.04 (s, 1H), 8.79 (s, 1H), 8.05 (d, 1H), 7.97 (d, 1H), 7.66 (t, 1H), 7.40 (d, 1H), 7.34 (d, 1H), 7.26-7.17 (m, 5H), 6.64-6.61 (m, 1H), 2.43 (s, 3H), 1.01 (s, 9H), 0.25 (S, 6H).

Step 2. 5-(Benzo[d]thiazol-6-yl)-N-(3-hydroxyphenyl)-1-(6-methylpyridin-2-yl)-1H-pyrazole-3-carboxyamide After dissolving 5-(benzo[d]thiazol-6-yl)-N-(3-((tert-butyldimethylsilyl)oxy)phenyl)-1-(6-methylpyridin-2-yl)-1H-pyrazole-3-carboxyamide (140 mg, 0.26 mmol) synthesized in Step 1 in tetrahydrofuran (2.5 mL), 1.0 M TBAF (0.78 mL, 0.78 mmol) was added dropwise thereto at room temperature, and the reaction solution was stirred for 1 hour. The reaction solution was removed under vacuum, and then ethyl acetate was added thereto. The organic layer was washed with sodium bicarbonate, and then dried using anhydrous magnesium sulfate, and after filtering, the filtrate was vacuum concentrated. The filtrate was purified using column chromatography to obtain a target compound (23 mg).

¹H NMR spectrum (300 MHz, CDCl₃) δ 9.06 (s, 1H), 8.93 (s, 1H), 8.05 (d, 1H), 8.00 (d, 2H), 7.67 (t, 1H), 7.38-7.18 (m, 5H), 6.90 (d, 1H), 6.68 (d, 1H), 2.44 (s, 3H). MS (ESI⁺): [M+H]⁺ m/z 428.1

Examples 83 to 85

Compounds of Examples 83 to 85 listed in the following [Table 2] were obtained in the same manner as in Step 2) of Example 82.

TABLE 2

| Example Number | Structure | Compound Name | ¹H NMR Spectrum (300 MHz, CDCl₃)δ | MS (ES) Actual Measurement Value [M + H]⁺/ Required Value |
|---|---|---|---|---|
| 83 | 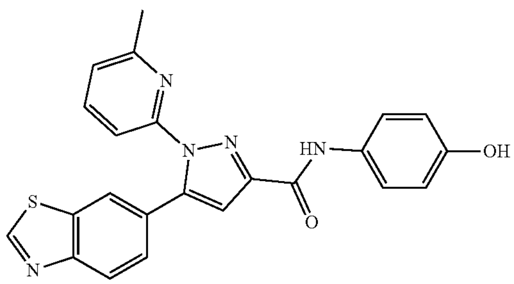 [SMILES: Cc1cccc(-n2nc(C(=O)Nc3ccc(O)cc3)cc2-c2ccc3ncsc3c2)n1] | 5-(benzo[d]thiazol-6-yl)-N-(4-hydroxyphenyl)-1-(6-methylpyridin-2-yl)-1H-pyrazole-3-carboxamide | 9.04(s, 1H), 8.71(s, 1H), 8.05(d, 1H), 7.98(d, 1H), 7.66(t, 1H), 7.57(d, 2H), 7.37(d, 1H), 7.19(t, 3H), 6.85(d, 2H), 4.93(s, 1H), 2.44(s, 3H) | 428.1/427.1 |
| 84 | 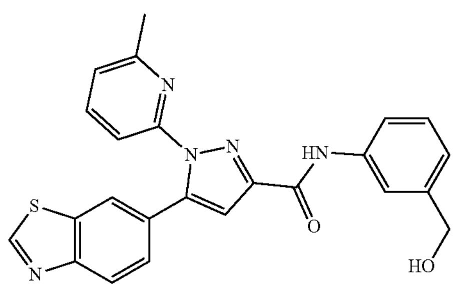 [SMILES: Cc1cccc(-n2nc(C(=O)Nc3cccc(CO)c3)cc2-c2ccc3ncsc3c2)n1] | 5-(benzo[d]thiazol-6-yl)-N-(3-(hydroxymethyl)phenyl)-1-(6-methylpyridin-2-yl)-1H-pyrazole-3-carboxamide | 9.05(s, 1H), 8.89(s, 1H), 8.05(d, 1H), 7.99(d, 1H), 7.77(s, 1H), 7.67(t, 2H), 7.37(t, 2H), 7.26-7.14(m, 4H), 7.43(d, 2H), 2.43(s, 3H), 1.80(s, 1H) | 442.1/441.1 |
| 85 | 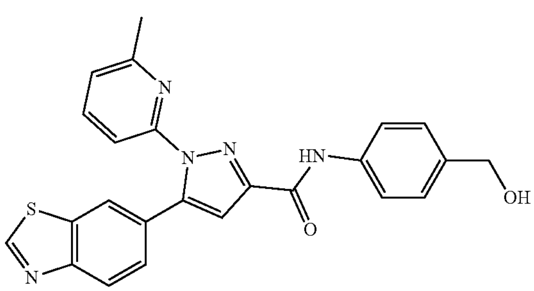 [SMILES: Cc1cccc(-n2nc(C(=O)Nc3ccc(CO)cc3)cc2-c2ccc3ncsc3c2)n1] | 5-(benzo[d]thiazol-6-yl)-N-(4-(hydroxymethyl)phenyl)-1-(6-methylpyridin-2-yl)-1H-pyrazole-3-carboxamide | 9.05(s, 1H), 8.88(s, 1H), 8.05(d, 1H), 7.98(d, 1H), 7.73(d, 2H), 7.67(t, 1H), 7.36(td, 3H), 7.20(t, 3H), 4.69(d, 2H), 2.44(s, 3H) | 442.1/441.1 |

[Example 86] N-(4-Aminophenyl)-5-(benzo[d]thiazol-6-yyl)-1-(6-methylpyridin-2-yl)-1H-pyrazole-3-carboxyamide After dissolving 5-(benzo[d]thiazol-6-yl)-1-(6-methylpyridin-2-yl)-N-(4-nitrophenyl)-1H-pyrazole-3-carboxyamide (65 mg, 0.14 mmol) synthesized in Example 14 in ethanol (1.5 mL) and dichloromethane (3 mL), 20% PdOH/C (20 mg, 30% w/w) was added thereto at room temperature, and the reaction solution was stirred for 13 hours under hydrogen gas. The reaction solution was vacuum filtered through celite, and the solvent was vacuum concentrated. The result was purified using column chromatography to obtain a target compound (20 mg).

$^1$H NMR spectrum (300 MHz, CDCl$_3$) δ 9.09 (s, 1H), 8.05 (d, 1H), 8.00 (d, 1H), 7.63 (t, 1H), 7.52 (d, 2H), 7.36 (d, 1H), 7.21 (d, 1H), 7.18 (s, 1H), 7.05 (d, 1H), 6.74 (d, 2H), 3.38 (s, 2H), 2.51 (s, 3H).

MS (ESI$^+$): [M+H]$^+$ m/z 427.1

[Example 87] 5-(Benzo[d]thiazol-6-yl)-N-(4-(butylamino)phenyl)-1-(6-methylpyridin-2-yl)-1H-pyrazole-3-carboxyamide

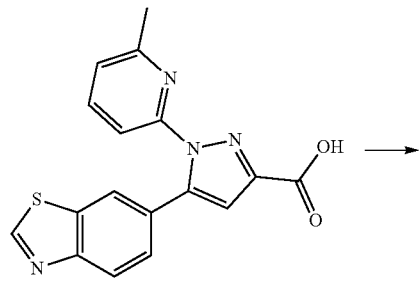

→

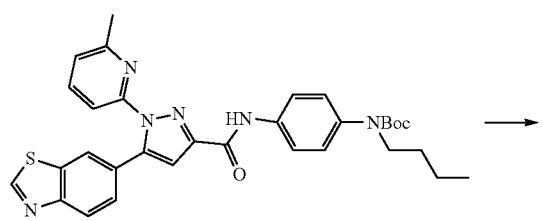

→

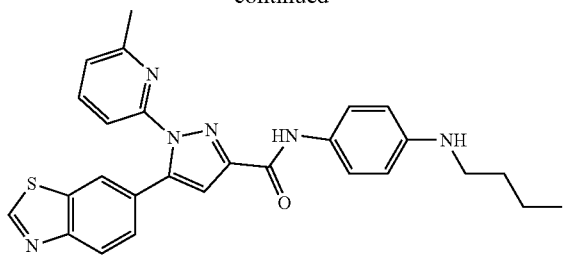

Step 1. Tert-butyl(4-(5-(benzo[d]thiazol-6-yl))-1-(6-methylpyridin-2-yl)-1H-pyrazole-3-carboxyamido)phenyl)(butyl)-carbamate A target compound (110 mg) was obtained in the same manner as in Example 1 except that tert-butyl(4-aminophenyl)(butyl)carbamate was used instead of p-anisidine.

$^1$H NMR spectrum (300 MHz, CDCl$_3$) δ 9.05 (s, 1H), 8.85 (s, 1H), 8.05 (d, 1H), 7.98 (d, 1H), 7.71-7.64 (m, 3H), 7.36 (d, 1H), 7.20 (td, 5H), 3.61 (t, 2H), 2.44 (s, 3H), 1.56-1.50 (m, 2H), 1.43 (s, 9H), 1.37-1.25 (m, 2H), 0.90 (t, 3H).

Step 2. 5-(Benzo[d]thiazol-6-yl)-N-(4-(butylamino)phenyl)-1-(6-methylpyridin-2-yl)-1H-pyrazole-3-carboxyamide After dissolving tert-butyl(4-(5-(benzo[d]thiazol-6-yl))-1-(6-methylpyridin-2-yl)-1H-pyrazole-3-carboxyamido)phenyl)(butyl)-carbamate (110 mg, 0.19 mmol) synthesized in Step 1 in dichloromethane (1.5 mL), a 4.0 M hydrochloric acid 1,4-dioxane solution (0.28 mL, 1.13 mmol) was added dropwise thereto at room temperature, and the reaction solution was stirred for 13 hours at room temperature. After adding dichloromethane to the reaction solution, the organic layer was washed with sodium bicarbonate, dried using anhydrous magnesium sulfate, and after filtering, the filtrate was vacuum concentrated. The filtrate was purified using column chromatography to obtain a target compound (70 mg).

$^1$H NMR spectrum (300 MHz, CDCl$_3$) δ 9.05 (s, 1H), 8.67 (s, 1H), 8.06 (d, 1H), 7.99 (d, 1H), 7.67 (t, 1H), 7.53 (d, 2H), 7.36 (d, 1H), 7.20 (t, 3H), 6.64 (d, 2H), 3.13 (t, 2H), 2.44 (s, 3H), 1.65-1.51 (m, 2H), 1.51-1.41 (m, 2H), 0.98 (t, 3H).

MS (ESI$^+$): [M+H]$^+$ m/z 483.2

Example 88

A compound of Example 88 listed in the following [Table 3] was obtained in the same manner as in Step 2) of Example 87.

TABLE 3

| Example Number | Structure | Compound Name | ¹H NMR Spectrum (300 MHz, CDCl$_3$)δ | MS (ES) Actual Measurement Value[M + H]$^+$/ Required Value |
|---|---|---|---|---|
| 88 | 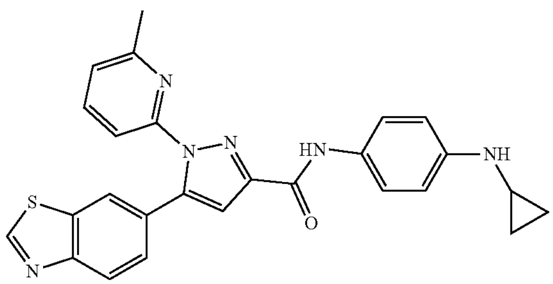 [SMILES: Cc1cccc(-n2nc(C(=O)Nc3ccc(NC4CC4)cc3)cc2-c2ccc3ncsc3c2)n1] | 5-(benzo[d]thiazol-6-yl)-N-(4-(cyclopropylamino)phenyl)-1-(6-methylpyridin-2-yl)-1H-pyrazole-3-carboxyamide | 9.04(s, 1H), 8.67(s, 1H), 8.05(d, 1H), 7.98(d, 1H), 7.66(t, 1H), 7.53(d, 2H), 7.37(d, 1H), 7.36(t, 3H), 6.80(d, 2H), 2.46-2.43 (m, 4H), 0.75-0.70 (m, 2H), 0.54-0.51(m, 2H) | 467.2/466.2 |

[Example 89] 5-(Benzo[d]thiazol-6-yl)-1-(6-methylpyridin-2-yl)-N-(4-(S-methylsulfonimidoyl)phenyl)-1H-pyrazole-3-carboxyamide Step 1. Ethyl-((4-(5-(benzo[d]thiazol-6-yl))-1-(6-methylpyridin-2-yl)-1H-pyrazole-3-carboxyamido)phenyl)(methyl)(oxo)-λ$^6$-sulfanylidine)carbamate A target compound (50 mg) was obtained in the same manner as in Example 1 except that ethyl ((4-aminophenyl)(methyl)(oxo)-λ$^6$-sulfanylidine)carbamate was used instead of p-anisidine.

¹H NMR spectrum (300 MHz, CDCl$_3$) δ 9.16 (s, 1H), 9.06 (s, 1H), 8.06 (d, 1H), 8.00-7.98 (m, 5H), 7.67 (t, 1H), 7.35 (d, 1H), 7.23-7.17 (m, 3H), 4.15-4.07 (m, 2H), 3.33 (s, 3H), 2.46 (s, 3H), 1.24 (t, 3H).

Step 2. 5-(Benzo[d]thiazol-6-yl)-1-(6-methylpyridin-2-yl)-N-(4-(S-methylsulfonimidoyl)phenyl)-1H-pyrazole-3-carboxamide After dissolving ethyl-((4-(5-(benzo[d]thiazol-6-yl))-1-(6-methylpyridin-2-yl)-1H-pyrazole-3-carboxyamido)phenyl)(methyl)(oxo)-λ$^6$-sulfanylidine)carbamate (50 mg, 0.09 mmol) synthesized in Step 1 in ethanol (1.0 mL), a 1.5 M sodium ethoxide ethanol solution (0.30 mL, 0.45 mmol) was added dropwise thereto at room temperature, and the reaction solution was stirred for 5 hours at 60□. After adding saline to the reaction solution, the result was extracted using a mixed solution of dichloromethane and methanol. The organic layer was dried using anhydrous magnesium sulfate, and after filtering, the filtrate was vacuum concentrated. The filtrate was purified using column chromatography to obtain a target compound (10 mg).

¹H NMR spectrum (300 MHz, CDCl$_3$) δ 9.16 (s, 1H), 9.06 (s, 1H), 8.08-7.92 (m, 6H), 7.67 (t, 1H), 7.35 (d, 1H), 7.23-7.15 (m, 3H), 3.13 (t, 2H), 2.47 (s, 3H).

MS (ESI$^+$): [M+H]$^+$ m/z 489.1

[Example 90] Preparation of 5-([1,2,4]triazolo[1,5-α]pyridin-6-yl)-N-(2-methoxyphenyl)-1-(6-methylpyridin-2-yl)-1H-pyrazole-3-carboxyamide Step 1. Preparation of 5-([1,2,4]triazolo[1,5-α]pyridin-6-yl)-N-(4-methoxyphenyl)-1-(6-methylpyridin-2-yl)-1H-pyrazole-3-carboxyamide -continued

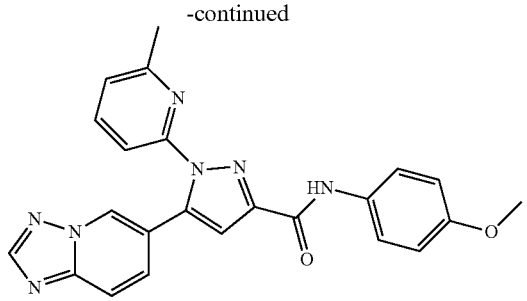

After dissolving 5-([1,2,4]triazolo[1,5-α]pyridin-6-yl)-1-(6-methylpyridin-2-yl)-1H-pyrazole-3-carboxylic acid (30 mg, 0.09 mmol) synthesized in Step 4) of Preparation Example 2 in N,N-dimethylformamide (1 mL), HATU (42 mg, 0.11 mmol) and DIPEA (34 μL, 0.28 mmol) were introduced thereto, and the result was stirred for 30 minutes at room temperature. To the reaction solution, p-anisidine (11 μL, 0.09 mmol) was introduced, and the result was stirred for 12 hours at room temperature. The result was extracted with ethyl acetate, and the obtained organic layer was dried using anhydrous magnesium sulfate and then filtered. The filtrate was concentrated and purified using column chromatography to obtain a target compound (20 mg, 50%).

$^1$H NMR (300 MHz, DMSO-$d_6$) δ 10.17 (s, 1H), 9.18 (s, 1H), 8.56 (s, 1H), 7.96 (m, 1H), 7.83-7.72 (m, 3H), 7.54 (m, 1H), 7.32 (br, 2H), 6.96 (d, 2H), 3.76 (s, 3H), 2.17 (s, 3H).
MS (ESI$^+$): m/z 426 [M+H]$^+$.

Examples 91 to 163

Compounds of Examples 91 to 163 listed in the following [Table 4] were obtained in the same manner as in Step 1) of Example 1 using various amine derivatives instead of p-anisidine.

TABLE 4

| Example | Structural Formula | Compound Name | Analysis Data |
|---|---|---|---|
| 91 | | 5-([1,2,4]triazolo[1,5-α]pyridin-6-yl)-N-(3-methoxyphenyl)-1-(6-methylpyridin-2-yl)-1H-pyrazole-3-carboxyamide | $^1$H NMR (300 MHz, CDCl$_3$) δ 8.79 (brs, 1H), 8.72 (s, 1H), 8.38 (s, 1H), 7.76-7.69 (m, 2H), 7.57-7.47 (m, 3H), 7.27-7.15 (m, 4H), 6.72 (d, J = 8.1 Hz, 1H), 3.84 (s, 3H), 2.31 (s, 3H), MS (ESI$^+$): m/z 426 [M + H]$^+$. |
| 92 | | 5-([1,2,4]triazolo[1,5-α]pyridin-6-yl)-N-(2-methoxyphenyl)-1-(6-methylpyridin-2-yl)-1H-pyrazole-3-carboxyamide | $^1$H NMR (300 MHz, CDCl$_3$) δ 9.42 (brs, JH), 8.73 (s, 1H), 8.54 (d, J = 7.8 Hz, 1H), 8.39 (s, 1H), 7.80-7.64 (m, 3H), 7.49 (d, J = 9.0 Hz, 1H), 7.19 (s, 1H), 7.15-7.02 (m, 3H), 6.94 (d, J = 7.8 Hz, 1H), 3.95 (s, 3H), 2.26 (s, 3H). MS (ESI$^+$): m/z 426 [M + H]$^+$. |
| 93 | | 5-([1,2,4]triazolo[1,5-α]pyridin-6-yl)-N-(4-hydroxyphenyl)-1-(6-methylpyridin-2-yl)-1H-pyrazole-3-carboxyamide | $^1$H NMR (300 MHz, DMSO-$d_6$) δ 10.0(s, 1H), 9.28(s, 1H), 9.18(s, 1H), 8.56 (s, 1H), 7.98-7.93(m, 1H), 7.79(m, 2H), 7.61-7.51(m, 3H), 7.32(d, 1H), 7.29(d, 1H), 6.77(d, 2H), 2.27(s, 3H). MS (ESI$^+$): m/z 412 [M + H]$^+$. |

TABLE 4-continued

| Example | Structural Formula | Compound Name | Analysis Data |
|---|---|---|---|
| 94 | | 5-([1,2,4]triazolo[1,5-α]pyridin-6-yl)-N-(4-isopropylphenyl)-1-(6-methylpyridin-2-yl)-1H-pyrazole-3-carboxyamide | $^1$H NMR (300 MHz, CDCl$_3$) δ 8.71 (brs, 1H), 8.37 (s, 1H), 7.74-7.68 (m, 2H), 7.61-7.53 (m, 3H), 7.46 (d, J = 9.3 Hz, 1H), 7.18-7.13 (m, 2H), 6.90 (d, J = 8.1 Hz, 2H), 4.52 (q, J = 6.0 Hz, 1H), 2.29 (s, 3H), 1.33 (d, J = 6.0 Hz, 6H). MS (ESI$^+$): m/z 454 [M + H]$^+$. |
| 95 | | 5-([1,2,4]triazolo[1,5-α]pyridin-6-yl)-N-(4-(2-methoxyethoxy)phenyl)-1-(6-methylpyridin-2-yl)-1H-pyrazole-3-carboxyamide | $^1$H NMR (300 MHz, CDCl$_3$) δ 8.71 (brs, 1H), 8.37 (s, 1H), 7.74-7.68 (m, 2H), 7.62 (d, J = 9.0 Hz, 2H), 7.55 (d, J = 8.4 Hz, 1H), 7.46 (d, J = 9.3 Hz, 1H), 7.18-7.13 (m, 2H), 6.96 (d, J = 9.0 Hz, 2H), 4.12 (t, J = 4.8 Hz, 2H), 3.75 (t, J = 4.8 Hz, 2H), 3.45 (s, 3H), 2.29 (s, 3H). MS (ESI$^+$): m/z 454 [M + H]$^+$. |
| 96 | | 5-([1,2,4]triazolo[1,5-α]pyridin-6-yl)-N-(benzo[d][1,3]dioxol-5-yl)-1-(6-methylpyridin-2-yl)-1H-pyrazole-3-carboxyamide | $^1$H NMR (300 MHz, CDCl$_3$) δ 8.72 (brs, 1H), 8.39 (s, 1H), 7.76-7.69 (m, 2H), 7.56-7.44 (m, 3H), 7.19-7.15 (m, 2H), 7.00 (d, J = 8.1 Hz, 1H), 6.81 (d, J = 7.8 Hz, 1H), 5.98 (s, 2H), 2.31 (s, 3H). MS (ESI$^+$): m/z 440 [M + H]$^+$. |
| 97 | | 5-{[1,2,4]triazolo[1,5-α]pyridin-6-yl)-N-(2-fluoro-4-methoxyphenyl)-1-(6-methylpyridin-2-yl)-1H-pyrazole-3-carboxyamide | $^1$H NMR (300 MHz, CDCl$_3$) δ 8.86 (brs, 1H), 8.73 (m, 1H), 8.39 (s, 1H), 8.31 (t, 1H), 7.80-7.69 (m, 2H), 7.63 (d, 1H), 7.48 (d, 1H), 7.19 (s, 1H), 7.15 (d, 1H), 6.76-6.72 (m, 2H), 3.81 (s, 3H), 2.27 (s, 3H). MS (ESI$^+$): m/z 444.2 [M + H]$^+$ |
| 98 | | 5-([1,2,4]triazolo[1,5-α]pyridin-6-yl)-N-(3-fluoro-4-methoxyphenyl)-1-(6-methylpyridin-2-yl)-1H-pyrazole-3-carboxyamide | $^1$H NMR (300 MHz, CDCl$_3$) δ 8.72-8.70 (m, 2H), 8.39 (s, 1H), 7.76-7.70 (m, 2H), 7.63 (d, 1H), 7.54 (d, 1H), 7.46 (d, 1H), 7.34 (d, 1H), 7.20-7.16 (m, 2H), 6.97 (t, 1H), 3.90 (s, 3H), 2.32 (s, 3H). MS (ESI$^+$): m/z 444.2 [M + H]$^+$ |

TABLE 4-continued

| Example | Compound Name | Analysis Data |
|---|---|---|
| 99 | 5-([1,2,4]triazolo[1,5-α]pyridin-6-yl)-1-(6-methylpyridin-2-yl)-N-(2-(trifluoromethoxy)phenyl)-1H-pyrazole-3-carboxamide | $^1$H NMR (300 MHz, CDCl$_3$) δ 9.33 (s, 1H), 8.75 (m, 1H), 8.60 (d, 1H), 8.39 (s, 1H), 7.79-7.68 (m, 3H), 7.50 (d, 1H), 7.40-7.32 (m, 2H), 7.18 (s, 2H), 7.13 (d, 1H), 2.23 (s, 3H). MS (ESI$^+$): m/z 480.1 [M + H]$^+$ |
| 100 | 5-([1,2,4]triazolo[1,5-α]pyridin-6-yl)-1-(6-methylpyridin-2-yl)-N-(3-(trifluoromethoxy)phenyl)-1H-pyrazole-3-carboxamide | $^1$H NMR (300 MHz, CDCl$_3$) δ 8.86 (s, 1H), 8.73 (s, 1H), 8.39 (s, 1H), 7.80-7.70 (m, 3H), 7.62 (d, 1H), 7.55 (d, 1H), 7.46 (d, 1H), 7.39 (t, 1H), 7.21 (s, 1H), 7.18 (d, 1H), 7.03 (d, 1H), 2.32 (s, 3H). MS (ESI$^+$): m/z 480.1 [M + H]$^+$ |
| 101 | 5-([1,2,4]triazolo[1,5-α]pyridin-6-yl)-1-(6-methylpyridin-2-yl)-N-(4-(trifluoromethoxy)phenyl)-1H-pyrazole-3-carboxamide | $^1$H NMR (300 MHz, CDCl$_3$) δ 8.86 (s, 1H), 8.73 (m, 1H), 8.39 (s, 1H), 7.80-7.70 (m, 4H), 7.54 (d, 1H), 7.46 (d, 1H), 7.23-7.17 (m, 4H), 2.32 (s, 3H), MS (ESI$^+$): m/z 480.1 [M + H]$^+$ |
| 102 | 5-([1,2,4]triazolo[1,5-α]pyridin-6-yl)-N-(3-(dimethylamino)phenyl)-1-(6-methylpyridin-2-yl)-1H-pyrazole-3-carboxamide | $^1$H NMR (300 MHz, CDCl$_3$) δ 8.74 (s, 1H), 8.72 (m, 1H), 8.39 (s, 1H), 7.76-7.69 (m, 2H), 7.58 (d, 1H), 7.46 (d, 1H), 7.31-7.15 (m, 4H), 6.96 (d, 1H), 6.55 (d, 1H), 2.99 (s, 6H), 2.31 (s, 3H). MS (ESI$^+$): m/z 439.2 [M + H]$^+$ |
| 103 | 5-([1,2,4]triazolo[1,5-α]pyridin-6-yl)-N-(4-aminophenyl)-1-(6-methylpyridin-2-yl)-1H-pyrazole-3-carboxamide | $^1$H NMR (300 MHz, DMSO-d$_6$) δ 9.91(s, 1H), 9.18(s, 1H), 8.56 (s, 1H), 7.97(t, 1H), 7.82-7.79 (m, 2H), 7.54(d, 1H), 7.45(d, 2H), 7.31(d, 1H), 7.24(s, 1H), 6.54(d, 2H), 4.95(br, —NH$_2$), 2.16(s, 3H) MS (ESI$^+$): m/z 411 [M + H]$^+$. |

TABLE 4-continued

| Example | Structural Formula | Compound Name | Analysis Data |
|---|---|---|---|
| 104 | | 5-([1,2,4]triazolo[1,5-α]pyridin-6-yl)-N-(4-(dimethylamino)phenyl)-1-(6-methylpyridin-2-yl)-1H-pyrazole-3-carboxamide | $^1$H NMR (300 MHz, DMSO-d$_6$) δ 9.99(s, 1H), 9.17(s, 1H), 8.55 (s, 1H), 7.95(m, 1H), 7.95-7.93 (m, 2H), 7.78(d, 2H), 7.53(d, 1H), 7.30-7.25(m, 2H), 6.72 (d, 2H), 2.87(s, 6H), 2.16(s, 3H). MS (ESI$^+$): m/z 439 [M + H]$^+$. |
| 105 | | 5-([1,2,4]triazolo[1,5-α]pyridin-6-yl)-N-(4-(pyrrolidin-1-yl)phenyl)-1-(6-methylpyridin-2-yl)-1H-pyrazole-3-carboxamide | $^1$H NMR (300 MHz, CDCl$_3$) δ 8.72 (s, 1H), 8.60 (s, 1H), 8.38 (s, 1H), 7.75-7.69 (m, 2H), 7.58-7.53 (m, 3H), 7.47 (d, 1H), 7.19 (s, 1H), 7.15 (d, 1H), 6.57 (d, 2H), 3.32-3.27(m, 4H), 2.30 (s, 3H), 2.03-1.99 (m, 4H). MS (ESI$^+$): m/z 465.2 [M + H]$^+$ |
| 106 | | 5-([1,2,4]triazolo(1,5-α]pyridin-6-yl)-N-(4-((2-(dimethylamino)ethyl)(methyl)amino)phenyl)-1-(6-methylpyridin-2-yl)-1H-pyrazole-3-carboxamide | $^1$H NMR (300 MHz, CDCl$_3$) δ 8.71 (brs, 1H), 8.64 (s, 1H), 7.78-7.69 (m, 2H), 7.57-7.55 (m, 3H), 7.46 (d, J = 9.3 Hz, 1H), 7.19-7.14 (m, 2H), 6.74 (d, J = 9.0 Hz, 2H), 3.51 (t, J = 7.5 Hz, 2H), 3.96 (s, 3H), 2.57 (t, J = 7.2 Hz, 2H), 2.36 (s, 6H), 2.30 (s, 3H). MS (ESI$^+$): m/z 496 [M + H]$^+$. |
| 107 | | 5-([1,2,4]triazolo[1,5-α]pyridin-6-yl)-N-(4-(4-methylpiperazin-1-yl)phenyl)-1-(6-methylpyridin-2-yl)-1H-pyrazole-3-carboxamide | $^1$H NMR (300 MHz, CDCl$_3$) δ 8.72 (s, 1H), 8.70 (s, 1H), 8.38 (s, 1H), 7.77-7.69 (m, 2H), 7.62-7.54 (m, 3H), 7.47 (d, 1H), 7.19-7.14 (m, 2H), 6.95 (d, 2H), 3.21 (m, 4H), 2.60 (m, 4H), 2.36 (s, 3H), 2.31 (s, 3H). MS (ESI$^+$): m/z 494.2 [M + H]$^+$ |
| 108 | | 5-([1,2,4]triazolo[1,5-α]pyridin-6-yl)-N-(4-(4-acetylpiperazin-1-yl)phenyl)-1-(6-methylpyridin-2-yl)-1H-pyrazole-3-carboxamide | $^1$H NMR (300 MHz, CDCl$_3$) δ 8.72 (s, 1H), 8.70 (s, 1H), 8.39 (s, 1H), 7.79-7.69 (m, 2H), 7.63 (d, 2H), 7.55 (d, 1H), 7.47 (d, 1H), 7.20-7.15 (m, 2H), 6.95 (d, 2H), 3.80-3.77 (m, 2H), 3.65-3.62 (m, 2H), 3.19-3.12 (m, 4H), 2.31 (s, 3H), 2.15 (s, 3H). MS (ESI$^+$): m/z 522.2 [M + H]$^+$ |

TABLE 4-continued

| Example | Structural Formula | Compound Name | Analysis Data |
|---|---|---|---|
| 109 | | 5-([1,2,4]triazolo[1,5-α]pyridin-6-yl)-N-(4-((1,1-dioxidotetrahydrothiophen-3-yl)amino)phenyl)-1-(6-methylpyridin-2-yl)-1H-pyrazole-3-carboxamide | $^1$H NMR (300 MHz, CDCl$_3$) δ 8.72 (brs, 1H), 8.66 (s, 1H), 8.39 (s, 1H), 7.79-7.69 (m, 2H), 7.58-7.54 (m, 3H), 7.46 (d, J = 9.0 Hz, 1H), 7.19-7.15 (m, 2H), 6.66 (d, J = 9.0 Hz, 2H), 4.41-4.36 (m, 1H), 4.01-3.98 (m, 1H), 3.76-3.69 (m, 1H), 3.30-3.28 (m, 1H), 3.04-3.00 (m, 1H), 2.70-2.50 (m, 1H), 2.36-2.31 (m, 1H), 2.31 (s, 3H). MS (ESI$^+$): m/z 496 [M+H]+. |
| 110 | | 5-([1,2,4]triazolo[1,5-α]pyridin-6-yl)-N-(4-acetamidophenyl)-1-(6-methylpyridin-2-yl)-1H-pyrazole-3-carboxamide | $^1$H NMR (300 MHz, DMSO-d$_6$) δ 10.22 (brs, 1H), 9.93 (s, 1H), 9.19 (s, 1H), 8.56 (s, 1H), 7.96 (d, J = 7.8 Hz, 1H), 7.84-7.73 (m, 4H), 7.57-7.50 (m, 3H), 7.32-7.29 (m, 2H), 2.17 (s, 3H), 2.03 (s, 3H). MS (ESI$^+$): m/z 453 [M + H]$^+$. |
| 111 | | 5-([1,2,4]triazolo[1,5-α]pyridin-6-yl)-N-(4-((dimethylamino)methyl)phenyl)-1-(6-methylpyridin-2-yl)-1H-pyrazole-3-carboxamide | $^1$H NMR (300 MHz, CDCl$_3$) δ 8.82 (s, 1H), 8.73 (s, 1H), 8.39 (s, 1H), 7.79-7.69 (m, 4H), 7.56 (d, 1H), 7.47 (d, 1H), 7.35 (d, 2H), 7.21 (s, 1H), 7.17 (d, 1H), 3.50 (s, 2H), 2.31 (s, 9H). MS (ESI$^+$): m/z 453.2 [M + H]$^+$ |
| 112 | | 5-([1,2,4]triazolo[1,5-α]pyridin-6-yl)-N-(2-(methylcarbamoyl)phenyl)-1-(6-methylpyridin-2-yl)-1H-pyrazole-3-carboxamide | $^1$H NMR (300 MHz, DMSO-d$_6$) δ 12.66 (brs, 1H), 9.21 (s, 1H), 8.77 (brs, 1H), 8.65 (d, J = 8.1 Hz, 1H), 8.57 (s, 1H), 8.01 (t, J = 8.1 Hz, 1H), 7.83-7.77 (m, 3H), 7.59-7.53 (m, 2H), 7.34-7.31 (m, 2H), 7.23-7.18 (m, 1H), 2.83 (s, 3H), 2.15 (s, 3H). MS (ESI$^+$): m/z 453 [M + H]$^+$. |
| 113 | | 5-([1,2,4]triazolo[1,5-α]pyridin-6-yl)-N-(4-(methylcarbamoyl)phenyl)-1-(6-methylpyridin-2-yl)-1H-pyrazole-3-carboxamide | $^1$H NMR (300 MHz, DMSO-d$_6$) δ 10.46 (brs, 1H), 9.18 (s, 1H), 8.55 (s, 1H), 8.35 (brs, 1H), 7.98-7.91 (m, 3H), 7.84-7.78 (m, 4H), 7.51 (d, J = 9.3 Hz, 1H), 7.32-7.29 (m, 2H), 2.77 (s, 3H), 2.16 (s, 3H). MS (ESI$^+$): m/z 453 [M + H]$^+$. |

TABLE 4-continued

| Example | Structural Formula | Compound Name | Analysis Data |
|---|---|---|---|
| 114 | | 5-([1,2,4]triazolo[1,5-α]pyridin-6-yl)-1-(6-methylpyridin-2-yl)-N-phenyl-1H-pyrazole-3-carboxyamide | $^1$H NMR (300 MHz, DMSO-d$_6$) δ 10.29(s, 1H), 9.20(s, 1H), 8.57(s, 1H), 7.95(t, 1H), 7.86-7.80(m, 4H), 7.54(d, 1H), 7.40-7.31(m, 4H), 7.12(t, 1H), 2.18(s, 3H). MS (ESI$^+$): m/z 396 [M + H]$^+$. |
| 115 | | 5-([1,2,4]triazolo[1,5-α]pyridin-6-yl)-1-(6-methylpyridin-2-yl)-N-(o-tolyl)-1H-pyrazole-3-carboxyamide | $^1$H NMR (300 MHz, CDCl$_3$) δ 8.77 (s, 1H), 8.73 (s, 1H), 8.48 (m, 1H), 8.39 (s, 1H), 8.14-8.11 (m, 3H), 7.77-7.70 (m, 2H), 7.61 (d, 1H), 7.56 (d, 1H), 7.23-7.14 (m, 2H), 2.40 (s, 3H), 2.27 (s, 3H), MS (ESI$^+$): m/z 410.2 [M + H]$^+$ |
| 116 | | 5-([1,2,4]triazolo[1,5-α]pyridin-6-yl)-1-(6-methylpyridin-2-yl)-N-(m-tolyl)-1H-pyrazole-3-carboxyamide | $^1$H NMR (300 MHz, CDCl$_3$) δ 8.74 (s, 1H), 8.73 (s, 1H), 8.39 (s, 1H), 7.76-7.69 (m, 2H), 7.59-7.45 (m, 4H), 7.29-7.25 (m, 1H), 7.20 (s, 1H), 7.16 (d, 1H), 6.99 (s, 1H), 2.39 (s, 3H), 2.30 (s, 3H). MS (ESI$^+$): m/z 10.2 [M + H]$^+$ |
| 117 | | 5-([1,2,4]triazolo[1,5-α]pyridin-6-yl)-1-(6-methylpyridin-2-yl)-N-(p-tolyl)-1H-pyrazole-3-carboxyamide | $^1$H NMR (300 MHz, CDCl$_3$) δ 8.72 (s, 2H), 8.38 (s, 1H), 7.78-7.69 (m, 2H), 7.61-7.55 (m, 3H), 7.46 (dd, 1H), 7.19-7.14 (m, 4H), 2.34 (s, 3H), 2.30 (s, 3H). MS (ESI$^+$): m/z 410.2 [M + H]$^+$ |
| 118 | | 5-([1,2,4]triazolo[1,5-α]pyridin-6-yl)-1-(6-methylpyridin-2-yl)-N-(3-(trifluoromethyl)phenyl)-1H-pyrazole-3-carboxyamide | $^1$H NMR (300 MHz, CDCl$_3$) δ 8.91 (s, 1H), 8.73 (s, 1H), 8.39 (s, 1H), 8.00-7.96 (m, 2H), 7.78-7.70 (m, 2H), 7.58-7.40 (m, 4H), 7.21 (s, 1H), 7.18 (d, 1H), 2.32 (s, 3H). MS (ESI$^+$): m/z 464.1 [M + H]$^+$ |

TABLE 4-continued

| Example | Structural Formula | Compound Name | Analysis Data |
| --- | --- | --- | --- |
| 119 | | 5-([1,2,4]triazolo[1,5-α]pyridin-6-yl)-1-(6-methylpyridin-2-yl)-N-(4-vinylphenyl)-1H-pyrazole-3-carboxyamide | $^1$H NMR (300 MHz, CDCl$_3$) δ 8.80 (s, 1H), 8.73 (s, 1H), 8.39 (s, 1H), 7.80-7.70 (m, 4H), 7.61-7.56 (m, 2H), 7.46 (d, 1H), 7.34 (t, 1H), 7.22-7.15 (m, 2H), 6.73 (dd, 1H), 5.80 (d, 1H), 5.29 (d, 1H), 2.31 (s, 3H). MS (ESI$^+$): m/z 422.2 [M + H]$^+$ |
| 120 | | 5-([1,2,4]triazolo[1,5-α]pyridin-6-yl)-N-(3-cyanophenyl)-1-(6-methylpyridin-2-yl)-1H-pyrazole-3-carboxyamide | $^1$H NMR (300 MHz, CDCl$_3$) δ 8.90 (s, 1H), 8.73 (s, 1H), 8.40 (s, 1H), 8.12 (m, 1H), 7.95 (d, 1H), 7.78-7.71 (m, 2H), 7.55-7.44 (m, 4H), 7.22 (s, 1H), 7.20 (d, 1H), 2.33 (s, 3H). MS (ESI$^+$): m/z 421.1 [M + H]$^+$ |
| 121 | | 5-([1,2,4]triazolo[1,5-α]pyridin-6-yl)-N-(4-cyanophenyl)-1-(6-methylpyridin-2-yl)-1H-pyrazole-3-carboxyamide | $^1$H NMR (300 MHz, DMSO-d$_6$) δ 10.70 (s, 1H), 9.18 (s, 1H), 8.55 (s, 1H), 8.08-8.05 (m, 2H), 7.95-7.92 (m, 2H), 7.84-7.78 (m, 3H), 7.52 (d, 1H), 7.35-7.30 (m, 2H), 2.25 (s, 3H). MS (ESI$^+$): m/z 421 [M + H]$^+$. |
| 122 | | 5-([1,2,4]triazolo[1,5-α]pyridin-6-yl)-N-(3-acetylphenyl)-1-(6-methylpyridin-2-yl)-1H-pyrazole-3-carboxyamide | $^1$H NMR (300 MHz, DMSO-d$_6$) δ 10.50 (s, 1H), 9.18 (s, 1H), 8.55 (s, 1H), 8.43 (s, 1H), 8.12 (d, 1H), 7.98-7.93 (m,1H), 7.84-7.73(m, 2H), 7.73 (d, 1H), 7.70-7.52 (m, 2H), 7.32 (br, 2H), 2.58 (s, 3H), 2.16 (s, 3H). MS (ESI$^+$): m/z 438 [M + H]$^+$. |
| 123 | | 5-([1,2,4]triazolo[1,5-α]pyridin-6-yl)-N-(4-acetylphenyl)-1-(6-methylpyridin-2-yl)-1H-pyrazole-3-carboxyamide | $^1$H NMR (300 MHz, DMSO-d$_6$) δ 10.59 (s, 1H), 9.18 (s, 1H), 8.55 (s, 1H), 7.99-7.95 (m, 5H), 7.83-7.78 (m, 2H), 7.53 (d, 1H), 7.34 (br, 2H), 2.54 (s, 3H), 2.25 (s, 3H). MS (ESI$^+$): m/z 438 [M + H]$^+$. |

TABLE 4-continued

| Example | Structural Formula | Compound Name | Analysis Data |
|---|---|---|---|
| 124 | | 5-([1,2,4]triazolo[1,5-α]pyridin-6-yl)-N-(2-fluorophenyl)-1-(6-methylpyridin-2-yl)-1H-pyrazole-3-carboxamide | $^1$H NMR (300 MHz, DMSO-d$_6$) δ 10.0 (s, 1H), 9.2 (Ks, 1H), 8.57 (s, 1H), 7.96 (t, 1H), 7.83-7.78 (m, 3H), 7.54 (d, 1H), 7.33-7.25 (m, 5H), 2.18 (s, 3H). MS (ESI$^+$): m/z 414 [M + H]$^+$. |
| 125 | | 5-([1,2,4]triazolo[1,5-α]pyridin-6-yl)-N-(3-fluorophenyl)-1-(6-methylpyridin-2-yl)-1H-pyrazole-3-carboxamide | $^1$H NMR (300 MHz, DMSO-d$_6$) δ 10.48 (s, 1H), 9.18 (s, 1H), 8.55 (s, 1H), 7.98 (t, 1H), 7.81-7.78 (m, 3H), 7.66 (d, 1H), 7.52 (d, 1H), 7.48-6.97 (m, 3H), 6.91 (t, 1H), 2.18 (s, 3H). MS (ESI$^+$): m/z 414 [M + H]$^+$. |
| 126 | | 5-([1,2,4]triazolo(1,5-α]pyridin-6-yl)-N-(4-fluorophenyl)-1-(6-methylpyridin-2-yl)-1H-pyrazole-3-carboxamide | $^1$H NMR (300 MHz, DMSO-d$_6$) δ 10.37 (s, 1H), 9.17 (s, 1H), 8.56 (s, 1H), 7.98-7.79 (m, 5H), 7.52 (d, 1H), 7.31-7.17 (m, 4H), 2.25 (s, 3H). MS (ESI$^+$): m/z 414 [M + H]$^+$. |
| 127 | | 5-([1,2,4]triazolo[1,5-α]pyridin-6-yl)-N-(2-chlorophenyl)-1-(6-methylpyridin-2-yl)-1H-pyrazole-3-carboxamide | $^1$H NMR (300 MHz, DMSO-d$_6$) δ 10.00 (s, 1H), 9.34 (s, 1H), 8.57 (s, 1H), 7.97 (m, 2H), 7.80 (m, 2H), 7.58 (m, 3H), 7.42-7.35 (m, 3H), 2.17 (s, 3H). MS (ESI$^+$): m/z 430 [M + H]$^+$. |
| 128 | | 5-([1,2,4]triazolo(1,5-α]pyridin-6-yl)-N-(3-chlorophenyl)-1-(6-methylpyridin-2-yl)-1H-pyrazole-3-carboxamide | $^1$H NMR (300 MHz, DMSO-d$_6$) δ 10.45 (s, 1H), 9.18 (s, 1H), 8.55 (s, 1H), 8.16 (s, 1H), 7.98 (t, 1H), 7.86-7.79 (m, 3H), 7.50 (d, 1H), 7.32 (br, 4H), 2.17 (s, 3H). MS (ESI$^+$): m/z 430 [M + H]$^+$. |

TABLE 4-continued

| Example | Structural Formula | Compound Name | Analysis Data |
|---|---|---|---|
| 129 | | 5-([1,2,4]triazolo[1,5-α]pyridin-6-yl)-N-(4-chlorophenyl)-1-(6-methylpyridin-2-yl)-1H-pyrazole-3-carboxamide | $^1$H NMR (300 MHz, DMSO-d$_6$) δ 10.45 (s, 1H), 9.19 (s, 1H), 8.57 (s, 1H), 7.99-7.80 (m, 5H), 7.53 (d, 1H), 7.44 (m, 2H), 7.31 (br, 2H), 2.25 (s, 3H). MS (ESI$^+$): m/z 430 [M + H]$^+$. |
| 130 | | 5-([1,2,4]triazolo[1,5-α]pyridin-6-yl)-N-(2-bromophenyl)-1-(6-methylpyridin-2-yl)-1H-pyrazole-3-carboxamide | $^1$H NMR (300 MHz, DMSO-d$_6$) δ 9.87 (s, 1H), 9.18 (s, 1H), 8.56 (s, 1H), 7.96-7.93 (m, 2H), 7.82-7.74 (m, 2H), 7.54-7.43 (m, 3H), 7.33 (br, 2H), 7.16 (t, 1H), 2.16 (s, 3H). MS (ESI$^+$): m/z 474 [M + H]$^+$. |
| 131 | | 5-([1,2,4]triazolo[1,5-α]pyridin-6-yl)-N-(3-bromophenyl)-1-(6-methylpyridin-2-yl)-1H-pyrazole-3-carboxamide | $^1$H NMR (300 MHz, DMSO-d$_6$) δ 10.45 (s, 1H), 9.18 (s, 1H), 8.55 (s, 1H), 8.16 (s, 1H), 7.98 (t, 1H), 7.86-7.79 (m, 3H), 7.50 (d, 1H), 7.32 (br, 4H), 2.17 (s, 3H). MS (ESI$^+$): m/z 474 [M + H]$^+$. |
| 132 | | 5-([1,2,4]triazolo[1,5-α]pyridin-6-yl)-N-(4-bromophenyl)-1-(6-methylpyridin-2-yl)-1H-pyrazole-3-carboxamide | $^1$H NMR (300 MHz, DMSO-d$_6$) δ 10.44 (s, 1H), 9.19 (s, 1H), 8.57 (s, 1H), 7.99 (t, 1H), 7.86-7.79 (m, 2H), 7.57-7.50 (m, 4H), 7.31 (br, 3H), 2.25 (s, 3H). MS (ESI$^+$): m/z 474 [M + H]$^+$. |
| 133 | | 5-([1,2,4]triazolo[1,5-α]pyridin-6-yl)-N-(2,3-difluorophenyl)-1-(6-methylpyridin-2-yl)-1H-pyrazole-3-carboxamide | $^1$H NMR (300 MHz, DMSO-d$_6$) δ 10.27 (s, 1H), 9.18 (s, 1H), 8.55 (s, 1H), 7.97 (t, 1H), 7.78 (t, 2H), 7.48 (d, 2H), 7.31-7.21 (m, 4H), 2.16 (s, 3H). MS (ESI$^+$): m/z 432 [M + H]$^+$. |

TABLE 4-continued

| Example | Structural Formula | Compound Name | Analysis Data |
|---|---|---|---|
| 134 | | 5-([1,2,4]triazolo[1,5-α]pyridin-6-yl)-N-(2,4-difluorophenyl)-1-(6-methylpyridin-2-yl)-1H-pyrazole-3-carboxamide | $^1$H NMR (300 MHz, DMSO-d$_6$) δ 10.08 (s, 1H), 9.18 (s, 1H), 8.55 (s, 1H), 7.97 (t, 1H), 7.78 (t, 2H), 7.68-7.66 (m, 1H), 7.52 (d, 1H), 7.37-7.29 (m, 3H), 7.13 (t, 1H), 2.06 (s, 3H). MS (ESI$^+$): m/z 432 [M + H]$^+$. |
| 135 | | 5-([1,2,4]triazolo[1,5-α]pyridin-6-yl)-N-(2,5-difluorophenyl)-1-(6-methylpyridin-2-yl)-1H-pyrazole-3-carboxamide | $^1$H NMR (300 MHz, DMSO-d$_6$) δ 10.04 (s, 1H), 9.18 (s, 1H), 8.55 (s, 1H), 7.95 (t, 1H), 7.81-7.71 (m, 3H), 7.52 (d, 1H), 7.41-7.33 (br, 3H), 7.13-7.09 (m, 1H), 2.17 (s, 3H). MS (ESI$^+$): m/z 432 [M + H]$^+$. |
| 136 | | 5-([1,2,4]triazolo[1,5-α]pyridin-6-yl)-N-(3,4-difluorophenyl)-1-(6-methylpyridin-2-yl)-1H-pyrazole-3-carboxamide | $^1$H NMR (300 MHz, DMSO-d$_6$) δ 10.64 (s, 1H), 9.20 (s, 1H), 8.55 (s, 1H), 7.95 (t, 2H), 7.65 (br, 2H), 7.49 (br, 1H), 7.49-7.39 (m, 2H), 7.32 (br, 2H), 2.25 (s, 3H). MS (ESI$^+$): m/z 432 [M + H]$^+$. |
| 137 | | 5-([1,2,4]triazolo[1,5-α]pyridin-6-yl)-N-(3,5-difluorophenyl)-1-(6-methylpyridin-2-yl)-1H-pyrazole-3-carboxamide | $^1$H NMR (300 MHz, CDCl$_3$) δ 9.19 (s, 1H), 8.98 (s, 1H), 8.24 (s, 1H), 7.80-7.73 (m, 2H), 7.70-7.60 (m, 3H), 7.55-7.44 (m, 3H), 6.64-6.57 (m, 1H), 2.25 (s, 3H), MS (ESI$^+$): m/z 432 [M + H]$^+$. |
| 138 | | 5-([1,2,4]triazolo[1,5-α]pyridin-6-yl)-N-(3-chloro-2-fluorophenyl)-1-(6-methylpyridin-2-yl)-1H-pyrazole-3-carboxamide | $^1$H NMR (300 MHz, DMSO-d$_6$) δ 10.24 (s, 1H), 9.18 (s, 1H), 8.55 (s, 1H), 7.94 (t, 2H), 7.78 (t, 2H), 7.66 (m, 1H), 7.51-7.43 (m, 2H), 7.31-7.25 (m, 3H), 2.16 (s, 3H). MS (ESI$^+$): m/z 448 [M + H]$^+$. |

TABLE 4-continued

| Example | Structural Formula | Compound Name | Analysis Data |
|---|---|---|---|
| 139 | 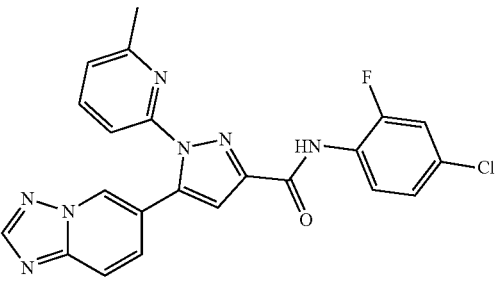 [SMILES: Cc1cccc(-n2nc(C(=O)Nc3ccc(Cl)cc3F)cc2-c2ccc3ncnn3c2)n1] | 5-([1,2,4]triazolo[1,5-α]pyridin-6-yl)-N-(4-chloro-2-fluorophenyl)-1-(6-methylpyridin-2-yl)-1H-pyrazole-3-carboxamide | $^1$H NMR (300 MHz, DMSO-$d_6$) δ 10.33 (s, 1H), 9.44 (s, 1H), 8.56 (s, 1H), 7.83 (t, 1H), 7.79-7.73 (m, 3H), 7.65-7.50 (m, 3H), 7.32 (br, 2H), 2.18 (s, 3H), MS (ESI$^+$): m/z 448 [M + H]$^+$. |
| 140 | 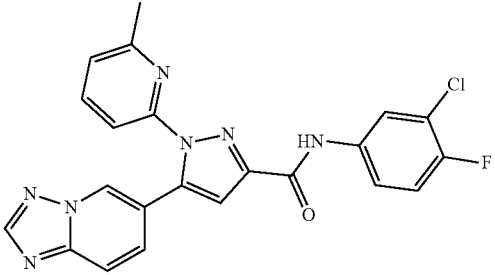 [SMILES: Cc1cccc(-n2nc(C(=O)Nc3ccc(F)c(Cl)c3)cc2-c2ccc3ncnn3c2)n1] | 5-([1,2,4]triazolo[1,5-α]pyridin-6-yl)-N-(3-chloro-4-fluorophenyl)-1-(6-methylpyridin-2-yl)-1H-pyrazole-3-carboxamide | $^1$H NMR (300 MHz, DMSO-$d_6$) δ 10.52 (s, 1H), 9.18 (s, 1H), 8.55 (s, 1H), 8.12 (d, 2H), 7.95 (t, 1H), 7.80-7.78 (br, 2H), 7.52-7.40 (m, 2H), 7.32 (br, 2H), 2.17 (s, 3H). MS (ESI$^+$): m/z 448 [M + H]$^+$. |
| 141 | 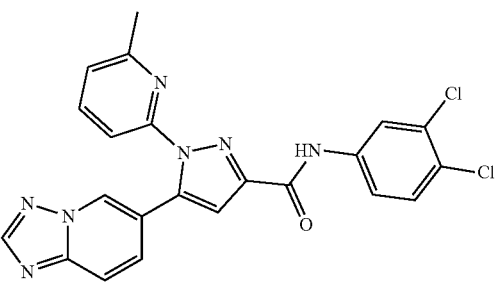 [SMILES: Cc1cccc(-n2nc(C(=O)Nc3ccc(Cl)c(Cl)c3)cc2-c2ccc3ncnn3c2)n1] | 5-([1,2,4]triazolo[1,5-α]pyridin-6-yl)-N-(3,4-dichlorophenyl)-1-(6-methylpyridin-2-yl)-1H-pyrazole-3-carboxamide | $^1$H NMR (300 MHz, DMSO-$d_6$) δ 10.59 (s, 1H), 9.18 (s, 1H), 8.55 (s, 1H), 7.98 (s, 1H), 7.98-7.78 (m, 4H), 7.64 (d, 1H), 7.61 (d, 1H), 7.21 (br, 2H), 2.17 (s, 3H). MS (ESI$^+$): m/z 464 [M + H]$^+$. |
| 142 | 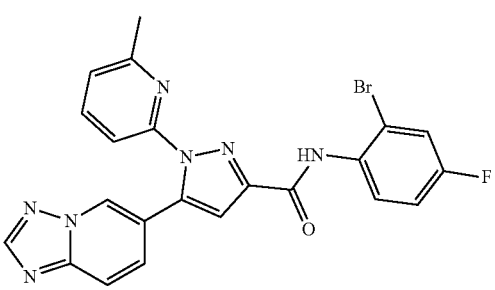 [SMILES: Cc1cccc(-n2nc(C(=O)Nc3ccc(F)cc3Br)cc2-c2ccc3ncnn3c2)n1] | 5-([1,2,4]triazolo[1,5-α]pyridin-6-yl)-N-(2-bromo-4-fluorophenyl)-1-(6-methylpyridin-2-yl)-1H-pyrazole-3-carboxamide | $^1$H NMR (300 MHz, DMSO-$d_6$) δ 10.17 (s, 1H), 9.14 (s, 1H), 8.49 (s, 1H), 7.96 (t, 1H), 7.85-7.70 (m, 4H), 7.5 l(m, 1H), 7.32(br, 3H), 2.17(s, 3H), MS (ESI$^+$): m/z 492 [M + H]$^+$. |
| 143 | 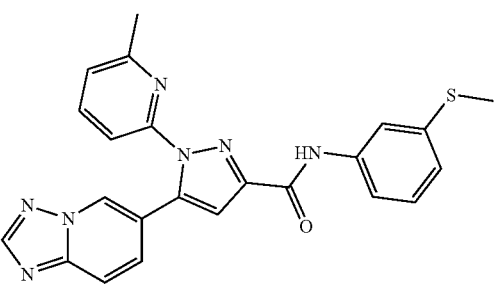 [SMILES: CSc1cccc(NC(=O)c2cc(-c3ccc4ncnn4c3)n(-c3cccc(C)n3)n2)c1] | 5-([1,2,4]triazolo[1,5-α]pyridin-6-yl)-N-(3-(methoxythio)phenyl)-1-(6-methylpyridin-2-yl)-1H-pyrazole-3-carboxamide | $^1$H NMR (300 MHz, CDCl$_3$) δ 8.80 (brs, 1H), 8.73 (s, 1H), 8.39 (s, 1H), 7.76-7.70 (m, 3H), 7.57 (d, J = 7.8 Hz, 1H), 7.48-7.43 (m, 2H), 7.28 (t, J = 7.8 Hz, 1H), 7.19-7.15 (m, 2H), 7.04 (d, J = 8.1Hz, 1H), 2.52 (s, 3H), 2.19 (s, 3H). MS (ESI$^+$): m/z 442 [M + H]$^+$. |

TABLE 4-continued

| Example | Structural Formula | Compound Name | Analysis Data |
|---|---|---|---|
| 144 | | 5-([1,2,4]triazolo[1,5-α]pyridin-6-yl)-N-(4-(methoxythio)phenyl)-1-(6-methylpyridin-2-yl)-1H-pyrazole-3-carboxamide | $^1$H NMR (300 MHz, CDCl$_3$) δ 8.77 (brs, 1H), 8.72 (s, 1H), 8.39 (s, 1H), 7.77-7.66 (m, 4H), 7.56 (d, J = 7.8 Hz, 1H), 7.47 (d, J = 7.8 Hz, 1H), 7.32-7.29 (m, 2H), 7.18-7.16 (m, 2H), 2.50 (s, 3H), 2.32 (s, 3H). MS (ESI$^+$): m/z 442 [M + H]$^+$. |
| 145 | | 5-([1,2,4]triazolo[1,5-α]pyridin-6-yl)-N-(3-(methylsulfinyl)phenyl)-1-(6-methylpyridin-2-yl)-1H-pyrazole-3-carboxamide | $^1$H NMR (300 MHz, CDCl$_3$) δ 9.03 (brs, 1H), 8.73 (s, 1H), 8.39 (s, 1H), 8.01-7.98 (m, 2H), 7.78-7.70 (m, 2H), 7.60-7.37 (m, 4H), 7.20-7.16 (m, 2H), 2.77 (s, 3H), 2.30 (s, 3H). MS (ESI$^+$): m/z 458 [M + H]$^+$. |
| 146 | | 5-([1,2,4]triazolo[1,5-α]pyridin-6-yl)-N-(4-(methylsulfinyl)phenyl)-1-(6-methylpyridin-2-yl)-1H-pyrazole-3-carboxamide | $^1$H NMR (300 MHz, CDCl$_3$) δ 8.98 (brs, 1H), 8.73 (s, 1H), 8.39 (s, 1H), 7.92 (d, J = 8.4 Hz, 2H), 7.79-7.66 (m, 4H), 7.55 (d, J = 7.8 Hz, 1H), 7.46 (d, J = 9.3 Hz, 1H), 7.21-7.17 (m, 2H), 2.74 (s, 3H), 2.32 (s, 3H). MS (ESI$^+$): m/z 458 [M + H]$^+$. |
| 147 | | 5-([1,2,4]triazolo[1,5-α]pyridin-6-yl)-N-(4-(methylsulfonyl)phenyl)-1-(6-methylpyridin-2-yl)-1H-pyrazole-3-carboxamide | $^1$H NMR (300 MHz, CDCl$_3$) δ 9.06 (brs, 1H), 8.75 (s, 1H), 8.41 (s, 1H), 7.97 (m, 4H), 7.82-7.72 (m, 2H), 7.55 (d, J = 8.1Hz, 1H), 7.48 (d, J = 9.3 Hz, 1H), 7.24-7.20 (m, 2H), 3.09 (s, 3H), 2.35 (s, 3H). MS (ESI$^+$): m/z 474 [M + H]$^+$. |
| 148 | | 5-([1,2,4]triazolo[1,5-α]pyridin-6-yl)-N-(4-sulfomoylphenyl)-1-(6-methylpyridin-2-yl)-1H-pyrazole-3-carboxamide | $^1$H NMR (300 MHz, DMSO-d$_6$) δ 10.63 (brs, 1H), 9.21 (s, 1H), 8.57 (s, 1H), 8.04-7.94 (m, 3H), 7.83-7.80 (m, 4H), 7.53 (d, J = 9.3 Hz, 1H), 7.35-7.30 (m, 4H), 2.19 (s, 3H). MS (ESI$^+$): m/z 475 [M + H]$^+$. |

TABLE 4-continued

| Example | Structural Formula | Compound Name | Analysis Data |
|---|---|---|---|
| 149 | | 5-([1,2,4]triazolo[1,5-a]pyridin-6-yl)-N-(4-(S-methylsulfonimidoyl)phenyl)-1-(6-methylpyridin-2-yl)-1H-pyrazole-3-carboxamide | $^1$H NMR (300 MHz, CDCl$_3$) δ 9.05 (brs, 1H), 8.73 (s, 1H), 8.39 (s, 1H), 7.04-7.91 (m, 4H), 7.77-7.70 (m, 2H), 7.53 (d, J = 7.8 Hz, 1H), 7.46 (d, J = 9.3 Hz, 1H), 7.22-7.18 (m, 2H), 3.12 (s, 3H), 2.33 (s, 3H). MS (ESI$^+$): m/z 473 [M + H]$^+$. |
| 150 | | 5-([1,2,4]triazolo[1,5-a]pyridin-6-yl)-N-(4-(propylsulfonyl)phenyl)-1-(6-methylpyridin-2-yl)-1H-pyrazole-3-carboxamide | $^1$H NMR (300 MHz, CDCl$_3$) δ 9.06 (brs, 1H), 8.75 (s, 1H), 8.41 (d, J = 6.9 Hz, 2H), 7.80-7.48 (m, 4H), 7.24-7.20 (m, 2H), 7.07 (d, J = 7.2 Hz, 1H), 6.84 (s, 1H), 3.12-3.07 (m, 1H), 2.20 (s, 3H), 1.81-1.71 (m, 2H), 1.02 (t, J = 7.5 Hz, 3H), MS (ESI$^+$): m/z 502 [M + H]$^+$. |
| 151 | | 5-([1,2,4]triazolo[1,5-a]pyridin-6-yl)-N-(4-(propylsulfonyl)phenyl)-1-(6-methylpyridin-2-yl)-1H-pyrazole-3-carboxamide | $^1$H NMR (300 MHz, CDCl$_3$) δ 9.04 (brs, 1H), 8.73 (s, 1H), 8.39 (s, 1H), 7.95-7.88 (m, 4H), 7.80-7.70 (m, 2H), 7.54 (d, J = 8.1Hz, 1H), 7.45 (d, J = 9.3 Hz, 1H), 7.43-7.18 (m, 2H), 2.50-2.44 (m, 1H), 2.33 (s, 3H), 1.38-1.32 (m, 2H), 1.07-1.00 (m, 3H). MS (ESI$^+$): m/z 502 [M + H]$^+$. |
| 152 | | 5-([1,2,4]triazolo[1,5-a]pyridin-6-yl)-N-(6-fluoropyridin-3-yl)-1-(6-methylpyridin-2-yl)-1H-pyrazole-3-carboxamide | $^1$H NMR (300 MHz, DMSO-d$_6$) δ 10.68 (brs, 1H), 9.21 (s, 1H), 8.67 (s, 1H), 8.57 (s, 1H), 8.40 (t, J = 6.9 Hz, 1H), 7.97 (t, J = 7.8 Hz, 1H), 7.83-7.78 (m, 2H), 7.51 (d, J= 9.3 Hz, 1H), 7.35-7.33 (m, 2H), 7.24 (d, J = 8.7 Hz, 1H), 2.20 (s, 3H). MS (ESI$^+$): m/z 415 [M + H]$^+$. |
| 153 | | 5-([1,2,4]triazolo[1,5-a]pyridin-6-yl)-N-(6-chloropyridin-3-yl)-1-(6-methylpyridin-2-yl)-1H-pyrazole-3-carboxamide | $^1$H NMR (300 MHz, DMSO-d$_6$) δ 9.42 (s, 1H), 8.74 (s, 1H), 8.49 (br, 2H), 7.91 (t, 1H), 7.75 (d, 1H), 7.64 (d, 2H), 7.50-7.48 (m, 2H), 7.37 (d, 1H), 7.27 (s, 1H), 2.13 (s, 3H). MS (ESI$^+$): m/z 431 [M + H]$^+$. |

TABLE 4-continued

| Example | Structural Formula | Compound Name | Analysis Data |
|---|---|---|---|
| 154 | 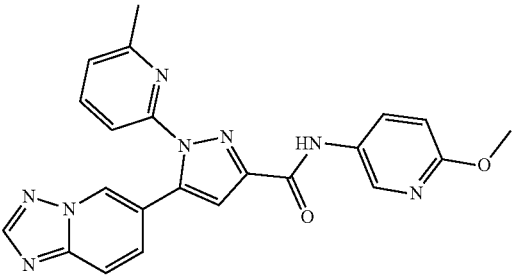 | 5-([1,2,4]triazolo[1,5-α]pyridin-6-yl)-N-(6-methoxypyridin-3-yl)-1-(6-methylpyridin-2-yl)-1H-pyrazole-3-carboxamide | $^1$H NMR (300 MHz, CDCl$_3$) δ 8.72 (brs, 1H), 8.71 (s, 1H), 8.68-8.36 (m, 2H), 8.11 (d, J = 9.0 Hz, 1H), 7.76-7.69 (m, 2H), 7.54 (d, J = 7.8 Hz, 1H), 7.45 (d, J = 9.0 Hz, 1H), 7.24-7.15 (m, 2H), 6.79 (d, J = 9.0 Hz, 1H), 3.94 (s, 3H), 2.32 (s, 3H). MS (ESI$^+$): m/z 427 [M + H]$^+$. |
| 155 | 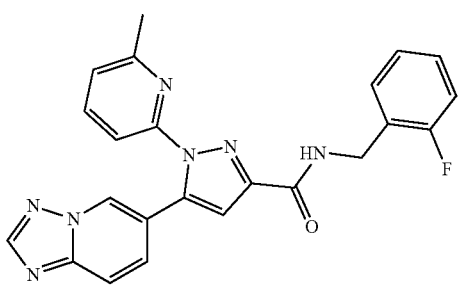 [SMILES: Cc1cccc(-n2nc(C(=O)NCc3ccccc3F)cc2-c2ccc3ncnn3c2)n1] | 5-([1,2,4]triazolo[1,5-α]pyridin-6-yl)-N-(2-fluorobenzyl)-1-(6-methylpyridin-2-yl)-1H-pyrazole-3-carboxamide | $^1$H NMR (300 MHz, DMSO-d$_6$) δ 9.25 (s, 1H), 9.01 (t, 1H), 8.54 (s, 1H), 7.89 (t, 1H), 7.77 (d, 1H), 7.70 (d, 1H), 7.51 (d, 1H), 7.38-7.27 (m, 3H), 7.14 (br, 2H), 4.54 (d, 2H), 2.15 (s, 3H). MS (ESI$^+$): m/z 428 [M + H]$^+$. |
| 156 | 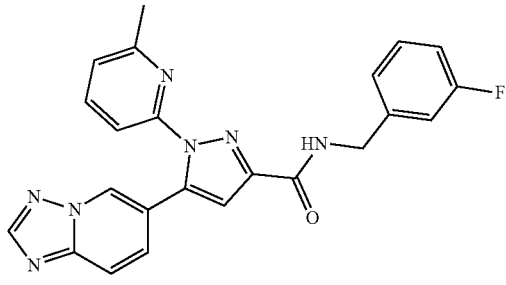 [SMILES: Cc1cccc(-n2nc(C(=O)NCc3cccc(F)c3)cc2-c2ccc3ncnn3c2)n1] | 5-([1,2,4]triazolo[1,5-α]pyridin-6-yl)-N-(3-fluorobenzyl)-1-(6-methylpyridin-2-yl)-1H-pyrazole-3-carboxamide | $^1$H NMR (300 MHz, DMSO-d$_6$) δ 9.15 (s, 1H), 9.00 (t, 1H), 7.95 (s, 1H), 7.81 (t, 1H), 7.78 (d, 1H), 7.71 (d, 1H), 7.52 (d, 1H), 7.48-7.28 (m, 3H), 7.15 (br, 2H), 4.55 (d, 2H), 2.15 (s, 3H). MS (ESI$^+$): m/z 428 [M + H]$^+$. |
| 157 | 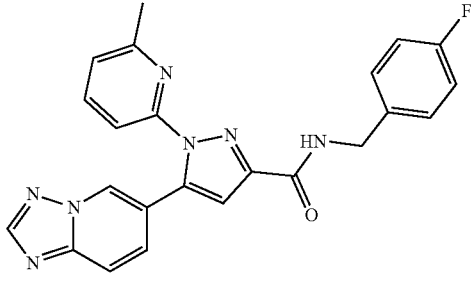 [SMILES: Cc1cccc(-n2nc(C(=O)NCc3ccc(F)cc3)cc2-c2ccc3ncnn3c2)n1] | 5-([1,2,4]triazolo[1,5-α]pyridin-6-yl)-N-(4-fluorobenzyl)-1-(6-methylpyridin-2-yl)-1H-pyrazole-3-carboxamide | $^1$H NMR (300 MHz, DMSO-d$_6$) δ 9.21 (s, 1H), 9.10 (t, 1H), 8.61 (s, 1H), 7.87 (t, 1H), 7.83 (d, 1H), 7.75 (d, 1H), 7.57 (d, 1H), 7.46-7.42 (m, 2H), 7.33 (d, 1H), 7.18 (br, 3H), 4.53 (d, 2H), 2.22 (s, 3H). MS (ESI$^+$): m/z 428 [M + H]$^+$. |
| 158 | 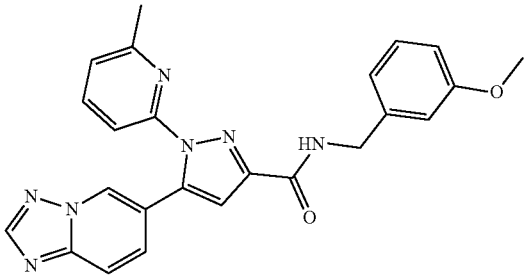 [SMILES: COc1cccc(CNC(=O)c2cc(-c3ccc4ncnn4c3)n(-c3cccc(C)n3)n2)c1] | 5-([1,2,4]triazolo[1,5-α]pyridin-6-yl)-N-(3-methoxybenzyl)-1-(6-methylpyridin-2-yl)-1H-pyrazole-3-carboxamide | $^1$H NMR (300 MHz, CDCl$_3$) δ 8.71 (brs, 1H), 8.39 (s, 1H), 7.72-7.69 (m, 2H), 7.52-7.45 (m, 2H), 7.31-7.11 (m, 3H), 6.99-6.87 (m, 3H), 4.66 (d, J = 4.0 Hz, 2H), 3.82 (s, 3H), 2.28 (s, 3H). MS (ESI$^+$): m/z 440 [M + H]$^+$. |

TABLE 4-continued

| Example | Structural Formula | Compound Name | Analysis Data |
|---|---|---|---|
| 159 | | 5-([1,2,4]triazolo[1,5-α]pyridin-6-yl)-N-(4-methoxybenzyl)-1-(6-methylpyridin-2-yl)-1H-pyrazole-3-carboxyamide | $^1$H NMR (300 MHz, CDCl$_3$) δ 8.71 (brs, 1H), 8.39 (s, 1H), 7.72-7.68 (m, 2H), 7.51-7.44 (m, 2H), 7.33 (d, J = 8.7 Hz, 2H), 7.15-7.11 (m, 2H), 6.91 (d, J = 8.7 Hz, 2H), 4.62 (d, J = 4.0 Hz, 2H), 3.82 (s, 3H), 2.28 (s, 3H). MS (ESI$^+$): m/z 440 [M + H]$^+$. |
| 160 | | 5-([1,2,4]triazolo[1,5-α]pyridin-6-yl)-N-(4-(dimethylamino)benzyl)-1-(6-methylpyridin-2-yl)-1H-pyrazole-3-carboxyamide | $^1$H NMR (300 MHz, CDCl$_3$) δ 8.70 (s, 1H), 8.37 (s, 1H), 7.70-7.66 (m, 2H), 7.47 (dd, 2H), 7.28-7.25 (m, 3H), 7.13 (s, 1H), 7.10 (d, 1H), 6.73 (d, 2H), 4.57 (d, 2H), 2.94 (s, 6H), 2.25 (s, 3H). MS (ESI$^+$): m/z 453.2 [M + H]$^+$. |
| 161 | | 5-([1,2,4]triazolo[1,5-α]pyridin-6-yl)-N-(4-acetamidobenzyl)-1-(6-methylpyridin-2-yl)-1H-pyrazole-3-carboxyamide | $^1$H NMR (300 MHz, DMSO-d$_6$) δ 8.90 (brs, 1H), 9.15 (s, 1H), 8.99 (t, 1H), 8.55 (s, 1H), 7.91 (t, J = 8.1Hz, 1H), 7.80 (d, J = 9.3 Hz, 1H), 7.72 (d, J = 8.1 Hz, 1H), 7.53-7.47 (m, 3H), 7.29-7.24 (m, 3H), 7.18 (s, 1H), 4.42 (d, J = 4.0 Hz, 2H), 2.15 (s, 3H), 2.01 (s, 3H). MS (ESI$^+$): m/z 467 [M + H]$^+$. |
| 162 | | 5-([1,2,4]triazolo[1,5-α]pyridin-6-yl)-1-(6-methylpyridin-2-yl)-N-(1-(methylsulfonyl)-1H-pyrazol-4-yl)-1H-pyrazole-3-carboxyamide | $^1$H NMR (300 MHz, DMSO-d$_6$) δ 8.76 (s, 1H), 8.73 (s, 1H), 8.62 (s, 1H), 8.39 (s, 1H), 8.01 (s, 1H), 7.79-7.70 (m, 2H), 7.53 (d, 1H), 7.45 (d, 1H), 7.20-7.17 (m, 2H), 3.33 (s, 3H), 2.33 (s, 3H). MS (ESI$^+$):m/z 464.1 [M + H]$^+$. |
| 163 | | 5-([1,2,4]triazolo[1,5-α]pyridin-6-yl)-N-(1-cyclopropylsulfonyl)-1H-pyrazol-4-yl)-1-(6-methylpyridin-2-yl)-1H-pyrazole-3-carboxyamide | $^1$H NMR (300 MHz, DMSO-d$_6$) δ 8.78 (s, 1H), 8.73 (s, 1H), 8.59 (s, 1H), 8.40 (s, 1H), 7.99 (s, 1H), 7.79-7.71 (m, 2H), 7.53 (d, 1H), 7.45 (d, 1H), 7.20-7.17 (m, 2H), 2.80-2.75 (m, 1H), 2.33 (s, 3H), 1.57-1.50 (m, 2H), 1.19-1.14 (m, 2H). MS (ESI$^+$): m/z 506.1 [M + H]$^+$. |

Example 164 Preparation of N-(4-methoxyphenyl)-1-(6-methylpyridin-2-yl)-5-(quinoxalin-6-yl)-1H-pyrazole-3-carboxyamide

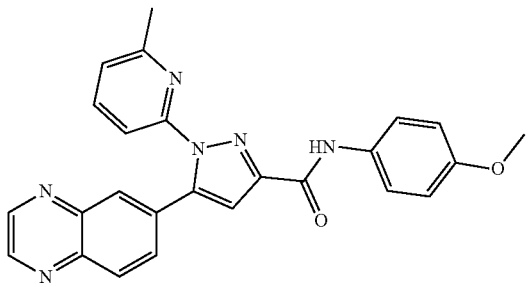 [SMILES: COc1ccc(NC(=O)c2cc(-c3ccc4nccnc4c3)n(-c3cccc(C)n3)n2)cc1]

After dissolving Intermediate 3 (50 mg, 0.15 mmol) in N,N-dimethylformamide, HATU (69 mg, 0.18 mmol) and DIPEA (79 μL, 0.45 mmol) were introduced thereto, and the result was stirred for 30 minutes at room temperature. To the reaction solution, p-anisidine (20 mg, 0.17 mmol) was introduced, and the result was stirred for 12 hours at room temperature. Produced solids were filtered, washed with ethyl acetate, and then vacuum dried to obtain a target compound (42 mg).

$^1$H NMR spectrum (300 MHz, DMSO-d$_6$) δ 10.1 (s, 1H), 8.96 (s, 2H), 8.07-7.93 (m, 3H), 7.78-7.73 (m, 4H), 7.37 (br, 2H), 6.92 (d, 2H), 3.75 (s, 3H), 2.17 (s, 3H).

MS (ESI$^+$): [M+H]$^+$ m/z 437.1

Examples 165 to 201

Compounds of Examples 161 to 198 listed in the following [Table 5] were obtained in the same manner as in Example 160 using various amine derivatives instead of p-anisidine.

TABLE 5

| Example Number | Structure | Compound Name | $^1$H NMR Spectrum (300 MHz, CDCl$_3$)δ | MS (ES) Actual Measurement Value[M+H]/ Required Value |
|---|---|---|---|---|
| 165 | 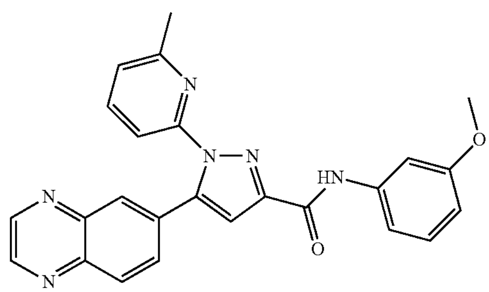 [SMILES: COc1cccc(NC(=O)c2cc(-c3ccc4nccnc4c3)n(-c3cccc(C)n3)n2)c1] | N-(3-methoxyphenyl)-1-(6-methylpyridin-2-yl)-5-(quinoxalin-6-yl)-1H-pyrazole-3-carboxyamide | 10.2(s, 1H), 8.96(s, 2H), 8.07-8.03(m, 2H), 7.96(t, 1H), 7.75(t, 2H), 7.53-7.46(m, 2H), 7.40-7.34(m, 2H), 7.26(t, 1H), 6.69(d, 1H), 3.76(s, 3H), 2.17(s, 3H) | 437.1/436.1 |
| 166 | 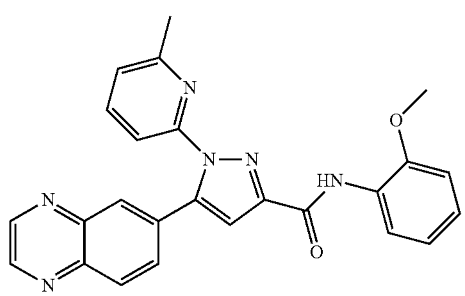 [SMILES: COc1ccccc1NC(=O)c1cc(-c2ccc3nccnc3c2)n(-c2cccc(C)n2)n1] | N-(2-methoxyphenyl)-1-(6-methylpyridin-2-yl)-5-(quinoxalin-6-yl)-1H-pyrazole-3-carboxyamide | 9.43(s, 1H), 8.97(s, 2H), 8.28(d, 1H), 8.07-7.95(m, 3H), 7.78(dd, 2H), 7.43(s, 1H), 7.39(d, 1H), 7.15(br, 2H), 7.13(m, 1H), 3.91(s, 3H), 2.19(s, 3H) | 437.1/436.1 |
| 167 | 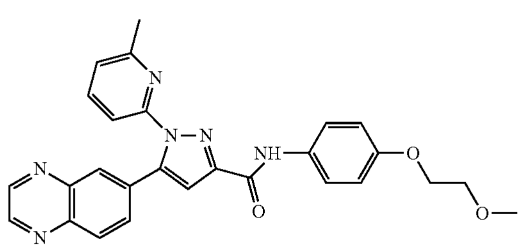 [SMILES: COCCOc1ccc(NC(=O)c2cc(-c3ccc4nccnc4c3)n(-c3cccc(C)n3)n2)cc1] | N-(4-(2-methoxyethoxy)phenyl)-1-(6-methylpyridin-2-yl)-5-(quinoxalin-6-yl)-1H-pyrazole-3-carboxyamide | 8.87(s, 2H), 8.78(s, 1H), 8.09-8.03(m, 2H), 7.70-7.63(m, 4H), 7.37(d, 1H), 7.29(s, 1H), 7.17(d, 1H), 6.95(d, 2H), 4.14(q, 2H), 3.76(q, 2H), 3.46(s, 3H), 2.34(s, 3H) | 481.2/480.2 |

TABLE 5-continued

| Example Number | Structure | Compound Name | ¹H NMR Spectrum (300 MHz, CDCl₃)δ | MS (ES) Actual Measurement Value[M+H]/ Required Value |
|---|---|---|---|---|
| 168 | 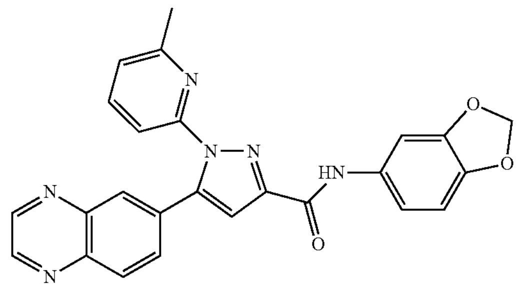 [SMILES: Cc1cccc(-n2nc(C(=O)Nc3ccc4c(c3)OCO4)cc2-c2ccc3nccnc3c2)n1] | N-(benzo[d][1,3]dioxol-5-yl)-1-(6-methylpyridin-2-yl)-5-(quinoxalin-6-yl)-1H-pyrazole-3-carboxyamide | 10.19(s, 1H), 8.95(s, 2H), 8.06-8.00(m, 2H), 7.94(t, 1H), 7.76-7.68(m, 2H), 7.48(d, 1H), 6.89(d, 1H), 5.99(s, 2H), 2.16(s, 3H) | 450.1/451.1 |
| 169 | 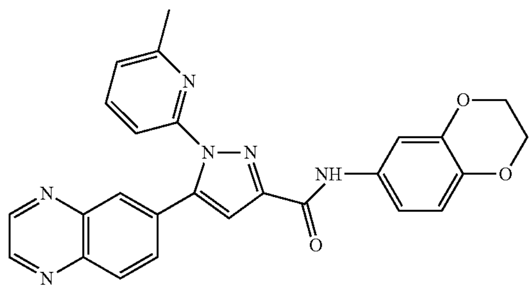 [SMILES: Cc1cccc(-n2nc(C(=O)Nc3ccc4c(c3)OCCO4)cc2-c2ccc3nccnc3c2)n1] | N-(2,3-dihydrobenzo[b][1,4]dioxin-6-yl)-1-(6-methylpyridin-2-yl)-5-(quinoxalin-6-yl)-1H-pyrazole-3-carboxyamide | 8.87(s, 2H), 8.71(s, 1H), 8.08-8.03(m, 2H), 7.70-7.64(m, 2H), 7.39-7.36(m, 2H), 7.29(s, 1H), 7.18-7.10(m, 2H), 6.86(d, 1H), 4.29-4.25(m, 4H), 2.34(s, 3H) | 465.2/464.2 |
| 170 | 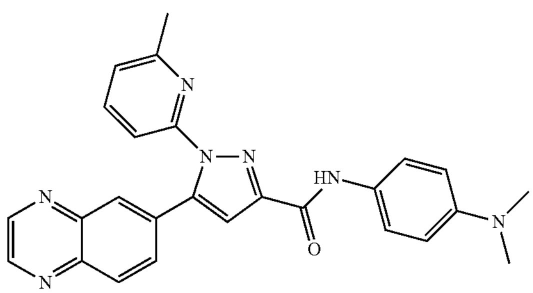 [SMILES: Cc1cccc(-n2nc(C(=O)Nc3ccc(N(C)C)cc3)cc2-c2ccc3nccnc3c2)n1] | N-(4-(dimethylamino)phenyl)-1-(6-methylpyridin-2-yl)-5-(quinoxalin-6-yl)-1H-pyrazole-3-carboxyamide | 9.97(s, 1H), 8.95(s, 2H), 8.05-7.91(m, 3H), 7.76-7.60(m, 4H), 7.33(br, 2H), 6.79-6.70(m, 3H), 2.86(s, 6H), 2.06(s, 3H) | 450.2/449.2 |
| 171 | 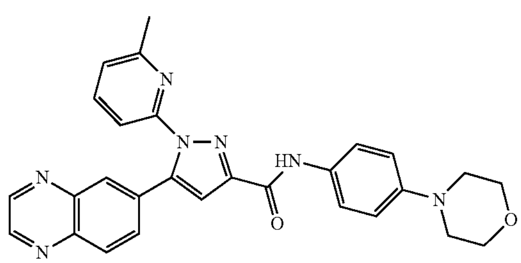 [SMILES: Cc1cccc(-n2nc(C(=O)Nc3ccc(N4CCOCC4)cc3)cc2-c2ccc3nccnc3c2)n1] | 1-(6-methylpyridin-2-yl)-N-(4-morpholinophenyl)-5-(quinoxalin-6-yl)-1H-pyrazole-3-carboxyamide | 8.87(s, 2H), 8.75(s, 1H), 8.09-8.04(m, 2H), 7.71-7.63(m, 4H), 7.38(d, 1H), 7.30(s, 1H), 7.18(d, 1H), 6.94(d, 2H), 3.88(t, 4H), 3.16(t, 4H), 2.35(s, 3H) | 492.2/491.2 |
| 172 | 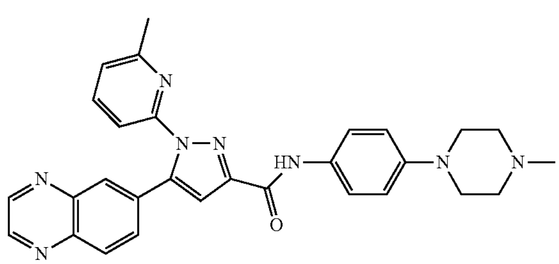 [SMILES: Cc1cccc(-n2nc(C(=O)Nc3ccc(N4CCN(C)CC4)cc3)cc2-c2ccc3nccnc3c2)n1] | N-(4-(4-methylpiperazin-1-yl)phenyl)-1-(6-methylpyridin-2-yl)-5-(quinoxalin-6-yl)-1H-pyrazole-3-carboxyamide | (300 MHz, DMSO-d₆) δ 10.07(s, 1H), 8.97(s, 2H), 8.07-8.03(m, 2H), 7.96(t, 1H), 7.78-7.66(m, 4H), 7.36(s, 2H), 6.93(d, 2H), 3.31(s, 3H), 3.12-3.11(m, 4H), 2.25-2.22(m, 4H), 2.17(s, 3H) | 505.2/504.2 |

TABLE 5-continued

| Example Number | Structure | Compound Name | ¹H NMR Spectrum (300 MHz, CDCl₃)δ | MS (ES) Actual Measurement Value[M+H]/ Required Value |
|---|---|---|---|---|
| 173 | 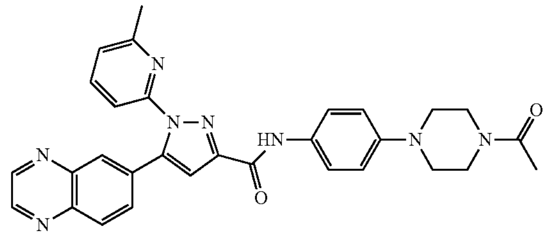 [SMILES: CC(=O)N1CCN(c2ccc(NC(=O)c3cc(-c4ccc5nccnc5c4)n(-c4cccc(C)n4)n3)cc2)CC1] | N-(4-(4-acetylpiperazin-1-yl)phenyl)-1-(6-methylpyridin-2-yl)-5-(quinoxalin-6-yl)-1H-pyrazole-3-carboxyamide | 8.91(s, 2H), 8.74(s, 1H), 8.08-8.03(m. 2H), 7.73-7.63(m. 4H), 7.37(d, 1H), 7.29(s, 1H), 7.17(d, 1H), 6.96(d. 2H), 3.80-3.79(m, 2H), 3.65-3.63(m, 2H), 3.19-3.14(m, 4H), 2.35(s, 3H), 2.15(s, 3H) | 533.3/532.3 |
| 174 | 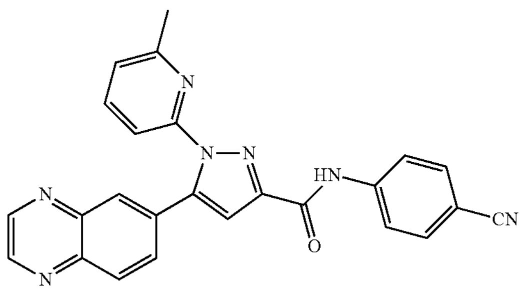 [SMILES: Cc1cccc(-n2nc(C(=O)Nc3ccc(C#N)cc3)cc2-c2ccc3nccnc3c2)n1] | N-(4-cyanophenyl)-1-(6-methylpyridin-2-yl)-5-(quinoxalin-6-yl)-1H-pyrazole-3-carboxyamide | 9.05(s, 1H), 8.88(s, 2H), 8.09-8.05(m, 2H), 7.88(d, 2H), 7.75-7.64(m, 4H), 7.35(d, 1H), 7.31(s, 1H), 7.21(d, 1H), 2.38(s, 3H) | 432.2/431.1 |
| 175 | 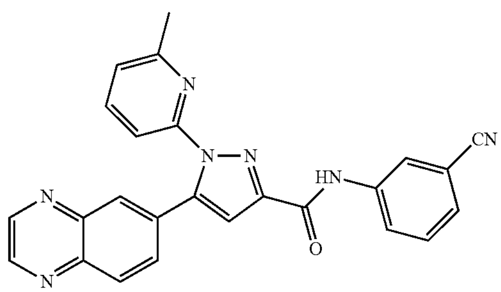 [SMILES: Cc1cccc(-n2nc(C(=O)Nc3cccc(C#N)c3)cc2-c2ccc3nccnc3c2)n1] | N-(3-cyanophenyl)-1-(6-methylpyridin-2-yl)-5-(quinoxalin-6-yl)-1H-pyrazole-3-carboxyamide | 8.97(s, 1H), 8.88(s, 2H), 8.15(s, 1H), 8.09-8.05(m, 2H), 7.96(d, 1H), 7.72-7.65(m, 2H), 7.49-7.44(m, 2H), 7.36(d, 1H), 7.31(s, 1H), 7.20(d, 1H), 2.37(s, 3H) | 432.2/431.1 |
| 176 | 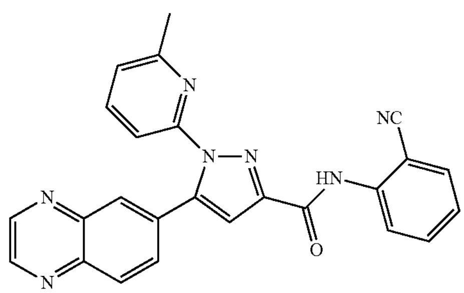 [SMILES: Cc1cccc(-n2nc(C(=O)Nc3ccccc3C#N)cc2-c2ccc3nccnc3c2)n1] | N-(2-cyanophenyl)-1-(6-methylpyridin-2-yl)-5-(quinoxalin-6-yl)-1H-pyrazole-3-carboxyamide | 9.56(s, 1H), 8.88(s, 2H), 8.66(d, 1H), 8.13(d, 1H), 8.05(d, 1H), 7.78(t, 1H), 7.71-7.64(m, 4H), 7.28(s, 1H), 7.21(t, 1H), 7.13(d, 1H), 2.19(s, 3H) | 432.2/431.1 |
| 177 | 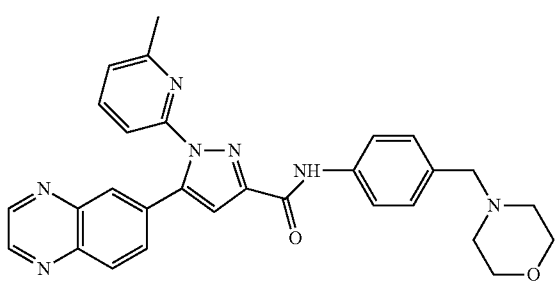 [SMILES: Cc1cccc(-n2nc(C(=O)Nc3ccc(CN4CCOCC4)cc3)cc2-c2ccc3nccnc3c2)n1] | 1-(6-methylpyridin-2-yl)-N-(4-(morpholinomethyl)phenyl)-5-(quinoxalin-6-yl)-1H-pyrazole-3-carboxyamide | 8.87(s, 3H), 8.09-8.04(m, 2H), 7.73-7.64(m, 4H), 7.38-7.30(m, 4H), 7.18(d, 1H), 3.76-3.71(m,4H), 3.50(s, 2H), 2.48-2.45(m, 4H), 2.36(s, 3H) | 506.2/505.2 |

TABLE 5-continued

| Example Number | Structure | Compound Name | ¹H NMR Spectrum (300 MHz, CDCl₃)δ | MS (ES) Actual Measurement Value[M+H]/ Required Value |
|---|---|---|---|---|
| 178 | 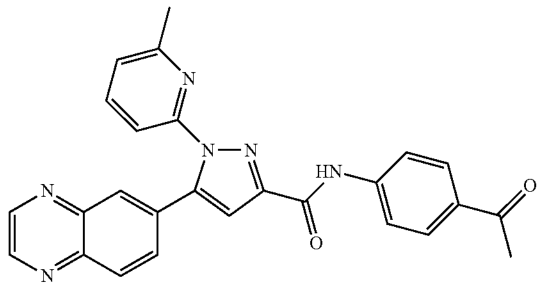 [SMILES: CC(=O)c1ccc(NC(=O)c2cc(-c3ccc4nccnc4c3)n(-c3cccc(C)n3)n2)cc1] | N-(4-acetylphenyl)-1-(6-methylpyridin-2-yl)-5-(quinoxalin-6-yl)-1H-pyrazole-3-carboxyamide | 9.04(s, 1H), 8.88(s, 2H), 8.10-8.00(m, 4H), 7.85(d, 2H), 7.75-7.65(m, 2H), 7.38(d, 1H), 7.32(s, 1H), 7.21(d, 1H), 2.61(s, 3H), 2.37(s, 3H) | 449.2/448.2 |
| 179 | 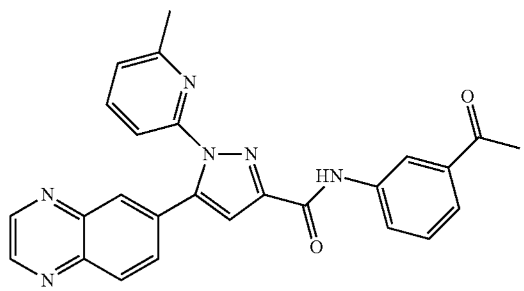 [SMILES: CC(=O)c1cccc(NC(=O)c2cc(-c3ccc4nccnc4c3)n(-c3cccc(C)n3)n2)c1] | N-(3-acetylphenyl)-1-(6-methylpyridin-2-yl)-5-(quinoxalin-6-yl)-1H-pyrazole-3-carboxyamide | (300 MHz, DMSO-d₆) 10.5(s, 1H), 8.97(s, 2H), 8.46(br, 1H), 8.17(d, 1H), 8.07-8.04(m, 2H), 7.97(t, 1H), 7.79-7.76(m, 3H), 7.56(t, 1H), 7.37(s, 1H), 7.35(d,1H), 2.59(s, 3H), 2.18(s, 3H) | 449.1/ 448.1 |
| 180 | 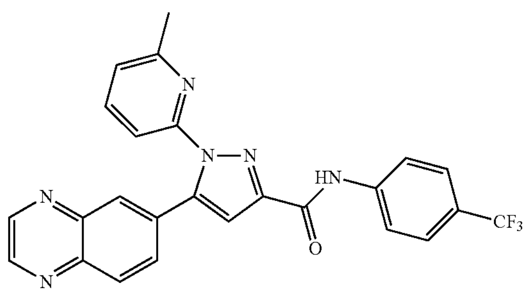 [SMILES: Cc1cccc(-n2nc(C(=O)Nc3ccc(C(F)(F)F)cc3)cc2-c2ccc3nccnc3c2)n1] | 1-(6-methylpyridin-2-yl)-5-(quinoxalin-6-yl)-N-(4-(trifluoromethyl)phenyl)-1H-pyrazole-3-carboxyamide | (300 MHz, DMSO-d₆) 10.6(s, 1H), 8.96(s, 2H), 8.11-7.93(m, 4H), 7.78-7.72(m, 3H), 7.44(s, 1H), 7.35(d, 1H), 2.07(s, 3H) | 475.1/474.1 |
| 181 | 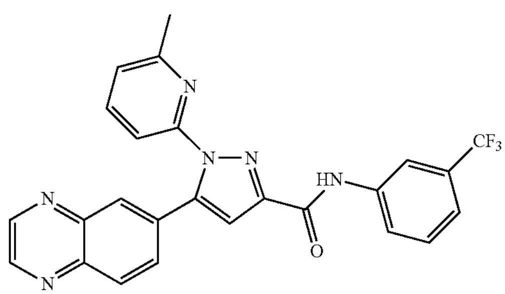 [SMILES: Cc1cccc(-n2nc(C(=O)Nc3cccc(C(F)(F)F)c3)cc2-c2ccc3nccnc3c2)n1] | 1-(6-methylpyridin-2-yl)-5-(quinoxalin-6-yl)-N-(3-(trifluoromethyl)phenyl)-1H-pyrazole-3-carboxyamide | (300 MHz, DMSO-d₆) 10.6(s, 1H), 8.97(s, 2H), 8.33(br, 1H), 8.15(d, 1H), 8.08-8.00(m, 2H), 7.94(t, 1H), 7.79-7.74(m, 2H), 7.72(t, 1H), 7.43(d,1H), 7.38(s, 1H), 7.35(d, 1H), 2.08(s, 3H) | 475.1/474.1 |
| 182 | 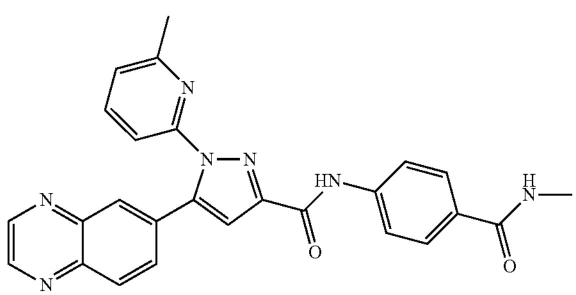 [SMILES: CNC(=O)c1ccc(NC(=O)c2cc(-c3ccc4nccnc4c3)n(-c3cccc(C)n3)n2)cc1] | N-(4-(methylcarbamoyl)phenyl)-1-(6-methylpyridin-2-yl)-5-(quinoxalin-6-yl)-1H-pyrazole-3-carboxyamide | (300 MHz, DMSO-d₆) 10.4(s, 1H), 8.94(s, 2H), 8.34(br, 1H), 8.06-7.91(m, 5H), 7.83-7.70(m, 4H), 7.40(s, 1H), 7.33(d, 1H), 2.77(s, 3H), 2.05(s, 3H) | 464.1/ 463.1 |

TABLE 5-continued

| Example Number | Structure | Compound Name | ¹H NMR Spectrum (300 MHz, CDCl₃)δ | MS (ES) Actual Measurement Value[M+H]/ Required Value |
|---|---|---|---|---|
| 183 | 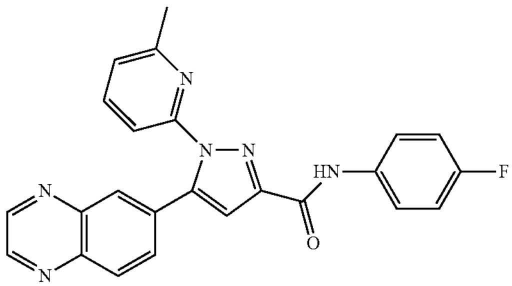 [SMILES: Cc1cccc(-n2nc(C(=O)Nc3ccc(F)cc3)cc2-c2ccc3nccnc3c2)n1] | N-(4-fluorophenyl)-1-(6-methylpyridin-2-yl)-5-(quinoxalin-6-yl)-1H-pyrazole-3-carboxyamide | 8.87-8.85(m, 3H), 8.08-8.04(m, 2H), 7.73-7.64(m, 4H), 7.35(d, 1H), 7.30(s, 1H), 7.18(d, 1H), 7.07(t, 2H), 2.36(s, 3H) | 425.1/424.1 |
| 184 | 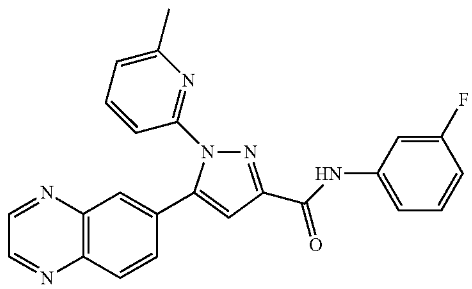 [SMILES: Cc1cccc(-n2nc(C(=O)Nc3cccc(F)c3)cc2-c2ccc3nccnc3c2)n1] | N-(3-fluorophenyl)-1-(6-methylpyridin-2-yl)-5-(quinoxalin-6-yl)-1H-pyrazole-3-carboxyamide | 10.50(s, 1H), 8.97(s, 2H), 8.08-7.94(m, 3H), 7.84-7.68(m, 4H), 7.42(s, 1H), 7.38-7.35(m, 2H), 6.95(t, 1H),2.12(s, 3H) | 425.2/421.1 |
| 185 | 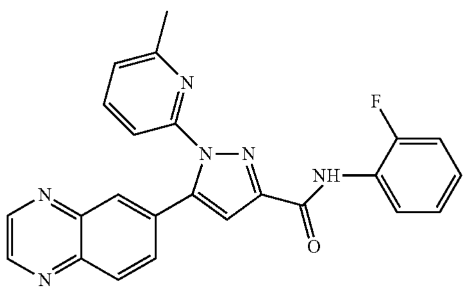 [SMILES: Cc1cccc(-n2nc(C(=O)Nc3ccccc3F)cc2-c2ccc3nccnc3c2)n1] | N-(2-fluorophenyl)-1-(6-methylpyridin-2-yl)-5-(quinoxalin-6-yl)-1H-pyrazole-3-carboxyamide | 9.11(s, 1H), 8.87(s, 2H), 8.53(t, 1H), 8.11-8.04(m, 2H), 7.77-7.66(m, 2H), 7.51 (d, 1H), 7.29(s, 1H), 7.20-7.11(m, 4H), 2.28(s, 3H) | 425.2/424.1 |
| 186 | 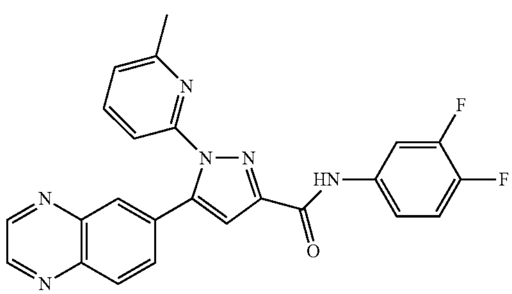 [SMILES: Cc1cccc(-n2nc(C(=O)Nc3ccc(F)c(F)c3)cc2-c2ccc3nccnc3c2)n1] | N-(3,4-difluorophenyl)-1-(6-methylpyridin-2-yl)-5-(quinoxalin-6-yl)-1H-pyrazole-3-carboxyamide | 8.87(s, 2H), 8.83(s, 1H), 8.08-8.04(m, 2H), 7.84-7.80(m, 1H), 7.71-7.63(m, 2H), 7.35(d, 1H), 7.28(s, 2H), 7.25-7.17 (m, 2H), 2.36(s, 3H) | 443.1/442.1 |
| 187 | 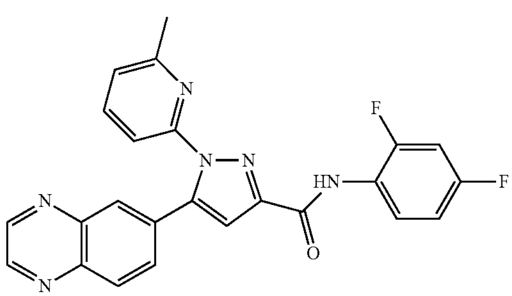 [SMILES: Cc1cccc(-n2nc(C(=O)Nc3ccc(F)cc3F)cc2-c2ccc3nccnc3c2)n1] | N-(2,4-difluorophenyl)-1-(6-methylpyridin-2-yl)-5-(quinoxalin-6-yl)-1H-pyrazole-3-carboxyamide | 8.98(s, 1H), 8.87(s, 2H), 8.48-8.45(m, 1H), 8.10(d, 1H), 8.05(d, 1H), 7.74(t, 1H), 7.66(dd, 1H), 7.48(d, 1H), 7.28(s, 1H), 7.16(d, 1H), 6.96-6.91(m, 2H), 2.28(s, 3H) | 443.1/442.1 |

TABLE 5-continued

| Example Number | Structure | Compound Name | ¹H NMR Spectrum (300 MHz, CDCl₃)δ | MS (ES) Actual Measurement Value[M+H]/ Required Value |
|---|---|---|---|---|
| 188 | 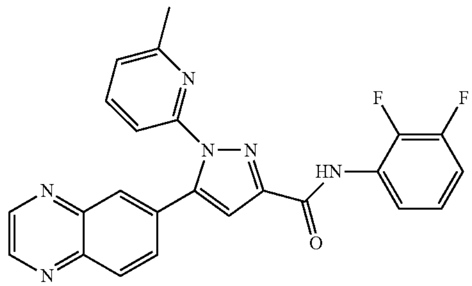 [SMILES: Cc1cccc(-n2nc(C(=O)Nc3cccc(F)c3F)cc2-c2ccc3nccnc3c2)n1] | N-(2,3-difluorophenyl)-1-(6-methylpyridin-2-yl)-5-(quinoxalin-6-yl)-1H-pyrazole-3-carboxamide | 9.13(s, 1H), 8.88(s, 2H), 8.30(t, 1H), 8.11-8.04(m, 2H), 7.75(t, 1H), 7.67(dd, 1H), 7.50(d, 1H), 7.29(s, 1H), 7.19-7.12 (m, 2H), 6.94(q, 1H), 2.28(s, 3H) | 443.1/442.1 |
| 189 | 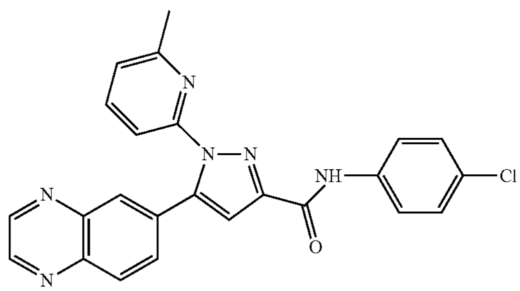 [SMILES: Cc1cccc(-n2nc(C(=O)Nc3ccc(Cl)cc3)cc2-c2ccc3nccnc3c2)n1] | N-(4-chlorophenyl)-1-(6-methylpyridin-2-yl)-5-(quinoxalin-6-yl)-1H-pyrazole-3-carboxamide | 8.87(s, 3H), 8.08-8.04(m, 2H), 7.73-7.63(m, 4H), 7.36-7.29(m, 4H), 7.18(d, 1H), 2.36(s, 3H) | 441.1/440.1 |
| 190 | 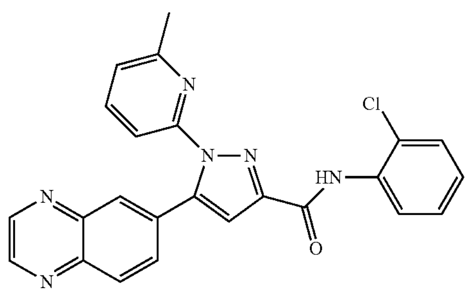 [SMILES: Cc1cccc(-n2nc(C(=O)Nc3ccccc3Cl)cc2-c2ccc3nccnc3c2)n1] | N-(2-chlorophenyl)-1-(6-methylpyridin-2-yl)-5-(quinoxalin-6-yl)-1H-pyrazole-3-carboxamide | 9.51(s, 1H), 8.87(s, 2H), 8.61(d, 1H), 8.12(d, 1H), 8.05(d, 1H), 7.77(t, 1H), 7.69(dd, 1H), 7.59(d, 1H), 7.43(dd, 1H), 7.34(t, 1H), 7.29(s, 1H), 7.15(d, 1H), 7.09(t, 1H), 2.23(s, 1H) | 441.1/440.1 |
| 191 | 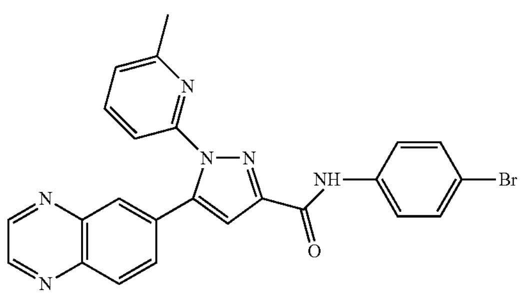 [SMILES: Cc1cccc(-n2nc(C(=O)Nc3ccc(Br)cc3)cc2-c2ccc3nccnc3c2)n1] | N-(4-bromophenyl)-1-(6-methylpyridin-2-yl)-5-(quinoxalin-6-yl)-1H-pyrazole-3-carboxamide | (300 MHz, DMSO-d₆) δ 10.44 (s, 1H), 8.97(s, 2H), 8.08-8.04(m, 2H), 7.96(t, 1H), 7.84(d, 2H), 7.78-7.71(m, 2H), 7.55(s, 2H), 7.41(s, 1H), 7.36(d, 1H), 2.18(s, 3H) | 485.1/484.1 |
| 192 | 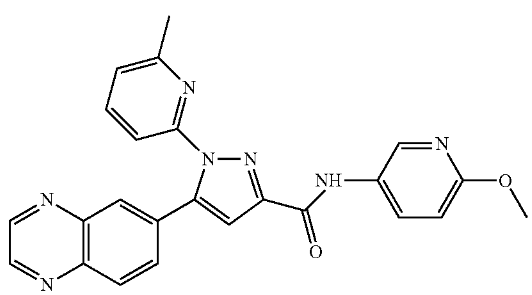 [SMILES: COc1ccc(NC(=O)c2cc(-c3ccc4nccnc4c3)n(-c3cccc(C)n3)n2)cn1] | N-(6-methoxypyridin-3-yl)-1-(6-methylpyridin-2-yl)-5-(quinoxalin-6-yl)-1H-pyrazole-3-carboxamide | (300 MHz, DMSO-d₆) δ 10.40 (s, 1H), 8.96(s, 2H), 8.59(d, 1H), 8.14-8.03(m, 3H), 7.96(t, 1H), 7.77(d, 1H), 7.70(d, 1H), 7.40(s, 1H), 7.36(d, 1H), 6.85(d, 1H), 3.85(s, 3H), 2.19(s, 3H) | 438.2/437.2 |

TABLE 5-continued

| Example Number | Structure | Compound Name | $^1$H NMR Spectrum (300 MHz, CDCl$_3$)δ | MS (ES) Actual Measurement Value[M+H]/ Required Value |
|---|---|---|---|---|
| 193 | 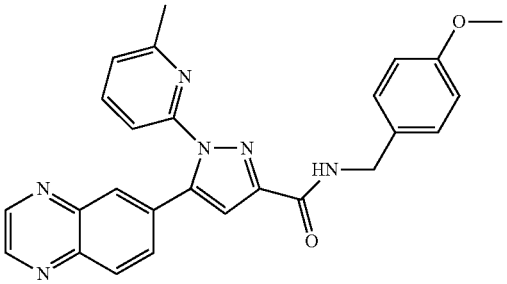 [SMILES: COc1ccc(CNC(=O)c2cc(-c3ccc4nccnc4c3)n(-c3cccc(C)n3)n2)cc1] | N-(4-methoxybenzyl)-1-(6-methylpyridin-2-yl)-5-(quinoxalin-6-yl)-1H-pyrazole-3-carboxyamide | 8.86(s, 2H), 8.06-8.02(m, 2H), 7.65(t, 2H), 7.33-7.24(m, 5H), 7.12(d, 1H), 6.89(d, 2H), 4.6l(d, 2H), 3.81(s, 3H), 2.29(s, 3H) | 451.2/450.2 |
| 194 | 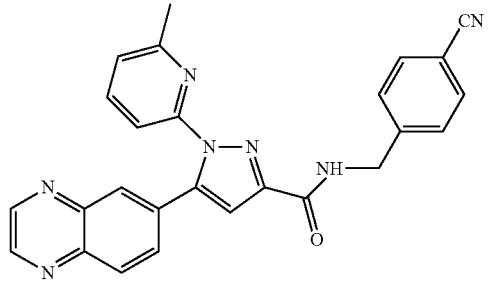 [SMILES: Cc1cccc(-n2nc(C(=O)NCc3ccc(C#N)cc3)cc2-c2ccc3nccnc3c2)n1] | N-(4-cyanobenzyl)-1-(6-methylpyridin-2-yl)-5-(quinoxalin-6-yl)-1H-pyrazole-3-carboxyamide | 8.87(s, 2H), 8.06(d, 1H), 8.03(s, 1H), 7.69-7.62(m, 4H), 7.51-7.49(m, 3H), 7.30(d, 1H), 7.25(s, 1H), 7.16(d, 1H), 4.74(d, 2H), 2.33(s, 3H) | 446.2/445.2 |
| 195 | 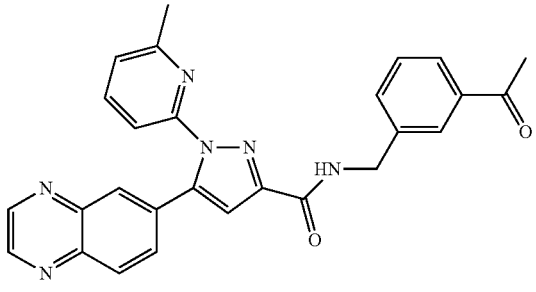 [SMILES: CC(=O)c1cccc(CNC(=O)c2cc(-c3ccc4nccnc4c3)n(-c3cccc(C)n3)n2)c1] | N-(3-acetylbenzyl)-1-(6-methylpyridin-2-yl)-5-(quinoxalin-6-yl)-1H-pyrazole-3-carboxyamide | 8.86(s, 2H), 8.07-8.02(m, 2H), 7.97(s, 1H), 7.88(d, 1H), 7.66-7.61(m, 3H), 7.49-7.44(m, 2H), 7.32(d, 1H), 7.25(s, 1H), 7.14(d, 1H), 4.74(d, 2H), 2.62(s, 3H), 2.31(s, 3H) | 463.2/462.2 |
| 196 | 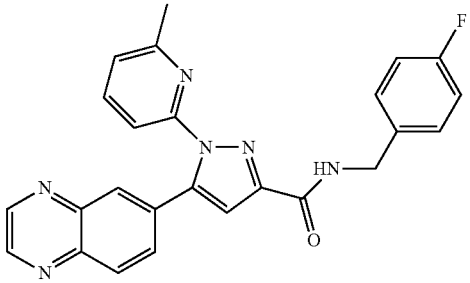 [SMILES: Cc1cccc(-n2nc(C(=O)NCc3ccc(F)cc3)cc2-c2ccc3nccnc3c2)n1] | N-(4-fluorobenzyl)-1-(6-methylpyridin-2-yl)-5-(quinoxalin-6-yl)-1H-pyrazole-3-carboxyamide | 8.86(s, 2H), 8.06-8.02(m, 2H), 7.65-7.62(m, 2H), 7.38-7.29(m, 4H), 7.25(s, 1H), 7.14(d, 1H), 7.04(t, 2H), 4.65(d, 2H), 2.31 (s, 3H) | 439.2/438.2 |
| 197 | 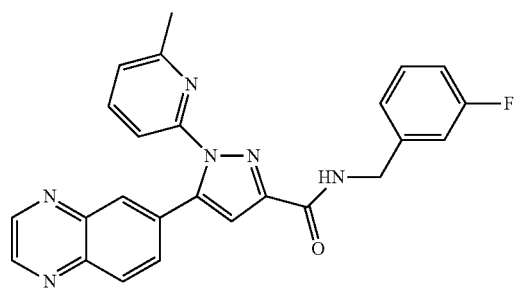 [SMILES: Cc1cccc(-n2nc(C(=O)NCc3cccc(F)c3)cc2-c2ccc3nccnc3c2)n1] | N-(3-fluorobenzyl)-1-(6-methylpyridin-2-yl)-5-(quinoxalin-6-yl)-1H-pyrazole-3-carboxyamide | 8.86(s, 2H), 8.07-8.03(m, 2H), 7.66-7.63(m, 2H), 7.42(t, 1H), 7.34-7.30(m, 2H), 7.25(s, 1H), 7.18-7.13(m, 3H), 6.98(t, 1H), 4.68(d, 2H), 2.31(s, 3H) | 439.2/438.2 |

TABLE 5-continued

| Example Number | Compound Name | ¹H NMR Spectrum (300 MHz, CDCl₃)δ | MS (ES) Actual Measurement Value[M+H]/ Required Value |
|---|---|---|---|
| 198 | N-(2-fluorobenzyl)-1-(6-methylpyridin-2-yl)-5-(quinoxalin-6-yl)-1H-pyrazole-3-carboxyamide | 8.86(s, 2H), 8.06-8.02 (m, 2H), 7.67-7.62 (m, 2H), 7.49-7.33(m, 3H), 7.23(s, 1H), 7.15-7.04(m, 3H), 4.74(d, 2H), 2.30(s, 3H) | 439.2/438.2 |
| 199 | N-(4-chlorobenzyl)-1-(6-methylpyridin-2-yl)-5-(quinoxalin-6-yl)-1H-pyrazole-3-carboxyamide | 8.86(s, 2H), 8.06-8.02(m, 2H), 7.68-7.62(m, 2H), 7.40(t, 1H), 7.32-7.30(m, 3H), 7.25(d, 2H), 7.14(d, 1H), 4.65(d, 2H), 2.31(s, 3H) | 455.1/454.1 |
| 200 | N-(3-chlorobenzyl)-1-(6-methylpyridin-2-yl)-5-(quinoxalin-6-yl)-1H-pyrazole-3-carboxyamide | 8.84(s, 2H), 8.05-8.01 (m, 2H), 7.67-7.61 (m, 2H), 7.36(s, 1H), 7.25-7.23 (m, 5H), 7.13(d, 1H), 4.63(d, 2H), 2.78(s, 3H) | 455.1/454.1 |
| 201 | N-(2-chlorobenzyl)-1-(6-methylpyridin-2-yl)-5-(quinoxalin-6-yl)-1H-pyrazole-3-carboxyamide | 8.86(s, 2H), 8.06-8.02 (m, 2H), 7.67-7.62 (m, 2H), 7.51 7.49(m, 2H), 7.37-7.34(m, 2H), 7.26-7.23(m 2H), 7.14(d, 2H), 4.78(d, 2H), 2.80(s, 3H) | 455.1/454.1 |

[Example 202] Preparation of N-(2-fluorophenyl)-5-(quinoxalin-6-yl)-1-(m-tolyl)-1H-pyrazole-3-carboxamide

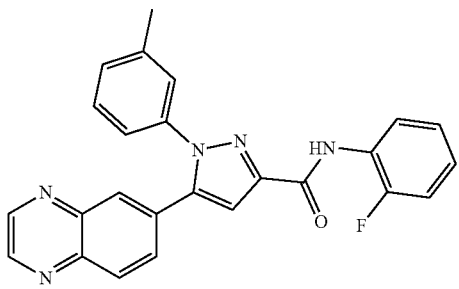 [SMILES: Cc1cccc(-n2nc(C(=O)Nc3ccccc3F)cc2-c2ccc3nccnc3c2)c1]

A target compound (3 mg) was obtained in the same manner as in Example 160 except that phenylhydrazine was used instead of 2-hydrazinyl-6-methylpyridine hydrochloric acid in Step 3 of Preparation Example 3, and 2-fluoroaniline was used instead of p-anisidine of Example 160.

$^1$H NMR spectrum (300 MHz, CDCl$_3$) δ 9.08 (s, 1H), 8.87 (s, 2H), 8.53 (t, 1H), 8.07-8.03 (m, 2H), 7.59 (dd, 1H), 7.32 (s, 2H), 7.24-7.07 (m, 6H), 2.37 (s, 3H).

MS (ESI$^+$): [M+H]$^+$ m/z 424.2

Examples 203 to 208

Compounds of Examples 203 to 208 listed in the following [Table 6] were obtained in the same manner as in Example 202.

TABLE 6

| Example Number | Structure | Compound Name | $^1$H NMR Spectrum (300 MHz, CDCl$_3$)δ | MS (ES) Actual Measurement Value [M+H]$^+$/ Required Value |
|---|---|---|---|---|
| 203 | 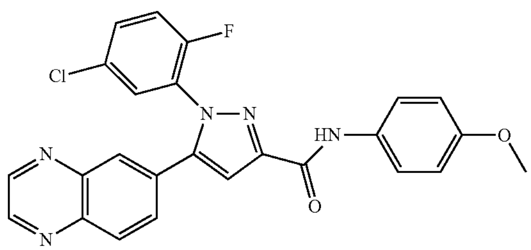 [SMILES: COc1ccc(NC(=O)c2cc(-c3ccc4nccnc4c3)n(-c3cc(Cl)ccc3F)n2)cc1] | 1-(5-chloro-2-fluorophenyl)-N-(4-methoxyphenyl)-5-(quinoxalin-6-yl)-1H-pyrazole-3-carboxamide | 8.87-8.85(m, 2H), 8.67(s, 1H), 8.10 (d, 1H), 7.97(d, 1H), 7.71-7.62 (m, 4H), 7.40-7.35(m, 1H), 7.33 (s, 1H), 7.04(t, 1H), 6.92(d, 2H), 3.82(s, 3H) | 474.1/473.1 |
| 204 | 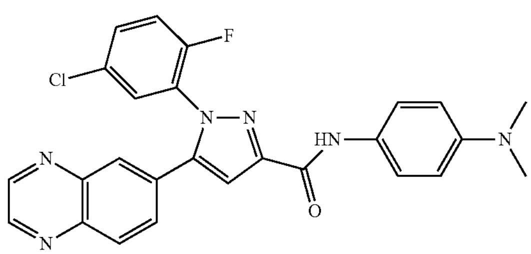 [SMILES: CN(C)c1ccc(NC(=O)c2cc(-c3ccc4nccnc4c3)n(-c3cc(Cl)ccc3F)n2)cc1] | 1-(5-chloro-2-fluorophenyl)-N-(4-(dimethylamino)phenyl)-5-(quinoxalin-6-yl)-1H-pyrazole-3-carboxamide | 8.86-8.85(m, 2H), 8.60(s, 1H), 8.10 (d, 1H), 7.97(d, 1H), 7.71-7.68 (m, 2H), 7.57(d, 2H), 7.43-7.40(m, 1H), 7.32(s, 1H), 7.03(t, 1H), 6.75 (d, 2H), 2.95(s, 3H) | 487.1/486.1 |
| 205 | 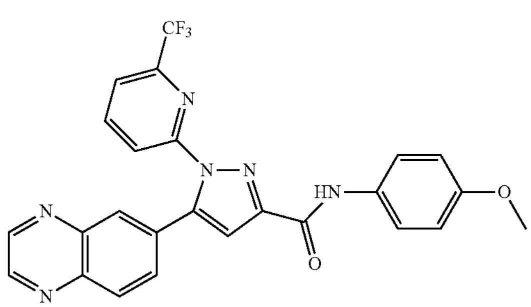 [SMILES: COc1ccc(NC(=O)c2cc(-c3ccc4nccnc4c3)n(-c3cccc(C(F)(F)F)n3)n2)cc1] | N-(4-methoxyphenyl)-5-(quinoxalin-6-yl)-1-(6-trifluoromethyl)pyridin-2-yl)-1H-pyrazole-3-carboxamide | 8.89-8.86(m, 2H), 8.73(s, 1H), 8.14-8.02 (m, 4H), 7.73(d, 1H), 7.65(d, 2H), 7.60(d, 1H), 6.93(d, 2H), 3.82(s, 3H) | 491.1/490.1 |

TABLE 6-continued

| Example Number | Structure | Compound Name | ¹H NMR Spectrum (300 MHz, CDCl₃)δ | MS (ES) Actual Measurement Value [M+H]⁺/ Required Value |
|---|---|---|---|---|
| 206 | 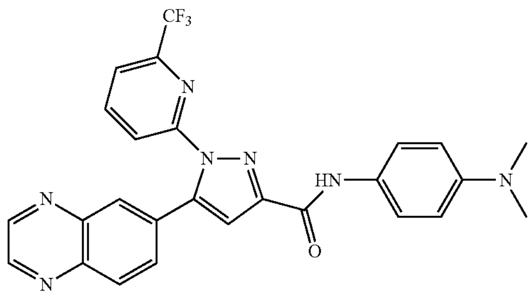 [SMILES: CN(C)c1ccc(NC(=O)c2cc(-c3ccc4nccnc4c3)n(-c3cccc(C(F)(F)F)n3)n2)cc1] | N-4-(dimethylamino)phenyl)-5-(quinoxalin-6-yl)-1-(6-trifluoromethyl)pyridin-2-yl)-1H-pyrazole-3-carboxyamide | 8.89-8.86(m, 2H), 8.65(s, 1H), 8.15-8.03 (m, 4H), 7.74 (d, 1H), 7.61-7.58(m, 3H), 6.77(d, 2H), 2.96(s, 6H) | 504.2/503.2 |
| 207 | 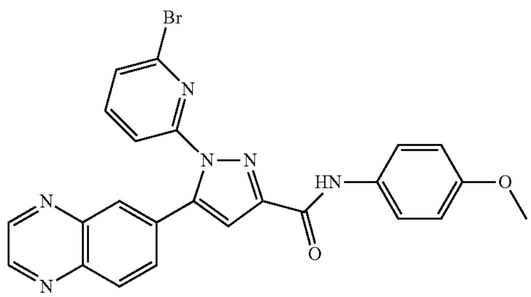 [SMILES: COc1ccc(NC(=O)c2cc(-c3ccc4nccnc4c3)n(-c3cccc(Br)n3)n2)cc1] | 1-(6-bromopyridin-2-yl)-N-(4-methoxyphenyl)-5-(quinoxalin-6-yl)-1H-pyrazole-3-carboxyamide | 8.89(s, 2H), 8.75(s, 1H), 8.13-8.10(m, 2H), 7.72-7.63(m, 5H), 7.46-7.44 (m, 1H), 6.93(d, 2H), 3.82(s, 3H) | 501.1/500.1 |
| 208 | 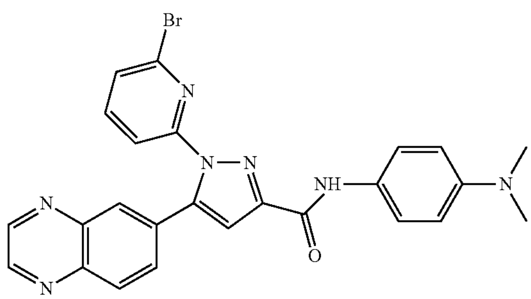 [SMILES: CN(C)c1ccc(NC(=O)c2cc(-c3ccc4nccnc4c3)n(-c3cccc(Br)n3)n2)cc1] | 1-(6-bromopyridin-2-yl)-N-(4-(dimethylamino)phenyl)-5-(quinoxalin-6-yl)-1H-pyrazole-3-carboxyamide | 8.88(s, 2H), 8.65 (s, 1H), 8.12-8.09 (m, 2H), 7.70(dd, 3H), 7.59(d, 2H), 7.44(d, 1H), 6.77(d, 2H), 2.95(s, 6H) | 514.1/513.1 |

[Example 209] N-(2-Fluorophenyl)-1-(6-methylpyridin-2-yl)-5-(quinolin-4-yl)-1H-pyrazole-3-carboxyamide

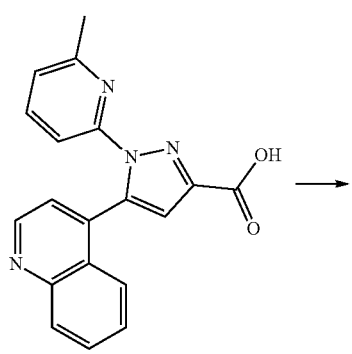

→

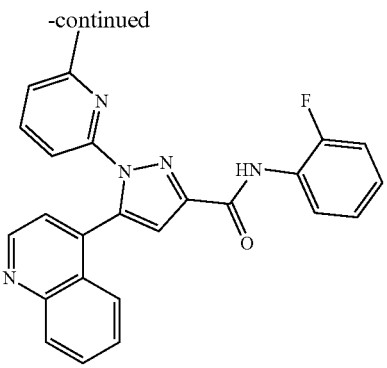

After dissolving 1-(6-methylpyridin-2-yl)-5-(quinolin-4-yl)-1H-pyrazole-3-carboxylic acid (40 mg, 0.1 mmol) synthesized in Step 5 of Preparation Example 4 in dichloromethane, HATU (55 mg, 0.1 mmol) and DIPEA (47 μL, 0.4 mmol) were introduced thereto and the result was stirred for 20 minutes at room temperature. To the reaction solution, 2-fluoroaniline (13 mg, 0.1 mmol) was introduced, and the result was stirred for 12 hours at room temperature. After terminating the reaction, ethyl acetate was added thereto. The result was washed with sodium bicarbonate, then dried using anhydrous magnesium sulfate, and after filtering, the filtrate was concentrated. The filtrate was purified using column chromatography to obtain a target compound (16 mg).

¹H NMR spectrum (300 MHz, CDCl₃) δ 9.17 (s, 1H), 8.93 (d, 1H), 8.55 (t, 1H), 8.15 (d, 1H), 7.69-7.60 (m, 4H), 7.41 (t, 1H), 7.33 (d, 1H), 7.25-7.12 (m, 4H), 6.95 (d, 1H), 1.83 (s, 3H).

MS (ESI⁺): [M+H]⁺ m/z 424.2

Examples 210 to 217

Compounds of Examples 210 to 217 listed in the following [Table 7] were obtained in the same manner as in Example 209 using various amine derivatives instead of 2-fluoroaniline.

TABLE 7

| Example | Structure | Compound Name | Material Information |
|---|---|---|---|
| 210 | 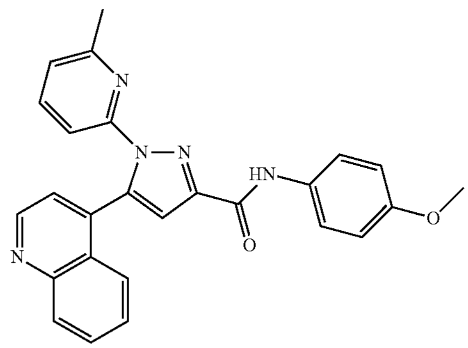 [SMILES: COc1ccc(NC(=O)c2cc(-c3ccnc4ccccc34)n(-c3cccc(C)n3)n2)cc1] | N-(4-methoxyphenyl)-1-(6-methylpyridin-2-yl)-5-(quinolin-4-yl)-1H-pyrazole-3-carboxyamide | ¹H NMR (300 MHz, CDCl₃) δ 8.92(d, 1H), 8.78(s, 1H), 8.15(d, 1H), 7.72-7.57(m, 5H), 7.48-7.40(m, 2H), 7.32(d, 1H), 7.26(s, 1H), 6.95(d, 3H), 3.83 (s, 3H), 1.92(s, 3H). MS (ESI⁺): [M+H]⁺ m/z436 |
| 211 | 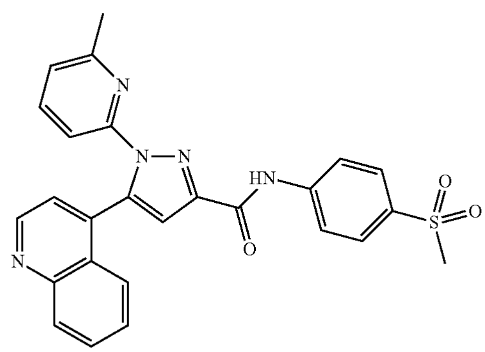 [SMILES: Cc1cccc(-n2nc(C(=O)Nc3ccc(S(C)(=O)=O)cc3)cc2-c2ccnc3ccccc23)n1] | 1-(6-methylpyridin-2-yl)-N-(4-(methylsulfonyl)phenyl)-5-(quinolin-4-yl)-1H-pyrazole-3-carboxyainide | ¹H NMR (300 MHz, CDCl₃) δ 9.13(s, 1H), 8.93(d, 1H), 8.16(d, 1H), 7.98 (s, 4H), 7.7l(t, 1H), 7.65-7.58(m, 2H), 7.44(d, 2H), 7.33-7.28(m, 2H), 6.98(d, 1H), 3.08(s, 3H), 1.96(s, 3H). MS (ESI⁺): [M+H]⁺ m/z 484 |
| 212 | 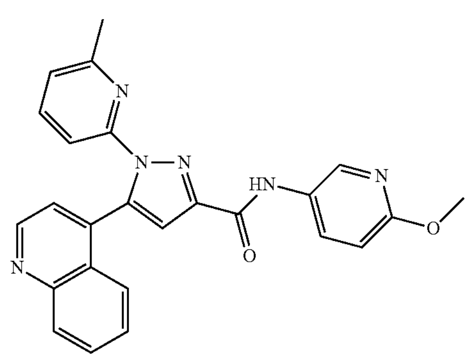 [SMILES: COc1ccc(NC(=O)c2cc(-c3ccnc4ccccc34)n(-c3cccc(C)n3)n2)cn1] | N-(6-methoxypyridin-3-yl)-1-(6-methylpyridin-2-yl)-5-(quinolin-4-yl)-1H-pyrazole-3-carboxyamide | ¹H NMR (300 MHz, CDCl₃) δ 8.92(d, 1H), 8.81(s, 1H), 8.41(d, 1H), 8.17-8.13(m, 2H), 7.70-7.57(m, 3H), 7.45-7.41(m, 2H), 7.31(d, 1H), 7.26(s, 1H), 6.96(d, 1H), 6.81(d, 1H), 3.96(s, 3H), 1.95(s, 3H). MS (ESI⁺): [M+H]⁺ m/z 437 |

TABLE 7-continued

| Example | Structure | Compound Name | Material Information |
|---|---|---|---|
| 213 | 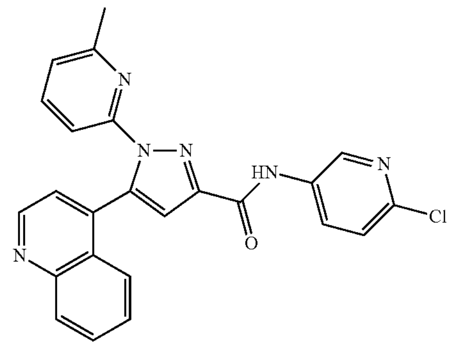 [SMILES: Cc1cccc(-n2nc(C(=O)Nc3ccc(Cl)nc3)cc2-c2ccnc3ccccc23)n1] | N-(6-chloropyridin-3-yl)-1-(6-methylpyridin-2-yl)-5-(quinolin-4-yl)-1H-pyrazole-3-carboxyamide | $^1$H NMR (300 MHz, CDCl$_3$) δ 8.99(s, 1H), 8.92(d, 1H), 8.62(d, 1H), 8.40 (d, 1H), 8.15(d, 1H), 7.70-7.58 (m, 3H), 7.45-7.26(m, 5H), 6.97 (d, 1H), 1.95(s, 3H). MS (ESI$^+$): [M+H]$^+$ m/z 441 |
| 214 | 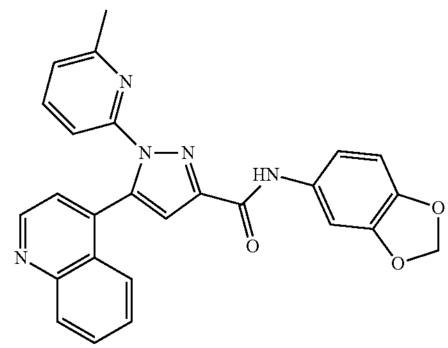 [SMILES: Cc1cccc(-n2nc(C(=O)Nc3ccc4c(c3)OCO4)cc2-c2ccnc3ccccc23)n1] | N-(benzo[d][1,3]dioxol-5-yl)-1-(6-methylpyridin-2-yl)-5-(quinolin-4-yl)-1H-pyrazole-3-carboxyamide | $^1$H NMR (300 MHz, CDCl$_3$) δ 8.92 (d, 1H), 8.80(s, 1H), 8.15(d, 1H), 7.69-7.56(m, 3H), 7.49-7.42 (m, 3H), 7.31(d, 1H), 7.24(s, 1H), 7.05(d, 1H), 6.94(d, 1H), 6.81(d, 1H), 5.99(s, 2H), 1.95(s, 3H). MS (ESI$^+$): [M+H]$^+$ m/z 450 |
| 215 | 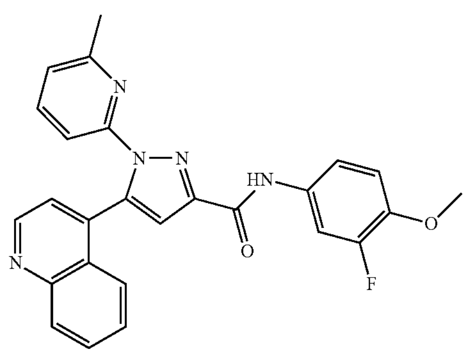 [SMILES: COc1ccc(NC(=O)c2cc(-c3ccnc4ccccc34)n(-c3cccc(C)n3)n2)cc1F] | N-(3-fluoro-4-methoxyphenyl)-1-(6-methylpyridin-2-yl)-5-(quinolin-4-yl)-1H-pyrazole-3-carboxyamide | $^1$H NMR (300 MHz, CDCl$_3$) δ 8.90(d, 1H), 8.85(s, 1H), 8.15 (d, 1H), 7.70-7.59(m, 4H), 7.46-7.41(m, 3H), 7.32-7.24(m, 2H), 6.97-6.93 (m, 2H), 3.93(s, 3H), 1.95 (s, 3H). MS (ESI$^+$): [M+H]$^+$ m/z 454 |
| 216 | 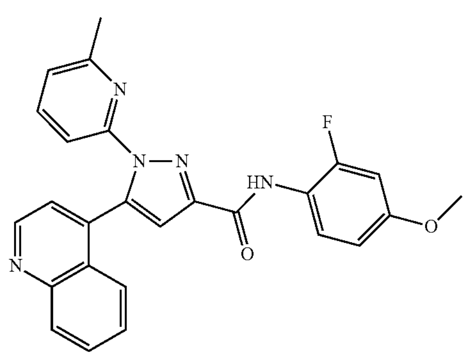 [SMILES: COc1ccc(NC(=O)c2cc(-c3ccnc4ccccc34)n(-c3cccc(C)n3)n2)c(F)c1] | N-(2-fluoro-4-methoxyphenyl)-1-(6-methylpyridin-2-yl)-5-(quinolin-4-yl)-1H-pyrazole-3-carboxyamide | $^1$H NMR (300 MHz, CDCl$_3$) δ 8.94-8.92(m, 2H), 8.34(t, 1H), 8.15(d, 1H), 7.69-7.59(m, 4H), 7.41(t, 1H), 7.31(d, 1H), 7.23 (s, 1H), 6.92(d, 1H), 6.76(d, 2H), 3.82(s, 3H), 1.83(s, 3H). MS (ESI$^+$): [M+H]$^+$ m/z 454 |

| Example | Structure | Compound Name | Material Information |
|---|---|---|---|
| 217 | 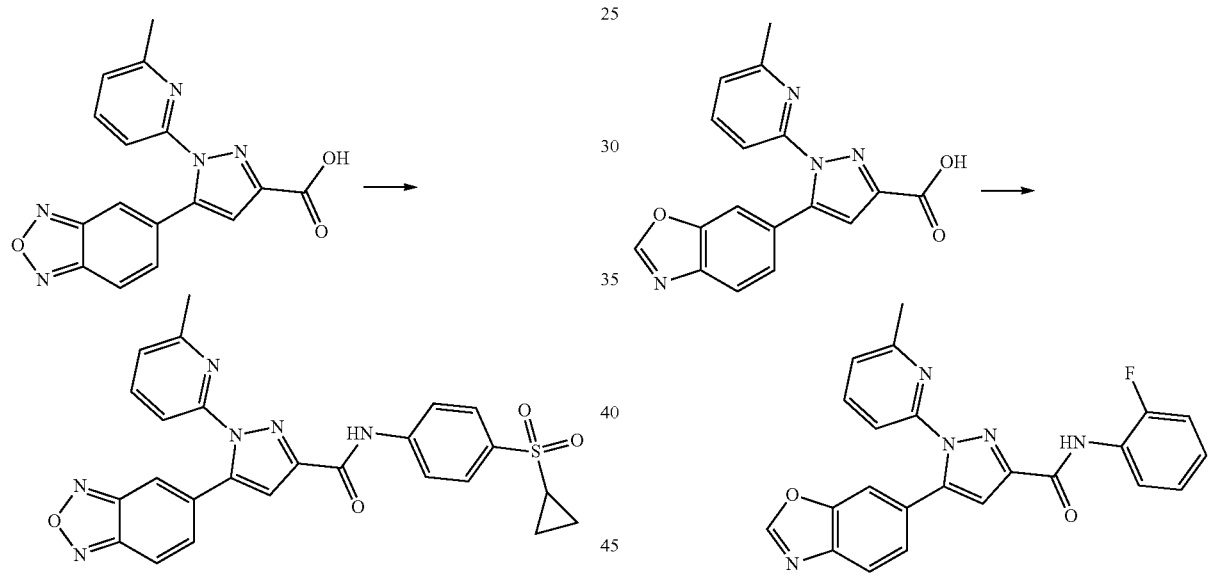 | N-(4-(2-methoxyethoxy)phenyl)-1-(6-methylpyridin-2-yl)-5-(quinolin-4-yl)-1H-pyrazole-3-carboxyamide | ¹H NMR (300 MHz, CDCl₃) δ 8.92(d, 1H). 8.84(s, 1H), 8.15 (d, 1H), 7.70-7.55(m, 5H), 7.48-7.41(m, 2H), 7.32-¹H NMR (300 MHz, CDCl₃) δ 7.24(m, 2H), 6.98-6.91 (m, 3H), 4.15-4.10(m, 2H), 3.78-3.75(m, 2H), 3.46 (s, 3H), 1.90(s, 3H). MS (ESI⁺): [M+H]⁺ m/z 480 |

[Example 218] 5-(Benzo[c][1,2,5]oxadiazol-5-yl)-N-(4-(cyclopropylsulfonyl)phenyl)-1-(6-methylpyridin-2-yl)-1H-pyrazole-3-carboxyamide

[Example 219] 5-(Benzo[d]oxazol-6-yl)-N-(2-fluorophenyl)-1-(6-methylpyridin-2-yl)-1H-pyrazole-3-carboxyamide After dissolving 5-(benzo[c][1,2,5]oxadiazol-5-yl)-1-(6-methylpyridin-2-yl)-1H-pyrazole-3-carboxylic acid (30 mg, 0.1 mmol) synthesized in Step 5 of Preparation Example 5 in dichloromethane, HATU (43 mg, 0.1 mmol) and DIPEA (48 L, 0.3 mmol) were introduced thereto, and the result was stirred for 20 minutes at room temperature. To the reaction solution, 4-(cyclopropylsulfonyl)aniline (21 mg, 0.1 mmol) was introduced, and the result was stirred for 12 hours at room temperature. After terminating the reaction, ethyl acetate was added thereto. The result was washed with sodium bicarbonate, then dried using anhydrous magnesium sulfate, and after filtering, the filtrate was concentrated. The filtrate was purified using column chromatography to obtain a target compound (5 mg).

¹H NMR spectrum (300 MHz, CDCl₃) δ 9.02 (s, 1H), 7.93 (s, 4H), 7.84-7.75 (m, 3H), 7.60 (s, 1H), 7.31-7.26 (m, 2H), 7.18 (d, 1H), 2.50-2.45 (m, 1H), 2.28 (s, 3H), 1.39-1.34 (m, 2H), 1.06-1.03 (m, 2H).

MS (ESI⁺): [M+H]⁺ m/z 501

After dissolving 5-(benzo[d]oxazol-6-yl)-1-(6-methylpyridin-2-yl)-1H-pyrazole-3-carboxylic acid (50 mg, 0.2 mmol) synthesized in Step 6 of Preparation Example 6 in dichloromethane, HATU (71 mg, 0.2 mmol) and DIPEA (81 μL, 0.5 mmol) were introduced thereto, and the result was stirred for 20 minutes at room temperature. To the reaction solution, 2-fluoroaniline (17 mg, 0.2 mmol) was introduced, and the result was stirred for 12 hours at room temperature. After terminating the reaction, ethyl acetate was added thereto. The result was washed with sodium bicarbonate, then dried using anhydrous magnesium sulfate, and after filtering, the filtrate was concentrated. The filtrate was purified using column chromatography to obtain a target compound (29 mg).

¹H NMR spectrum (300 MHz, CDCl₃) δ 9.09 (s, 1H), 8.51 (t, 1H), 8.13 (s, 1H), 7.74-7.70 (m, 2H), 7.58 (d, 1H), 7.34-7.26 (m, 2H), 7.18-7.11 (m, 5H), 2.37 (s, 3H).

MS (ESI⁺): [M+H]⁺ m/z 414

Examples 220 to 227

Using compounds prepared in the preparation examples, compounds of Examples 220 to 227 listed in the following [Table 8] were obtained in the same manner as in Example 219 using various amines instead of 2-fluoroaniline.

TABLE 8

| Example | Structure | Compound Name | Material Information |
|---|---|---|---|
| 220 | 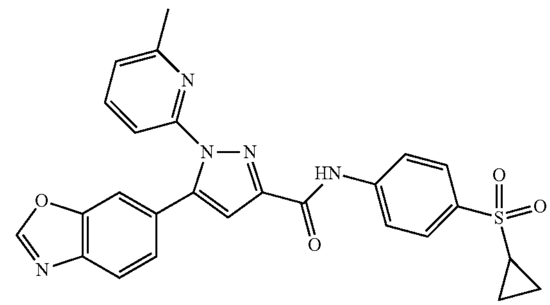 [SMILES: Cc1cccc(-n2nc(C(=O)Nc3ccc(S(=O)(=O)C4CC4)cc3)cc2-c2ccc3ncoc3c2)n1] | 5-(benzo[d]oxazol-6-yl)-N-(4-(cyclopropylsulfonyl)phenyl)-1-(6-methylpyridin-2-yl)-1H-pyrazole-3-carboxyamide | $^1$H NMR (300 MHz, CDCl$_3$) δ 9.10(s, 1H), 8.14(s, 1H), 7.95-7.90(m, 4H), 7.75-7.65(m, 2H), 7.57(s, 1H), 7.29-7.15(m, 4H), 2.50-2.45(m, 4H), 1.37-1.35(m, 2H), 1.05-1.02(m, 2H). MS (ESI$^+$): [M+H]$^+$ m/z 500 |
| 221 | 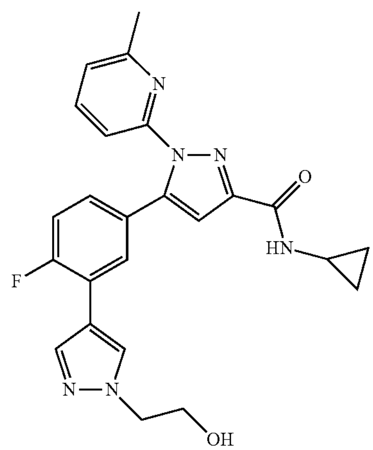 [SMILES: Cc1cccc(-n2nc(C(=O)NC3CC3)cc2-c2ccc(F)c(-c3cnn(CCO)c3)c2)n1] | N-cyclopropyl-5-(4-fluoro-3-(1-(2-hydroxyethyl)-1H-pyrazol-4-yl)phenyl)-1-(6-methylpyridin-2-yl)-1H-pyrazole-3-carboxyamide | $^1$H NMR (300 MHz, CDCl$_3$) δ 7.82 (s, 1H), 7.69-7.64 (m, 2H), 7.45 (d, 1H), 7.20-7.15 (m, 3H), 7.05-7.02 (m, 3H), 4.28 (t, 2H), 4.03 (t, 2H), 2.70 (q, 1H), 2.47 (s, 3H), 0.88 (q, 2H), 0.69 (q, 2H). MS (ESI$^+$): [M+H]$^+$ m/z 447 |
| 222 | 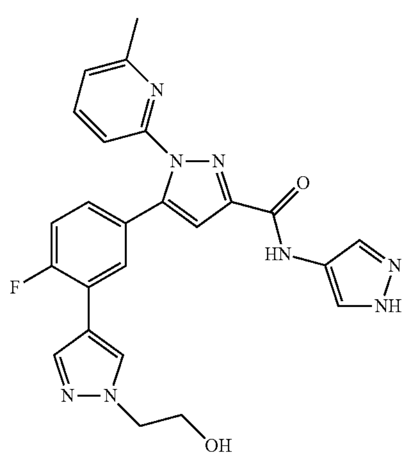 [SMILES: Cc1cccc(-n2nc(C(=O)Nc3cn[nH]c3)cc2-c2ccc(F)c(-c3cnn(CCO)c3)c2)n1] | N-(1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxyamlde | $^1$H NMR (300 MHz, MeOD) δ 8.52 (s, 2H), 8.20 (s, 1H), 8.00 (s, 1H), 7.94 (t, 1H), 7.69 (d, 1H), 7.53 (d, 1H), 7.40 (d, 1H), 7.21-7.18 (m, 3H), 4.35 (t, 2H), 3.94 (t, 2H), 2.43 (s, 3H). MS (ESI$^+$): [M+H]$^+$ m/z 473 |

TABLE 8-continued

| Example | Structure | Compound Name | Material Information |
|---|---|---|---|
| 223 | 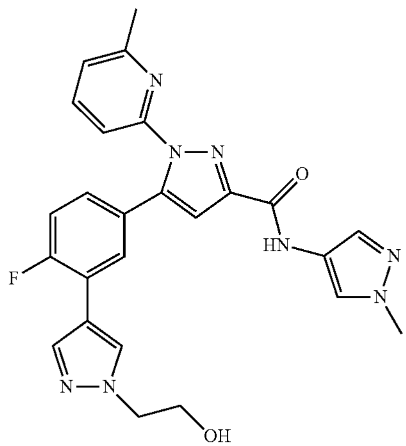 [SMILES: Cc1cccc(-n2nc(C(=O)Nc3cnn(C)c3)cc2-c2ccc(F)c(-c3cnn(CCO)c3)c2)n1] | N-(1-methyl-1H-pyrazol-4-yl)-5-(4-fluoro-3-(1-(2-hydroxyethyl)-1H-pyrazol -4-yl)phenyl)-1-(6-methylpyridin-2-yl)-1H-pyrazole-3-carboxyamide | $^1$H NMR (300 MHz, MeOD) δ 8.80 (s, 1H), 8.03 (s, 1H), 7.81 (s, 1H), 7.72-7.64 (m, 2H), 7.50-7.44 (m, 2H), 7.19-7.03 (m, 5H), 4.26 (t, 2H), 4.04 (t, 2H), 3.89 (s, 3H), 2.48 (s, 3H). MS (ESI$^+$): [M+H]$^+$ m/z 487 |
| 224 | 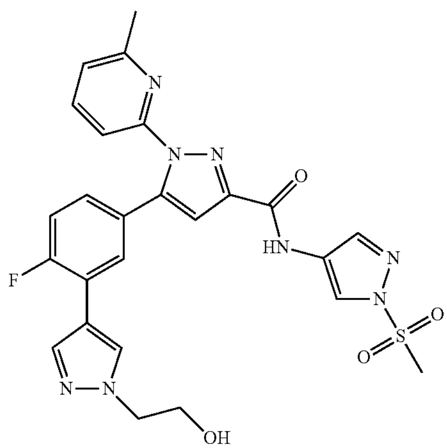 [SMILES: Cc1cccc(-n2nc(C(=O)Nc3cnn(S(C)(=O)=O)c3)cc2-c2ccc(F)c(-c3cnn(CCO)c3)c2)n1] | N-(1-(methylsulfonyl)-1H-pyrazol-4-yl)-5-(4-fluoro-3-(1-(2-hydroxy ethyl)-1H-pyrazol-4-yl)phenyl)-1-(6-methylpyridin-2-yl)-1H-pyrazole-3-carboxyamide | $^1$H NMR (300 MHz, CDCl$_3$) δ 9.04 (s, 1H), 8.60 (s, 1H), 7.99 (s, 1H), 7.83 (s, 1H), 7.71-7.66 (m, 2H), 7.46 (d, 1H), 7.24-7.05 (m, 5H), 4.30 (t, 2H), 4.05 (t, 2H), 3.33 (s, 3H), 2.51 (s, 3H). MS (ESI$^+$): [M+H]$^+$ m/z 551 |
| 225 | 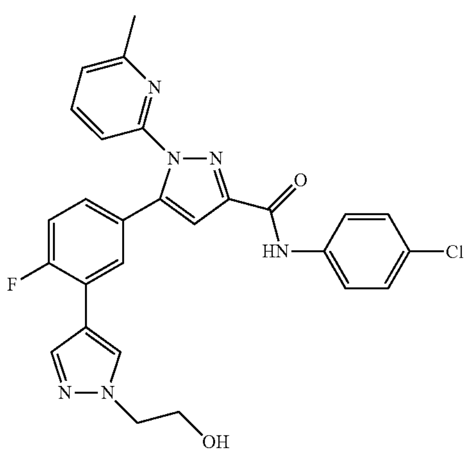 [SMILES: Cc1cccc(-n2nc(C(=O)Nc3ccc(Cl)cc3)cc2-c2ccc(F)c(-c3cnn(CCO)c3)c2)n1] | N-(4-chlorophenyl)-5-(4-fluoro-3-(1-(2-hydroxyethyl)-1H-pyrazol-4-yl)phenyl)-1-(6-methylpyridin-2-yl)-1H-pyrazole-3-carboxyamide | $^1$H NMR (300 MHz, CDCl$_3$) δ 8.89 (s, 1H), 7.84 (s, 1H), 7.74-7.69 (m, 3H), 7.52 (d, 1H), 7.35 (d, 2H), 7.25-7.16 (m, 2H), 7.09 (d, 2H), 4.31 (t, 2H), 4.06 (t, 2H), 3.33 (s, 3H), 2.52 (s, 3H). MS (ESI$^+$): [M+H]$^+$ m/z 517 |

TABLE 8-continued

| Example | Structure | Compound Name | Material Information |
|---|---|---|---|
| 226 | 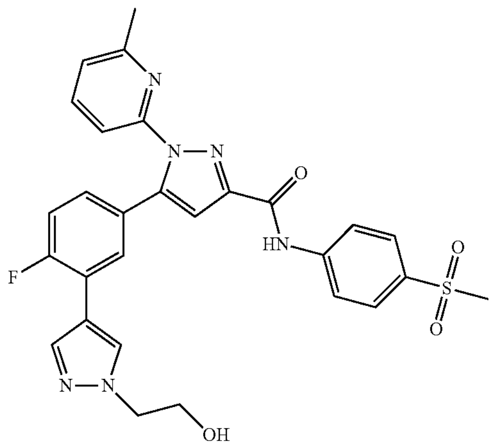 [SMILES: Cc1cccc(-n2nc(C(=O)Nc3ccc(S(C)(=O)=O)cc3)cc2-c2ccc(F)c(-c3cnn(CCO)c3)c2)n1] | N-(4-(methylsulfonyl)phenyl)-5-(4-fluoro-3-(1-(2-hydroxyethyl)-1H-pyrazol-4-yl)phenyl)-1-(6-methylpyridin-2-yl)-1H-pyrazole-3-carboxyamide | $^1$H NMR (300 MHz, CDCl$_3$) δ 9.13 (s, 1H), 7.96 (s, 3H), 7.84 (s, 1H), 7.75-7.70 (m, 2H), 7.50 (d, 1H), 7.24-6.77 (m, 6H), 4.31 (t, 2H), 4.06 (t, 2H), 3.08 (s, 3H), 2.53 (s, 3H). MS (ESI$^+$): [M+H]$^+$ m/z 561 |
| 227 | 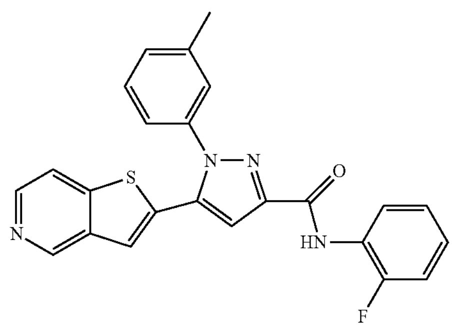 [SMILES: Cc1cccc(-n2nc(C(=O)Nc3ccccc3F)cc2-c2cc3cnccc3s2)c1] | N-(2-fluorophenyl)-5-(thieno[3,2,c]pyridin-2-yl)-1-(m-tolyl)-1H-pyrazole-3-carboxyamide | $^1$H NMR (300 MHz, CDCl$_3$) δ 9.98(s, 1H), 9.1 l(s, 1H), 8.41 (s, 1H), 7.95(d, 2H), 7.80(s, 1H), 7.80(s, 2H), 7.70(d, 1H), 7.50(d, 1H), 7.28-7.23(m, 4H), 2.42(s, 3H) MS (ESI$^+$): [M+H]$^+$ m/z 429 |

Formulation Example 1: Preparation of Tablet

In accordance with common methods, a single tablet for oral administration containing each of the compounds prepared in Examples 1 to 227 as an active compound was prepared using ingredients of the following Table 9 in amounts corresponding thereto.

TABLE 9

| Ingredient | Amount per Tablet |
|---|---|
| Active Compound | 100 mg |
| Corn Starch | 80 mg |
| Lactose | 80 mg |
| Magnesium Stearate | 5 mg |

Formulation Example 2: Preparation of Capsule

In accordance with common methods, a hard gelatin capsule for oral administration containing each of the compounds prepared in Examples 1 to 227 as an active compound was prepared using ingredients of the following Table 10 in amounts corresponding thereto.

TABLE 10

| Ingredient | Amount per Capsule |
|---|---|
| Active Compound | 100 mg |
| Corn Starch | 80 mg |
| Lactose | 80 mg |

TABLE 10-continued

| Ingredient | Amount per Capsule |
|---|---|
| Crystalline Cellulose | 80 mg |
| Magnesium Stearate | 5 mg |

Formulation Example 3: Preparation of Formulation for Injection

In accordance with common methods, a formulation for injection containing each of the compounds prepared in Examples 1 to 227 as an active compound was prepared using ingredients of the following Table 11 in amounts corresponding thereto. However, a pH was not adjusted when using a salt of the compound of Chemical Formula 1 as the active compound.

TABLE 11

| Ingredient | Amount per Formulation for Injection |
|---|---|
| Active Compound | 20 mg |
| 5% Glucose Solution | 10 mL |
| HCl (1N) | Suitable Amount to Make pH to 4 |

Formulation Example 4: Preparation of Formulation for Injection

In accordance with common methods, a formulation for injection containing each of the compounds prepared in Examples 1 to 227 as an active compound was prepared using ingredients of the following Table 12 in amounts corresponding thereto.

TABLE 12

| Ingredient | Amount per Formulation for Injection |
|---|---|
| Active Compound | 20 mg |
| Polyethylene Glycol 400 | 2 mL |
| Sterilized Water | 8 mL |

Experimental Example 1: Activity Inhibition Test on ALK5 Enzyme

For each of the compounds obtained in Examples 1 to 227, inhibitory activity against ALK5 kinase was measured.

For this, a LanthaScreen Eu binding kinase assay method was used, and ALK5 kinase, a kinase buffer, a kinase tracer 178, and a LanthaScreen Eu-GST binding antibody were all purchased from Thermo Fisher Scientific Solutions. Each of the compounds was made into a 10 mM DMSO solution, and diluted by 1/10 to a concentration of 1 μM to 0.0001 μM with an aqueous solution containing 4% DMSO. The test was performed in 384 well plates (well polystyrene low volume round-bottomed plates). First, 5 μL of the diluted compound solution was added, then 5 μL of the kinase/antibody mixture solution was introduced thereto, and 5 μL of the tracer was introduced thereto. Herein, these were added to each well so that the final kinase concentration became 5 nM, the final Eu-GST binding antibody concentration 2 nM, and the kinase tracer 178 concentration 10 nM, and the result was reacted in a stirrer for 60 minutes at room temperature. Then a fluorescence value was measured using a fluorescence meter (molecular device) (620 nm excitation filter, 665 nm emission filter). Herein, as for the degree of compound activity to inhibit the kinase reaction, a phosphorylate rate was calculated from 0% to 100% with respect to a control group according to the protocol included in the kit, and a 50% inhibitory concentration ($IC_{50}$) value was calculated by obtaining the x-axis concentration in the region where 50% activity was inhibited. The $IC_{50}$ results for each of the compounds are shown in the following Table 13.

TABLE 13

| Example | $IC_{50}$ (nM) ALK5 |
|---|---|
| 1 | 5.0 |
| 2 | 4.7 |
| 3 | 12 |
| 4 | 4.4 |
| 5 | 10-100 |
| 6 | 11 |
| 7 | <10 |
| 8 | 4.7 |
| 9 | 19 |
| 10 | 10 |
| 11 | 2.2 |
| 12 | 6.1 |
| 13 | 10-100 |
| 14 | 17 |
| 15 | 6.4 |
| 16 | 2.3 |
| 17 | 14 |
| 18 | 10-100 |
| 19 | 10-100 |
| 20 | 10-100 |
| 21 | ~100 |

TABLE 13-continued

| Example | $IC_{50}$ (nM) ALK5 |
|---|---|
| 22 | 10-100 |
| 23 | ~10 |
| 24 | ~100 |
| 25 | <10 |
| 26 | 10-100 |
| 27 | 6.2 |
| 28 | 4.5 |
| 29 | 3.9 |
| 30 | 5.8 |
| 31 | >100 |
| 32 | 10-100 |
| 33 | 10-100 |
| 34 | 10-100 |
| 35 | 10-100 |
| 36 | <10 |
| 37 | 40 |
| 38 | 1.8 |
| 39 | 2.4 |
| 40 | 3.3 |
| 41 | 5.2 |
| 42 | 2.2 |
| 43 | 4.4 |
| 44 | 13 |
| 45 | 2.4 |
| 46 | 1.3 |
| 47 | 1.2 |
| 48 | 4.1 |
| 49 | 5.6 |
| 50 | 6.6 |
| 51 | 6.5 |
| 52 | 2.5 |
| 53 | 2.4 |
| 54 | 2.0 |
| 55 | 4.2 |
| 56 | 2.4 |
| 57 | 45 |
| 58 | 5.6 |
| 59 | 20 |
| 60 | 13 |
| 61 | 10-100 |
| 62 | 16 |
| 63 | 3.7 |
| 64 | <10 |
| 65 | <10 |
| 66 | 3.2 |
| 67 | 9.6 |
| 68 | 65 |
| 69 | 4.9 |
| 70 | 4.6 |
| 71 | 8.0 |
| 72 | 11 |
| 73 | 5.8 |
| 74 | 2.3 |
| 75 | 7.4 |
| 76 | ~10 |
| 77 | 7.2 |
| 78 | 3.4 |
| 79 | 5.6 |
| 80 | 1.3 |
| 81 | 1.5 |
| 82 | 2.7 |
| 83 | 0.7 |
| 84 | 3.9 |
| 85 | 3.8 |
| 86 | 1.1 |
| 87 | 9.1 |
| 88 | 3.5 |
| 89 | 3.5 |
| 90 | 5.0 |
| 91 | 10-100 |
| 92 | 10-100 |
| 93 | 3.9 |
| 94 | ~10 |
| 95 | 25 |
| 96 | 3.5 |
| 97 | 10-100 |

TABLE 13-continued

| Example | IC$_{50}$ (nM) ALK5 |
|---|---|
| 98 | 5.3 |
| 99 | ~10 |
| 100 | 10-100 |
| 101 | 10-100 |
| 102 | 10-100 |
| 103 | 9.1 |
| 104 | 7.0 |
| 105 | 7.0 |
| 106 | 14 |
| 107 | 10-100 |
| 108 | ~10 |
| 109 | 9.7 |
| 110 | 10-100 |
| 111 | >100 |
| 112 | 10-100 |
| 113 | 10-100 |
| 114 | 9.5 |
| 115 | 10-100 |
| 116 | ~10 |
| 117 | 10-100 |
| 118 | 10-100 |
| 119 | <10 |
| 120 | 10-100 |
| 121 | 10-100 |
| 122 | 10-100 |
| 123 | 10-100 |
| 124 | 31 |
| 125 | 10-100 |
| 126 | ~10 |
| 127 | ~100 |
| 128 | 10-100 |
| 129 | 10-100 |
| 130 | 10-100 |
| 131 | 10-100 |
| 132 | ~10 |
| 133 | 10-100 |
| 134 | 10-100 |
| 135 | 10-100 |
| 136 | ~10 |
| 137 | 10-100 |
| 138 | 10-100 |
| 139 | 10-100 |
| 140 | ~10 |
| 141 | 10-100 |
| 142 | 10-100 |
| 143 | 6.6 |
| 144 | 10-100 |
| 145 | 15 |
| 146 | 6.0 |
| 147 | 3.7 |
| 148 | 8.3 |
| 149 | 7.7 |
| 150 | 4.8 |
| 151 | 2.7 |
| 152 | 4.6 |
| 153 | 25 |
| 154 | ~10 |
| 155 | 13 |
| 156 | 22 |
| 157 | 10-100 |
| 158 | 10-100 |
| 159 | 10-100 |
| 160 | 10-100 |
| 161 | 10-100 |
| 162 | 2.0 |
| 163 | 4.6 |
| 164 | 18 |
| 165 | 24 |
| 166 | ~100 |
| 167 | ≤100 |
| 168 | ≤100 |
| 169 | 10-100 |
| 170 | <100 |
| 171 | 10-100 |
| 172 | 10-100 |
| 173 | 10-100 |
| 174 | <100 |
| 175 | <100 |
| 176 | 100 |
| 177 | ~100 |
| 178 | 10-100 |
| 179 | <100 |
| 180 | 100-1,000 |
| 181 | ~100 |
| 182 | <100 |
| 183 | 10-100 |
| 184 | 10-100 |
| 185 | <100 |
| 186 | 10-100 |
| 187 | 10-100 |
| 188 | 100 |
| 189 | 10-100 |
| 190 | 100-1,000 |
| 191 | 10-100 |
| 192 | 10-100 |
| 193 | ~100 |
| 194 | >100 |
| 195 | 10-100 |
| 196 | 100 |
| 197 | 10-100 |
| 198 | <100 |
| 199 | >100 |
| 200 | 10-100 |
| 201 | 10-100 |
| 202 | >1,000 |
| 203 | >100 |
| 204 | ~100 |
| 205 | >100 |
| 206 | >100 |
| 207 | 10-100 |
| 208 | 10-100 |
| 209 | >100 |
| 210 | 10-100 |
| 211 | <10 |
| 212 | 36 |
| 213 | 23 |
| 214 | 30 |
| 215 | 91 |
| 216 | ~100 |
| 217 | 18 |
| 218 | 10-100 |
| 219 | 27 |
| 220 | 3.2 |
| 221 | 4.3 |
| 222 | 1.0 |
| 223 | 2.8 |
| 224 | 3.1 |
| 225 | 33 |
| 226 | 4.7 |
| 227 | ~100 |

Hereinbefore, the present disclosure has been described with reference to the examples, however, these are for illustrative purposes only, and it is to be understood that various modified and equivalent other examples of the present disclosure obvious to those skilled in the art may be implemented within the scope of the attached claims.

The invention claimed is:
1. A compound of the following Chemical Formula 1 or a pharmaceutically acceptable salt thereof:

[Chemical Formula 1]

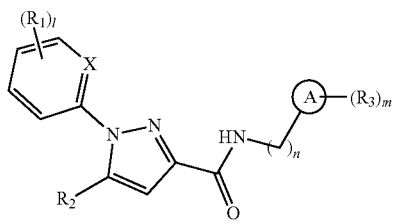

wherein, in Chemical Formula 1,
X is N or CH;
a ring A is $C_{3-6}$ cycloalkylene, $C_{6-10}$ arylene, $C_{5-10}$ heteroarylene containing 1 to 4 heteroatoms selected from among N, O and S atoms, or a non-aromatic fused heteropolycyclic ring containing 1 to 4 heteroatoms selected from among N, O and S;
$R_1$s are each independently hydrogen, halogen, or linear or branched $C_{1-6}$ alkyl, or halo $C_{1-6}$ alkyl, and when there are a plurality of $R_1$s, these are the same as or different from each other;
$R_2$s are each independently

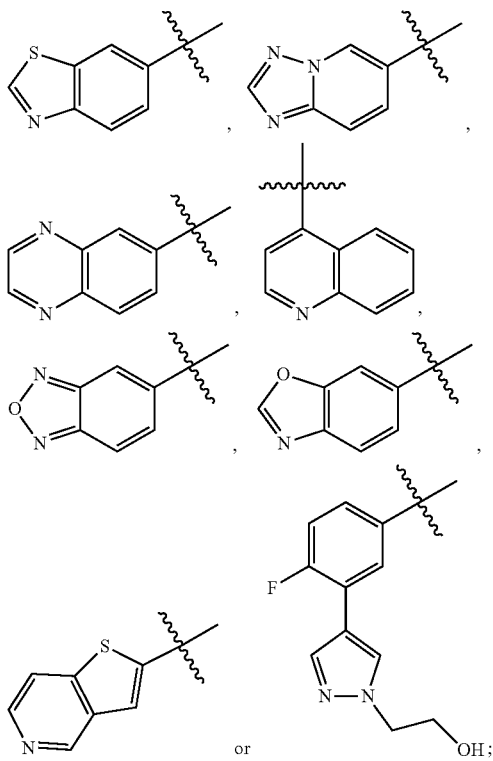

$R_3$ is hydrogen, halogen, linear or branched $C_{1-6}$ alkyl, linear or branched halo $C_{1-6}$ alkyl, $C_{3-10}$ cycloalkyl, $C_{3-10}$ heterocycloalkyl unsubstituted or substituted with $R_4$, $C_{6-10}$ heterobicycloalkyl, linear or branched $C_{2-6}$ alkenyl, $C_{2-6}$ alkynyl, —$(CH_2)_a$—$R_4$, —$(CH_2)_a$—$OR_4$, —$(CH_2)_a$—$O$—$(CH_2)_a$—$R_4$, —$(CH_2)_a$—$S$—$(CH_2)_a$—$R_4$, —$(CH_2)_a$—$O$—$(CH_2)_a$—$OR_4$, —$(CH_2)_a$—$NR_4R_5$, —$(CH_2)_a$—$NO_2$, —$(CH_2)_a$—$CN$, —$(CH_2)_a$—$COR_4$, —$(CH_2)_a$—$CO_2R_4$, —$(CH_2)_a$—$CONR_4R_5$, —$(CH_2)_a$—$NHCOR_4$, —$(CH_2)_a$—$SR_4$, —$(CH_2)_a$—$NHSO_2R_4$, —$(CH_2)_a$$SOR_6$, —$(CH_2)_a$—$SO_2R_6$, —$(CH_2)_a$—$SO_2NHR_6$, —$(CH_2)_a$—$SO(NH)R_6$ or —$(CH_2)_a$—$SO_2NR_4R_5$, or when there are a plurality of $R_3$s and they are adjacent to each other, they are linked to each other to form a 5-membered or 6-membered ring with the ring A, one or more heteroatoms selected from among N, O and S atoms are included in the ring, and the heteroatoms are further oxidized;
$R_4$ and $R_5$ are each independently hydrogen, linear or branched $C_{1-6}$ alkyl, linear or branched halo $C_{1-6}$ alkyl, $C_{3-10}$ cycloalkyl, $C_{3-6}$ cycloalkenyl, $C_{1-6}$ carbonyl, $C_{6-12}$ aryl, —$(CH_2)_b$—$NR_6R_7$, or saturated or partially unsaturated 5-membered to 10-membered monocyclic or bicyclic heterocycloalkyl or heteroaryl containing 1 to 4 heteroatoms selected from among N, O and S;
$R_6$ and $R_7$ are each independently hydrogen, hydroxy, $C_{1-6}$ alkyl, halo $C_{1-6}$ alkyl or $C_{3-6}$ cycloalkyl;
a and b are an integer of 0 to 4; and
l, m and n are each independently an integer of 0 to 4.
2. The compound or a pharmaceutically acceptable salt thereof of claim 1, wherein X is N, and $R_1$ is $C_{1-6}$ alkyl.
3. The compound or a pharmaceutically acceptable salt thereof of claim 1, wherein the ring A is phenyl, pyrazole, pyridinyl or benzo[d][1,3]dioxol.
4. The compound or a pharmaceutically acceptable salt thereof of claim 1, wherein the compound of Chemical Formula 1 is a compound selected from the group consisting of the following compounds:
(1) 5-(benzo[d]thiazol-6-yl)-N-(4-methoxyphenyl)-1-(6-methylpyridin-2-yl)-1H-pyrazole-3-carboxyamide;
(2) 5-(benzo[d]thiazol-6-yl)-N-(4-ethoxyphenyl)-1-(6-methylpyridin-2-yl)-1H-pyrazole-3-carboxyamide;
(3) 5-(benzo[d]thiazol-6-yl)-N-(4-(cyclopropylmethoxy)phenyl)-1-(6-methylpyridin-2-yl)-1H-pyrazole-3-carboxyamide;
(4) 5-(benzo[d]thiazol-6-yl)-N-(4-(2-methoxyethoxy)phenyl)-1-(6-methylpyridin-2-yl)-1H-pyrazole-3-carboxyamide;
(5) 5-(benzo[d]thiazol-6-yl)-1-(6-methylpyridin-2-yl)-N-(4-(trifluoromethoxy)phenyl)-1H-pyrazole-3-carboxyamide;
(6) 5-(benzo[d]thiazol-6-yl)-N-(4-(benzyloxy)phenyl)-1-(6-methylpyridin-2-yl)-1H-pyrazole-3-carboxyamide;
(7) N-(benzo[d][1,3]dioxol-5-yl)-5-(benzo[d]thiazol-6-yl)-1-(6-methylpyridin-2-yl)-1-H-pyrazole-3-carboxyamide;
(8) 5-(benzo[d]thiazol-6-yl)-N-(4-fluoro-3-methoxyphenyl)-1-(6-methylpyridin-2-yl)-1H-pyrazole-3-carboxyamide;
(9) 5-(benzo[d]thiazol-6-yl)-N-(2-fluoro-4-methoxyphenyl)-1-(6-methylpyridin-2-yl)-1H-pyrazole-3-carboxyamide;
(10) 5-(benzo[d]thiazol-6-yl)-N-(3-fluoro-4-methoxyphenyl)-1-(6-methylpyridin-2-yl)-1H-pyrazole-3-carboxyamide;
(11) 5-(benzo[d]thiazol-6-yl)-N-(3-aminophenyl)-1-(6-methylpyridin-2-yl)-1H-pyrazole-3-carboxyamide;
(12) 5-(benzo[d]thiazol-6-yl)-N-(3-(methylamino)phenyl)-1-(6-methylpyridin-2-yl)-1H-pyrazole-3-carboxyamide;
(13) 5-(benzo[d]thiazol-6-yl)-N-(4-(dimethylamino)phenyl)-1-(6-methylpyridin-2-yl)-1H-pyrazole-3-carboxyamide;

(14) 5-(benzo[d]thiazol-6-yl)-1-(6-methylpyridin-2-yl)-N-(4-nitrophenyl)-1H-pyrazole-3-carboxamide;
(15) 5-(benzo[d]thiazol-6-yl)-N-(4-((2-(dimethylamino)ethyl)(methyl)amino)phenyl)-1-(6-methylpyridin-2-yl)-1H-pyrazole-3-carboxyamide;
(16) 5-(benzo[d]thiazol-6-yl)-N-(4-(3-(dimethylamino)pyrrolidin-1-yl)phenyl)-1-(6-methylpyridin-2-yl)-1H-pyrazole-3-carboxyamide;
(17) 5-(benzo[d]thiazol-6-yl)-N-(3-chloro-4-(octahydro-6H-pyrrolo[3,4-b]pyridin-6-yl)phenyl)-1-(6-methylpyridin-2-yl)-1H-pyrazole-3-carboxyamide;
(18) 5-(benzo[d]thiazol-6-yl)-1-(6-methylpyridin-2-yl)-N-phenyl-1H-pyrazole-3-carboxyamide;
(19) 5-(benzo[d]thiazol-6-yl)-N-(3-tolyl)-1-(6-methylpyridin-2-yl)-1H-pyrazole-3-carboxyamide;
(20) 5-(benzo[d]thiazol-6-yl)-1-(6-methylpyridin-2-yl)-N-(3-vinylphenyl)-1H-pyrazole-3-carboxyamide;
(21) 5-(benzo[d]thiazol-6-yl)-N-(3-(trifluoromethyl)phenyl)-1-(6-methylpyridin-2-yl)-1H-pyrazole-3-carboxyamide;
(22) 5-(benzo[d]thiazol-6-yl)-N-(3-(cyanophenyl)-1-(6-methylpyridin-2-yl)-1H-pyrazole-3-carboxyamide;
(23) 5-(benzo[d]thiazol-6-yl)-N-(3-acetylphenyl)-1-(6-methylpyridin-2-yl)-1H-pyrazole-3-carboxyamide;
(24) ethyl 3-(5-(benzo[d]thiazol-6-yl)-1-(6-methylpyridin-2-yl)-1H-pyrazole-3-carboxyamido)benzoate;
(25) 5-(benzo[d]thiazol-6-yl)-N-(4-(methylcarbamoyl)phenyl)-1-(6-methylpyridin-2-yl)-1H-pyrazole-3-carboxyamide;
(26) 5-(benzo[d]thiazol-6-yl)-N-(4-acetamidophenyl)-1-(6-methylpyridin-2-yl)-1H-pyrazole-3-carboxyamide;
(27) 5-(benzo[d]thiazol-6-yl)-N-(2-fluorophenyl)-1-(6-methylpyridin-2-yl)-1H-pyrazole-3-carboxyamide;
(28) 5-(benzo[d]thiazol-6-yl)-N-(3-fluorophenyl)-1-(6-methylpyridin-2-yl)-1H-pyrazole-3-carboxyamide;
(29) 5-(benzo[d]thiazol-6-yl)-N-(4-fluorophenyl)-1-(6-methylpyridin-2-yl)-1H-pyrazole-3-carboxyamide;
(30) 5-(benzo[d]thiazol-6-yl)-N-(3,4-difluorophenyl)-1-(6-methylpyridin-2-yl)-1H-pyrazole-3-carboxyamide;
(31) 5-(benzo[d]thiazol-6-yl)-N-(2-chlorophenyl)-1-(6-methylpyridin-2-yl)-1H-pyrazole-3-carboxyamide;
(32) 5-(benzo[d]thiazol-6-yl)-N-(3-chlorophenyl)-1-(6-methylpyridin-2-yl)-1H-pyrazole-3-carboxyamide;
(33) 5-(benzo[d]thiazol-6-yl)-N-(4-chlorophenyl)-1-(6-methylpyridin-2-yl)-1H-pyrazole-3-carboxyamide;
(34) 5-(benzo[d]thiazol-6-yl)-N-(4-bromophenyl)-1-(6-methylpyridin-2-yl)-1H-pyrazole-3-carboxyamide;
(35) 5-(benzo[d]thiazol-6-yl)-1-(6-methylpyridin-2-yl)-N-(3-(methylthio)phenyl)-1H-pyrazole-3-carboxyamide;
(36) 5-(benzo[d]thiazol-6-yl)-1-(6-methylpyridin-2-yl)-N-(4-(methylthio)phenyl)-1H-pyrazole-3-carboxyamide;
(37) 5-(benzo[d]thiazol-6-yl)-N-(4-(cyclopropylthio)phenyl)-1-(6-methylpyridin-2-yl)-1H-pyrazole-3-carboxyamide;
(38) 5-(benzo[d]thiazol-6-yl)-1-(6-methylpyridin-2-yl)-N-(3-(methylsulfinyl)phenyl)-1H-pyrazole-3-carboxyamide;
(39) 5-(benzo[d]thiazol-6-yl)-1-(6-methylpyridin-2-yl)-N-(4-(methylsulfinyl)phenyl)-1H-pyrazole-3-carboxyamide;
(40) 5-(benzo[d]thiazol-6-yl)-1-(6-methylpyridin-2-yl)-N-(3-(methylsulfonyl)phenyl)-1H-pyrazole-3-carboxamide;
(41) 5-(benzo[d]thiazol-6-yl)-1-(6-methylpyridin-2-yl)-N-(4-(methylsulfonyl)phenyl)-1H-pyrazole-3-carboxyamide;
(42) 5-(benzo[d]thiazol-6-yl)-1-(6-methylpyridin-2-yl)-N-(4-(propylsulfonyl)phenyl)-1H-pyrazole-3-carboxyamide;
(43) 5-(benzo[d]thiazol-6-yl)-N-(4-(cyclopropylsulfonyl)phenyl)-1-(6-methylpyridin-2-yl)-1H-pyrazole-3-carboxyamide;
(44) 5-(benzo[d]thiazol-6-yl)-N-(2-fluoro-4-(methylsulfonyl)phenyl)-1-(6-methylpyridin-2-yl)-1H-pyrazole-3-carboxyamide;
(45) 5-(benzo[d]thiazol-6-yl)-1-(6-methylpyridin-2-yl)-N-(3-sulfamoylphenyl)-1H-pyrazole-3-carboxyamide;
(46) 5-(benzo[d]thiazol-6-yl)-1-(6-methylpyridin-2-yl)-N-(4-sulfamoylphenyl)-1H-pyrazole-3-carboxyamide;
(47) 5-(benzo[d]thiazol-6-yl)-1-(6-methylpyridin-2-yl)-N-(3-(N-methylsulfamoyl)phenyl)-1H-pyrazole-3-carboxyamide;
(48) 5-(benzo[d]thiazol-6-yl)-1-(6-methylpyridin-2-yl)-N-(4-(N-methylsulfamoyl)phenyl)-1H-pyrazole-3-carboxyamide;
(49) 5-(benzo[d]thiazol-6-yl)-N-(3-(N-cyclopropylsulfamoyl)phenyl)-1-(6-methylpyridin-2-yl)-1H-pyrazole-3-carboxyamide;
(50) 5-(benzo[d]thiazol-6-yl)-N-(4-(N-cyclopropylsulfamoyl)phenyl)-1-(6-methylpyridin-2-yl)-1H-pyrazole-3-carboxyamide;
(51) 5-(benzo[d]thiazol-6-yl)-N-(3-(N,N-dimethylsulfamoyl)phenyl)-1-(6-methylpyridin-2-yl)-1H-pyrazole-3-carboxyamide;
(52) 5-(benzo[d]thiazol-6-yl)-N-(4-(N,N-dimethylsulfamoyl)phenyl)-1-(6-methylpyridin-2-yl)-1H-pyrazole-3-carboxyamide;
(53) 5-(benzo[d]thiazol-6-yl)-1-(6-methylpyridin-2-yl)-N-(3-(methylsulfonamido)phenyl)-1H-pyrazole-3-carboxyamide;
(54) 5-(benzo[d]thiazol-6-yl)-N-(3-(cyclopropanesulfonamido)phenyl)-1-(6-methylpyridin-2-yl)-1H-pyrazole-3-carboxyamide;
(55) 5-(benzo[d]thiazol-6-yl)-N-(4-(cyclopropanesulfonamido)phenyl)-1-(6-methylpyridin-2-yl)-1H-pyrazole-3-carboxyamide;
(56) 4-(5-(benzo[d]thiazol-6-yl)-1-(6-methylpyridin-2-yl)-1H-pyrazole-3-carboxyamido)benzenesulfonic acid;
(57) 5-(benzo[d]thiazol-6-yl)-1-(6-methylpyridin-2-yl)-N-(4-((trifluoromethyl)sulfonyl)phenyl)-1H-pyrazole-3-carboxyamide;
(58) 5-(benzo[d]thiazol-6-yl)-1-(6-methylpyridin-2-yl)-N-(4-(N-(2,2,2-trifluoroethyl)sulfamoyl)phenyl)-1H-pyrazole-3-carboxyamide;
(59) 5-(benzo[d]thiazol-6-yl)-1-(6-methylpyridin-2-yl)-N-(4-((methylsulfonyl)methyl)phenyl)-1H-pyrazole-3-carboxyamide;
(60) 5-(benzo[d]thiazol-6-yl)-1-(6-methylpyridin-2-yl)-N-(3-(sulfamoylmethyl)phenyl)-1H-pyrazole-3-carboxyamide;
(61) 5-(benzo[d]thiazol-6-yl)-1-(6-methylpyridin-2-yl)-N-(4-(sulfamoylmethyl)phenyl)-1H-pyrazole-3-carboxyamide;
(62) 5-(benzo[d]thiazol-6-yl)-N-(4-fluoro-3-(sulfamoylmethyl)phenyl)-1-(6-methylpyridin-2-yl)-1H-pyrazole-3-carboxyamide;
(63) 5-(benzo[d]thiazol-6-yl)-N-(4-((1,1-dioxidotetrahydrothiophen-3-yl)amino)phenyl)-1-(6-methylpyridin-2-yl)-1H-pyrazole-3-carboxyamide;

(64) 5-(benzo[d]thiazol-6-yl)-1-(6-methylpyridin-2-yl)-N-(pyridin-4-yl)-1H-pyrazole-3-carboxamide;
(65) 5-(benzo[d]thiazol-6-yl)-N-(6-methoxypyridin-3-yl)-1-(6-methylpyridin-2-yl)-1H-pyrazole-3-carboxamide;
(66) 5-(benzo[d]thiazol-6-yl)-N-(2-methoxypyridin-4-yl)-1-(6-methylpyridin-2-yl)-1H-pyrazole-3-carboxamide;
(67) 5-(benzo[d]thiazol-6-yl)-N-(6-(methylthio)pyridin-3-yl)-1-(6-methylpyridin-2-yl)-1H-pyrazole-3-carboxamide;
(68) 5-(benzo[d]thiazol-6-yl)-1-(6-methylpyridin-2-yl)-N-(6-(methylsulfonyl)pyridin-2-yl)-1H-pyrazole-3-carboxamide;
(69) 5-(benzo[d]thiazol-6-yl)-N-(6-(methylsulfonyl)pyridin-3-yl)-1-(6-methylpyridin-2-yl)-1H-pyrazole-3-carboxamide;
(70) 5-(benzo[d]thiazol-6-yl)-1-(6-methylpyridin-2-yl)-N-(2-(methylsulfonyl)pyridin-4-yl)-1H-pyrazole-3-carboxamide;
(71) 5-(benzo[d]thiazol-6-yl)-N-(6-fluoropyridin-3-yl)-1-(6-methylpyridin-2-yl)-1H-pyrazole-3-carboxamide;
(72) 5-(benzo[d]thiazol-6-yl)-N-(2-fluoropyridin-4-yl)-1-(6-methylpyridin-2-yl)-1H-pyrazole-3-carboxamide;
(73) 5-(benzo[d]thiazol-6-yl)-N-(6-chloropyridin-3-yl)-1-(6-methylpyridin-2-yl)-1H-pyrazole-3-carboxamide;
(74) 5-(benzo[d]thiazol-6-yl)-N-(2-chloropyridin-4-yl)-1-(6-methylpyridin-2-yl)-1H-pyrazole-3-carboxamide;
(75) 5-(benzo[d]thiazol-6-yl)-1-(6-methylpyridin-2-yl)-N-(thiazol-2-yl)-1H-pyrazole-3-carboxamide;
(76) 5-(benzo[d]thiazol-6-yl)-N-benzyl-1-(6-methylpyridin-2-yl)-1H-pyrazole-3-carboxamide;
(77) 5-(benzo[d]thiazol-6-yl)-N-(2-fluorobenzyl)-1-(6-methylpyridin-2-yl)-1H-pyrazole-3-carboxamide;
(78) 5-(benzo[d]thiazol-6-yl)-N-(3-fluorobenzyl)-1-(6-methylpyridin-2-yl)-1H-pyrazole-3-carboxamide;
(79) 5-(benzo[d]thiazol-6-yl)-N-(4-fluorobenzyl)-1-(6-methylpyridin-2-yl)-1H-pyrazole-3-carboxamide;
(80) 5-(benzo[d]thiazol-6-yl)-1-(6-methylpyridin-2-yl)-N-(1-(methylsulfonyl)-1H-pyrazol-4-yl)-1H-pyrazole-3-carboxamide;
(81) 5-(benzo[d]thiazol-6-yl)-N-(1-(cyclopropylsulfonyl)-1H-pyrazol-4-yl)-1-(6-methylpyridin-2-yl)-1H-pyrazole-3-carboxamide;
(82) 5-(benzo[d]thiazol-6-yl)-N-(3-hydroxyphenyl)-1-(6-methylpyridin-2-yl)-1H-pyrazole-3-carboxamide;
(83) 5-(benzo[d]thiazol-6-yl)-N-(4-hydroxyphenyl)-1-(6-methylpyridin-2-yl)-1H-pyrazole-3-carboxamide;
(84) 5-(benzo[d]thiazol-6-yl)-N-(3-(hydroxymethyl)phenyl)-1-(6-methylpyridin-2-yl)-1H-pyrazole-3-carboxamide;
(85) 5-(benzo[d]thiazol-6-yl)-N-(4-(hydroxymethyl)phenyl)-1-(6-methylpyridin-2-yl)-1H-pyrazole-3-carboxamide;
(86) N-(4-aminophenyl)-5-(benzo[d]thiazol-6-yl)-1-(6-methylpyridin-2-yl)-1H-pyrazole-3-carboxamide;
(87) 5-(benzo[d]thiazol-6-yl)-N-(4-(butylamino)phenyl)-1-(6-methylpyridin-2-yl)-1H-pyrazole-3-carboxamide;
(88) 5-(benzo[d]thiazol-6-yl)-N-(4-(cyclopropylamino)phenyl)-1-(6-methylpyridin-2-yl)-1H-pyrazole-3-carboxamide;
(89) 5-(benzo[d]thiazol-6-yl)-1-(6-methylpyridin-2-yl)-N-(4-(S-methylsulfonimidoyl)phenyl)-1H-pyrazole-3-carboxamide;
(90) 5-([1,2,4]triazolo[1,5-α]pyridin-6-yl)-N-(2-methoxyphenyl)-1-(6-methylpyridin-2-yl)-1H-pyrazole-3-carboxamide;
(91) 5-([1,2,4]triazolo[1,5-α]pyridin-6-yl)-N-(3-methoxyphenyl)-1-(6-methylpyridin-2-yl)-1H-pyrazole-3-carboxamide;
(92) 5-([1,2,4]triazolo[1,5-α]pyridin-6-yl)-N-(2-methoxyphenyl)-1-(6-methylpyridin-2-yl)-1H-pyrazole-3-carboxamide;
(93) 5-([1,2,4]triazolo[1,5-α]pyridin-6-yl)-N-(4-hydroxyphenyl)-1-(6-methylpyridin-2-yl)-1H-pyrazole-3-carboxamide;
(94) 5-([1,2,4]triazolo[1,5-α]pyridin-6-yl)-N-(4-isopropylphenyl)-1-(6-methylpyridin-2-yl)-1H-pyrazole-3-carboxamide;
(95) 5-([1,2,4]triazolo[1,5-α]pyridin-6-yl)-N-(4-(2-methoxyethoxy)phenyl)-1-(6-methylpyridin-2-yl)-1H-pyrazole-3-carboxamide;
(96) 5-([1,2,4]triazolo[1,5-α]pyridin-6-yl)-N-(benzo[d][1,3]dioxol-5-yl)-1-(6-methylpyridin-2-yl)-1H-pyrazole-3-carboxamide;
(97) 5-([1,2,4]triazolo[1,5-α]pyridin-6-yl)-N-(2-fluoro-4-methoxyphenyl)-1-(6-methylpyridin-2-yl)-1H-pyrazole-3-carboxamide;
(98) 5-([1,2,4]triazolo[1,5-α]pyridin-6-yl)-N-(3-fluoro-4-methoxyphenyl)-1-(6-methylpyridin-2-yl)-1H-pyrazole-3-carboxamide;
(99) 5-([1,2,4]triazolo[1,5-α]pyridin-6-yl)-1-(6-methylpyridin-2-yl)-N-(2-(trifluoromethoxy)phenyl)-1H-pyrazole-3-carboxamide;
(100) 5-([1,2,4]triazolo[1,5-α]pyridin-6-yl)-1-(6-methylpyridin-2-yl)-N-(3-(trifluoromethoxy)phenyl)-1H-pyrazole-3-carboxamide;
(101) 5-([1,2,4]triazolo[1,5-α]pyridin-6-yl)-1-(6-methylpyridin-2-yl)-N-(4-(trifluoromethoxy)phenyl)-1H-pyrazole-3-carboxamide;
(102) 5-([1,2,4]triazolo[1,5-α]pyridin-6-yl)-N-(3-(dimethylamino)phenyl)-1-(6-methylpyridin-2-yl)-1H-pyrazole-3-carboxamide;
(103) 5-([1,2,4]triazolo[1,5-α]pyridin-6-yl)-N-(4-aminophenyl)-1-(6-methylpyridin-2-yl)-1H-pyrazole-3-carboxamide;
(104) 5-([1,2,4]triazolo[1,5-α]pyridin-6-yl)-N-(4-(dimethylamino)phenyl)-1-(6-methylpyridin-2-yl)-1-H-pyrazole-3-carboxamide;
(105) 5-([1,2,4]triazolo[1,5-α]pyridin-6-yl)-N-(4-(pyrrolidin-1-yl)phenyl)1-(6-methylpyridin-2-yl)-1H-pyrazole-3-carboxamide;
(106) 5-([1,2,4]triazolo[1,5-α]pyridin-6-yl)-N-(4-((2-(dimethylamino)ethyl)(methyl)amino)phenyl)-1-(6-methylpyridin-2-yl)-1H-pyrazole-3-carboxamide;
(107) 5-([1,2,4]triazolo[1,5-α]pyridin-6-yl)-N-(4-(4-methylpiperazin-1-yl)phenyl)-1-(6-methylpyridin-2-yl)-1H-pyrazole-3-carboxamide;
(108) 5-([1,2,4]triazolo[1,5-α]pyridin-6-yl)-N-(4-(4-acetylpiperazin-1-yl)phenyl)-1-(6-methylpyridin-2-yl)-1H-pyrazole-3-carboxamide;
(109) 5-([1,2,4]triazolo[1,5-α]pyridin-6-yl)-N-(4-((1,1-dioxidotetrahydrothiophen-3-yl)amino)phenyl)-1-(6-methylpyridin-2-yl)-1H-pyrazole-3-carboxamide;
(110) 5-([1,2,4]triazolo[1,5-α]pyridin-6-yl)-N-(4-acetamidophenyl)-1-(6-methylpyridin-2-yl)-1H-pyrazole-3-carboxamide;
(111) 5-([1,2,4]triazolo[1,5-α]pyridin-6-yl)-N-(4-((dimethylamino)methyl)phenyl)-1-(6-methylpyridin-2-yl)-1H-pyrazole-3-carboxamide;

(112) 5-([1,2,4]triazolo[1,5-α]pyridin-6-yl)-N-(2-(methylcarbamoyl)phenyl)-1-(6-methylpyridin-2-yl)-1H-pyrazole-3-carboxamide;
(113) 5-([1,2,4]triazolo[1,5-α]pyridin-6-yl)-N-(4-(methylcarbamoyl)phenyl)-1-(6-methylpyridin-2-yl)-1H-pyrazole-3-carboxamide;
(114) 5-([1,2,4]triazolo[1,5-α]pyridin-6-yl)-1-(6-methylpyridin-2-yl)-N-phenyl-1H-pyrazole-3-carboxamide;
(115) 5-([1,2,4]triazolo[1,5-α]pyridin-6-yl)-1-(6-methylpyridin-2-yl)-N-(o-tolyl)-1H-pyrazole-3-carboxamide;
(116) 5-([1,2,4]triazolo[1,5-α]pyridin-6-yl)-1-(6-methylpyridin-2-yl)-N-(m-tolyl)-1H-pyrazole-3-carboxamide;
(117) 5-([1,2,4]triazolo[1,5-α]pyridin-6-yl)-1-(6-methylpyridin-2-yl)-N-(p-tolyl)-1H-pyrazole-3-carboxamide;
(118) 5-([1,2,4]triazolo[1,5-α]pyridin-6-yl)-1-(6-methylpyridin-2-yl)-N-(3-(trifluoromethyl)phenyl)-1H-pyrazole-3-carboxamide;
(119) 5-([1,2,4]triazolo[1,5-α]pyridin-6-yl)-1-(6-methylpyridin-2-yl)-N-(4-vinylphenyl)-1H-pyrazole-3-carboxamide;
(120) 5-([1,2,4]triazolo[1,5-α]pyridin-6-yl)-N-(3-cyanophenyl)-1-(6-methylpyridin-2-yl)-1H-pyrazole-3-carboxamide;
(121) 5-([1,2,4]triazolo[1,5-α]pyridin-6-yl)-N-(4-cyanophenyl)-1-(6-methylpyridin-2-yl)-1-H-pyrazole-3-carboxamide;
(122) 5-([1,2,4]triazolo[1,5-α]pyridin-6-yl)-N-(3-acetylphenyl)-1-(6-methylpyridin-2-yl)-1H-pyrazole-3-carboxamide;
(123) 5-([1,2,4]triazolo[1,5-α]pyridin-6-yl)-N-(4-acetylphenyl)-1-(6-methylpyridin-2-yl)-1H-pyrazole-3-carboxamide;
(124) 5-([1,2,4]triazolo[1,5-α]pyridin-6-yl)-N-(2-fluorophenyl)-1-(6-methylpyridin-2-yl)-1H-pyrazole-3-carboxamide;
(125) 5-([1,2,4]triazolo[1,5-α]pyridin-6-yl)-N-(3-fluorophenyl)-1-(6-methylpyridin-2-yl)-1H-pyrazole-3-carboxamide;
(126) 5-([1,2,4]triazolo[1,5-α]pyridin-6-yl)-N-(4-fluorophenyl)-1-(6-methylpyridin-2-yl)-1H-pyrazole-3-carboxamide;
(127) 5-([1,2,4]triazolo[1,5-α]pyridin-6-yl)-N-(2-chlorophenyl)-1-(6-methylpyridin-2-yl)-1H-pyrazole-3-carboxamide;
(128) 5-([1,2,4]triazolo[1,5-α]pyridin-6-yl)-N-(3-chlorophenyl)-1-(6-methylpyridin-2-yl)-1H-pyrazole-3-carboxamide;
(129) 5-([1,2,4]triazolo[1,5-α]pyridin-6-yl)-N-(4-chlorophenyl)-1-(6-methylpyridin-2-yl)-1H-pyrazole-3-carboxamide;
(130) 5-([1,2,4]triazolo[1,5-α]pyridin-6-yl)-N-(2-bromophenyl)-1-(6-methylpyridin-2-yl)-1H-pyrazole-3-carboxamide;
(131) 5-([1,2,4]triazolo[1,5-α]pyridin-6-yl)-N-(3-bromophenyl)-1-(6-methylpyridin-2-yl)-1H-pyrazole-3-carboxamide;
(132) 5-([1,2,4]triazolo[1,5-α]pyridin-6-yl)-N-(4-bromophenyl)-1-(6-methylpyridin-2-yl)-1H-pyrazole-3-carboxamide;
(133) 5-([1,2,4]triazolo[1,5-α]pyridin-6-yl)-N-(2,3-difluorophenyl)-1-(6-methylpyridin-2-yl)-1H-pyrazole-3-carboxamide;
(134) 5-([1,2,4]triazolo[1,5-α]pyridin-6-yl)-N-(2,4-difluorophenyl)-1-(6-methylpyridin-2-yl)-1H-pyrazole-3-carboxamide;
(135) 5-([1,2,4]triazolo[1,5-α]pyridin-6-yl)-N-(2,5-difluorophenyl)-1-(6-methylpyridin-2-yl)-1H-pyrazole-3-carboxamide;
(136) 5-([1,2,4]triazolo[1,5-α]pyridin-6-yl)-N-(3,4-difluorophenyl)-1-(6-methylpyridin-2-yl)-1H-pyrazole-3-carboxamide;
(148) 5-([1,2,4]triazolo[1,5-α]pyridin-6-yl)-N-(4-sulfamoylphenyl)-1-(6-methylpyridin-2-yl)-1H-pyrazole-3-carboxamide;
(149) 5-([1,2,4]triazolo[1,5-α]pyridin-6-yl)-N-(4-(S-methylsulfonimidoyl)phenyl)-1-(6-methylpyridin-2-yl)-1H-pyrazole-3-carboxamide;
(150) 5-([1,2,4]triazolo[1,5-α]pyridin-6-yl)-N-(4-(propylsulfonyl)phenyl)-1-(6-methylpyridin-2-yl)-1H-pyrazole-3-carboxamide;
(151) 5-([1,2,4]triazolo[1,5-α]pyridin-6-yl)-N-(4-(propylsulfonyl)phenyl)-1-(6-methylpyridin-2-yl)-1H-pyrazole-3-carboxamide;
(152) 5-([1,2,4]triazolo[1,5-α]pyridin-6-yl)-N-(6-fluoropyridin-3-yl)-1-(6-methylpyridin-2-yl)-1H-pyrazole-3-carboxamide;
(153) 5-([1,2,4]triazolo[1,5-α]pyridin-6-yl)-N-(6-chloropyridin-3-yl)-1-(6-methylpyridin-2-yl)-1H-pyrazole-3-carboxamide;
(154) 5-([1,2,4]triazolo[1,5-α]pyridin-6-yl)-N-(6-methoxypyridin-3-yl)-1-(6-methylpyridin-2-yl)-1H-pyrazole-3-carboxamide;
(155) 5-([1,2,4]triazolo[1,5-α]pyridin-6-yl)-N-(2-fluorobenzyl)-1-(6-methylpyridin-2-yl)-1H-pyrazole-3-carboxamide;
(156) 5-([1,2,4]triazolo[1,5-α]pyridin-6-yl)-N-(3-fluorobenzyl)-1-(6-methylpyridin-2-yl)-1H-pyrazole-3-carboxamide;
(157) 5-([1,2,4]triazolo[1,5-α]pyridin-6-yl)-N-(4-fluorobenzyl)-1-(6-methylpyridin-2-yl)-1H-pyrazole-3-carboxamide;
(158) 5-([1,2,4]triazolo[1,5-α]pyridin-6-yl)-N-(3-methoxybenzyl)-1-(6-methylpyridin-2-yl)-1H-pyrazole-3-carboxamide;
(137) 5-([1,2,4]triazolo[1,5-α]pyridin-6-yl)-N-(3,5-difluorophenyl)-1-(6-methylpyridin-2-yl)-1H-pyrazole-3-carboxamide;
(138) 5-([1,2,4]triazolo[1,5-α]pyridin-6-yl)-N-(3-chloro-2-fluorophenyl)-1-(6-methylpyridin-2-yl)-1H-pyrazole-3-carboxamide;
(139) 5-([1,2,4]triazolo[1,5-α]pyridin-6-yl)-N-(4-chloro-2-fluorophenyl)-1-(6-methylpyridin-2-yl)-1H-pyrazole-3-carboxamide;
(140) 5-([1,2,4]triazolo[1,5-α]pyridin-6-yl)-N-(3-chloro-4-fluorophenyl)-1-(6-methylpyridin-2-yl)-1H-pyrazole-3-carboxamide;
(141) 5-([1,2,4]triazolo[1,5-α]pyridin-6-yl)-N-(3,4-dichlorophenyl)-1-(6-methylpyridin-2-yl)-1H-pyrazole-3-carboxamide;
(142) 5-([1,2,4]triazolo[1,5-α]pyridin-6-yl)-N-(2-bromo-4-fluorophenyl)-1-(6-methylpyridin-2-yl)-1H-pyrazole-3-carboxamide;
(143) 5-([1,2,4]triazolo[1,5-α]pyridin-6-yl)-N-(3-(methoxythio)phenyl)-1-(6-methylpyridin-2-yl)-1H-pyrazole-3-carboxamide;
(144) 5-([1,2,4]triazolo[1,5-α]pyridin-6-yl)-N-(4-(methoxythio)phenyl)-1-(6-methylpyridin-2-yl)-1H-pyrazole-3-carboxamide;

(145) 5-([1,2,4]triazolo[1,5-α]pyridin-6-yl)-N-(3-(methylsulfinyl)phenyl)-1-(6-methylpyridin-2-yl)-1H-pyrazole-3-carboxamide;
(146) 5-([1,2,4]triazolo[1,5-α]pyridin-6-yl)-N-(4-(methylsulfinyl)phenyl)-1-(6-methylpyridin-2-yl)-1H-pyrazole-3-carboxamide;
(147) 5-([1,2,4]triazolo[1,5-α]pyridin-6-yl)-N-(4-(methylsulfonyl)phenyl)-1-(6-methylpyridin-2-yl)-1H-pyrazole-3-carboxamide;
(159) 5-([1,2,4]triazolo[1,5-α]pyridin-6-yl)-N-(4-methoxybenzyl)-1-(6-methylpyridin-2-yl)-1H-pyrazole-3-carboxamide;
(160) 5-([1,2,4]triazolo[1,5-α]pyridin-6-yl)-N-(4-(dimethylamino)benzyl)-1-(6-methylpyridin-2-yl)-1H-pyrazole-3-carboxamide;
(161) 5-([1,2,4]triazolo[1,5-α]pyridin-6-yl)-N-(-acetamidobenzyl)-1-(6-methylpyridin-2-yl)-1H-pyrazole-3-carboxamide;
(162) 5-([1,2,4]triazolo[1,5-α]pyridin-6-yl)-1-(6-methylpyridin-2-yl)-N-(1-(methylsulfonyl)-1H-pyrazol-4-yl)-1H-pyrazole-3-carboxamide;
(163) 5-([1,2,4]triazolo[1,5-α]pyridin-6-yl)-N-(1-cyclopropyl sulfonyl)-1H-pyrazol-4-yl)-1-(6-methylpyridin-2-yl)-1H-pyrazole-3-carboxamide;
(164) N-(4-methoxyphenyl)-1-(6-methylpyridin-2-yl)-5-(quinoxalin-6-yl)-1H-pyrazole-3-carboxamide;
(165) N-(3-methoxyphenyl)-1-(6-methylpyridin-2-yl)-5-(quinoxalin-6-yl)-1H-pyrazole-3-carboxamide;
(166) N-(2-methoxyphenyl)-1-(6-methylpyridin-2-yl)-5-(quinoxalin-6-yl)-1H-pyrazole-3-carboxamide;
(167) N-(4-(2-methoxyethoxy)phenyl)-1-(6-methylpyridin-2-yl)-5-(quinoxalin-6-yl)-1H-pyrazole-3-carboxamide;
(168) N-(benzo[d][1,3]dioxol-5-yl)-1-(6-methylpyridin-2-yl)-5-(quinoxalin-6-yl)-1H-pyrazole-3-carboxamide;
(169) N-(2,3-dihydrobenzo[b][1,4]dioxin-6-yl)-1-(6-methylpyridin-2-yl)-5-(quinoxalin-6-yl)-1H-pyrazole-3-carboxamide;
(170) N-(4-(dimethylamino)phenyl)-1-(6-methylpyridin-2-yl)-5-(quinoxalin-6-yl)-1H-pyrazole-3-carboxamide;
(171) 1-(6-methylpyridin-2-yl)-N-(4-morpholinophenyl)-5-(quinoxalin-6-yl)-1H-pyrazole-3-carboxamide;
(172) N-(4-(4-methylpiperazin-1-yl)phenyl)-1-(6-methylpyridin-2-yl)-5-(quinoxalin-6-yl)-1H-pyrazole-3-carboxamide;
(173) N-(4-(4-acetylpiperazin-1-yl)phenyl)-1-(6-methylpyridin-2-yl)-5-(quinoxalin-6-yl)-1H-pyrazole-3-carboxamide;
(174) N-(4-cyanophenyl)-1-(6-methylpyridin-2-yl)-5-(quinoxalin-6-yl)-1H-pyrazole-3-carboxamide;
(175) N-(3-cyanophenyl)-1-(6-methylpyridin-2-yl)-5-(quinoxalin-6-yl)-1H-pyrazole-3-carboxamide;
(176) N-(2-cyanophenyl)-1-(6-methylpyridin-2-yl)-5-(quinoxalin-6-yl)-1H-pyrazole-3-carboxamide;
(177) 1-(6-methylpyridin-2-yl)-N-(4-(morpholinomethyl)phenyl)-5-(quinoxalin-6-yl)-1H-pyrazole-3-carboxamide;
(178) N-(4-acetylphenyl)-1-(6-methylpyridin-2-yl)-5-(quinoxalin-6-yl)-1H-pyrazole-3-carboxamide;
(179) N-(3-acetylphenyl)-1-(6-methylpyridin-2-yl)-5-(quinoxalin-6-yl)-1H-pyrazole-3-carboxamide;
(180) 1-(6-methylpyridin-2-yl)-5-(quinoxalin-6-yl)-N-(4-(trifluoromethyl)phenyl)-1H-pyrazole-3-carboxamide;
(181) 1-(6-methylpyridin-2-yl)-5-(quinoxalin-6-yl)-N-(3-(trifluoromethyl)phenyl)-1H-pyrazole-3-carboxamide;
(182) N-(4-(methylcarbamoyl)phenyl)-1-(6-methylpyridin-2-yl)-5-(quinoxalin-6-yl)-1H-pyrazole-3-carboxamide;
(183) N-(4-fluorophenyl)-1-(6-methylpyridin-2-yl)-5-(quinoxalin-6-yl)-1H-pyrazole-3-carboxamide;
(184) N-(3-fluorophenyl)-1-(6-methylpyridin-2-yl)-5-(quinoxalin-6-yl)-1H-pyrazole-3-carboxamide;
(185) N-(2-fluorophenyl)-1-(6-methylpyridin-2-yl)-5-(quinoxalin-6-yl)-1H-pyrazole-3-carboxamide;
(186) N-(3,4-difluorophenyl)-1-(6-methylpyridin-2-yl)-5-(quinoxalin-6-yl)-1H-pyrazole-3-carboxamide;
(187) N-(2,4-difluorophenyl)-1-(6-methylpyridin-2-yl)-5-(quinoxalin-6-yl)-1H-pyrazole-3-carboxamide;
(188) N-(2,3-difluorophenyl)-1-(6-methylpyridin-2-yl)-5-(quinoxalin-6-yl)-1H-pyrazole-3-carboxamide;
(189) N-(4-chlorophenyl)-1-(6-methylpyridin-2-yl)-5-(quinoxalin-6-yl)-1H-pyrazole-3-carboxamide;
(190) N-(2-chlorophenyl)-1-(6-methylpyridin-2-yl)-5-(quinoxalin-6-yl)-1H-pyrazole-3-carboxamide;
(191) N-(4-bromophenyl)-1-(6-methylpyridin-2-yl)-5-(quinoxalin-6-yl)-1H-pyrazole-3-carboxamide;
(192) N-(6-methoxypyridin-3-yl)-1-(6-methylpyridin-2-yl)-5-(quinoxalin-6-yl)-1H-pyrazole-3-carboxamide;
(193) N-(4-methoxybenzyl)-1-(6-methylpyridin-2-yl)-5-(quinoxalin-6-yl)-1H-pyrazole-3-carboxamide;
(194) N-(4-cyanobenzyl)-1-(6-methylpyridin-2-yl)-5-(quinoxalin-6-yl)-1H-pyrazole-3-carboxamide;
(195) N-(3-acetylbenzyl)-1-(6-methylpyridin-2-yl)-5-(quinoxalin-6-yl)-1H-pyrazole-3-carboxamide;
(196) N-(4-fluorobenzyl)-1-(6-methylpyridin-2-yl)-5-(quinoxalin-6-yl)-1H-pyrazole-3-carboxamide;
(197) N-(3-fluorobenzyl)-1-(6-methylpyridin-2-yl)-5-(quinoxalin-6-yl)-1H-pyrazole-3-carboxamide;
(198) N-(2-fluorobenzyl)-1-(6-methylpyridin-2-yl)-5-(quinoxalin-6-yl)-1H-pyrazole-3-carboxamide;
(199) N-(4-chlorobenzyl)-1-(6-methylpyridin-2-yl)-5-(quinoxalin-6-yl)-1H-pyrazole-3-carboxamide;
(200) N-(3-chlorobenzyl)-1-(6-methylpyridin-2-yl)-5-(quinoxalin-6-yl)-1H-pyrazole-3-carboxamide;
(201) N-(2-chlorobenzyl)-1-(6-methylpyridin-2-yl)-5-(quinoxalin-6-yl)-1H-pyrazole-3-carboxamide;
(202) N-(2-fluorophenyl)-5-(quinoxalin-6-yl)-1-(m-tolyl)-1H-pyrazole-3-carboxamide;
(203) 1-(5-chloro-2-fluorophenyl)-N-(4-methoxyphenyl)-5-(quinoxalin-6-yl)-1H-pyrazole-3-carboxamide;
(204) 1-(5-chloro-2-fluorophenyl)-N-(4-(dimethylamino)phenyl)-5-(quinoxalin-6-yl)-1H-pyrazole-3-carboxamide;
(205) N-(4-methoxyphenyl)-5-(quinoxalin-6-yl)-1-(6-trifluoromethyl)pyridin-2-yl)-1H-pyrazole-3-carboxamide;
(206) N-(4-(dimethylamino)phenyl)-5-(quinoxalin-6-yl)-1-(6-trifluoromethyl)pyridin-2-yl)-1H-pyrazole-3-carboxamide;
(207) 1-(6-bromopyridin-2-yl)-N-(4-methoxyphenyl)-5-(quinoxalin-6-yl)-1H-pyrazole-3-carboxamide;
(208) 1-(6-bromopyridin-2-yl)-N-(4-(dimethylamino)phenyl)-5-(quinoxalin-6-yl)-1H-pyrazole-3-carboxamide;
(209) N-(2-fluorophenyl)-1-(6-methylpyridin-2-yl)-5-(quinolin-4-yl)-1H-pyrazole-3-carboxamide;
(210) N-(4-methoxyphenyl)-1-(6-methylpyridin-2-yl)-5-(quinolin-4-yl)-1H-pyrazole-3-carboxamide;

(211) 1-(6-methylpyridin-2-yl)-N-(4-(methylsulfonyl)phenyl)-5-(quinolin-4-yl)-1H-pyrazole-3-carboxamide;

(212) N-(6-methoxypyridin-3-yl)-1-(6-methylpyridin-2-yl)-5-(quinolin-4-yl)-1H-pyrazole-3-carboxyamide;

(213) N-(6-chloropyridin-3-yl)-1-(6-methylpyridin-2-yl)-5-(quinolin-4-yl)-1H-pyrazole-3-carboxyamide;

(214) N-(benzo[d][1,3]dioxol-5-yl)-1-(6-methylpyridin-2-yl)-5-(quinolin-4-yl)-1H-pyrazole-3-carboxyamide;

(215) N-(3-fluoro-4-methoxyphenyl)-1-(6-methylpyridin-2-yl)-5-(quinolin-4-yl)-1H-pyrazole-3-carboxamide;

(216) N-(2-fluoro-4-methoxyphenyl)-1-(6-methylpyridin-2-yl)-5-(quinolin-4-yl)-1H-pyrazole-3-carboxyamide;

(217) N-(4-(2-methoxyethoxy)phenyl)-1-(6-methylpyridin-2-yl)-5-(quinolin-4-yl)-1H-pyrazole-3-carboxyamide;

(218) 5-(benzo[c][1,2,5]oxadiazol-5-yl)-N-(4-(cyclopropyl sulfonyl)phenyl)-1-(6-methylpyridin-2-yl)-1H-pyrazole-3-carboxyamide;

(219) 5-(benzo[d]oxazol-6-yl)-N-(2-fluorophenyl)-1-(6-methylpyridin-2-yl)-1H-pyrazole-3-carboxyamide;

(220) 5-(benzo[d]oxazol-6-yl)-N-(4-(cyclopropylsulfonyl)phenyl)-1-(6-methylpyridin-2-yl)-1H-pyrazole-3-carboxyamide;

(221) N-cyclopropyl-5-(4-fluoro-3-(1-(2-hydroxyethyl)-1H-pyrazol-4-yl)phenyl)-1-(6-methylpyridin-2-yl)-1H-pyrazole-3-carboxyamide;

(222) N-(1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxyamide;

(223) N-(1-methyl-1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxyamide;

(224) N-(1-(methylsulfonyl)-1H-pyrazol-4-yl)-5-(4-fluoro-3-(1-(2-hydroxyethyl)-1H-pyrazol-4-yl)phenyl)-1-(6-methylpyridin-2-yl)-1H-pyrazole-3-carboxyamide;

(225) N-(4-chlorophenyl)-5-(4-fluoro-3-(1-(2-hydroxyethyl)-1H-pyrazol-4-yl)phenyl)-1-(6-methylpyridin-2-yl)-1H-pyrazole-3-carboxyamide;

(226) N-(4-(methylsulfonyl)phenyl)-5-(4-fluoro-3-(1-(2-hydroxyethyl)-1H-pyrazol-4-yl)phenyl)-1-(6-methylpyridin-2-yl)-1H-pyrazole-3-carboxyamide; and (227) N-(2-fluorophenyl)-5-(thieno[3,2,c]pyridin-2-yl)-1-(m-tolyl)-1H-pyrazole-3-carboxamide.

5. A pharmaceutical composition comprising the compound or pharmaceutically acceptable salt thereof of claim 1 in a pharmaceutically effective amount.

6. A pharmaceutical composition comprising the compound or pharmaceutically acceptable salt thereof of claim 4 in a pharmaceutically effective amount.

7. A method for inhibiting a TGF-β signaling pathway in a subject or a cell, the method comprising administering a pharmaceutically effective amount of the compound of claim 1 to the subject in need.

8. A method for inhibiting a TGF-β signaling pathway in a subject or a cell, the method comprising administering a pharmaceutically effective amount of the compound of claim 4 to the subject in need.

9. A method for inhibiting metastasis of cancer cells in a subject, the method comprising administering a pharmaceutically effective amount of the compound of claim 1 to the subject in need.

10. A method for treating a carcinoma mediated by overexpression of TGFβ, the method comprising administering a pharmaceutically effective amount of the compound of claim 1 to a subject in need of treatment of a carcinoma mediated by overexpression of TGFβ.

11. The method of claim 10, wherein the carcinoma is selected from the group consisting of carcinomas of lung, breast, liver, biliary, gastrointestinal tract, head and neck, pancreas, prostate and cervix, multiple myeloma, melanoma, glioma and glioblastoma.

12. The pharmaceutical composition of claim 5, which is for treating a cancer or a tumor.

13. The pharmaceutical composition of claim 12, wherein the cancer is selected from the group consisting of liver cancer, hepatocellular carcinoma, thyroid cancer, colorectal cancer, testicular cancer, bone cancer, oral cancer, basal cell carcinoma, ovarian cancer, brain tumor, gallbladder carcinoma, biliary tract cancer, head and neck cancer, colorectal cancer, vesical carcinoma, tongue cancer, esophageal cancer, glioma, glioblastoma, renal cancer, malignant melanoma, gastric cancer, breast cancer, sarcoma, pharynx carcinoma, uterine cancer, cervical cancer, prostate cancer, rectal cancer, pancreatic cancer, lung cancer, skin cancer, fibrous cancer, and a metastatic tumor.

* * * * *